(12) United States Patent
Kenyon et al.

(10) Patent No.: US 10,124,135 B2
(45) Date of Patent: Nov. 13, 2018

(54) BLOWER

(75) Inventors: Barton John Kenyon, Sydney (AU);
Jeegarkumar Kapadia, Sydney (AU);
Melanie Lucia Cariola, Sydney (AU);
Michael Bruce Moir, Newbury Park,
CA (US); Aleksandr S. Nagorny,
Canoga Park, CA (US); **Christopher
Scott Edwards**, Canoga Park, CA (US);
James McKensey Bencke, Sydney
(AU); Paul Andrews Dickens, Blue
Mountains (AU)

(73) Assignee: ResMed Motor Technologies Inc.,
Chatsworth, CA (US)

( * ) Notice: Subject to any disclaimer, the term of this
patent is extended or adjusted under 35
U.S.C. 154(b) by 218 days.

(21) Appl. No.: 14/236,766

(22) PCT Filed: Aug. 2, 2012

(86) PCT No.: PCT/AU2012/000918
§ 371 (c)(1),
(2), (4) Date: Feb. 3, 2014

(87) PCT Pub. No.: WO2013/020167
PCT Pub. Date: Feb. 14, 2013

(65) Prior Publication Data
US 2014/0158131 A1 Jun. 12, 2014

Related U.S. Application Data

(60) Provisional application No. 61/573,019, filed on Aug. 5, 2011.

(51) Int. Cl.
*A61M 16/00* (2006.01)
*F04D 17/16* (2006.01)
(Continued)

(52) U.S. Cl.
CPC .... *A61M 16/0066* (2013.01); *A61M 16/0069* (2014.02); *A61M 16/0858* (2014.02);
(Continued)

(58) Field of Classification Search
CPC .......... A61M 16/0066; A61M 16/0069; A61M 2205/42; A61M 2016/0039; F04D 29/444;
(Continued)

(56) References Cited

U.S. PATENT DOCUMENTS 2,287,822 A 6/1942 Odor et al.
3,066,850 A 12/1962 Coron et al.
(Continued)

FOREIGN PATENT DOCUMENTS

EP 1297772 A2 4/2003
JP 3577763 B2 7/2004
(Continued)

OTHER PUBLICATIONS

First Office Action issued in corresponding Chinese Application No. 201280049272.X dated Nov. 4, 2015, with English translation thereof.
(Continued)

*Primary Examiner* — Gregory Anderson
*Assistant Examiner* — Margaret Luarca
(74) *Attorney, Agent, or Firm* — Nixon & Vanderhye P.C.

(57) ABSTRACT

A blower includes a housing including an inlet and an outlet, a motor to drive a rotatable shaft, first and second impellers provided to the shaft, the first and second impellers each including a plurality of impeller blades, a first stationary component provided to the housing and including stator vanes downstream of the first impeller, and a second stationary component provided to the housing and including stator vanes downstream of the second impeller. A first set of stator vanes of the first stationary component is provided
(Continued)

around the motor and are configured and arranged to direct airflow along the motor, to de-swirl the airflow and to decelerate air to increase pressure. A blower including a third impeller and third stationary component positioned above the first impeller is also described.

53 Claims, 98 Drawing Sheets

(51) Int. Cl.
    *F04D 25/06*     (2006.01)
    *F04D 25/08*     (2006.01)
    *F04D 29/42*     (2006.01)
    *F04D 29/44*     (2006.01)
    *F04D 29/66*     (2006.01)
    *A61M 16/08*     (2006.01)

(52) U.S. Cl.
    CPC ......... *F04D 17/164* (2013.01); *F04D 17/165* (2013.01); *F04D 25/0606* (2013.01); *F04D 25/082* (2013.01); *F04D 29/4226* (2013.01); *F04D 29/444* (2013.01); *F04D 29/668* (2013.01); *A61M 2016/0027* (2013.01); *A61M 2016/0039* (2013.01); *A61M 2205/42* (2013.01); *F05D 2250/52* (2013.01)

(58) Field of Classification Search
    CPC ............... F04D 29/4226; F04D 29/668; F04D 25/0606; F04D 17/165; F04D 29/663; F05D 2250/52; F05D 2260/96; F05D 2260/963; H02K 5/24
    USPC .......................................................... 29/665
    See application file for complete search history.

(56) References Cited

U.S. PATENT DOCUMENTS

| | | | |
|---|---|---|---|
| 3,171,353 A | 3/1965 | McMahan | |
| 4,635,752 A | 1/1987 | Jennings | |
| 4,950,133 A | 8/1990 | Sargent | |
| 5,110,266 A | 5/1992 | Toyoshima et al. | |
| 6,451,097 B1 | 9/2002 | Andreani et al. | |
| 6,910,483 B2 | 5/2005 | Daly et al. | |
| 7,789,194 B2 | 9/2010 | Lathrop et al. | |
| 7,866,944 B2 | 1/2011 | Kenyon et al. | |
| 2003/0172931 A1 | 9/2003 | Kerechanin, II et al. | |
| 2005/0103339 A1* | 5/2005 | Daly ................ | A61M 16/0057 128/204.18 |
| 2005/0123398 A1 | 6/2005 | Tam et al. | |
| 2005/0166921 A1 | 8/2005 | De Vries et al. | |
| 2006/0144396 A1 | 7/2006 | DeVries et al. | |
| 2007/0007271 A1 | 1/2007 | Heidmann et al. | |
| 2008/0257346 A1* | 10/2008 | Lathrop ............ | A61M 16/0066 128/204.17 |
| 2008/0304986 A1 | 12/2008 | Kenyon et al. | |
| 2009/0246013 A1* | 10/2009 | Kenyon ............ | A61M 16/0057 415/208.2 |
| 2010/0307498 A1* | 12/2010 | Jones ................ | A61M 16/0066 128/204.21 |
| 2012/0167879 A1* | 7/2012 | Bowman ........... | A61M 16/0066 128/201.22 |
| 2012/0199129 A1* | 8/2012 | Kenyon ............ | A61M 16/0066 128/205.25 |
| 2013/0152918 A1* | 6/2013 | Rummery ............ | A61M 16/00 128/201.22 |

FOREIGN PATENT DOCUMENTS

| | | |
|---|---|---|
| JP | 2006-527324 | 11/2006 |
| JP | 2008-509331 | 3/2008 |
| WO | 98/33433 A1 | 8/1998 |
| WO | WO 99/22794 | 5/1999 |
| WO | WO 02/070139 | 9/2002 |
| WO | WO 2004/108198 | 12/2004 |
| WO | WO 2006/017398 A2 | 2/2006 |
| WO | WO 2007/024955 | 3/2007 |
| WO | WO 2007/045017 | 4/2007 |
| WO | WO 2007/048205 | 5/2007 |
| WO | WO 2010/028121 | 3/2010 |
| WO | WO 2011/062633 | 5/2011 |
| WO | WO 2012/094230 | 7/2012 |
| WO | WO 2012/135912 | 10/2012 |
| WO | WO 2013/048238 | 4/2013 |
| WO | WO 2013/133889 | 9/2013 |

OTHER PUBLICATIONS

International Search Report for PCT/AU2012/000918, dated Dec. 14, 2012.
Further Examination Report issued in corresponding New Zealand Application No. 620412 dated Sep. 9, 2015.
International Preliminary Report on Patentability in PCT Application No. PCT/AU2012/000918 dated Feb. 11, 2014.
First Examination Report issued in corresponding New Zealand Application No. 711507 dated Sep. 17, 2015.
Patent Examination Report No. 2 issued in corresponding Australian Application No. 2012292950 dated Sep. 23, 2015.
First Examination Report issued in corresponding New Zealand Appln. No. 620412 dated Oct. 29, 2014.
International Preliminary Report on Patentability Chapter I for PCT Application No. PCT/AU2012/000918, dated Feb. 20, 2014.
Extended European Search Report issued in corresponding European Appln. No. 12 82 1650.4 dated Mar. 2, 2015.
Patent Examination Report No. 1 issued in corresponding Australian Appln. No. 2012292950 dated Mar. 8, 2015.
Further Examination Report issued in corresponding New Zealand Application No. 620412 dated Mar. 23, 2016.
First Office Action issued in corresponding Japanese Patent Application No. 2014-523146 dated Jul. 4, 2016, with English language translation thereof.
Second Office Action issued in corresponding Chinese Patent Application No. 201280049272.X dated Jul. 5, 2016, with English language translation thereof.
Communication pursuant to Article 94(3) EPC issued in corresponding European Application No. 12 821 650.4 dated Feb. 24, 2016.
Office Action dated Jul. 3, 2017 issued in Chinese Application No. 201280049272.X with English translation (4 pages).
Office Action dated Apr. 3, 2017 issued in Japanese Application No. 2014-523146 with English translation (15 pages).
First Examination Report dated Mar. 15, 2017 issued in New Zealand Application No. 729296 (2 pages).
Office Action dated Jan. 4, 2017 issued in Chinese Application No. 201280049272.X with English translation (8 pages).
Examination Report dated Jan. 5, 2017 issued in Australian Application No. 2016200222 (2 pages).
Extended European Search Report dated Jun. 23, 2017 issued in European Application No. 17154737.5 (11 pages).
Decision of Rejection dated Dec. 25, 2017 issued in Japanese Application No. 2014-523146 with English translation (7 pages).
Further Examination Report dated Jun. 5, 2018 issued in New Zealand Application No. 729296 (2 pages).
Pre-Appeal Examination Report dated Jul. 23, 2018 issued in Japanese Application No. 2014-523146 with English translation (6 pages).

\* cited by examiner

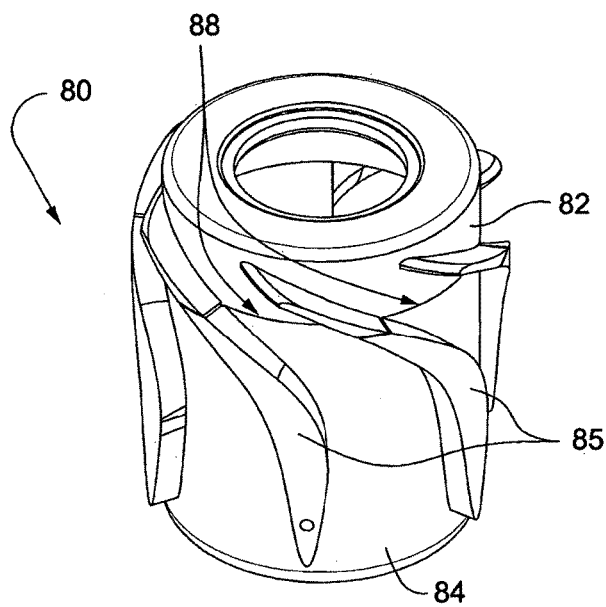
FIG. 49
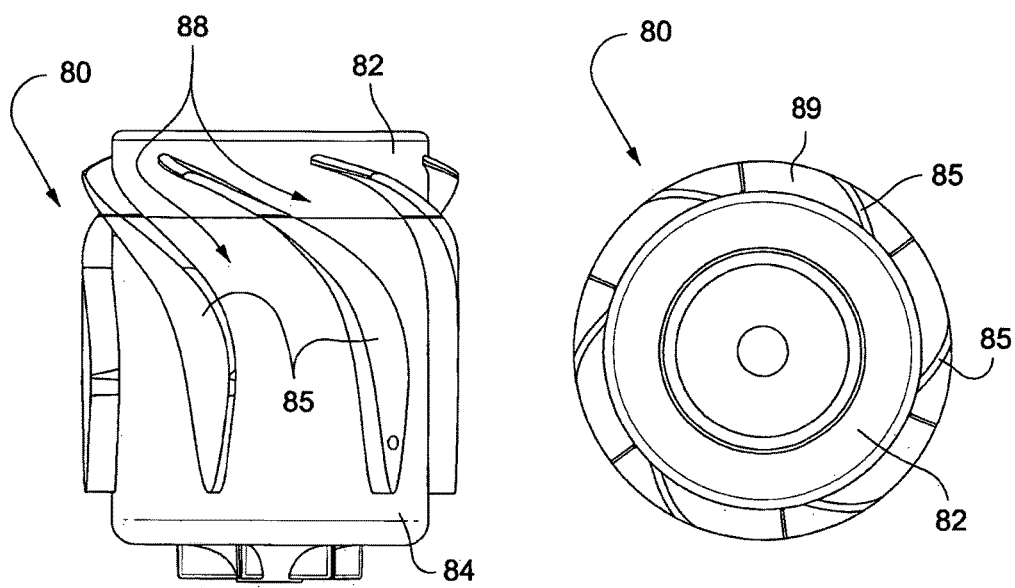
FIG. 50
FIG. 51

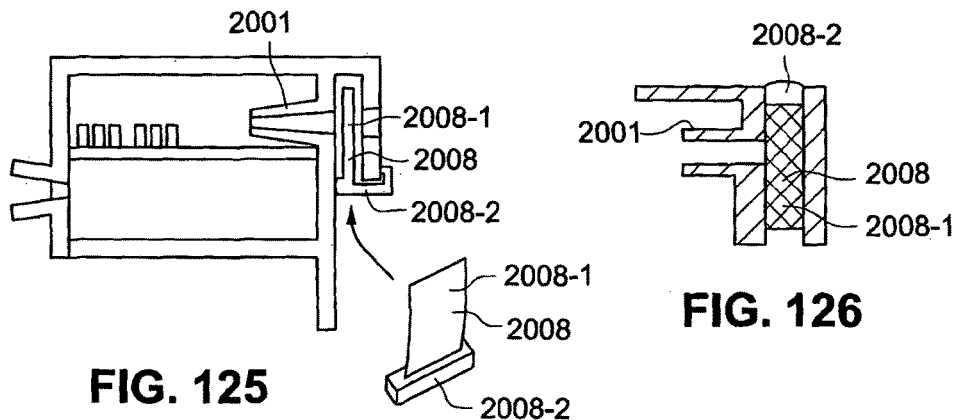
FIG. 125
FIG. 126
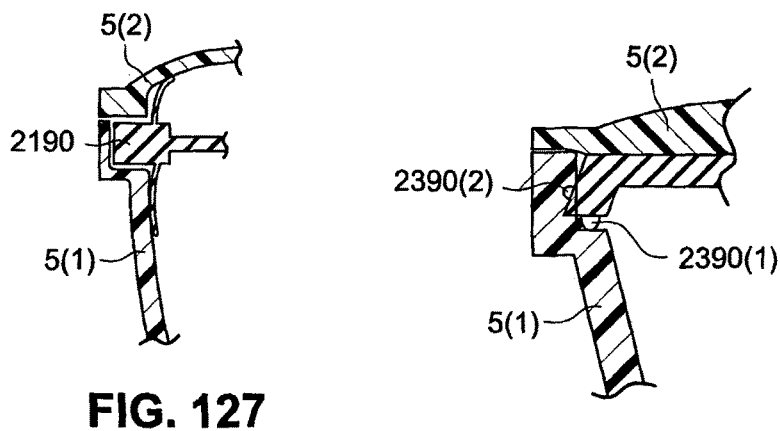
FIG. 127
FIG. 128
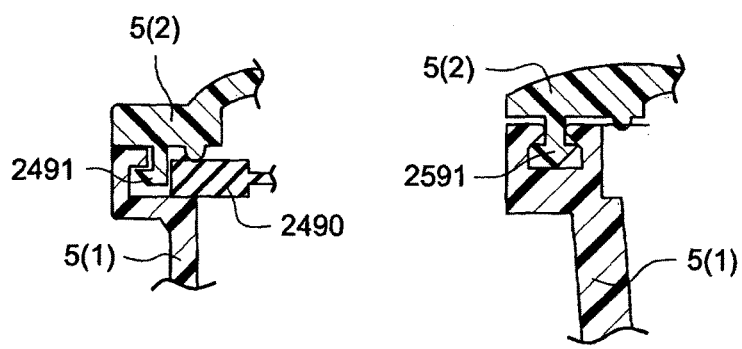
FIG. 129
FIG. 130

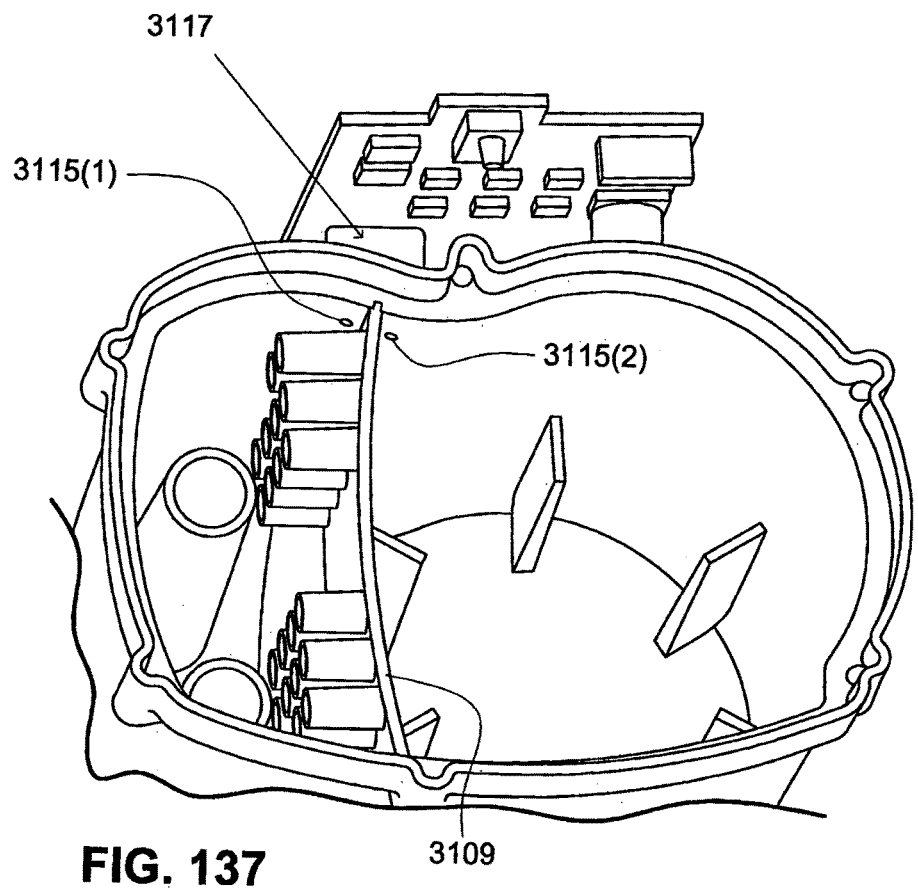
FIG. 137
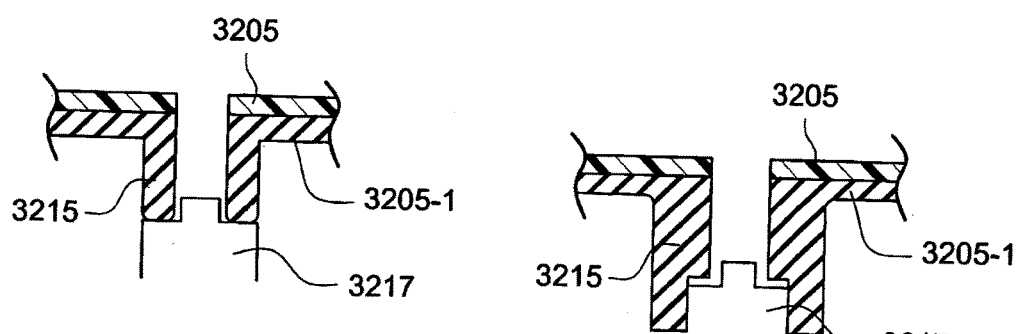
FIG. 138
FIG. 139

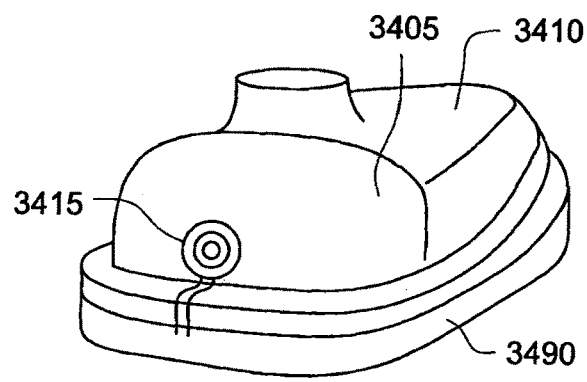
FIG. 148
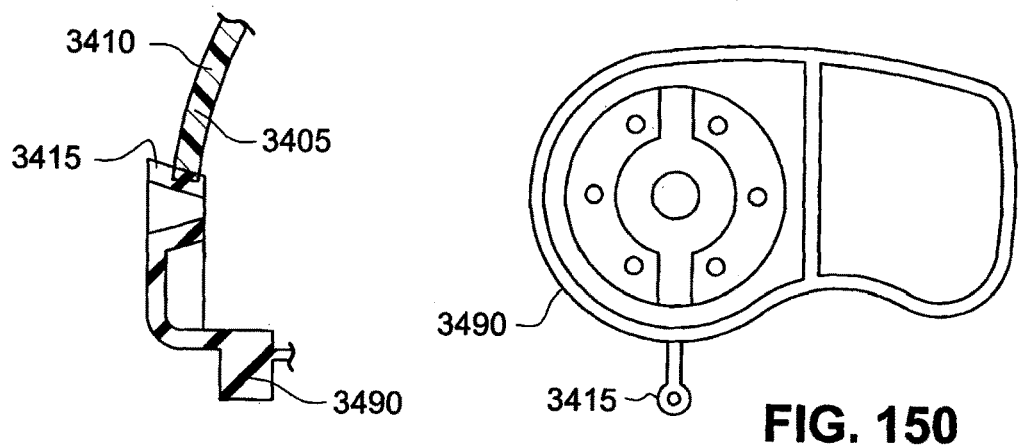
FIG. 149
FIG. 150
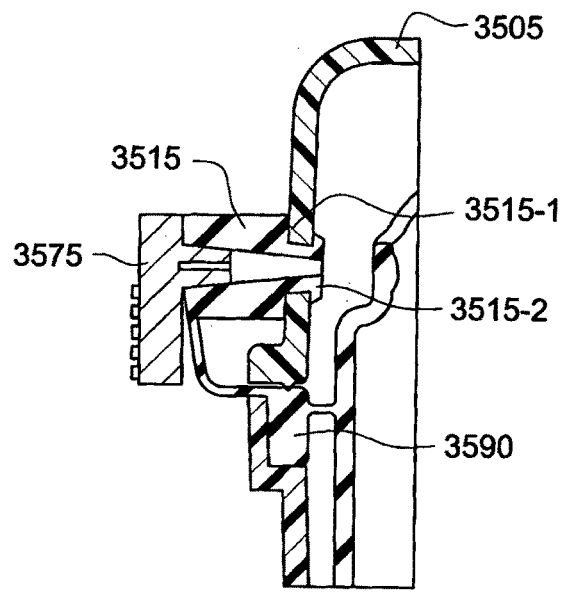
FIG. 151

BLOWER

CROSS-REFERENCE TO APPLICATION

This application is the U.S. national phase of International Application No. PCT/AU2012/000918 filed 2 Aug. 2012 which is designated the U.S. and claims the benefit of U.S. Provisional Application No. 61/573,019, filed Aug. 5, 2011, which is incorporated herein by reference in its entirety.

FIELD OF TECHNOLOGY

The present technology relates to a blower for generating a pressure differential and/or to a pressure generating device or positive airway pressure (PAP) device. In an example, the blower may be used in a positive airway pressure (PAP) device used for the delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) and more particularly Obstructive Sleep Apnea (OSA). However, the blower may be used in other applications (e.g., vacuum applications (medical or otherwise)).

BACKGROUND OF TECHNOLOGY

Examples of existing motor/blower designs are described in ResMed's U.S. Pat. Nos. 6,910,483 and 7,866,944, which are incorporated into ResMed's AutoSet CS2 and S9 series of sleep therapy products, respectively.

A need has developed in the art for blower designs that are quieter and more compact, all while retaining the same or equivalent air delivery capacity, e.g., in terms of pressure and flow. The present technology provides alternative arrangements of blowers that consider this need.

SUMMARY OF TECHNOLOGY

An aspect of the disclosed technology relates to a blower including a housing including an inlet and an outlet, a motor to drive a rotatable shaft, first and second impellers provided to the shaft, the first and second impellers each including a plurality of impeller blades, a first stationary component provided to the housing and including stator vanes downstream of the first impeller, and a second stationary component provided to the housing and including stator vanes downstream of the second impeller. A first set of stator vanes of the first stationary component is provided around the motor and are configured and arranged to direct airflow along the motor, to de-swirl the airflow and to decelerate air to increase pressure. In an example, the first impeller is positioned on one side of the motor and the second impeller is positioned on the other side of the motor. In an example, the blower includes a third impeller and a third stationary component provided to the housing and including stator vanes following the third impeller, the third impeller and the third stationary component positioned upstream of the first impeller.

An aspect of the disclosed technology relates to a blower including a housing including an inlet and an outlet, a motor to drive a rotatable shaft, first, second, and third impellers provided to the shaft (e.g., two provided to the shaft on one side of the motor and one provided to the shaft on the other side of the motor), a first stationary component provided to the housing and including stator vanes following the first impeller, a second stationary component provided to the housing and including stator vanes following the second impeller, and a third stationary component provided to the housing and including stator vanes following the third impeller. The second stationary component is provided around the motor and the stator vanes of the second stationary component are configured and arranged to direct airflow along the motor, de-swirl the airflow, and to decelerate the air to increase pressure.

Another aspect of the disclosed technology relates to a blower including at least one impeller and a stationary component following each impeller. Each stationary component includes a plurality of vanes that provide vane passages therebetween for airflow. Each vane passage includes an expanding cross-sectional area that increases from an upstream direction to a downstream direction to increase pressure.

Another aspect of the disclosed technology relates to a PAP device including a casing and a blower provided within the casing. The casing includes at least first and second chambers and a plurality of conduits or tubes that allow air to pass from the first chamber to the second chamber. The plurality of conduits are arranged to provide acoustic impedance and flow measurement by providing a defined pressure drop. In an alternative example, the casing may include a single chamber and plurality of conduits provided between the chamber and atmosphere, e.g., combine plurality of conduits and inlet into one piece.

Another aspect of the disclosed technology relates to a blower having a reduced size compared to prior art blowers while still providing high pressures with low noise and reliability. This may be enabled by one or more of the following: (i) ensuring high static regain—by using stator vane passages that expand in cross-sectional area while they turn the flow, employing stator vanes that extend all the way to the hub to prevent swirling into the next stage, forming the stator vanes in two halves to provide for a larger number of vanes that are still moldable (e.g., 8-20 stator vanes utilized), using skewed leading edges to soften acoustic interactions; (ii) run at faster speeds; (iii) include third stage; (iv) increasing impeller strength by extending the blades into the hub, impeller slightly tapered to reduce turbulence, less height at the outer tips of the impeller compared to the inner region of the impeller; (v) inlet housing includes chimney to provide acoustic resistance to reduce noise emitted from inlet; and/or (vi) thermally conductive plastics used for the housing and potentially the impeller to assist with removing heat, and air recirculated between the shaft and the first set of stator vanes to assist in removing heat from bearings and shaft.

Another aspect of the disclosed technology relates to a PAP device including a casing and a blower provided within the casing. The casing includes at least one chamber and one or more inlet conduits extending at least partially into the chamber to allow ambient air to enter the chamber, e.g., while providing acoustic impedance.

Another aspect of the disclosed technology relates to a PAP device including a casing and a blower provided within the casing. The casing includes at least an inlet chamber, e.g., to attenuate airborne radiated noise, having a casing inlet and a blower inlet chamber to support an inlet end of the blower. The blower is supported by a suspension system structured to divide low and high pressure sides of the blower.

Another aspect of the disclosed technology relates to a PAP device including a casing, a blower provided within the casing, and a suspension system to support the blower within the casing. At least a portion of the suspension system includes a plurality of strap members structured to clamp to an exterior of the blower to secure the portion to the blower and secure blower components of the blower in position.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 49-51 are various views of a stationary component according to an example of the disclosed technology;

FIGS. 122-1 and 122-2 show a single suspension system for a blower according to an example of the disclosed technology;

FIGS. 125 and 126 are schematic views showing a filter insert for a PAP device according to alternative examples of the disclosed technology;

FIGS. 127 to 133 are schematic views showing sealing arrangements for a cover of a PAP device according to alternative examples of the disclosed technology;

FIG. 137 is a cross-sectional view of a PAP device including flow sensor ports according to an example of the disclosed technology;

FIGS. 138-142 are cross-sectional views of flow sensor interfaces provided in an over-molded layer of the casing for a PAP device according to alternative examples of the disclosed technology;

FIGS. 148 to 153 show sensor interfaces or seals provided to the blower suspension of a PAP device according to alternative examples of the disclosed technology;

DETAILED DESCRIPTION OF ILLUSTRATED EXAMPLES

Figure 1:
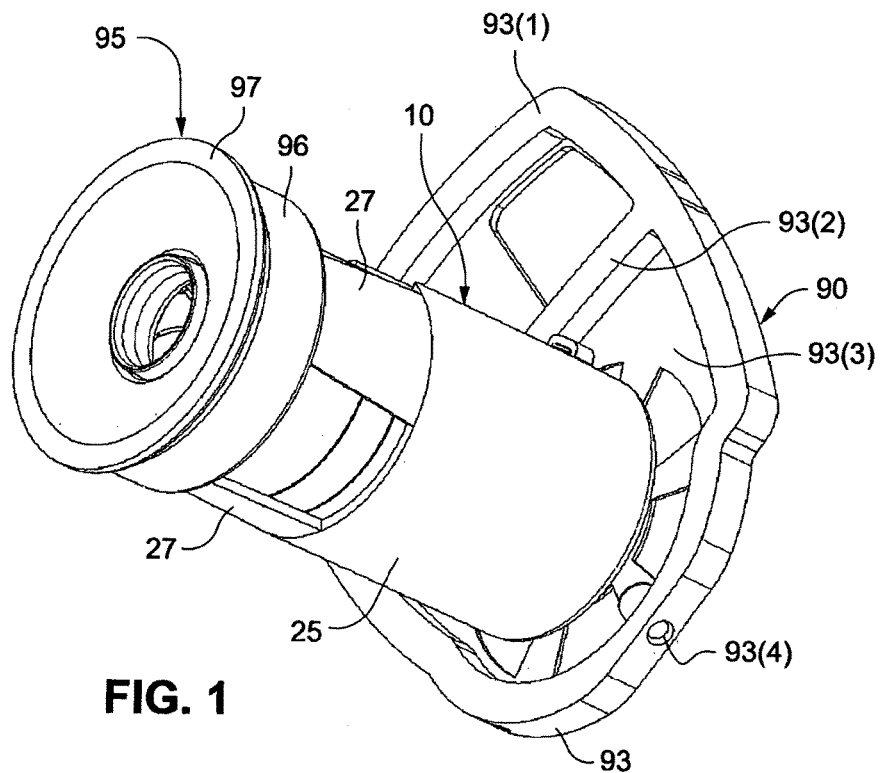
FIG. 1 is a perspective view of a blower including an inlet end suspension and an outlet end suspension according to an example of the disclosed technology.

The following description is provided in relation to several examples (some of which are illustrated, some of which may not be) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Aspects of the technology will be described herein in its application to non-invasive ventilation (NIVV) treatment apparatus (e.g., positive airway pressure (PAP) devices), such as CPAP, but it is to be understood that aspects of the technology may have application to other fields of application where blowers are used, e.g., in both positive pressure and negative pressure applications.

In this specification, the words "air pump" and "blower" may be used interchangeably. The term "air" may be taken to include breathable gases, for example air with supplemental oxygen. It is also acknowledged that the blowers described herein may be designed to pump fluids other than air.

Also, each blower example below is described as including a three stage design. However, it should be appreciated that examples of the technology may be applied to other stage designs, e.g., one, two, four, or more stages.

1. Blower

FIGS. 1-14 illustrate a three stage, centrifugal blower 10 according to an example of the technology. As described below, the blower provides a low inertia, axially symmetric, three-stage blower design. The blower is structured to provide high pressure values while maintaining a low noise and small size. In an example, the blower may be structured to provide pressurized air up to 45-50 cmH$_2$O, e.g., in the range of 2-50 cmH$_2$O, e.g., 3-45 cmH$_2$O, 4-30 cmH$_2$O.

The blower is relatively small (e.g., outer diameter of the blower may be about 30-40 mm, e.g., 35-36 mm) but minimizes the increase of rpm by providing three stages. The impellers and stator vanes of the blower are compressed axially to prevent the rotor or shaft from protruding too far. The blower has relatively low inertia (e.g., about 300-400 g·mm$^2$) so responds relatively quickly. In an example, the blower may be about 50% smaller and about 50-60% the inertia of the blower disclosed in U.S. Patent Publication No. US-2008-0304986.

In an example, a three stage blower according to an example of the present technology may include an overall length of about 63 mm and a diameter of about 35 mm, and a related two stage blower according to an example of the present technology may include a length of about 53 mm and a diameter of about 35 mm. In contrast, an exemplary two stage blower such as that disclosed in U.S. Patent Publication No. US-2008-0304986 includes a length of about 59 mm and a diameter of about 59 mm. In an example, an impeller according to an example of the present technology includes a diameter of about 25 mm on a 3 mm diameter shaft to provide low inertia, e.g., about 50-60% that of an exemplary blower such as that disclosed in U.S. Patent Publication No. US-2008-0304986 which includes an impeller having a diameter of about 42 mm on a 4 mm diameter shaft.

Total pressure is equal to pressure per stage times the number of stages. The pressure per stage is proportional to (impeller diameter)$^2$×(angular velocity)$^2$. As the impeller diameter decreases, the angular velocity (rpm) may be increased to maintain a desired pressure per stage. Alternatively, the blower may minimize the increase in angular velocity by providing extra stages, e.g., three stages.

The blower is structured to provide performance for a full range of products from continuous positive airway pressure to variable positive airway pressure, where the motor must react quickly to the patient's breathing pattern, e.g., increased speed during inspiration and reduced speed during expiration. Thus, the blower is structured to generate pressures up to 45-50 cmH$_2$O (e.g., and flows up to about 120 L/min) to allow for the high impedance of some patient circuits and different altitudes.

As illustrated, the blower 10 includes first and second housing parts 20, 25, a motor 30 adapted to drive a rotatable shaft of the rotor 50, first and second impellers 60-1, 60-2 provided to the rotor 50 and positioned on one side of the motor 30 and a third impeller 60-3 provided to the rotor 50 and positioned on the opposite side of the motor 30. The blower includes a first stationary component 70-1 including stage 1 stator vanes and following the first impeller 60-1, a second stationary component 80 including stage 2 stator vanes following the second impeller 60-2 and enclosing the motor 30, and a third stationary component 70-2 including stage 3 stator vanes and following the third impeller 60-3. Also, a suspension system (e.g., constructed of silicone) including an outlet end suspension 90 and an inlet end suspension 95 may optionally be provided to the blower 10, e.g., to support the blower within the casing of a PAP device as described below. In an alternative arrangement, the suspension may be formed as a single piece that encases at least a portion of the blower.

FIGS. 44 to 48 show alternative views of the blower 10 and FIGS. 49 to 51 show alternative views of the second stationary component 80. In FIGS. 44-48, the outlet end suspension 90 includes a more ring-shaped configuration, in contrast to the example shown in FIGS. 1-12.

In the illustrated example, the blower 10 includes an axial air inlet 21 and axial air outlet 26 between which are located three stages with three corresponding impellers, i.e., first and second impellers positioned on one side of the motor and a third impeller positioned on the other side of the motor. However, other suitable impeller arrangements are possible.

As described below, each stage includes an axially flat impeller (i.e., axially short or axially compact impeller, e.g., total axial height of the impeller may be about 4 mm) followed by a set of stator vanes structured to direct the air flow to the next stage (or air outlet for the third stage stator vanes). A shield 72 is provided between the first and third stage impellers 60-1, 60-3 and the first and third stage stator vanes 70-1, 70-2, e.g., to prevent blade pass tonal noise and to constrain the air within the stator vane passages. The shield 72 is preferably used when radially directed stator vanes or stator vanes configured in a substantially horizontal plane are positioned below the impeller. Preferably, no shield is used when axially directed stator vanes or stator vanes configured in a substantially vertical plane are positioned below the impeller as for the second stage stator vanes 80. However, a shield may be used with any stator vanes arrangement. The motor is located below the second impeller, and the second stage stator vanes are designed around and below the motor to direct the air flow in a substantially axial direction and then a radial direction to the third stage impeller below the motor and the bottom portion 86 of the second stage stator vanes. The second stage stator vanes are divided into two main sections, an upper section, including top and intermediate portions 82, 84 that surround the motor and includes vanes that are arranged in a substantially vertical plane or axially directed and a lower bottom portion 86 positioned below the motor that includes vanes that direct the airflow in a radial direction to the next stage. The stator vanes of the bottom portion 86 are arranged in a generally horizontal plane or are radially directed. In the illustrated example, the first and third stage stator vanes are the same.

Also, the blower may include a single stage design, a two stage design, or four or more stage designs. For example, the blower may include a two stage variant to provide lower pressures (e.g., at 30 cmH$_2$O, e.g., up to about 100 L/min), e.g., such as for a wearable device or a snore treatment device. In one example, the two stage variant may include only stages 2 and 3 (i.e., second and third impellers) with stage 1 (i.e., first impeller) being removed. In this example, maintaining an impeller on each side of the motor provides better balance and further reduces the size of the blower. In an alternative example, the stage 3 (i.e., third impeller) may be removed. In this example, a balancing ring may be provided below the motor to correctly balance the blower.

For example, FIGS. 59 to 62 illustrate a two stage blower 410 according to an example of the present technology. As illustrated, the blower includes first and second housing parts 420, 425, a motor 430 adapted to drive a rotatable shaft of the rotor 450, a first impeller 460-1 provided to the rotor 450 and positioned on one side of the motor 430 and a second impeller 460-2 provided to the rotor 450 and positioned on the opposite side of the motor 430. The blower includes a first stationary component 470 including stage 1 stator vanes and following the first impeller 460-1 and a second stationary component 480 including stage 2 stator vanes following the second impeller 460-2. The first stationary component 470 is provided around the motor and the stator vanes of the first stationary component are configured and arranged to direct airflow along the motor, to de-swirl the airflow and to decelerate air to increase pressure. The first stationary component 470 is similar to the second stationary component 80 of the three stage example described herein. The vanes of the second stationary component 480 are similar to the vanes of the third stator vanes 70-2 described herein. A shield 472 is provided between the second stage impeller 460-2 and the second stage stator vanes 480 to prevent blade pass tonal noise and to constrain the air within the stator vane passages. Also, a suspension system (e.g., constructed of silicone) including an outlet end suspension 490 may optionally be provided to the blower 410.

1.1 Housing

In the illustrated example, the first housing part 20 provides an inlet 21 and the second housing part 25 provides an outlet 26. The blower is operable to draw a supply of gas into the blower through the inlet and provide a pressurized flow of gas at the outlet. The blower has axial symmetry with both the inlet and outlet aligned with an axis of the blower. In use, gas enters the blower axially at one end and leaves the blower axially at the other end.

The first housing part 20 includes a chimney or inlet conduit portion 22 provided to the inlet 21. The chimney 22 is structured to provide acoustic resistance and reduce noise emitted from the inlet with no significant restriction to the air flow provided to the inlet. In an example, the chimney 22 may be formed with the first housing part 20 as a one-piece plastic component. Alternatively, the chimney may be overmolded to the first housing part 20 (e.g., chimney may be constructed of thermoplastic elastomer (TPE) or other suitable material). In an example, the first and second housing parts may be constructed from a liquid crystal polymer (LCP), or polypropylene (PP) or other acoustically dampened plastic. Also, the first and second housing parts may be relatively thin, e.g., to reduce the blower diameter, and help flow internally.

In the illustrated example, the first and second housing parts 20, 25 are coupled to one another and cooperate to retain and maintain alignment of the first, second, and third stationary components 70-1, 80, 70-2 with one another. As best shown in FIGS. 3, 5-8, and 10-12, the second housing part 25 includes at least two resilient arm members 27 (e.g., three arm members) each including tabs 27(1) adapted to engage an upper wall of the first housing part 20, e.g., with a snap fit. In addition, the side wall of the first housing part 20 includes hook members 23 (e.g., three hook members) adapted to engage within respective recesses 27(2) provided to the arm members 27 of the second housing part 25, e.g., see FIGS. 5-8, 10-12, and 16. However, it should be appreciated that the first and second housing parts may be secured to one another in other suitable manners.

1.2 Motor

Figure 3:
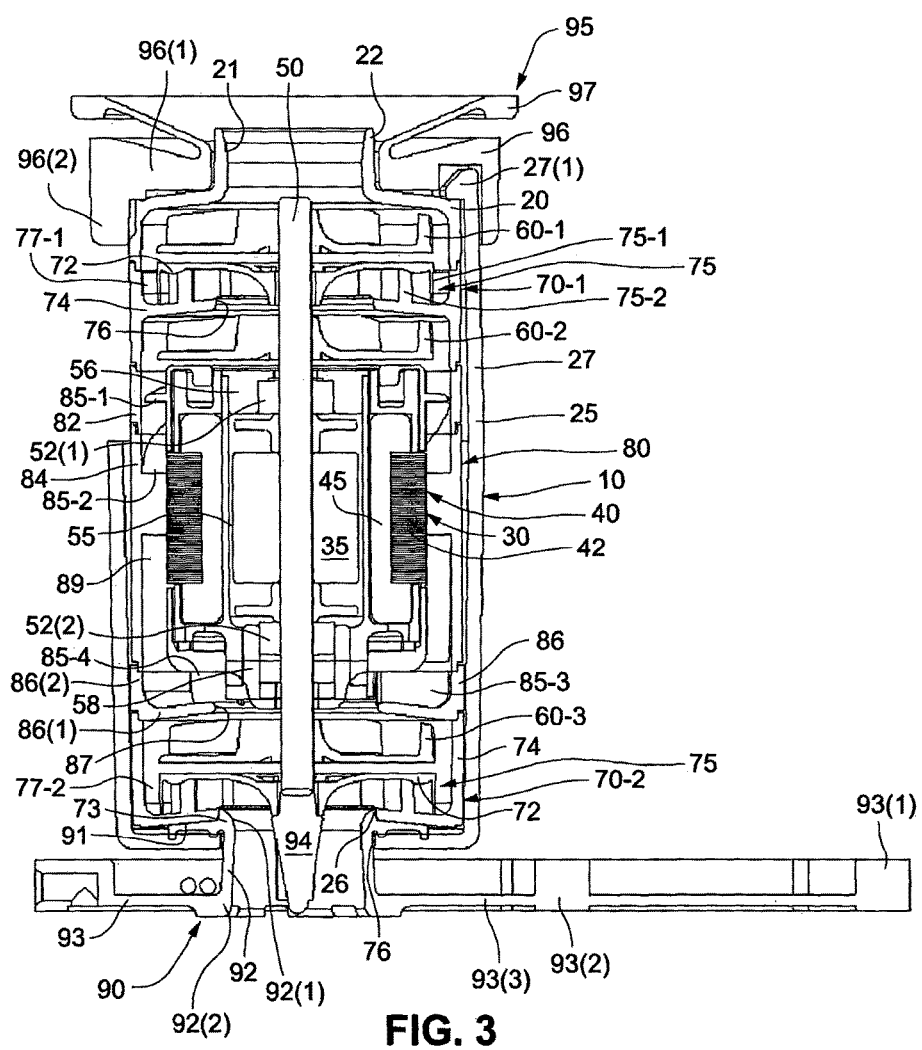
FIG. 3 is a cross-sectional view of the blower of FIG. 1.
Figure 4:
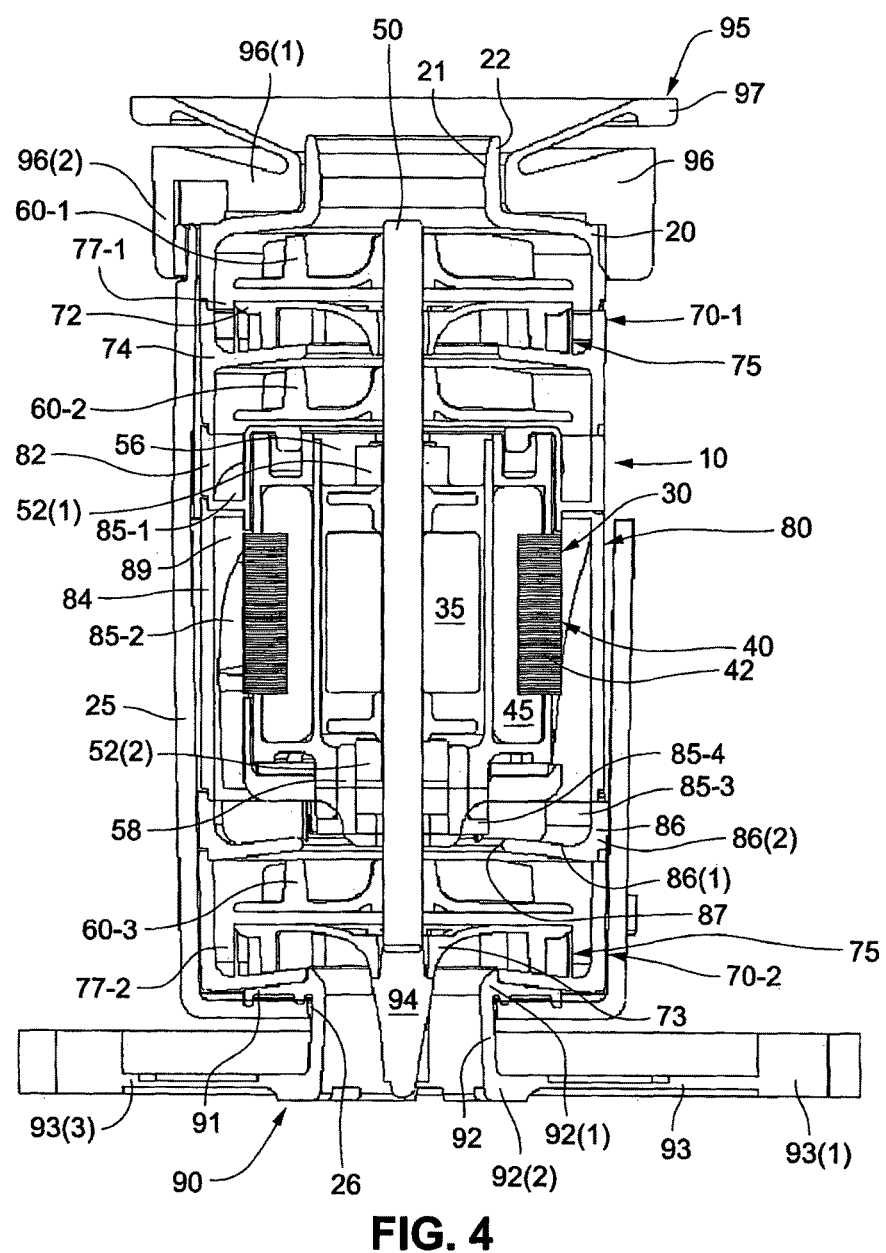
FIG. 4 is another cross-sectional view of the blower of FIG. 1.
Figure 5:
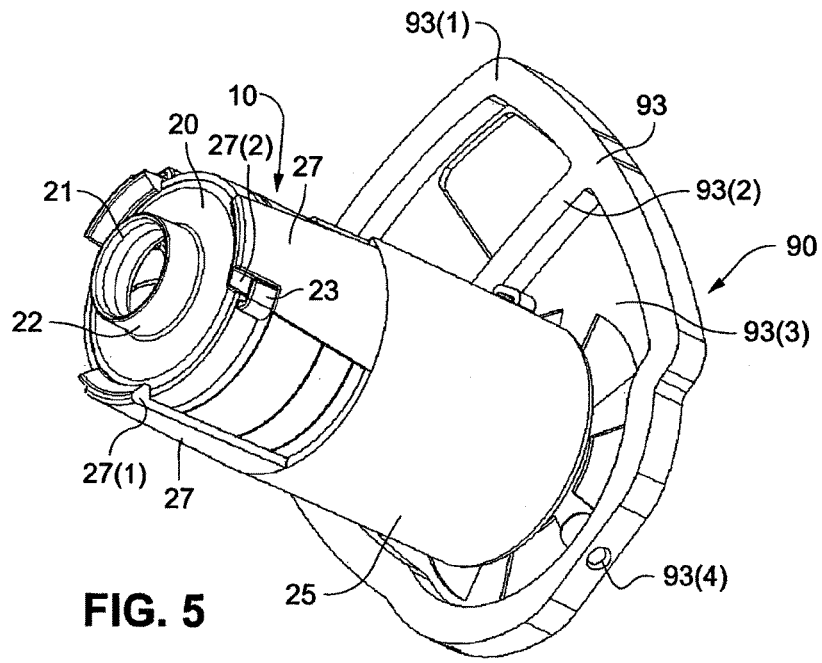
FIG. 5 is a perspective view of the blower of FIG. 1 without the inlet end suspension.
Figure 6:
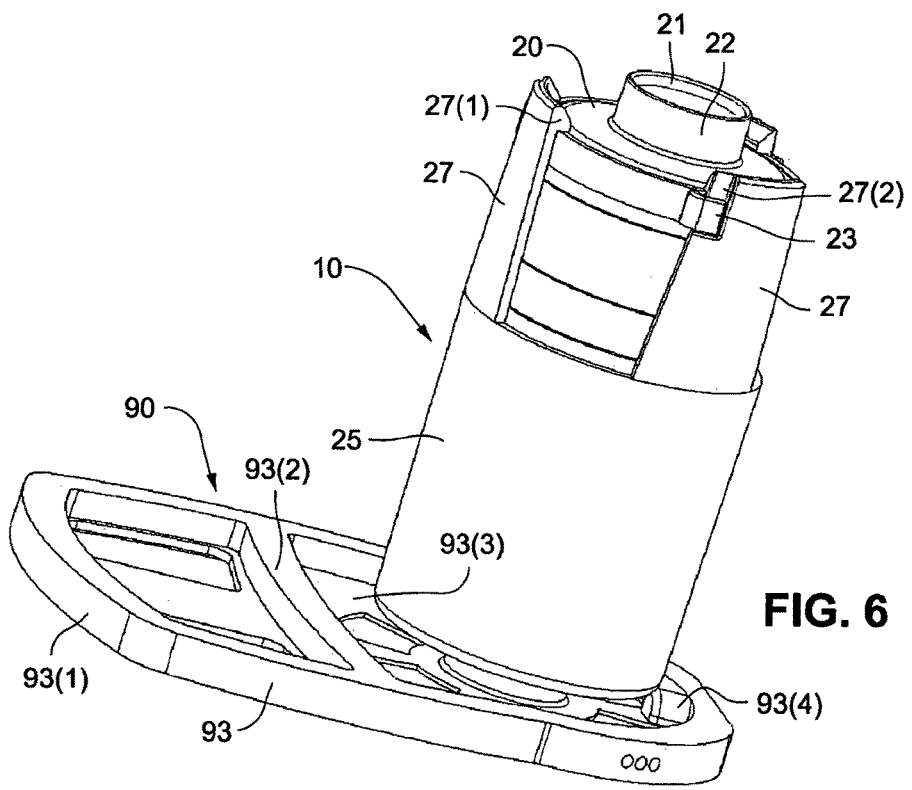
FIG. 6 is another perspective view of the blower of FIG. 5.
Figure 7:
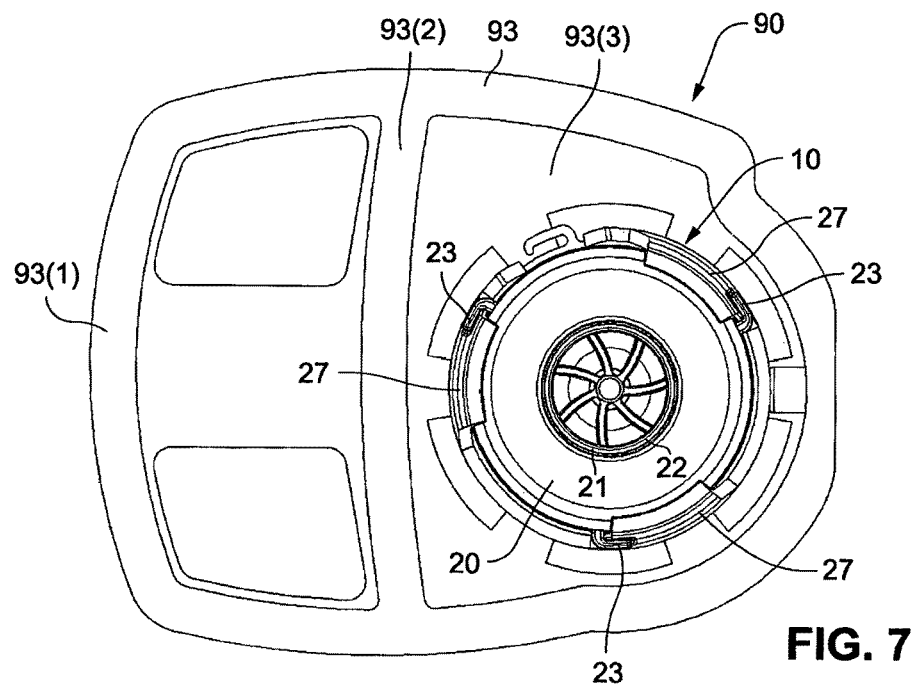
FIG. 7 is atop view of the blower of FIG. 5.
Figure 8:
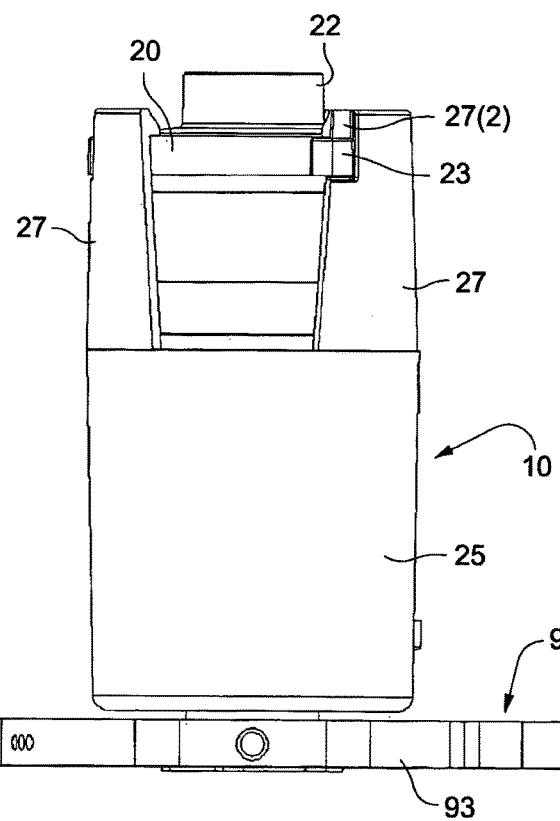
FIG. 8 is a side view of the blower of FIG. 5.
Figure 9:
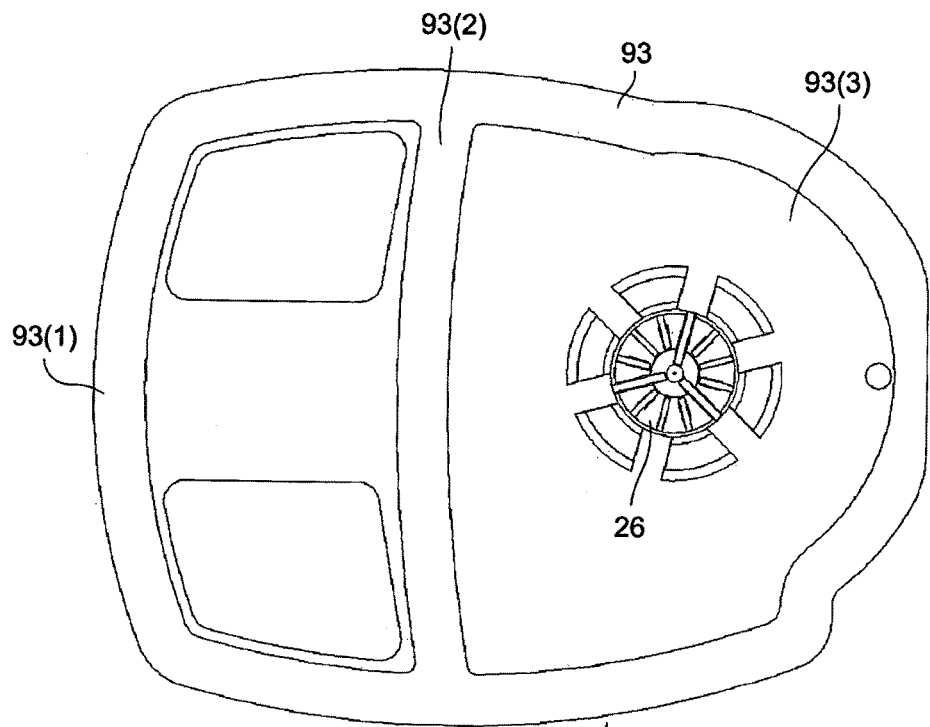
FIG. 9 is a bottom view of the blower of FIG. 5.
Figure 10:
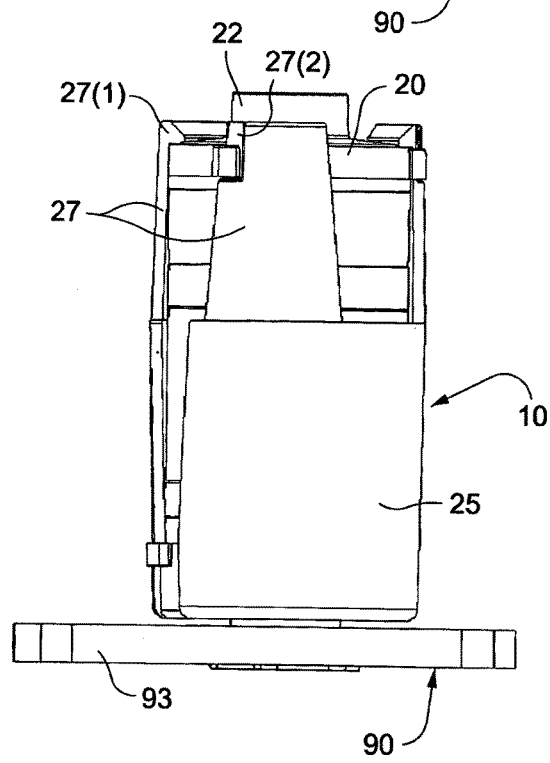
FIG. 10 is another side view of the blower if FIG. 5.
Figure 11:
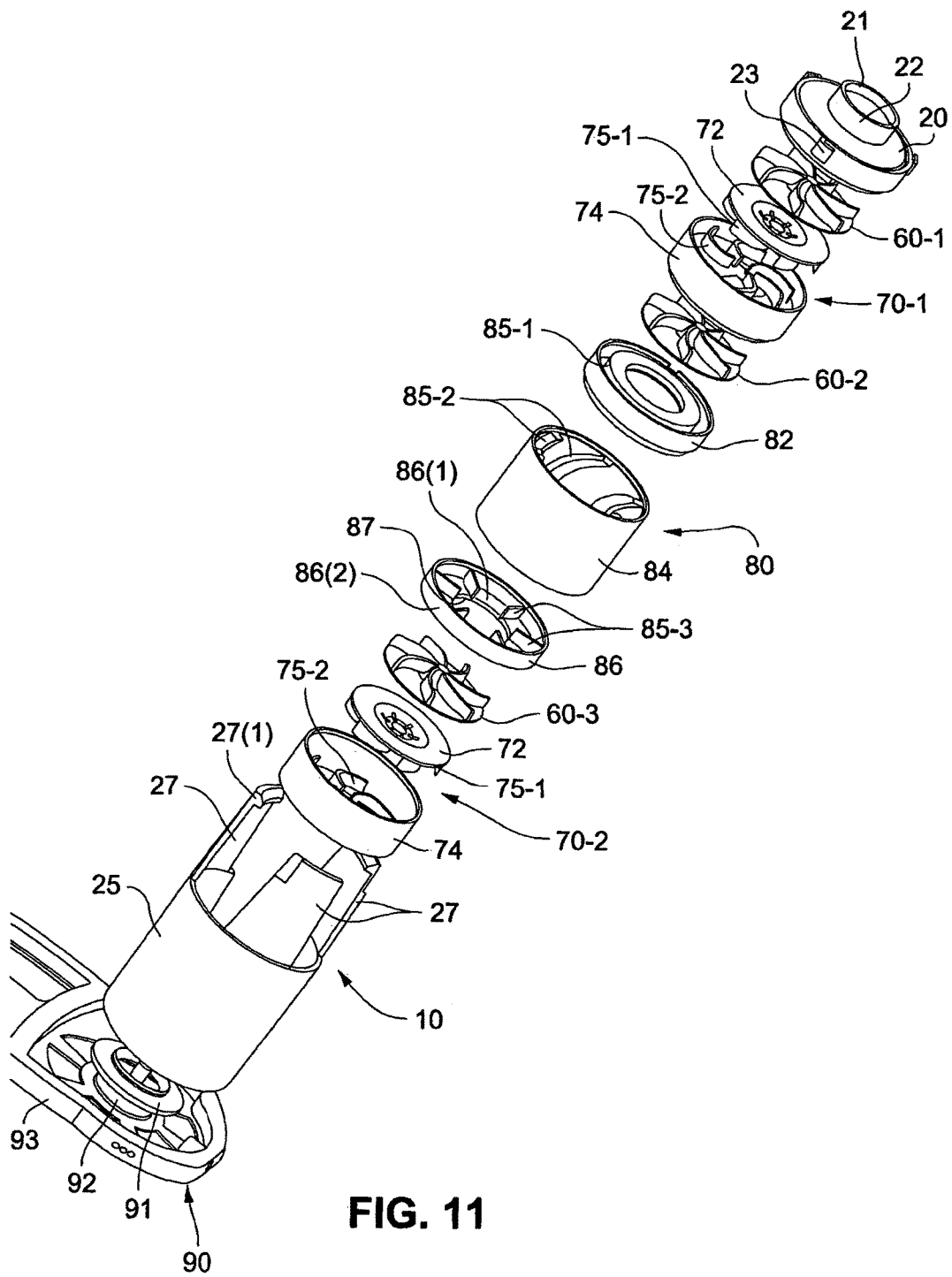
FIG. 11 is an exploded view of the blower of FIG. 5.
Figure 12:
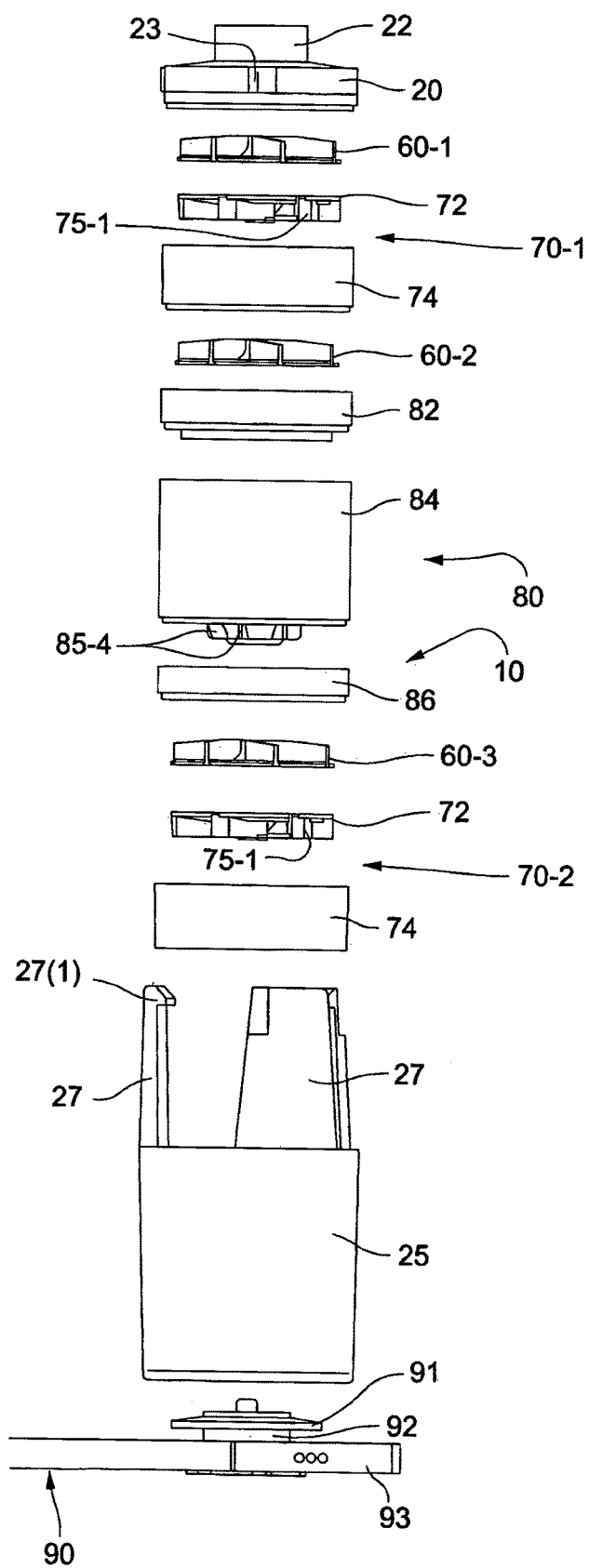
FIG. 12 is another exploded view of the blower of FIG. 5.

As best shown in FIGS. 3 and 4, the motor 30 includes magnet 35 provided to the rotor 50 and a stator assembly or stator component 40. The stator component 40 includes a lamination stack 42 (e.g., 45 laminations (e.g., constructed of iron)) and a stator coil or windings 45 (e.g., constructed of copper) provided to the lamination stack 42. In an example, the motor may spin up to 60,000 rpm, such as up to 50,000 rpm. In an example, the length of the motor may be in the range of about 21-30 mm.

In an example, one or more parameters (e.g., size, material) of the stator component and/or the windings may be adjusted to achieve desired performance (e.g., power output (e.g., speed, torque)), cost and/or size characteristics. For example, the stator component may be constructed of a sintered powder material (e.g., iron particles).

In an example, the magnet 35 may be constructed of different magnet materials (e.g., Neodymium (Neo), Iron Boron, Samarium Cobalt (SmCo), etc.) and different magnet grades (e.g., Neo 45 grade, Neo 38 grade, Neo 35 grade, Neo grade 30, SmCo 30 grade, etc.), e.g., to achieve desired performance, blower size, and/or cost characteristics. In an example, the magnet/magnet grade selected may adjust the blower size (e.g., blower volume) for a desired blower performance (e.g., up to 45-50 cmH$_2$O), e.g., higher grade magnet enhances motor performance and enables smaller blower volume and smaller blower outside diameter (e.g., smaller diameter impellers) for a desired blower performance. Also, the magnet/magnet grade selected may determine a size of the magnet (e.g., length, outside diameter) for a desired motor performance. The size of the flux getters may be adjusted to accommodate the adjusted size of the magnet.

In an example, the magnet may be constructed of a higher grade magnet material (e.g., Neo 45) to provide a higher concentrated energy capability which can be converted into a higher power capability. In an example, the magnet may be constructed of Neo 45 permanent magnet with size and performance characteristics to provide a relative permanent magnet volume of about 20-25%, e.g., 23%. For example, the permanent magnet volume (magnet and rotor) may be about 1200-1300 mm$^3$ (e.g., 1270 mm$^3$) and the total motor active volume (stator and everything inside stator) may be about 5400-5500 mm$^3$ (e.g., 5430 mm$^3$) to provide a relative permanent magnet volume (permanent magnet volume to total motor active volume ratio) of about 23%. Thus, the larger relative permanent magnet volume allows the motor to be smaller in size (e.g., smaller stator component thickness, smaller diameter impellers) while providing similar performance characteristics as larger motors.

In the illustrated example, the rotor 50 is rotatably supported by a pair of high speed bearings 52(1), 52(2), e.g., miniature deep groove ball bearings, that are retained or housed by a bearing tube assembly. The bearing tube assembly includes a tube portion 55 and end portions 56, 58 provided to respective ends of the tube portion 55. The end portions 56, 58 are structured to retain and align the bearings 52(1), 52(2) that rotatably support the rotor 50. In the illustrated example, the end portions are formed separately from the tube portion and attached thereto. In an alternative example, one or more portions of the end portions may be integrally formed in one piece with the tube portion, e.g., lower end portion formed in one piece with the tube portion with the upper end portion structured to be attached to the tube portion or vice versa.

In the illustrated example, the bearings 52(1), 52(2) are the same size (e.g., 3 mm ID by 7 mm OD by 3 mm high). As shown in FIGS. 3 and 4, the end portion is in the form of an adaptor 56 that increases the diameter of the bearing 52(1) so it fits within the tube portion 55. In an alternative example, the outside diameter of the bearing 52(2) may be increased (e.g., to 13 mm OD) so that it may fit within the tube portion 55 without the use of adaptor 56. That is, the bearing tube assembly may be structured to support different size bearings.

The tube portion 55 encloses the magnet 35 on the shaft 50 which is aligned in close proximity to the stator component 40 provided along an exterior surface of the tube portion 55. The tube portion 55 is constructed of a material that is sufficiently "magnetically transparent" to allow a magnetic field to pass through it, which allows the stator component 40 along its exterior surface to act on the magnet 35 positioned within the tube portion 55. Further details and examples of such arrangement are disclosed in U.S. Patent Publication No. US-2008-0304986, which is incorporated herein by reference in its entirety.

Figure 52:
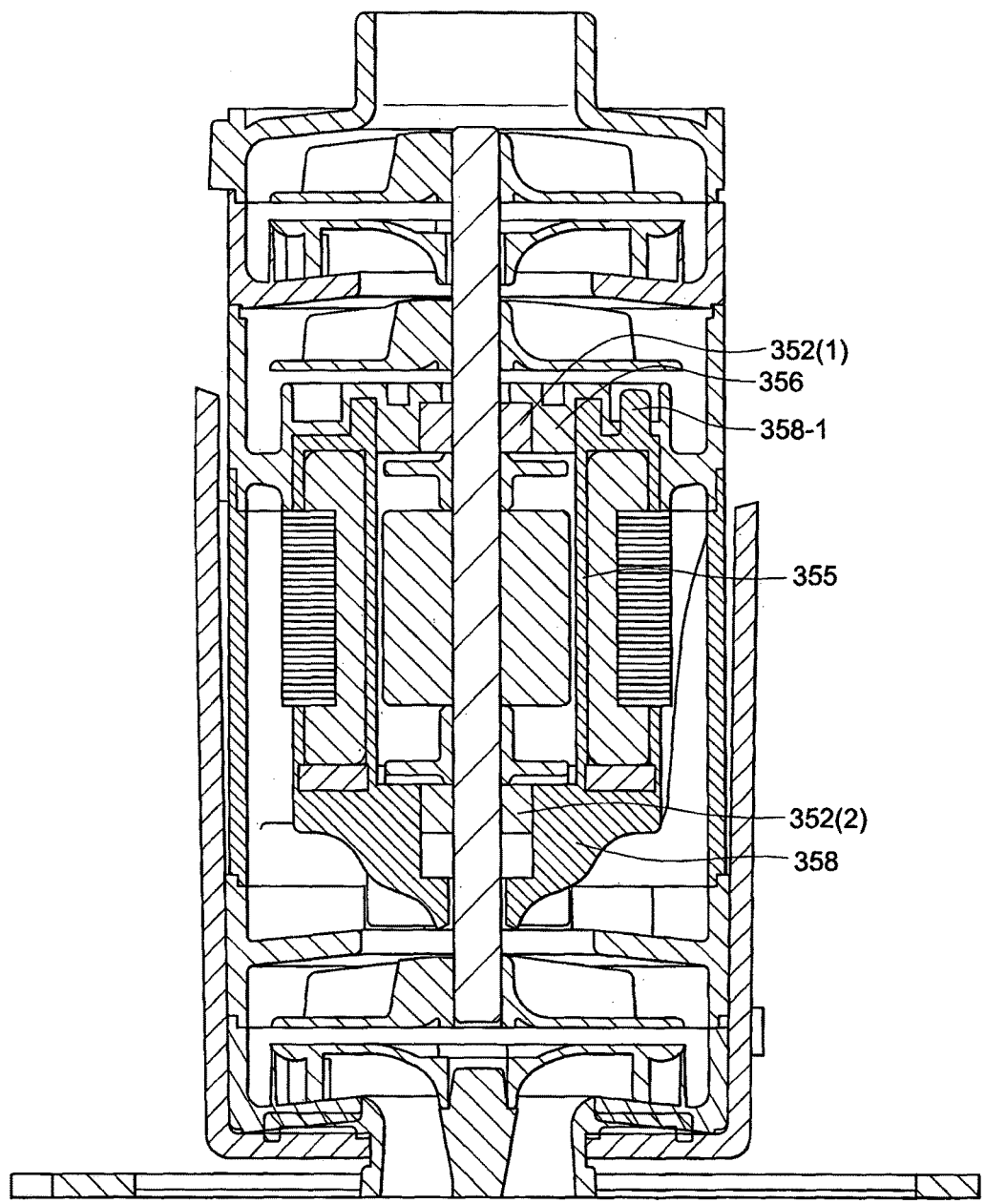
FIGS. 52-58 show various views of blowers and blower components according to alternative examples of the present technology.

FIGS. 52 to 58 show various views of blowers and blower components according to alternative examples of the present technology. For example, such figures illustrate examples of a bearing tube assembly including a lower end portion 358 formed in one piece with the tube portion 355 and an upper end portion 356 (e.g., also referred to as a rotor cap or end bell) provided to the lower end portion. In an example, as shown in FIG. 52, the lower end portion 358 may include one or more stakes 358-1 that may be heat staked to hold the upper end portion 356 in place. The end portions 356, 358 are structured to retain and align respective bearings 352(1), 352(2). As illustrated, the lower end portion may be overmolded to the stator component.

1.2.1 Dual or Single Toroid Coil Configuration

FIGS. 34 to 39 illustrate a motor 230 according to another example of the present technology. In this example, the motor or motor module 230 includes a stator component 240 (FIG. 35) with at least two separate lamination stacks 242(1), 242(2) separated by a spacer 249 (e.g., constructed of a non-conductive material such as plastic) and stator coils 245(1), 245(2) provided to the stators to form two stator windings. A common magnet 235 (e.g., 2 pole magnet) is provided to the rotor 250, which is rotatably supported by a pair of bearings 252(1), 252(2) that are retained or housed by a motor housing 232. Due to the ability to perform series of parallel connection of the two stator windings, the supply of DC voltage can be chosen from either 24 Volts or 12 Volts. Such motor arrangement provides a modular motor design capability, and allows use at home or on the road, e.g., for truckers using an adaptor.

The motor housing 232 includes first and second housing parts 232(1), 232(2) which are coupled to one another to enclose the motor components therewithin. Each housing part 232(1), 232(2) includes an end portion providing a cylindrical opening to support a respective bearing 252(1), 252(2). The opening of the first housing part provides a space 233 for a spring (e.g., crest to crest wave spring), e.g., to apply the preload force for bearings. Also, a flux getter 234(1), 234(2) (e.g., constructed of stainless steel) is provided between each of the bearings 252(1), 252(2) and the rotor magnet 235, e.g., to prevent flux from coming into bearings, inducing eddy current loss, heating up the bearings and reducing efficiency.

In the illustrated example, each lamination stack 242(1), 242(2) (also referred to as a stator core) includes a cylindrical or ring-shaped configuration (e.g., slotless) on which the magnetic wire or coils 245(1), 245(2) is wound, e.g., toroidal coil. Each lamination stack 242(1), 242(2) includes a plurality of laminations, e.g., 2-100 laminations or more, that are stacked on top of one another. The number of laminations may depend on the power requirement. In an example, the lamination stack includes about 40-50 laminations (e.g., 42 laminations) that are stacked on one another and affixed to one another using adhesives, dimples or other techniques. The lamination stack may be coated and/or provided with insulators to insulate the stack from the stator coils.

The stator coils 245(1), 245(2) of each stator are provided as three coils C1, C2, C3 for a three phase motor, i.e., 1 stator coil per phase. Each stator 242(1), 242(2) includes three stator teeth 243 that extend radially outwardly from the stator. The stator teeth 243 space the stator coils C1, C2, C3 on each stack apart from one another and are used for the centering of the stator inside the housings.

Figure 35:
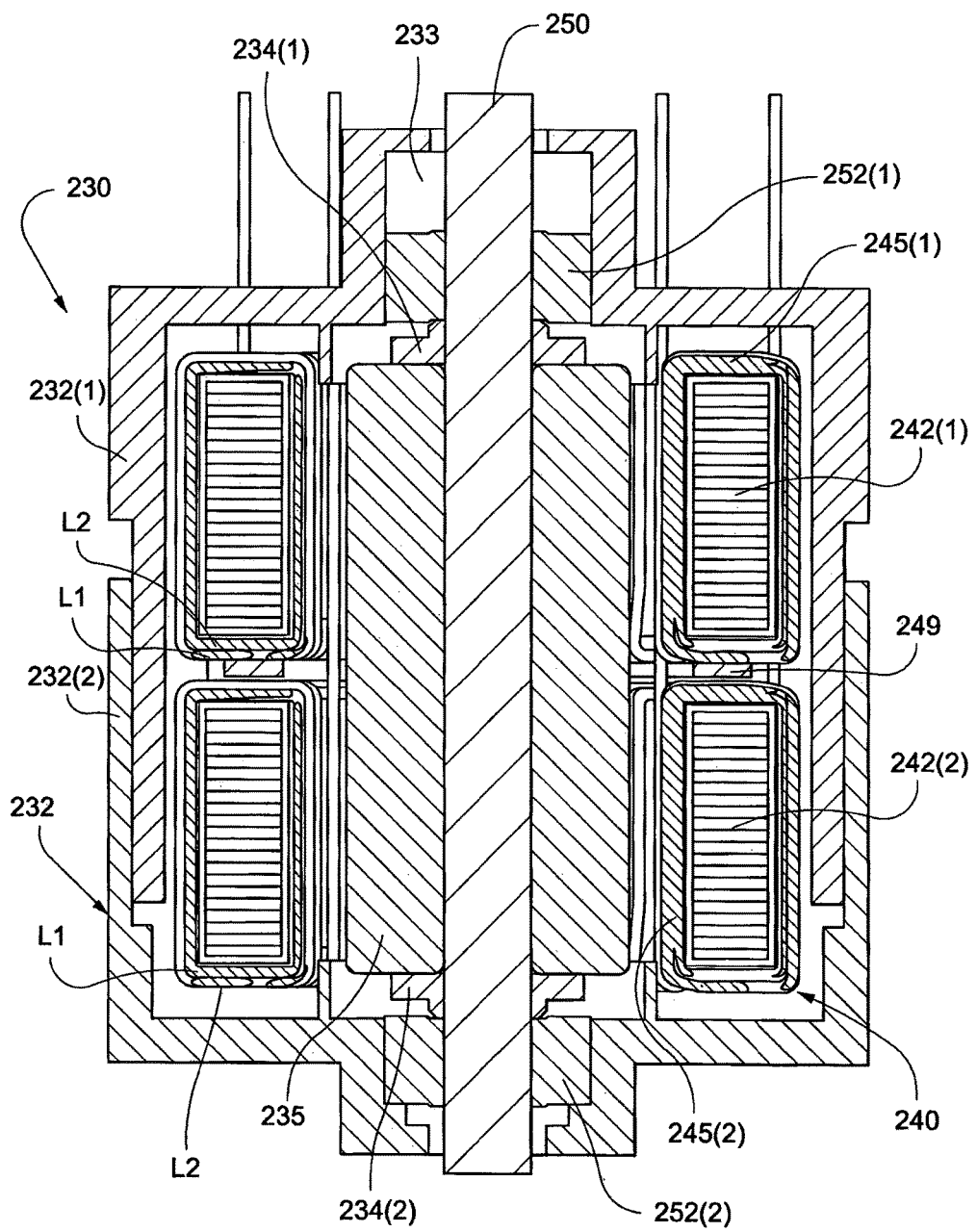
FIG. 35 is a cross-sectional view of the motor of FIG. 34.
Figure 36:
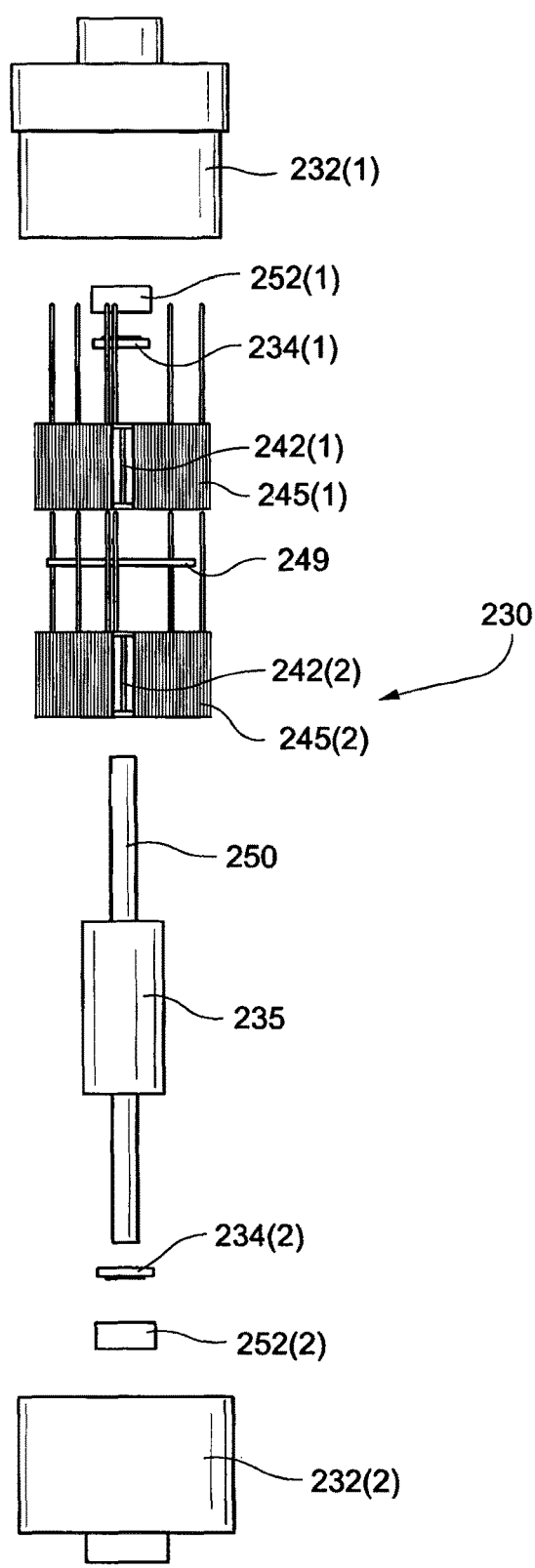
FIG. 36 is an exploded view of the motor of FIG. 34.
Figure 37:
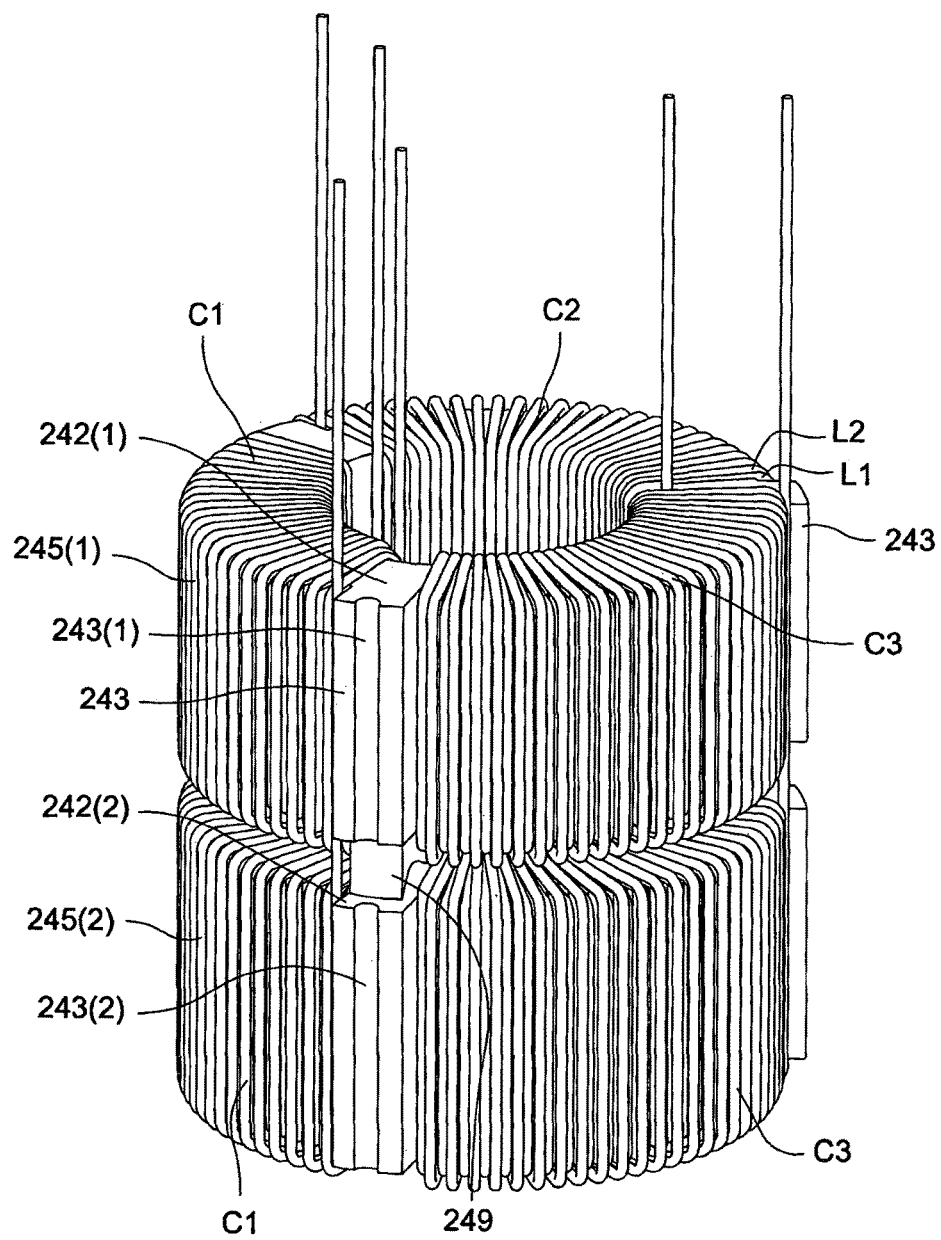
FIG. 37 is a perspective view of a stator component of the motor of FIG. 34 according to an example of the disclosed technology.
Figure 38:
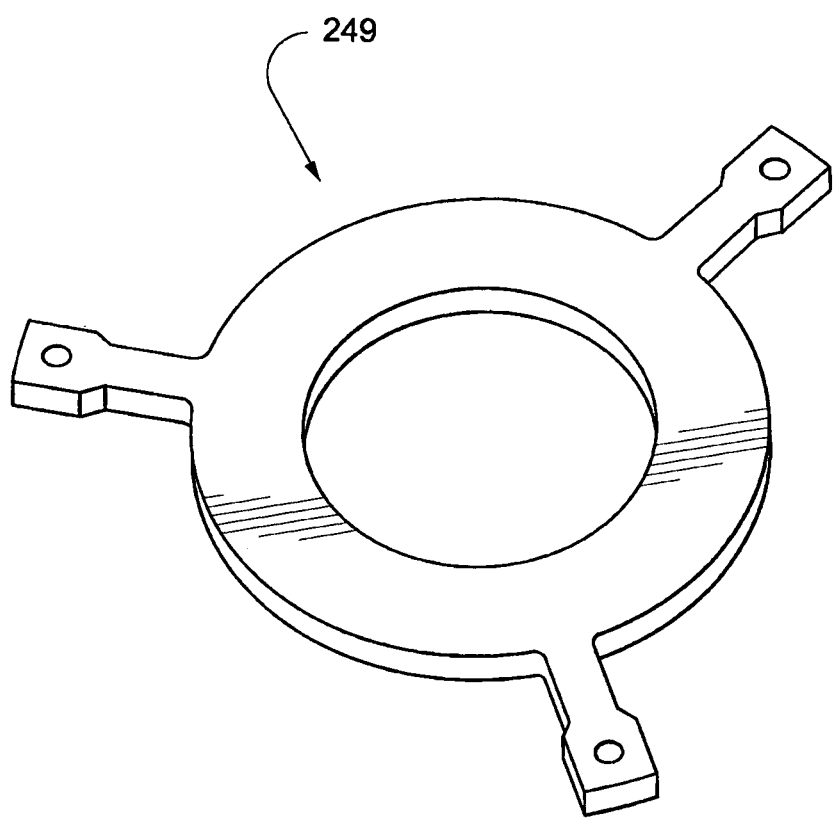
FIG. 38 is a perspective view of a termination PCB according to an example of the disclosed technology.
Figure 39:
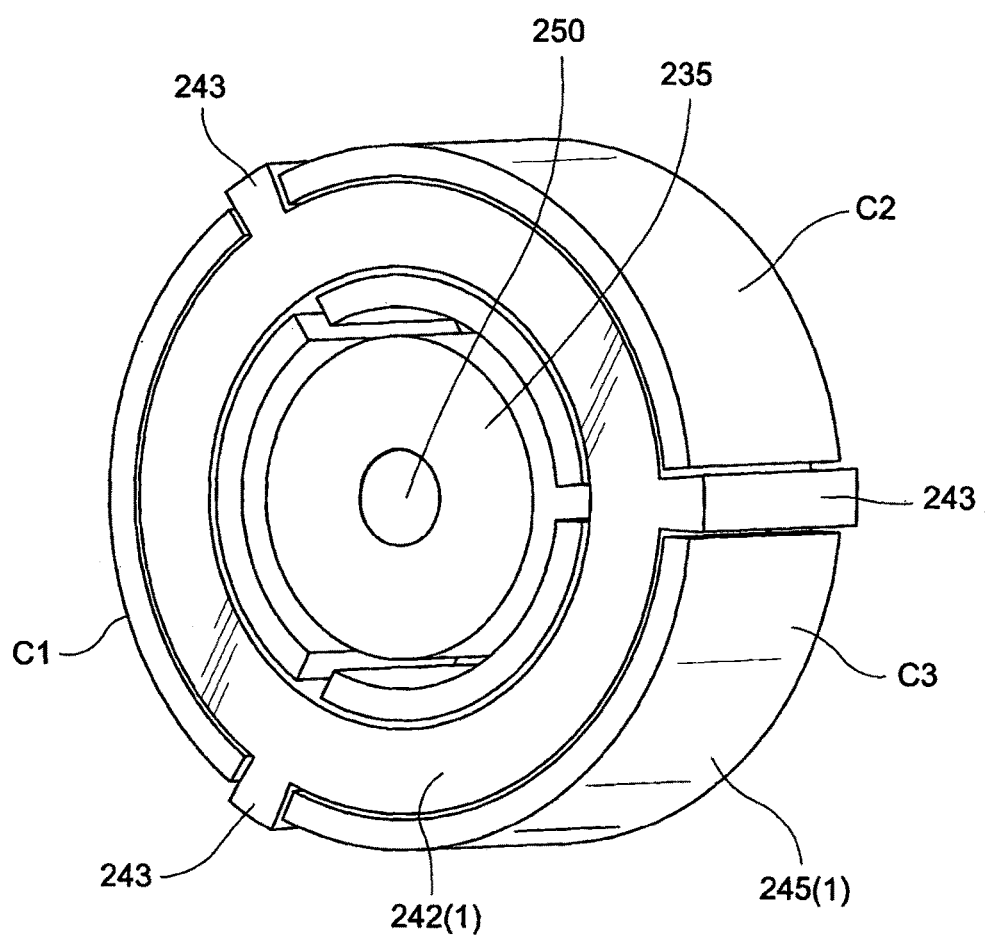
FIG. 39 is a perspective view of a portion of the motor of FIG. 34.

In an example, each coil C1, C2, C3 per stator includes 2 layers of magnet wire L1, L2, as best shown in FIGS. 35 and 37. In the illustrated example, each coil includes magnet wire wound around the stator with 51 turns total, including 26 turns in the first, inner layer L1 and 25 turns in the second, outer layer L2. However, it should be appreciated that each coil may include other suitable numbers of layers (e.g., one layer, three or more layers) and each layer may include any suitable numbers of turns.

Also, as shown in FIG. 37, one of the teeth 243 of the first stator 242(1) may include a notch 243(1) adapted to align with a notch 243(1) provided on one of the teeth 243 of the second stator 242(2). The notches may act as reference points to properly position and align the stator laminations during the stacking process, the stators with respect to one another and/or within the motor housing during assembly.

Figure 40:
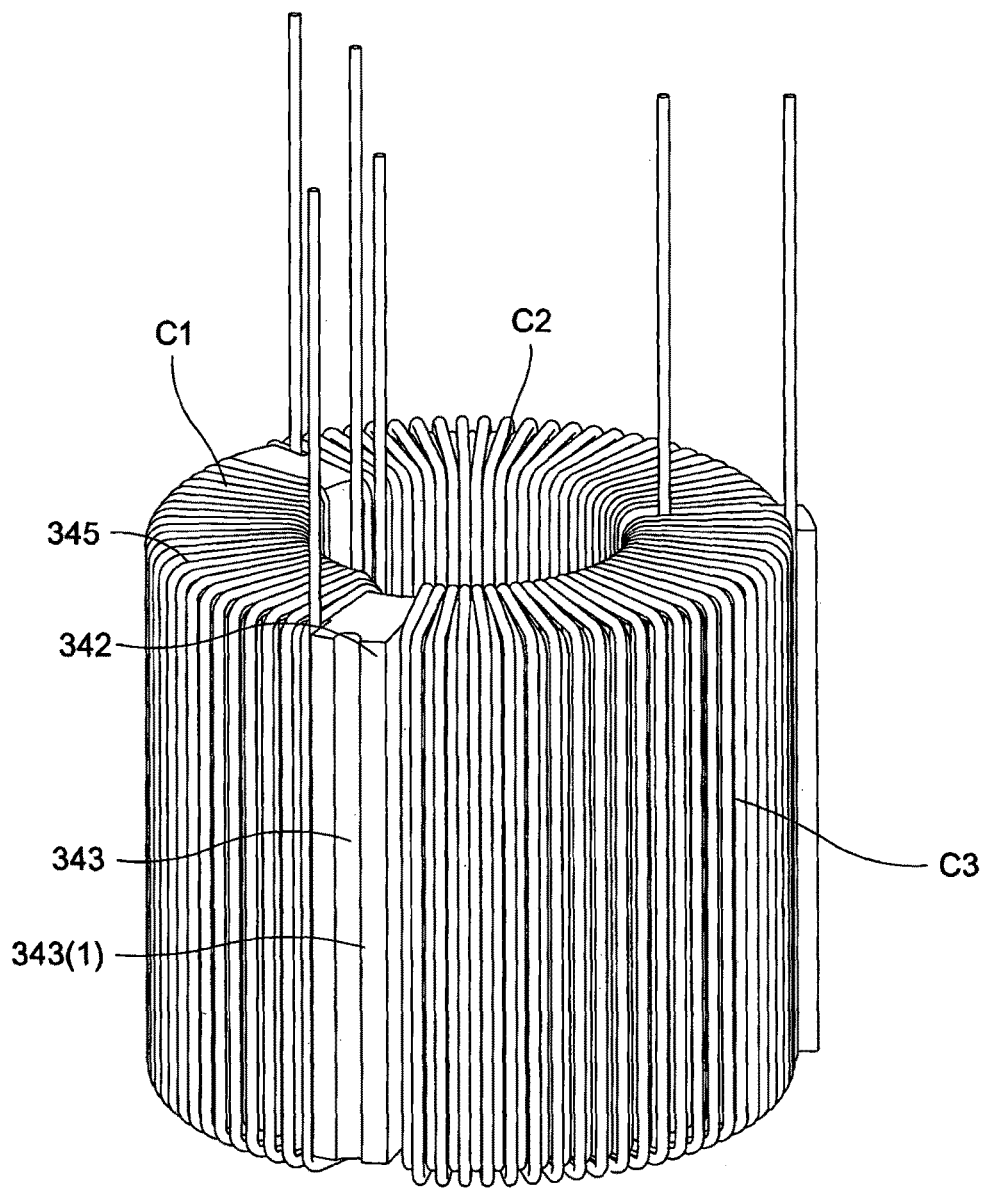
FIG. 40 is a perspective view of a stator component according to another example of the disclosed technology.

FIG. 40 illustrates another example in which the stator component includes a single lamination stack 342 and stator coils 345 provided to the stator. The lamination stack 342 is taller than each lamination stack 242 described above in FIGS. 35-37, e.g., lamination stack 342 includes about 80-90 laminations (e.g., 84 laminations). The stator component includes three stator coils C1, C2, C3 for a three phase motor, i.e., 1 stator coil per phase. The stator teeth 343 space the stator coils C1, C2, C3 apart from one another on the stator. Also, one of the teeth may include a notch 343(1) to act as a reference point for positioning and alignment.

Similar to the above, each coil C1, C2, C3 may include 2 layers of magnet wire. For example, each coil may include magnet wire wound around the stator with 51 turns total, including 26 turns in the first, inner layer and 25 turns in the second, outer layer. However, it should be appreciated that each coil may include other suitable numbers of layers (e.g., one layer, three or more layers) and each layer may include any suitable numbers of turns.

1.3 Impeller

In the illustrated example, the first, second, and third impellers 60-1, 60-2, 60-3 are the same. However, it should be appreciated that the impellers may be different for each stage.

Figure 18:
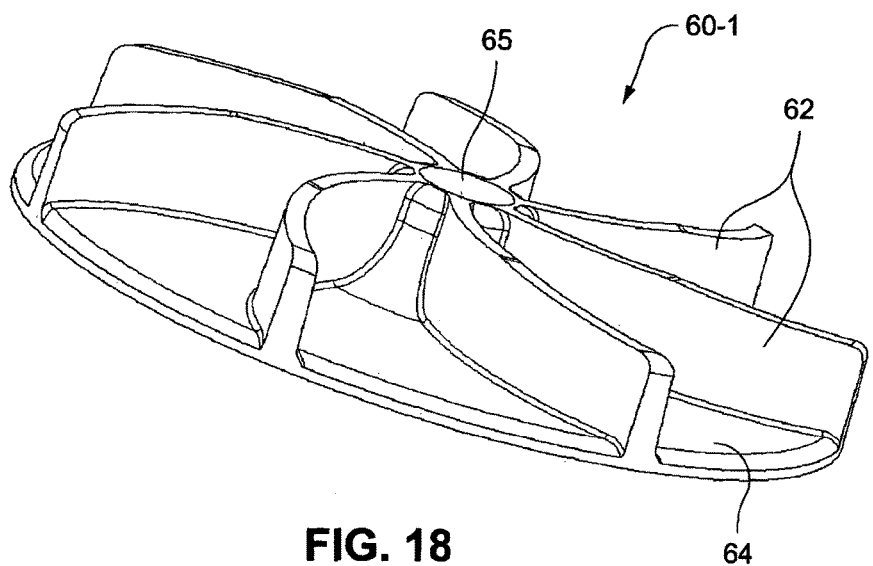
FIG. 18 is a perspective view of an impeller according to an example of the disclosed technology.
Figure 19:
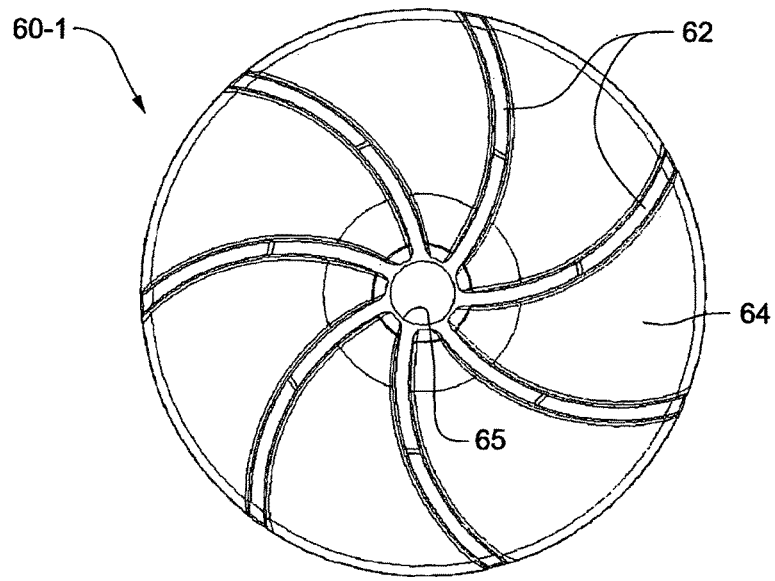
FIG. 19 is a top view of the impeller of FIG. 18.
Figure 20:
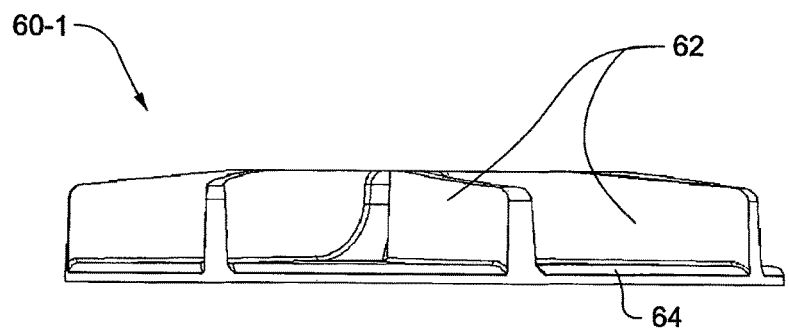
FIG. 20 is a side view of the impeller of FIG. 18.
Figure 21:
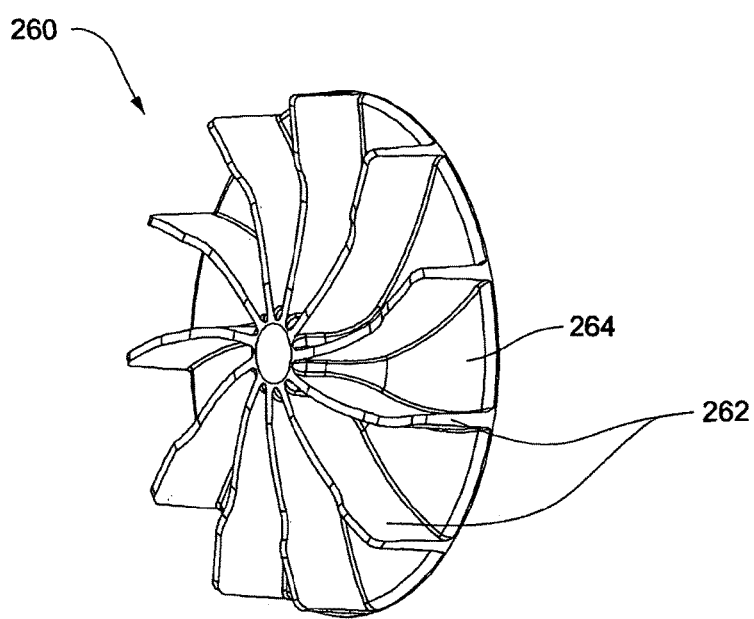
FIG. 21 is a perspective view of an impeller according to another example of the disclosed technology.
Figure 22:
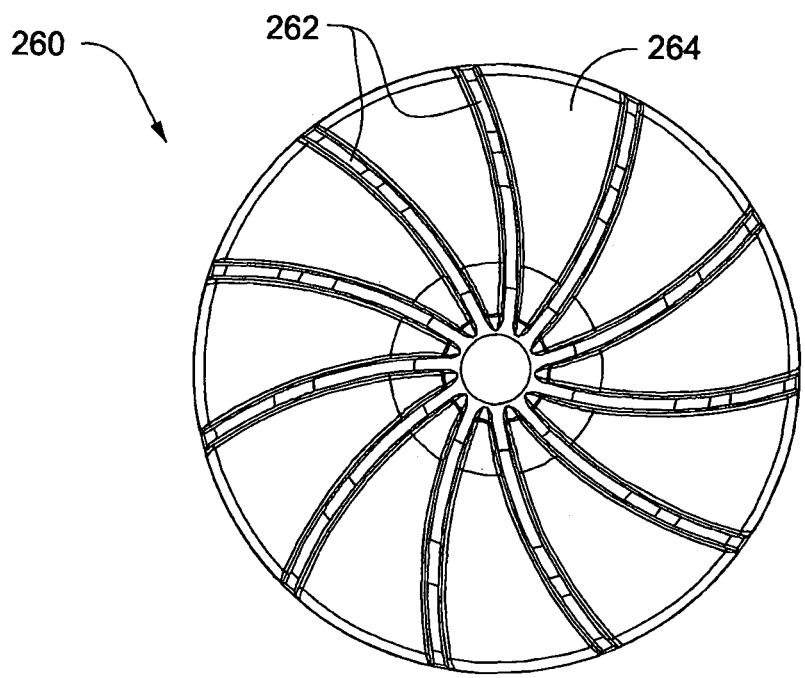
FIG. 22 is a top view of the impeller of FIG. 21.

As best shown in FIGS. 18-20, each impeller 60-1, 60-2, 60-3 includes a plurality of curved blades 62 provided to a disk-like shroud 64. The shroud 64 incorporates a hub 65 that is adapted to receive the shaft. The blades extend from the hub towards the edge of the shroud, e.g., for strength. In the illustrated example, the impeller includes 7 blades. However, it should be appreciated that the impeller may include other suitable numbers of blades, e.g., 3 or more blades, e.g., 5-20 blades, 7 blades, 11 blades, 13 blades. For example, FIGS. 21 and 22 illustrate an impeller 260 including 11 curved blades 262 provided to shroud 264.

Each impeller may be constructed of a plastic material, e.g., polymer thermoplastic such as Polyetheretherketone (PEEK) or polycarbonate (PC) for strength and damping properties. The shroud may have a scalloped shape (not shown). The blades may be slightly tapered from the hub to the outer tip to assist in reducing turbulence and thus noise. Thus, the height of the blades is lower at the tip than at the hub. For example, an exemplary height of the blade at the hub is about 3.5-4.5, e.g., 4 mm, and an exemplary height of the blade at the tip is about 2.5-3.5 mm, e.g., 3.3 mm. This feature assists in reducing the size of the blower. In an example, the impeller has a diameter of about 20-30 mm, e.g., 25.5 mm. However, it should be appreciated that other suitable dimensions are possible.

Figure 23:
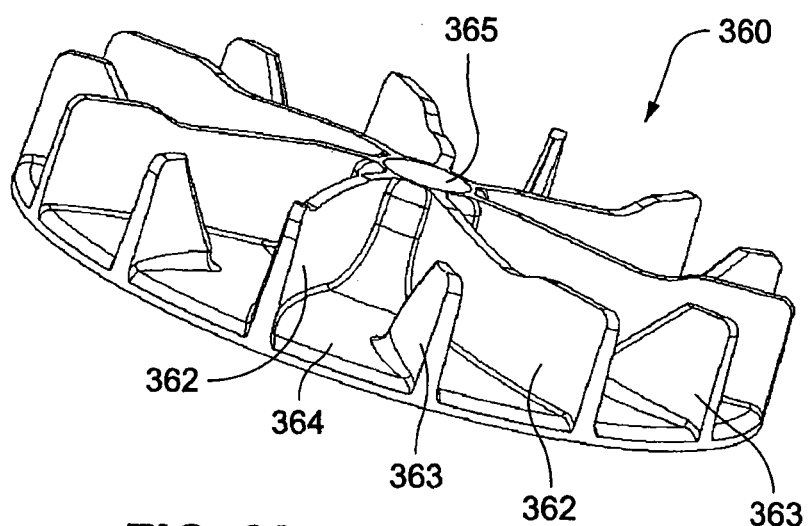
FIG. 23 is a perspective view of an impeller according to another example of the disclosed technology.
Figure 24:
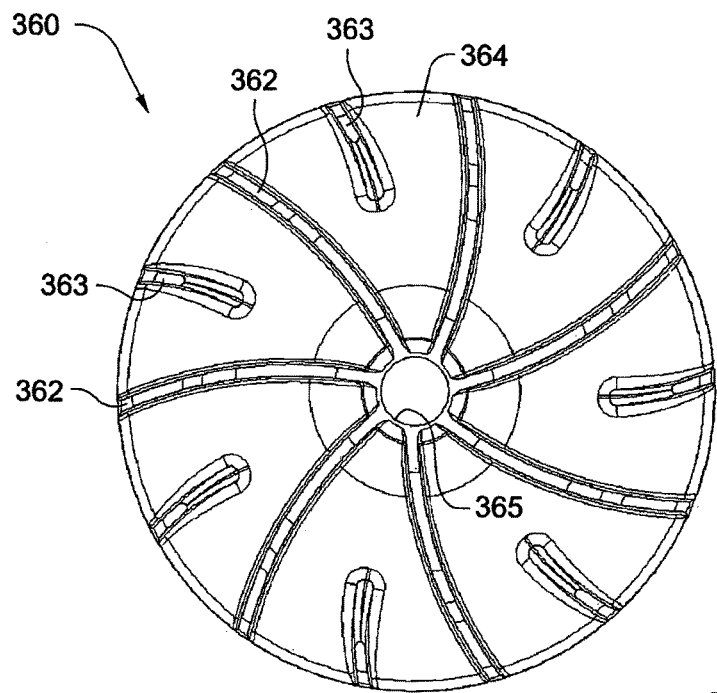
FIG. 24 is a top view of the impeller of FIG. 23.

In an alternative example, as shown in FIGS. 23 and 24, an impeller 360 may include a set of shorter secondary blades 363 each positioned between adjacent primary blades 362 provided to shroud 364. As illustrated, each short blade 363 extends from the edge of the shroud 364 and partially towards the hub 365. Each short blade 363 may include a shape similar to the primary blades starting at the tip (impeller outside diameter) and coming back towards the hub in the range of 20%-70%, such as approximately 33% of the distance from the impeller outside diameter to the impeller center line. In an alternative example, each short blade may include a circular arc shape.

Figure 66:
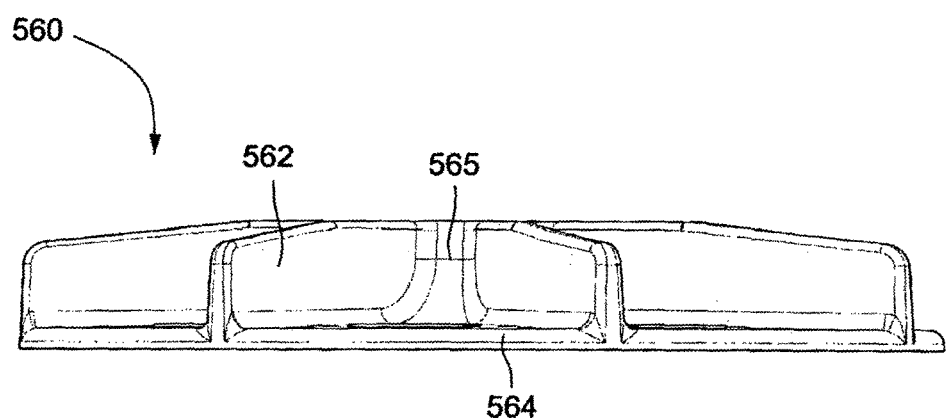

FIGS. 63-66 show an alternative example of an impeller 560 including 7 curved blades 562 provided to shroud 564. As illustrated, each blade 562 includes a smaller curvature than blades 62 shown in FIGS. 18-20. FIG. 66 shows the taper of each blade 562 height from the hub 565 to the outer tip, e.g., to assist in reducing turbulence and thus noise. Thus, the height of each blade 562 measured from the shroud 564 is larger at the hub 565 than the height of each blade at the outer tip. The height of each blade may be substantially constant for a first portion of the blade adjacent the hub 565 and then reduce in height along the blade length in a second portion that extends to the outer tip.

1.4 Stationary Components

In the illustrated example, the first and third stationary components 70-1, 70-2 used in stages 1 and 3 are similar to one another and include stator vanes structured to direct air flow from a tangential to radial direction and then from a radial to axial direction. These stages 1 and 3 stator vanes 75 are arranged in a substantially radial direction or on a substantially horizontal plane. The second stationary component 80 used in stage 2 comprises two main sections, an upper section including having stator vanes 85-1, 85-2 and a lower bottom portion 86 having stator vanes 85-3. The top and intermediate portions 82, 84 are provided around the motor 30 and structured to direct air flow from a tangential to axial direction without an intervening radial transition, e.g., flow straightener, and creating an expanding vane passage between the stator vanes to generate pressure via static regain. The lower bottom portion 86 is positioned below the motor and is structured to direct air flow in a radial direction to the next stage.

1.4.1 First and Third Stationary Components

In the illustrated example, as shown in FIGS. 3, 4, 11-14, and 25-32, each of the first and third stationary components 70-1, 70-2 is provided in two parts that are formed separately from one another (e.g., molded) and then assembled to one another. As illustrated, each component 70-1, 70-2 includes a shield 72 that provides a first set of stator vanes 75-1 and a housing 74 that provides a second set of stator vanes 75-2. When the shield 72 and housing 74 are assembled to one another, the first and second set of vanes 75-1, 75-2 provide the full or complete set of stator vanes 75 (e.g., see FIG. 32) and the correct expansion sizes for air flow are produced.

In the illustrated example, half of the complete set of stator vanes 75 are provided to the shield 72 and half of the complete set of stator vanes 75 are provided to the housing 74. This construction may make the stator vanes and each part stronger and easier to mold and stiffens both parts, by having vanes on both parts, to reduce part acoustic resonances. This construction also facilitates the molding of smaller stationary components. However, it should be appreciated that the complete set of stator vanes may be split between the shield and the housing in other suitable manners.

In the illustrated example, the shield 72 and the housing 74 each include six vanes, i.e., assembled component provides a complete set of twelve stator vanes. However, the assembly component may provide other suitable numbers of stator vanes, e.g., 8-20 total stator vanes, e.g., 10-16 total stator vanes. The housing 74 also includes an opening 76 for the air to exit from the stator vanes to the next stage or the outlet.

Figure 25:
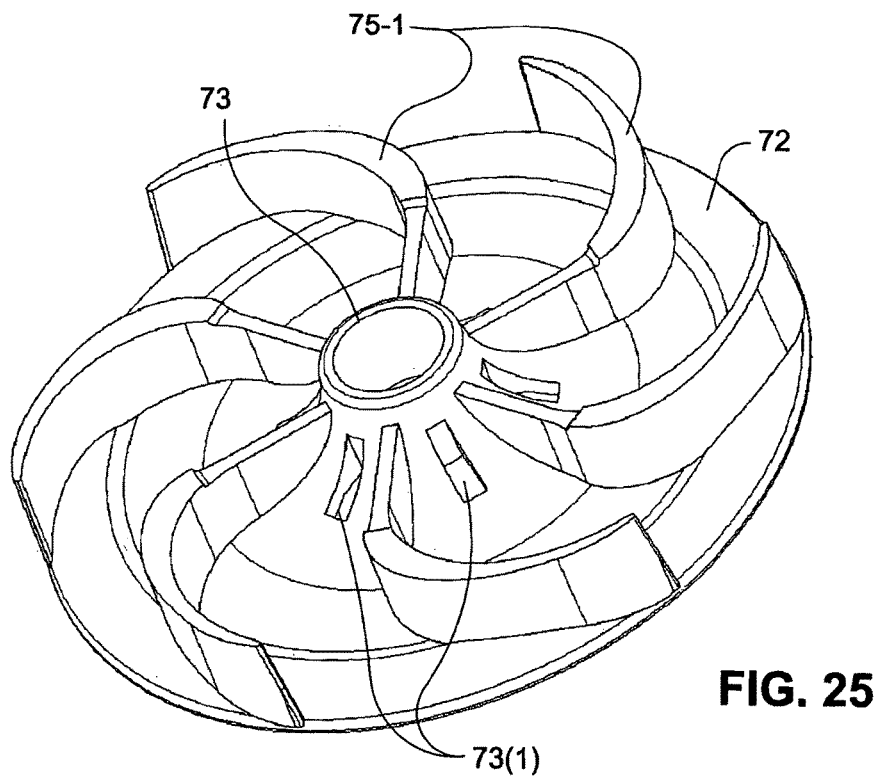
FIG. 25 is a bottom perspective view of a shield of a stationary component according to an example of the disclosed technology.
Figure 26:
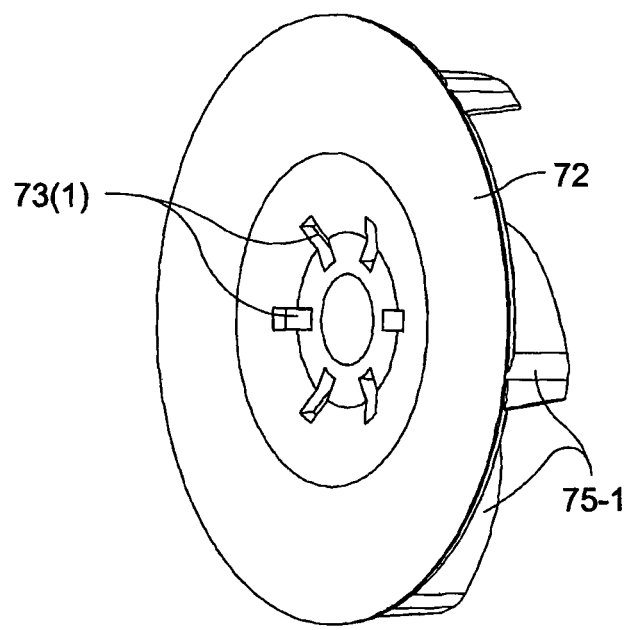
FIG. 26 is a top perspective view of the shield of FIG. 25.
Figure 27:
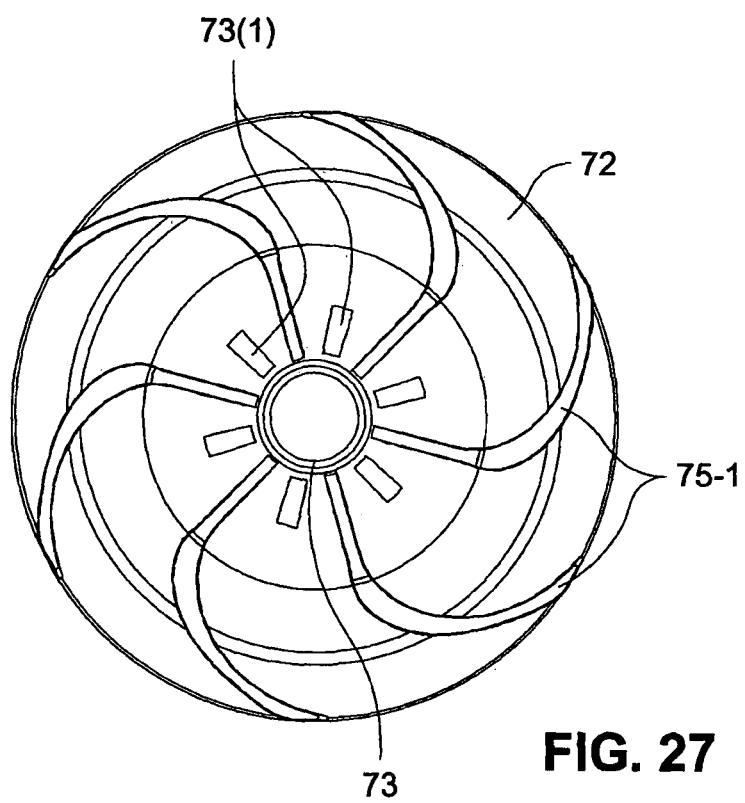
FIG. 27 is a bottom view of the shield of FIG. 25.
Figure 32:
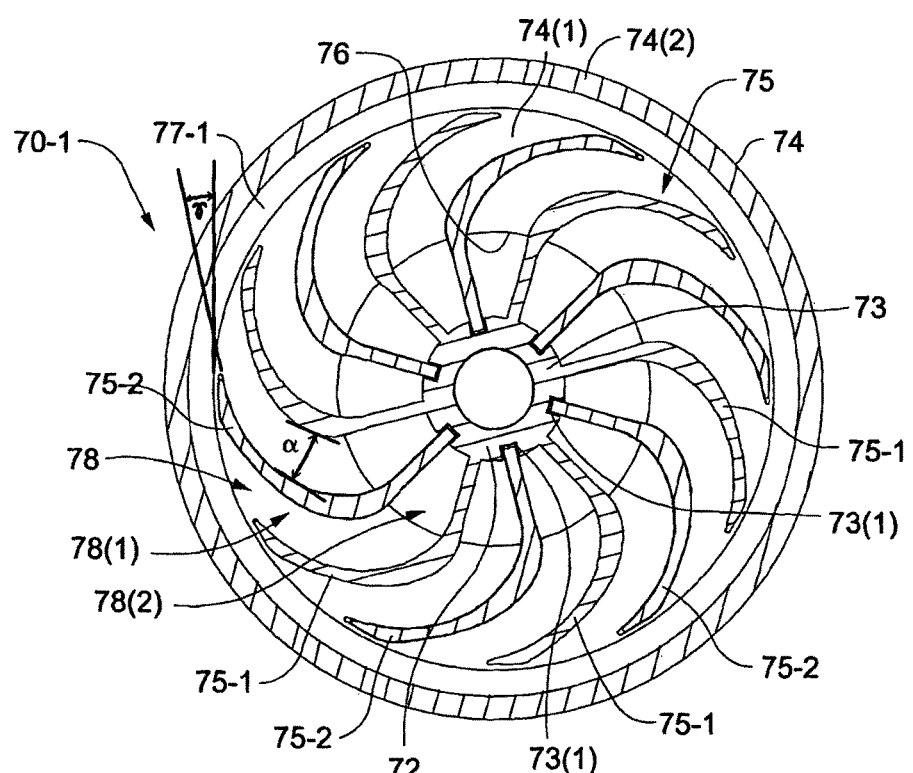
FIG. 32 is a cross-sectional view of the assembled stationary component of FIG. 31.
Figure 33:
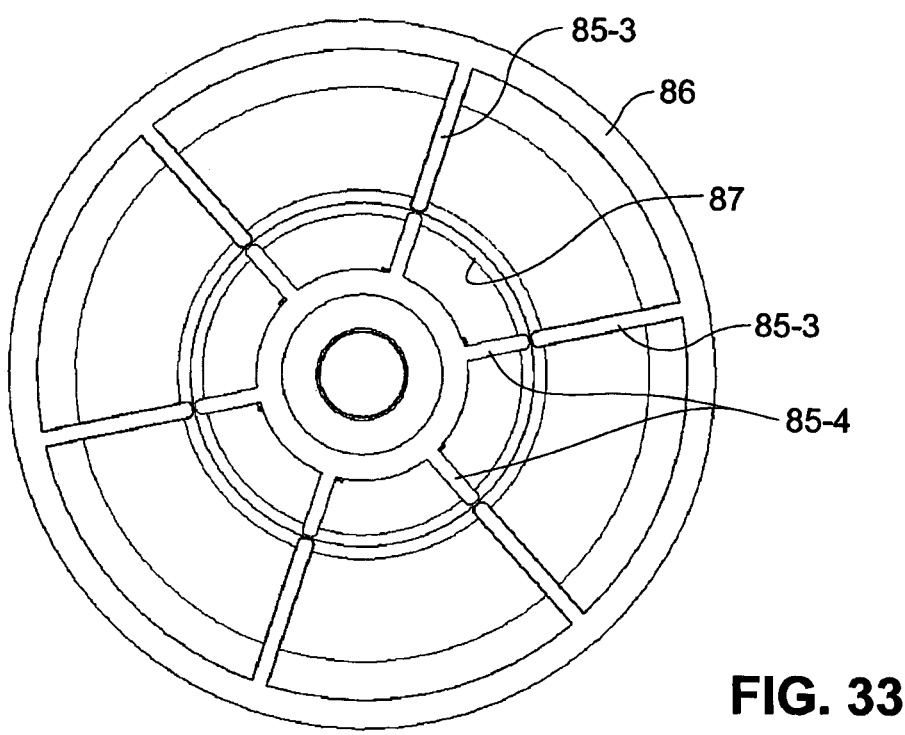
FIG. 33 is a top sectional view of a stationary component including straight vanes.
Figure 34:
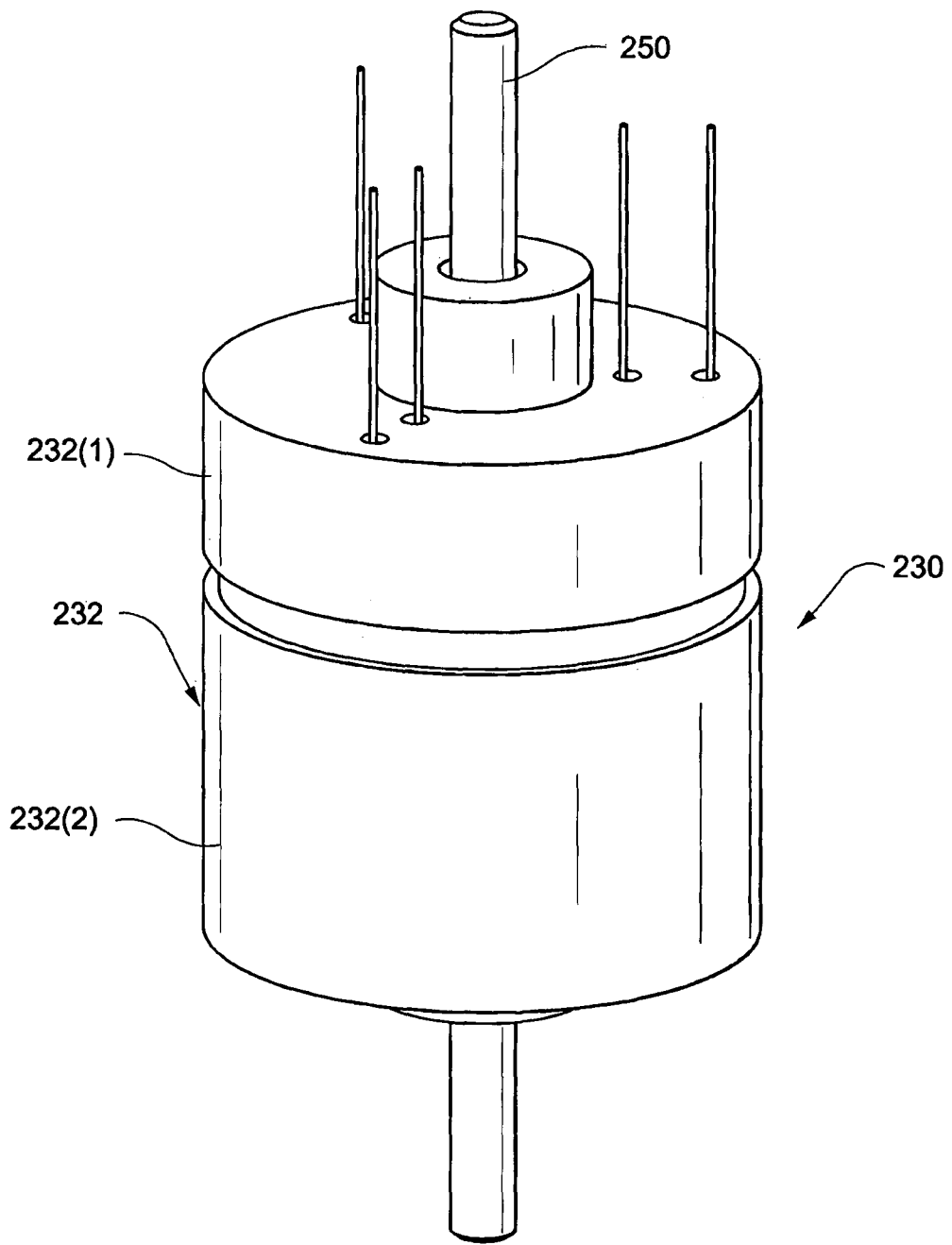
FIG. 34 is a perspective view of a motor according to an example of the disclosed technology.

As best shown in FIGS. 25, 27, and 32, the shield 72 includes a hub 73, adapted to receive the rotor 50 therethrough, and stator vanes 75-1 that extend from the hub 73 towards the edge of the shield 72. As best shown in FIGS. 28-30 and 32, the housing 74 includes a bottom wall 74(1) providing an outlet opening 76, an annular side wall 74(2) provided to the bottom wall 74(1), and stator vanes 75-2 that extend along the bottom wall 74(1) and at least partially across the outlet opening 76. As shown in FIGS. 3, 4, 31 and 32, when assembled, the shield 72 is supported on the housing stator vanes 75-2, and the hub 73 of the shield 72 includes recesses 73(1) adapted to receive trailing edges of the housing stator vanes 75-2 (e.g., see FIGS. 25-27 and 31-32) such that all the stator vanes 75-1, 75-2 extend from the hub 73 towards the side wall 74(2) of the housing 74. Air enters the stationary component via an annular gap 77-1, 77-2 (e.g., see FIGS. 3, 4, 31, and 32) provided between the edge of the shield and the side wall of the housing. In an example, the gap is in the range of 0.5 mm to 3 mm, such as about 1-1.5 mm. However, it is to be understood that the size of the gap may vary depending on the size of the blower.

As best shown in FIG. 32, each vane passage 78 defined between adjacent stator vanes 75-1, 75-2 (e.g., 12 vane passages defined by 12 vanes) is structured to provide an expanding passage along the vanes, e.g., each passage increases in cross-sectional area from the inlet to the outlet of the passage. The expansion of the vane passage is to slow down or decelerate the air and increase pressure, thereby effectively harnessing the radial speed component of the airflow.

The vanes provide a smooth transition along the path of the vane for the air flow. The width and/or shape of each vane may vary to control the expansion of the air path. As noted above, the stator vanes extend all the way to the hub, e.g., to prevent swirling of the airflow into the next stage.

In an example, the total cross-sectional area of the vane passages (i.e., total of all 12 vane passages) start at about 50-60 mm$^2$, e.g., 53 mm$^2$, and end at about 90-100 mm$^2$, e.g., 98 mm$^2$. The area of the vanes can also be defined by the inlet area. In an example, the inlet area between the 12 channels defined by the stator vanes may be equivalent to the area of a circle having a diameter of about 5-10 mm, e.g., 8 mm. The vanes have a finite thickness.

As shown in FIG. 32, each vane passage 78 includes two portions, i.e., a radial outer portion 78(1) and an inner straight portion 78(2). The radial outer portion includes an expanding cross-section that transitions the air from a generally tangential direction to a generally radial direction. The vanes defining each radial outer portion have a curved structure to provide the expanding air passage to slow down the airflow and allow the generation of pressure through static regain.

The inner straight portion transitions the airflow from a radial direction to an axial direction. The inner straight portions are located above the opening 76 to the next stage or outlet located in the housing 74. The inner straight portion is structured to prevent swirling of the airflow as it enters the next stage or outlet. The vanes defining the inner straight portion are structured to bend the airflow, e.g., at a generally right angle with respect to the radial outer portion. This portion of the vane passage is not generating or increasing the pressure, just bending the airflow toward the next stage or outlet through opening 76.

As shown in FIG. 32, each vane passage 78 includes a divergence angle or angle of expansion $\alpha$ which is defined between the radial outer portion of adjacent vanes, i.e., measured as the angle between the tangent of one vane compared to the adjacent vane tangent. In an example, the divergence angle $\alpha$ is in the range of 5-20°, such as 10-15°, e.g., 11°, 14°.

As shown in FIG. 32, the entry angle $\gamma$ of each vane is the angle at which the airflow is required to turn to enter the vane or passage (also referred to as the leading edge angle of the vane). The angle is measured between a tangent from the shield at the tip of the vane and a tangent out from the start of the vane tip. This angle is preferably small, e.g., not too low as this may result in large frictional losses and high impedance and not too large as this may result in large pressure losses due to sudden change of direction of air flow. In an example, the entry angle $\gamma$ is in the range of about 0-45°, e.g., 5-20°, e.g., 5-12°.

In an example, the stator vanes may all have skewed or angled leading edges to soften the blade pass pressure pulses from the airflow hitting the leading edges of the stator vanes. Thus, this arrangement reduces the blade pass acoustic tones. For example, the leading edges of the stator vanes may be angled at about 45°, although other angles such as 30-60° may be utilized.

Figure 15:
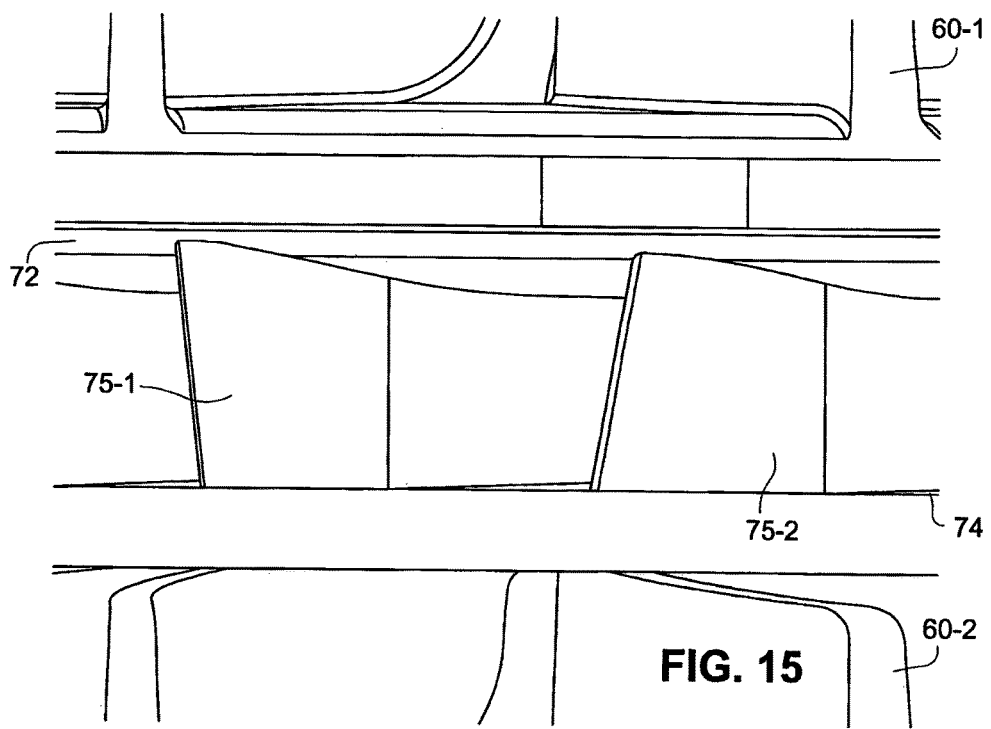
FIG. 15 is an enlarged view of stator vanes of the blower of FIG. 14.
Figure 16:
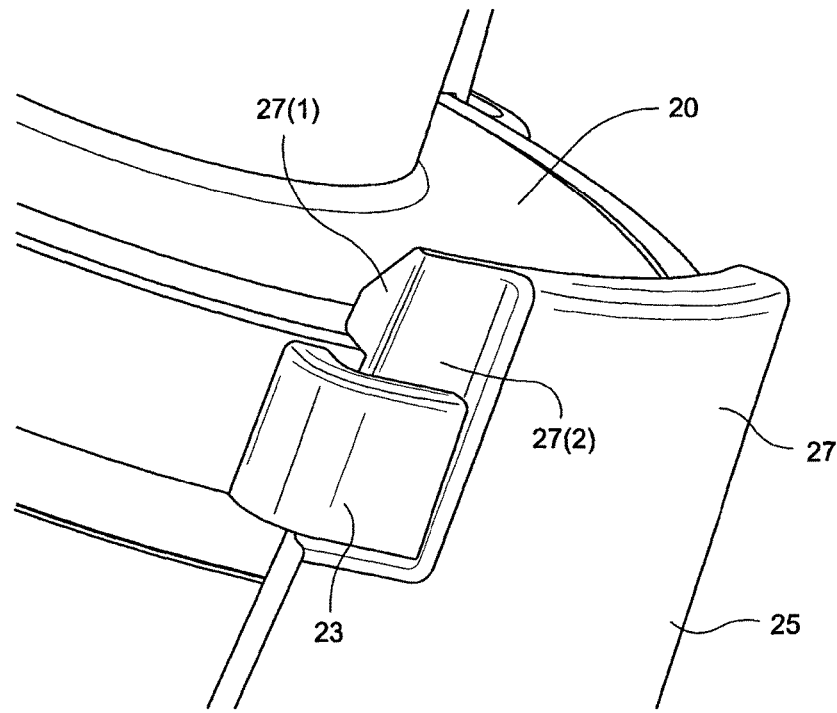
FIG. 16 is an enlarged view of housing parts of the blower of FIG. 1.

In an example, the stator vanes on the shield may be skewed or angled in the opposite direction from the stator vanes on the housing for manufacturing reasons. For example, as shown in FIG. 15, the stator vanes 75-1 on the shield 72 may be skewed with a forward angle and the stator vanes 75-2 on the housing 74 may be skewed with a backwards angle, or vice versa. However, the stator vanes of the shield and housing may all be skewed in the same direction.

1.4.2 Second Stationary Component

In the illustrated example, as shown in FIGS. 3, 4, and 11-14, the second stationary component 80 is provided in three parts that are formed separately from one another (e.g., molded) and then assembled to one another (e.g., mechanical interlock (e.g., tongue/groove), friction-fit, heat stake, etc.). As illustrated, the second stationary component 80 includes a top portion 82 providing a first set of stator vanes 85-1, an intermediate portion 84 providing a second set of stator vanes 85-2, and a bottom portion 86 providing a third set of stator vanes 85-3. The first and second sets of stator vanes 85-1, 85-2 are arranged in a substantially axial direction around the motor or in a substantially vertical plane around the motor. In contrast, the third set of stator vanes 85-3 are arranged in a substantially horizontal plane below the motor or in a radial direction.

The top and intermediate portions 82, 84 cooperate to support and maintain the motor 30 in an operative position. In addition, the vanes 85-1, 85-2 of the top and intermediate portions 82, 84 cooperate to define stator vanes 85 structured to direct airflow in a generally axial direction down and around the motor, i.e., first set of vanes 85-1 define a top portion of each vane 85 and second set of vanes 85-2 define a bottom portion of each vane 85. In the illustrated example, the top and intermediate portions 82, 84 cooperate to provide six stator vanes 85. However, other suitable numbers of stator vanes are possible, e.g., 3-20 stator vanes.

The stator vanes 85 are configured and arranged to collect air from the second impeller 60-2 and transition the airflow from a tangential direction to an axial direction without an intervening radial transition. The stator vanes 85 are configured and arranged to de-swirl the airflow and provide static regain to increase the pressure.

Each vane passage 88 defined between adjacent stator vanes 85 (e.g., six vane passages defined by six vanes) are structured to provide an increasing cross-sectional area that increases from the upstream direction (i.e., adjacent the second impeller 60-2) to the downstream direction (i.e., towards the third impeller 60-3). Thus, the ratio of the cross-section at the beginning of each vane passage to the end of each vane passage is less than 1. As the cross-sectional area of each passage increases, the air is decelerated and the pressure increases.

Figure 14:
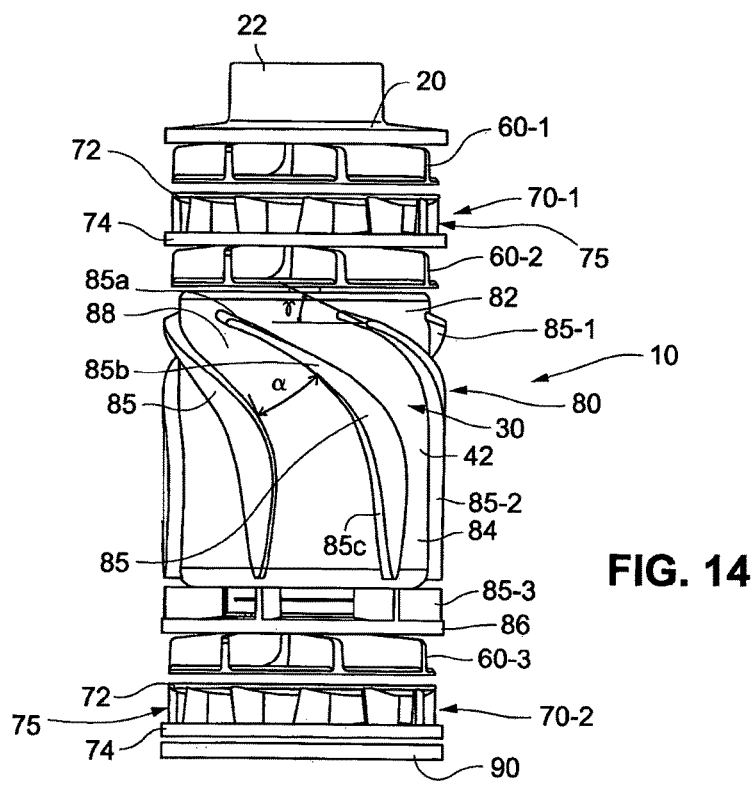
FIG. 14 is a side view of the blower of FIG. 13.

As best shown in FIG. 14, each vane 85 includes a leading edge portion 85a, an intermediate portion 85b, and a trailing edge portion 85c. The leading edge portion 85a extends generally tangentially from near the outer edges of the second impeller blades 60-2 to collect air exiting the second impeller. The intermediate portion 85b curves downwards from the leading edge portion to direct air from a tangential direction to an axial direction. The trailing edge portion 85c extends in the axial direction towards the base of the intermediate portion.

In an example, the total cross-sectional area of the vane passages (i.e., total of all six vane passages) start at about 50-60 mm², e.g., 56 mm², and end at about 120-130 mm², e.g., 123 mm².

In an example, as shown in FIG. 14, the entry angle γ of the airflow at the lead edge portion is about 10-20°, e.g., about 14°, away from horizontal or the plane of rotation of the impeller. The angle of expansion α of the vane passage is about 10-20°, e.g., about 14°, 15°, 16°, or 17°.

Static regain is related to the velocity, theoretical equation: $dP=air\ density*(V_1^2-V_2^2)/2$, wherein $V_1$=velocity at the start of the vane passage (this velocity is typically 70-90% or 80-90% of the velocity of the impeller tip speed, thus the leading edge portion of the vanes start relatively close to the impeller) and $V_2$=velocity at the end of the vane passage. For maximum static regain: $V_1$ should be maintained high; $V_2$ should be low; transition from $V_1$ to $V_2$ should be gradual; and angle of expansion α should be smooth.

Figure 13:
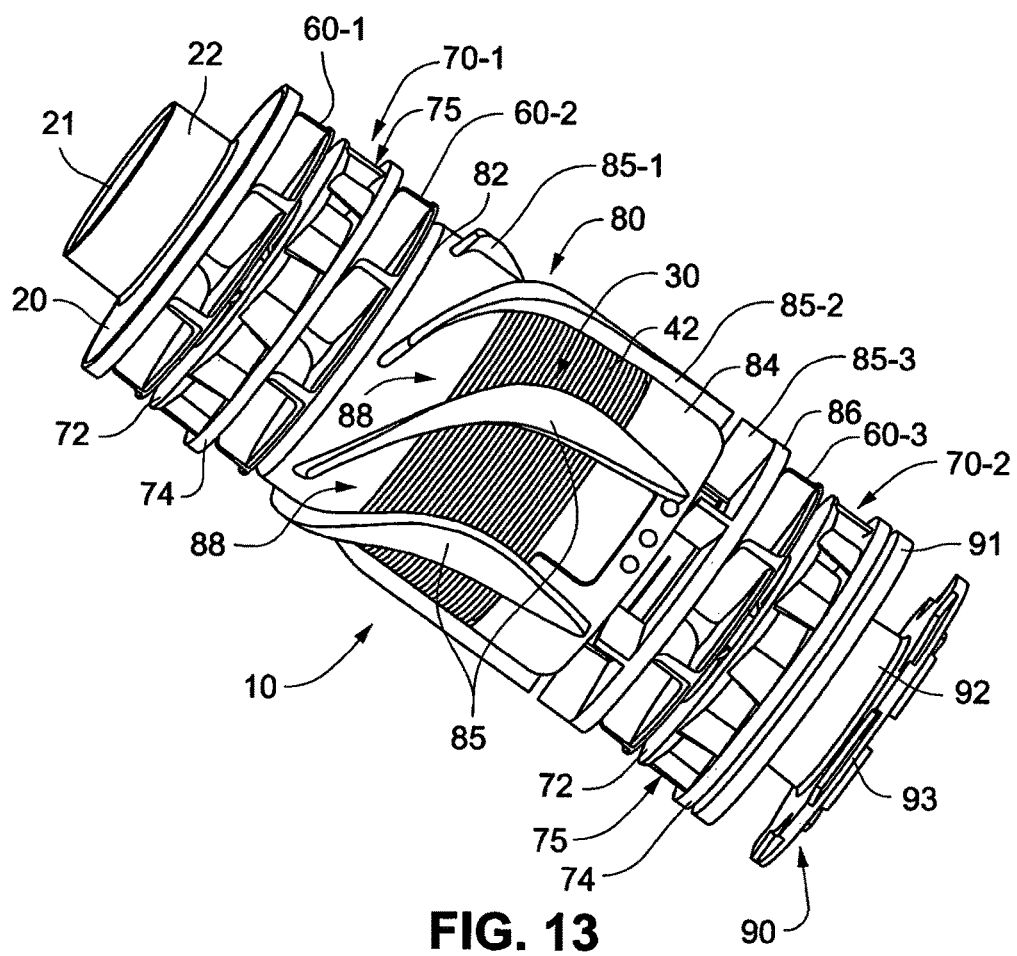
FIG. 13 is a perspective view of the blower of FIG. 1 with outer side walls removed.

The entire length of the vanes 85 provided by the top and intermediate portions 82, 84 are used for static regain down the annular gap 89 (e.g., see FIGS. 3 and 4) between inner and outer walls provided by the top and intermediate portions. FIGS. 13 and 14 illustrate the inner walls provided by the top and intermediate portions with their outer walls removed to more clearly illustrate the vanes 85.

Figure 53:
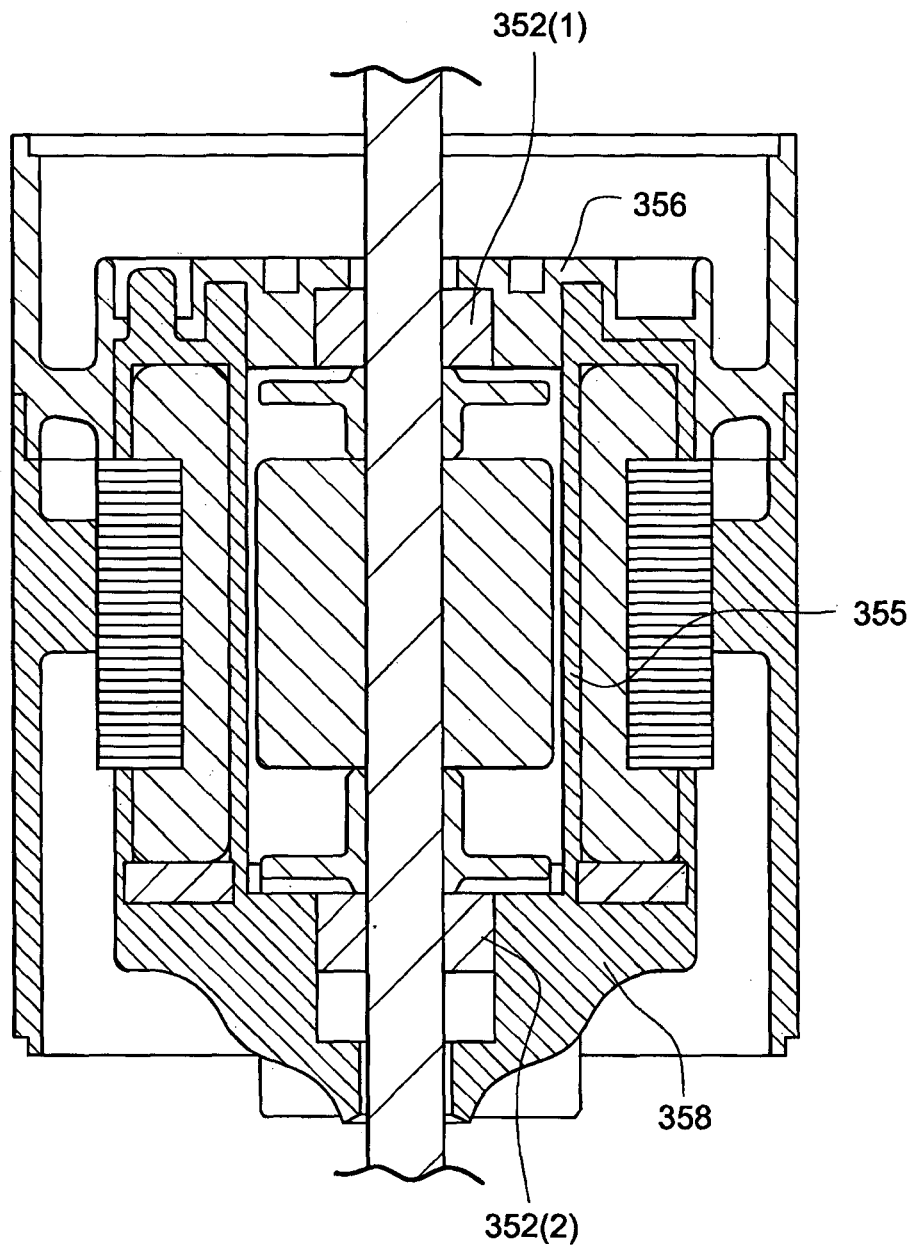
Figure 54:
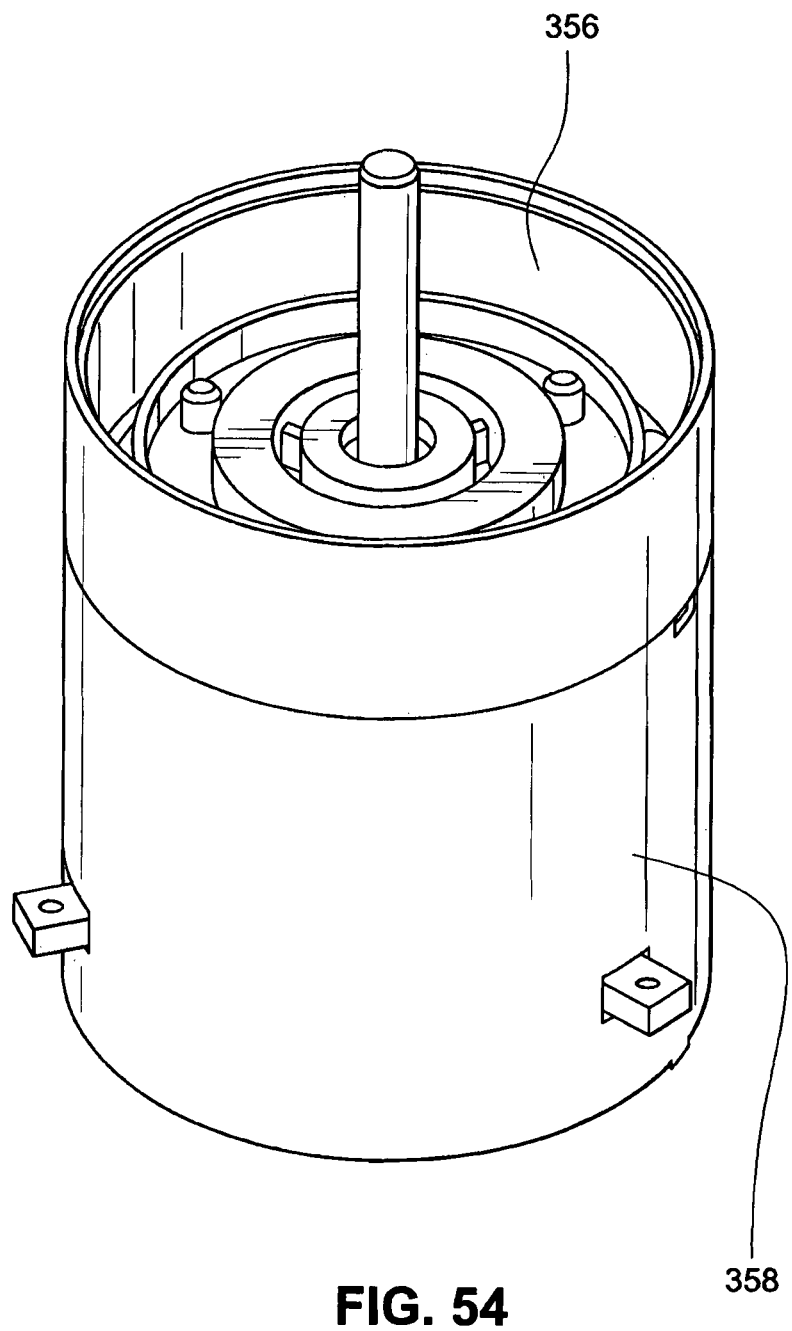
Figure 55:
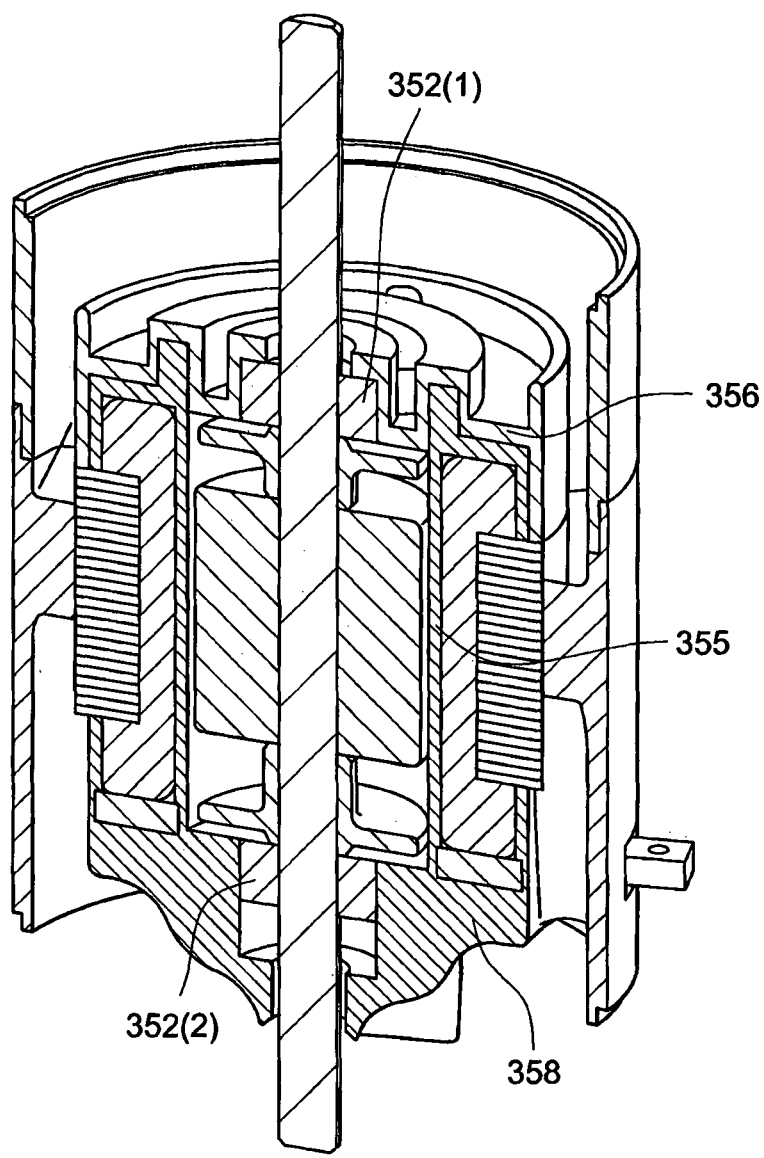
Figure 56:
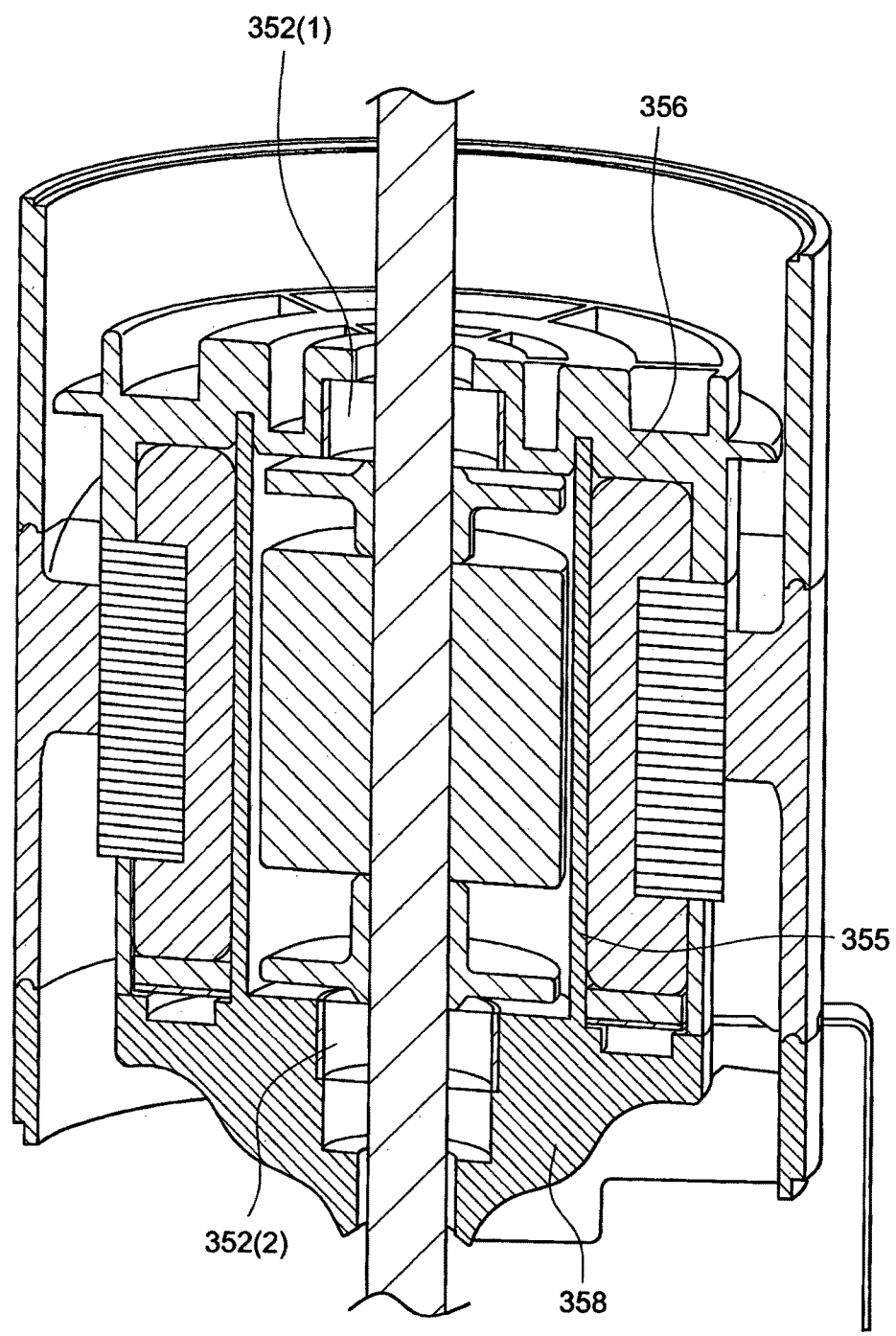
Figure 57:
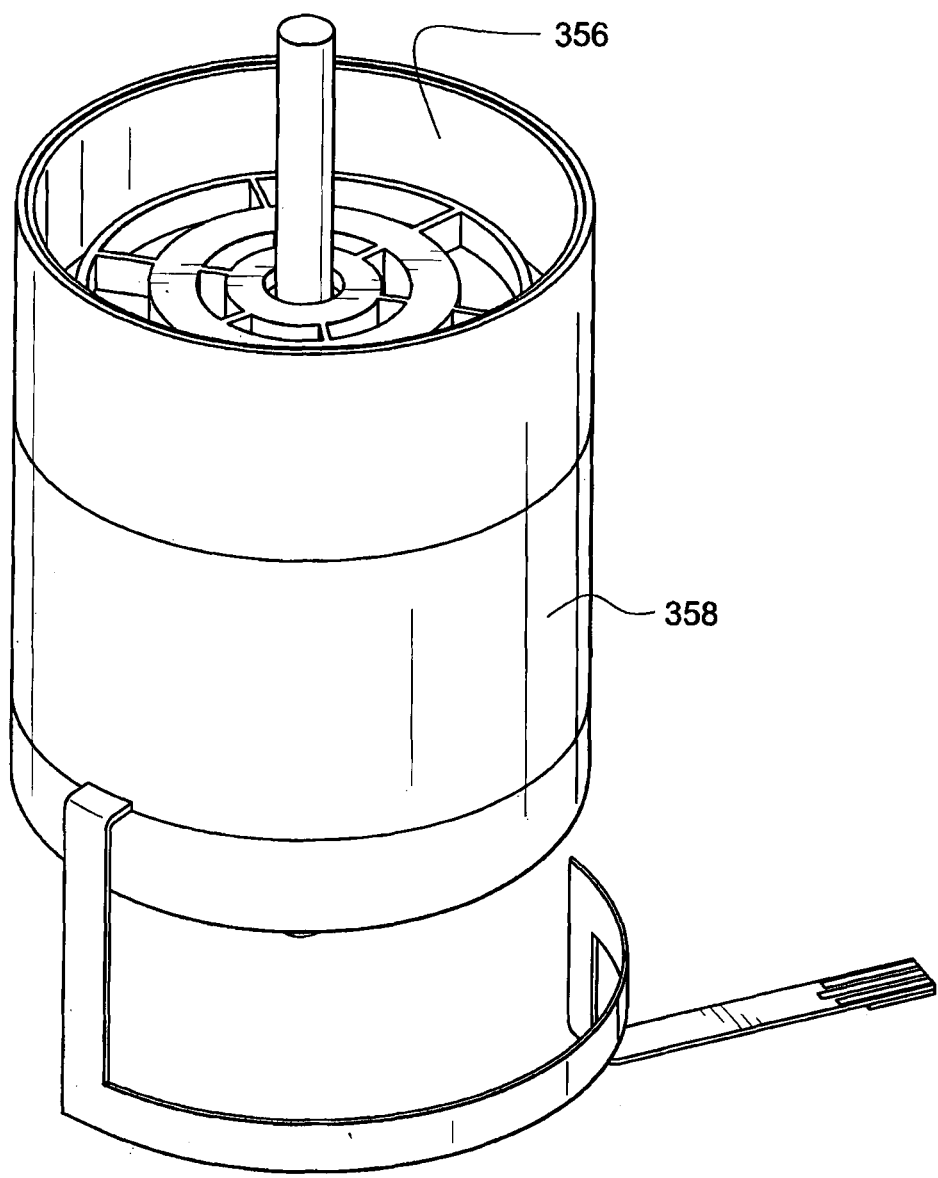
Figure 58:
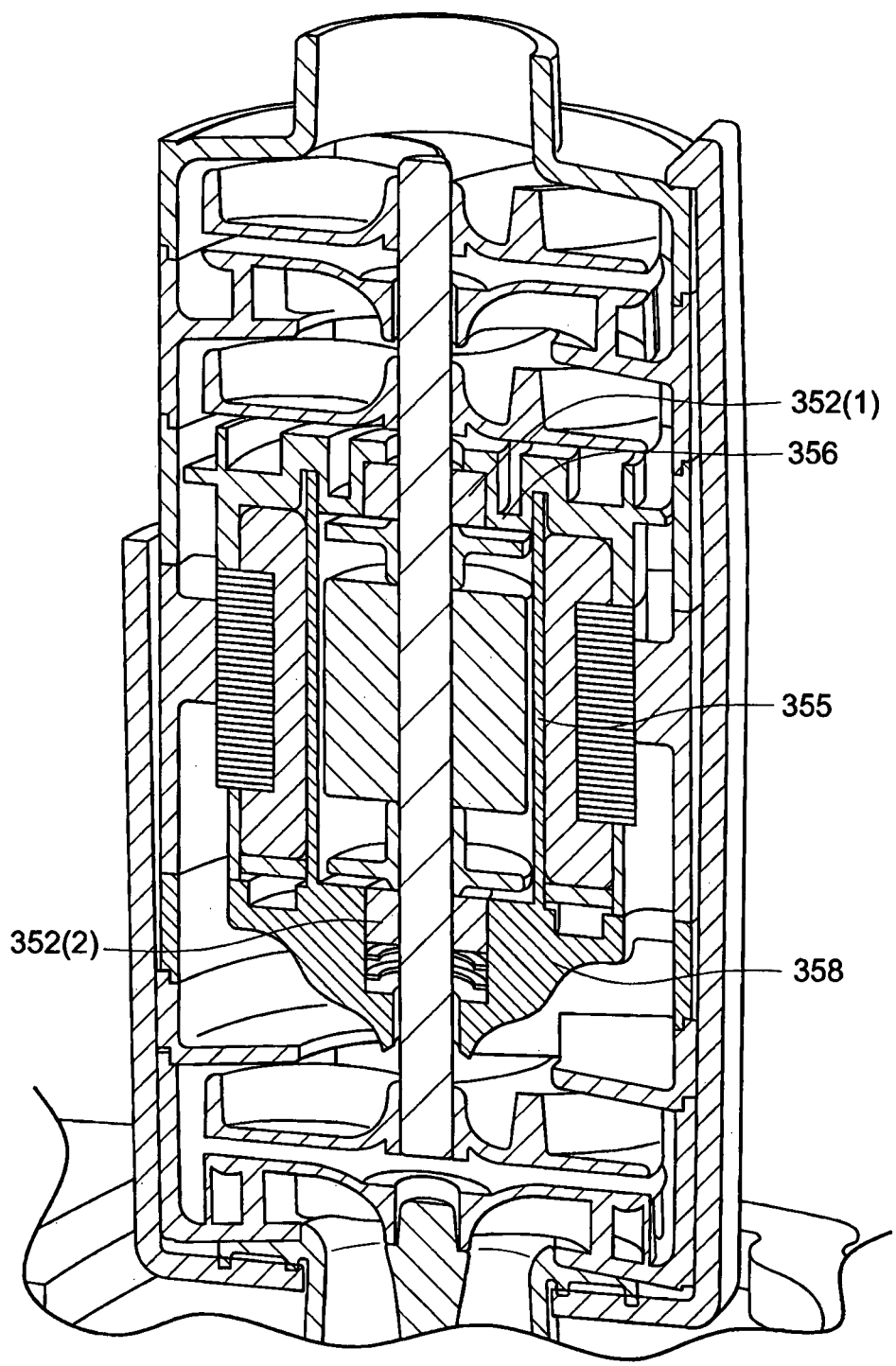
Figure 59:
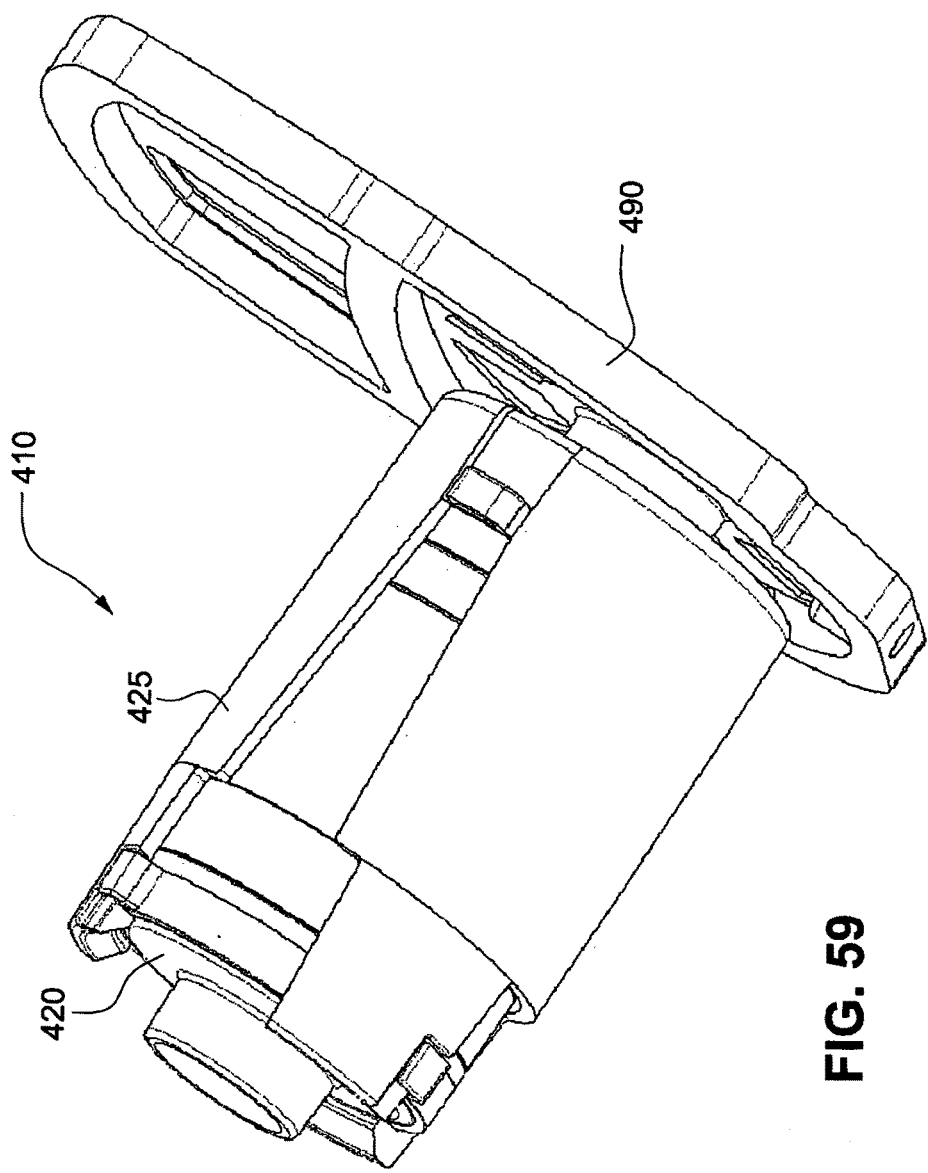
FIGS. 59-62 show various views of a two stage blower according to an example of the present technology.
Figure 60:
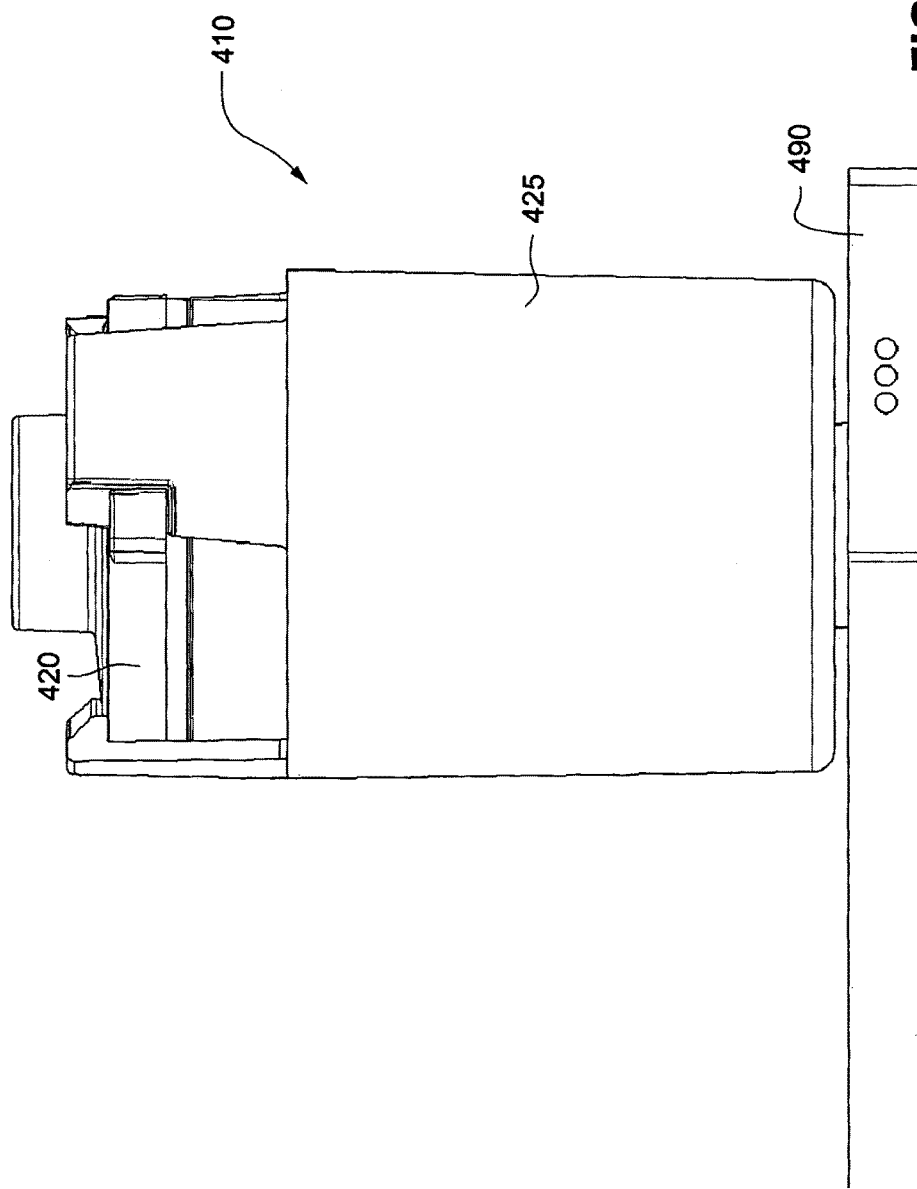
Figure 61:
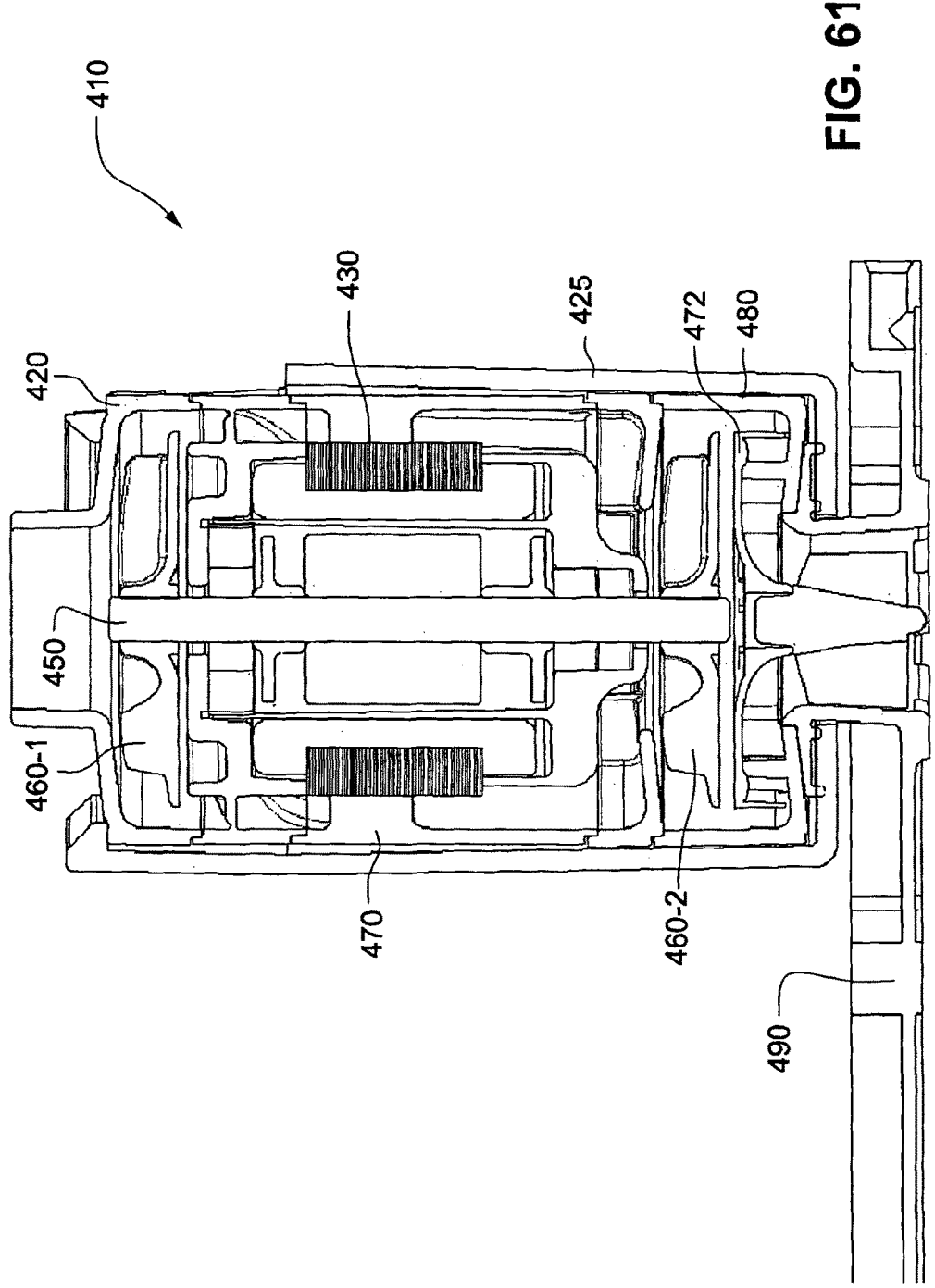
Figure 62:
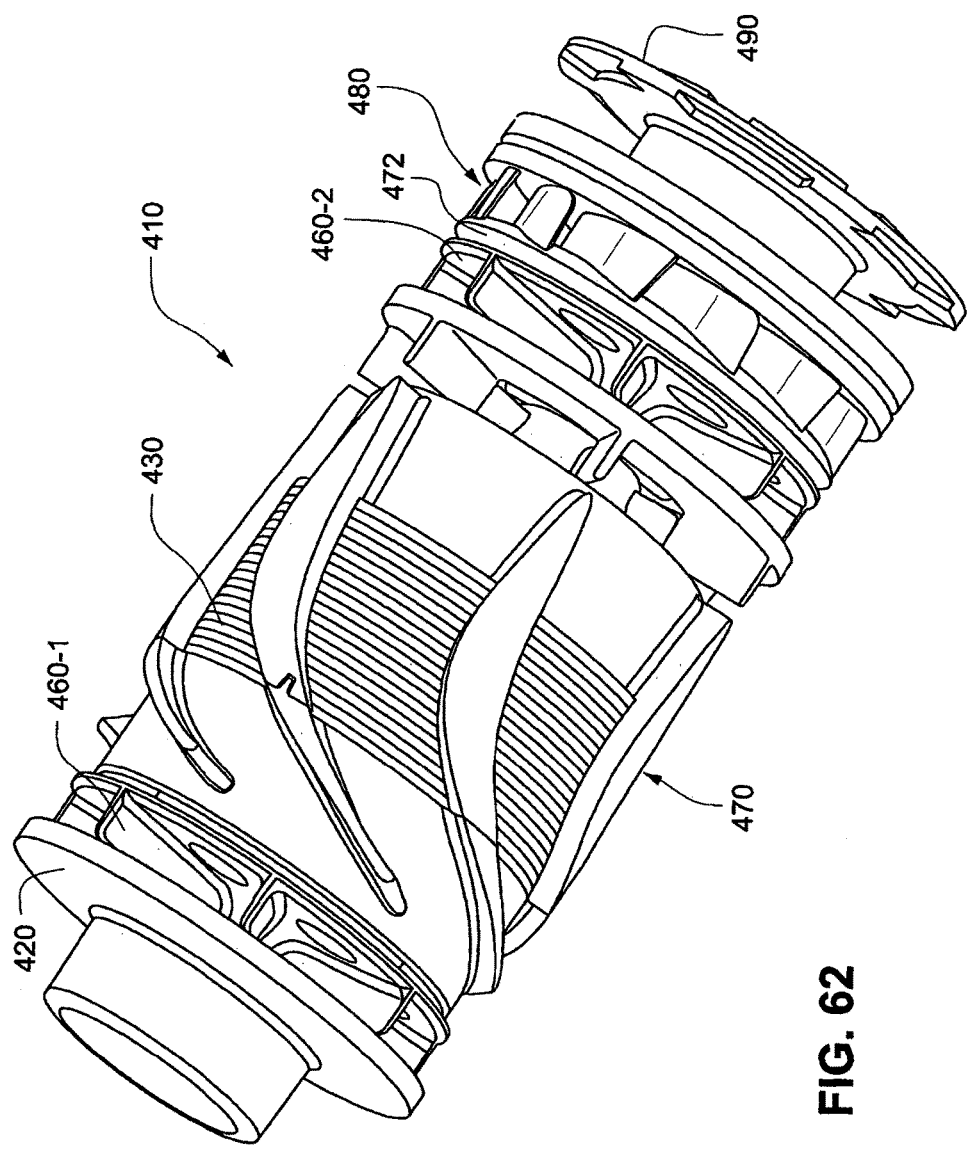
Figure 63:
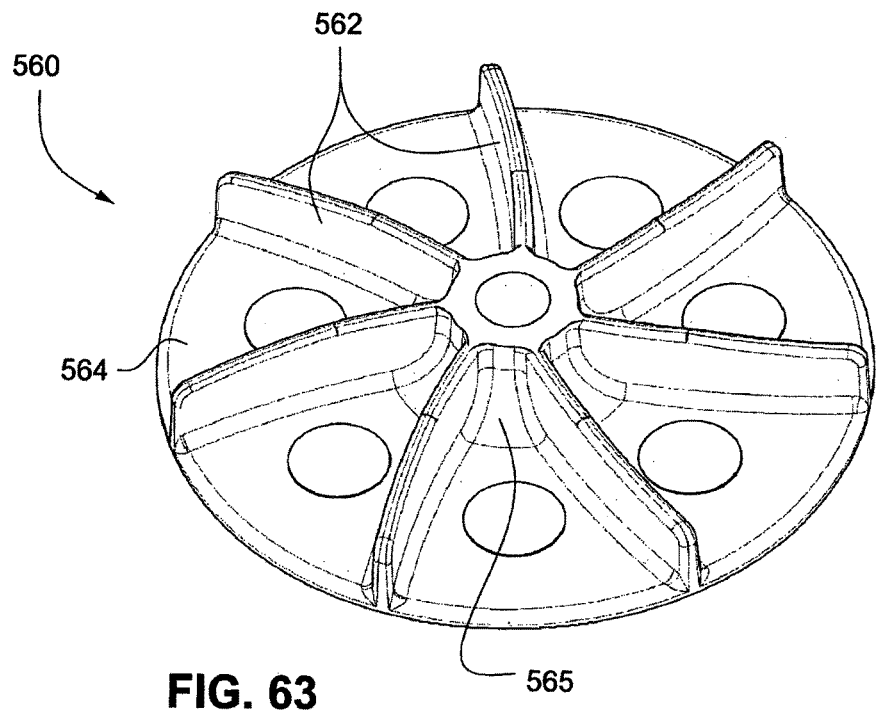
FIGS. 63-66 show various views of an impeller according to another example of the disclosed technology.
Figure 64:
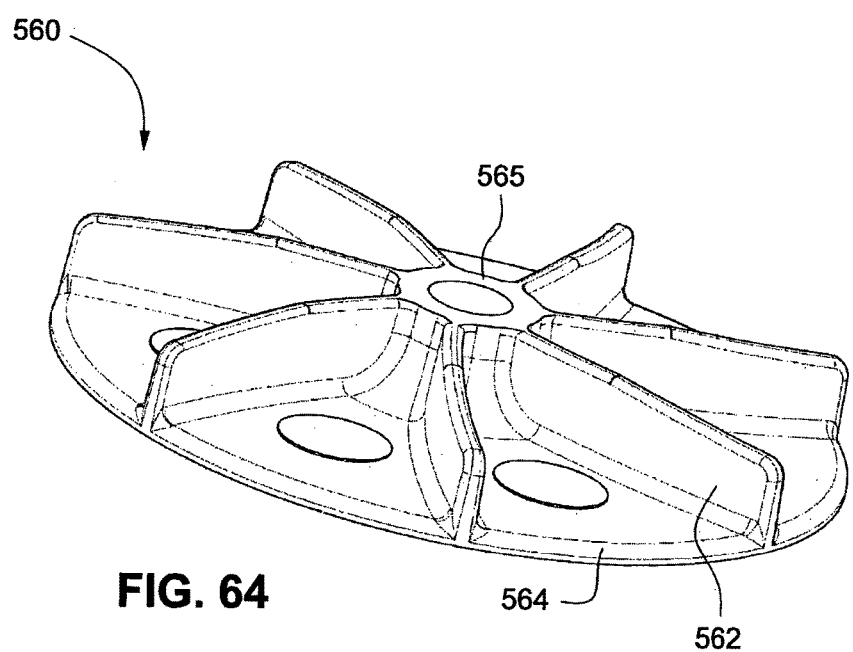
Figure 65:
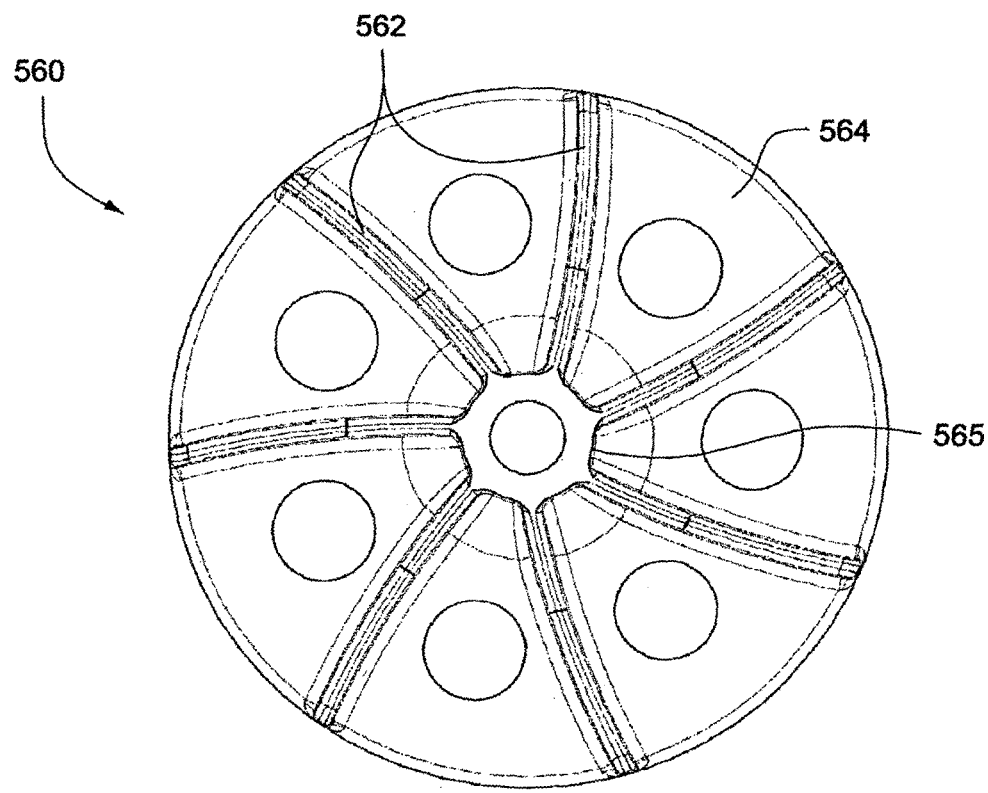

In an example, the leading edges of the stator vanes 85 may be skewed or angled in plane view to reduce blade pass pressure tones. For example, all the leading edges of the stator vanes 85 may be skewed in the same backwards direction. FIGS. 13 and 53 are exemplary views showing skewed leading edges of the stator vanes 85.

Additionally, the top and/or intermediate portions 82, 84 may be structured such that the lamination stack 42 of the stator component may be at least partially exposed to the flow of gas to help carry away heat produced from the motor, e.g., see FIGS. 13 and 14.

As shown in FIGS. 3, 4, 11-14, and 33, the bottom portion 86 located below the motor provides stator vanes 85-3 to direct airflow radially to ensure that the airflow does not swirl as it enters the third stage impeller 60-3. The bottom portion 86 includes a bottom wall 86(1) providing an outlet opening 87, an annular side wall 86(2) provided to the bottom wall, and stator vanes 85-3 that extend radially along the bottom wall from the side wall to the outlet opening 87. The outlet opening 87 allows the air to enter the third stage.

In the illustrated example, as shown in FIGS. 3, 4, 12, and 33, the intermediate portion 84 includes stator vanes 85-4 that extend radially along the bottom thereof. The stator vanes 85-4 are aligned and cooperate with the stator vanes 85-3 (see FIGS. 3, 4, 11 and 33) of the bottom portion 86 to direct airflow radially towards the outlet opening 87.

1.4.3 Alignment and Retention

Figure 87:
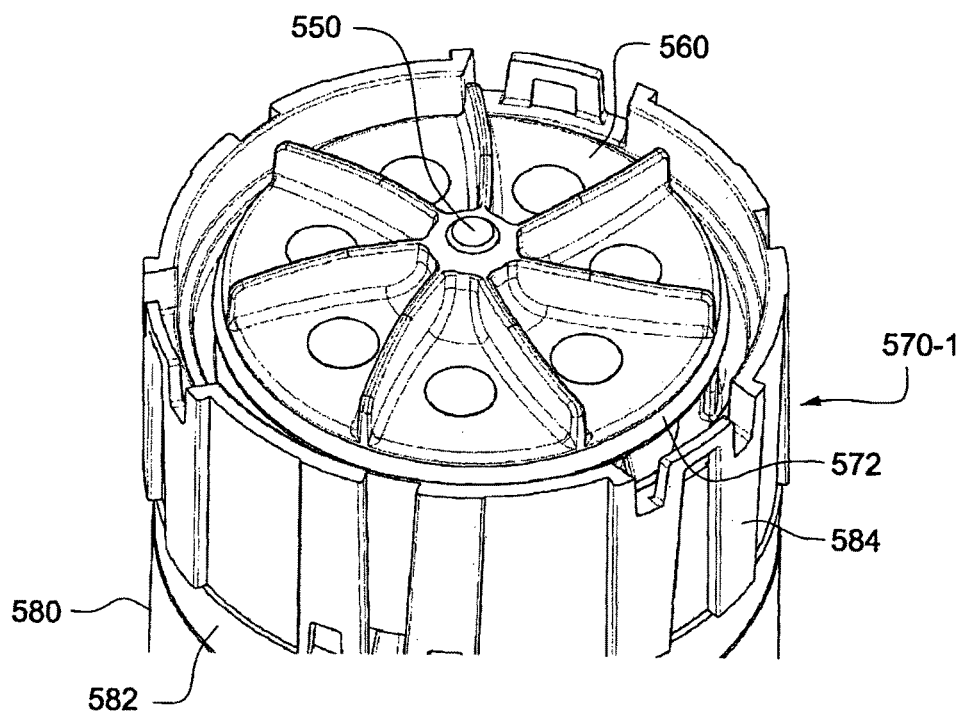
FIG. 87 is a perspective view showing an impeller provided to the rotor of the motor adjacent the shield of the first stationary component according to an example of the disclosed technology.

In an example, one or more of the housing parts and stationary components may provide structure to allow them to interlock with one another, e.g., with a snap-fit, to facilitate retention and alignment of such parts/components. In addition, a removable interlock arrangement (e.g., snap-fit) facilitates access to the impellers (e.g., see FIGS. 85, 87, and 89) during and/or after assembly, e.g., for blower balancing purposes.

Figure 67:
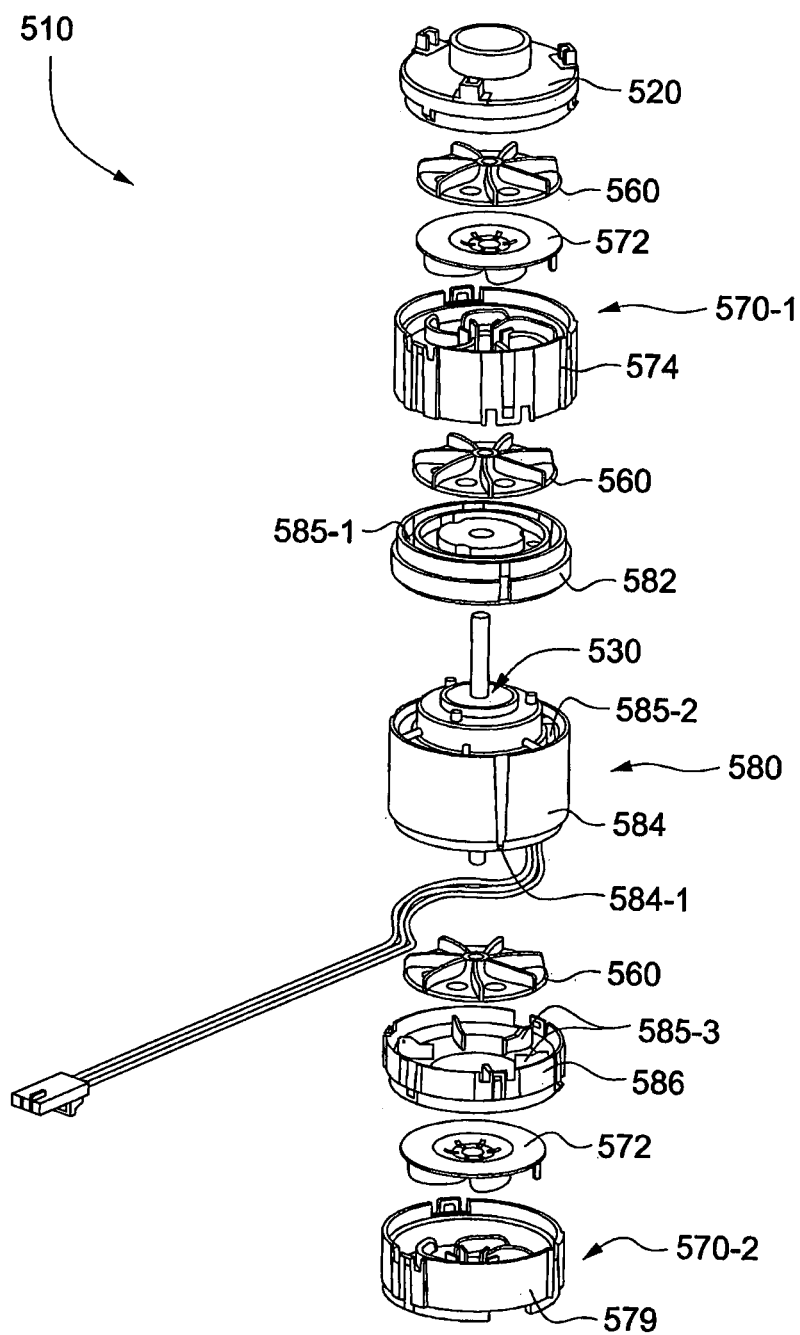
FIG. 67 is an exploded view of a blower according to another example of the disclosed technology.

For example, FIG. 67 shows a blower 510 including alternative examples of the first, second and third stationary components 570-1, 580, 570-2 as well as an alternative example of the first housing part 520. The first housing part 520, also referred to as an inlet portion, provides the inlet port into the blower. In this example, the first, second and third stationary components and the first housing part are interlocked with one another, e.g., via snap-fit arrangement as described below. As a result, a second housing part (as provided in the blower 10 described above) is not required for retention and alignment in this example.

Figure 68:
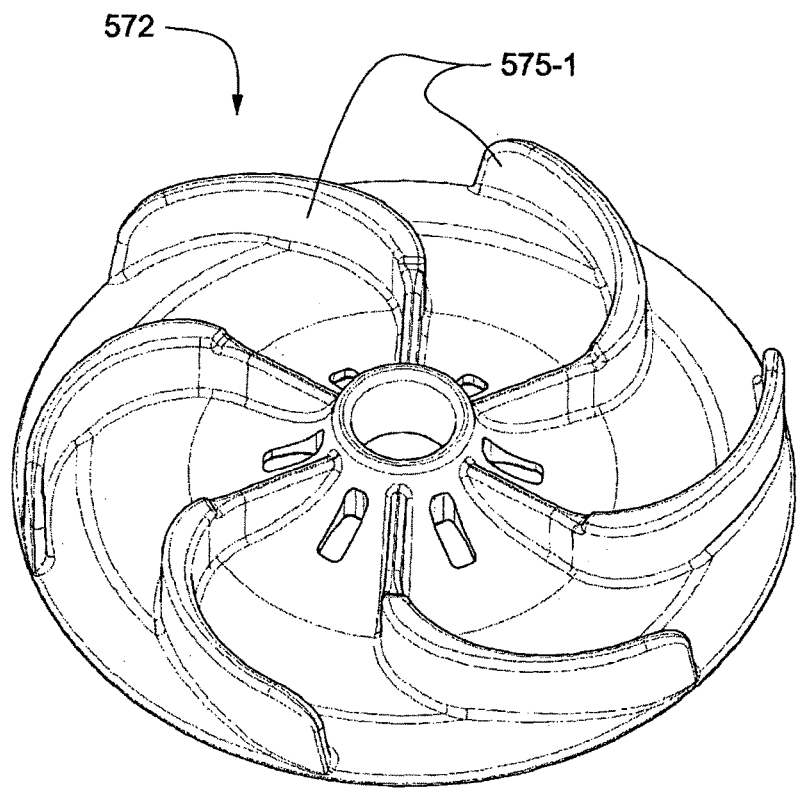
FIGS. 68-70 show various views of a shield of a stationary component according to an example of the disclosed technology.
Figure 69:
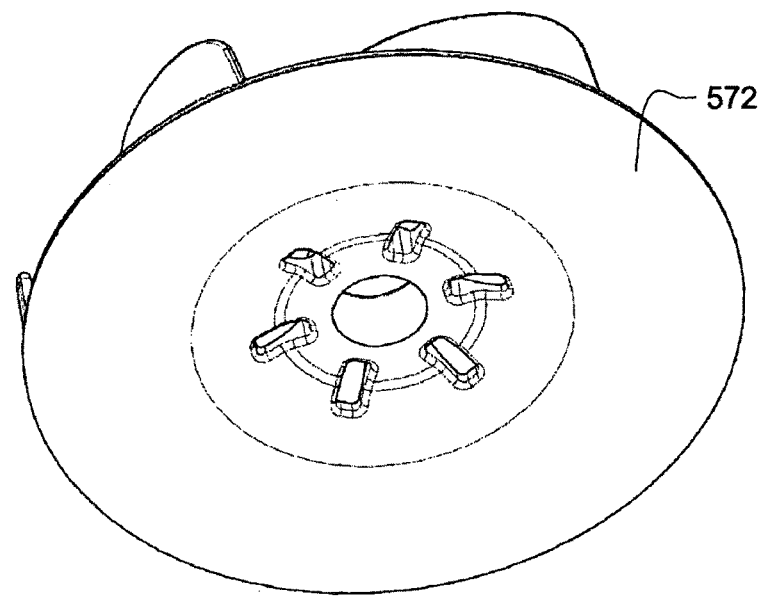
Figure 70:
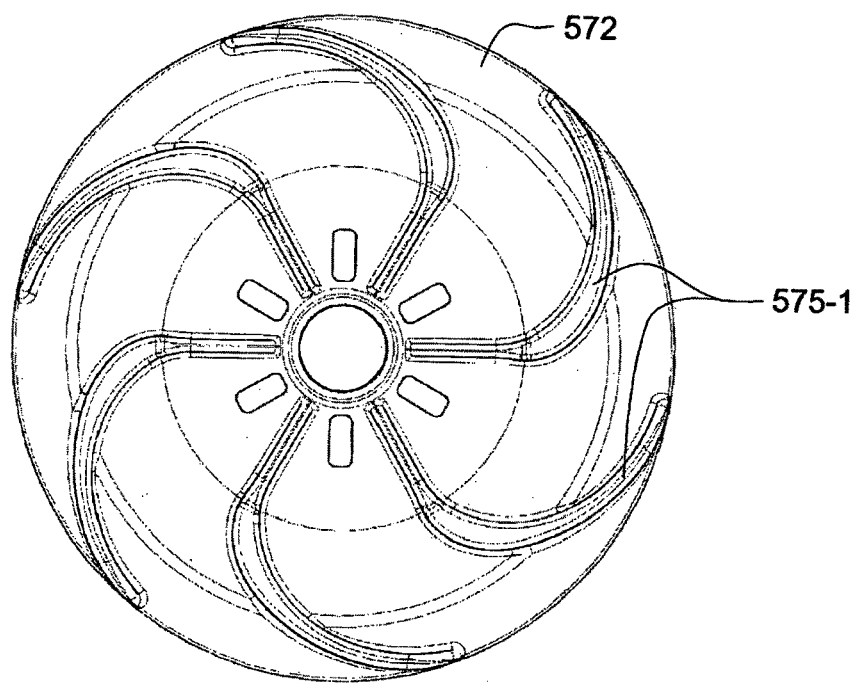
Figure 71:
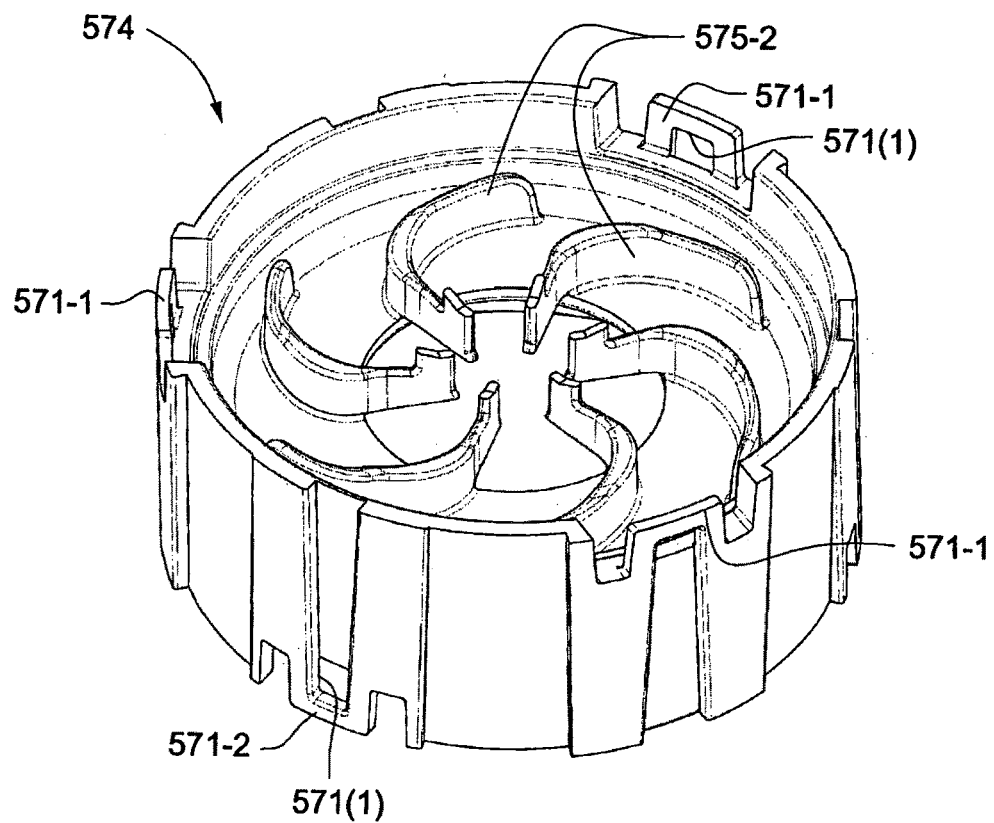
FIGS. 71-73 show various views of a housing of a first stationary component according to an example of the disclosed technology.
Figure 72:
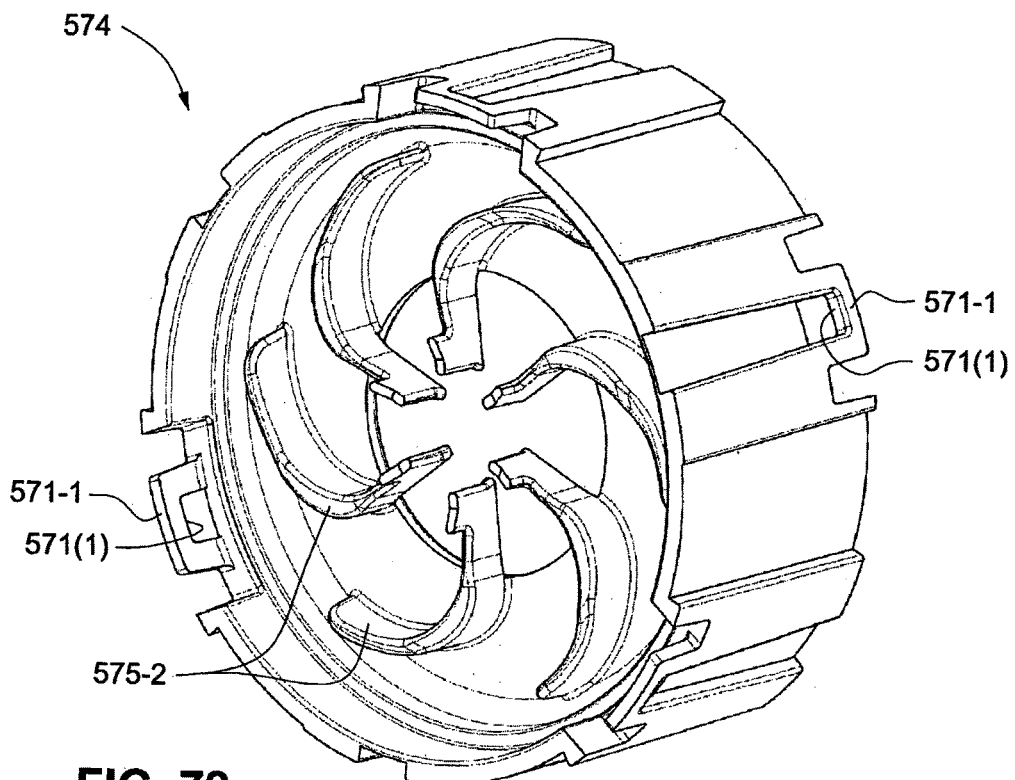
Figure 73:
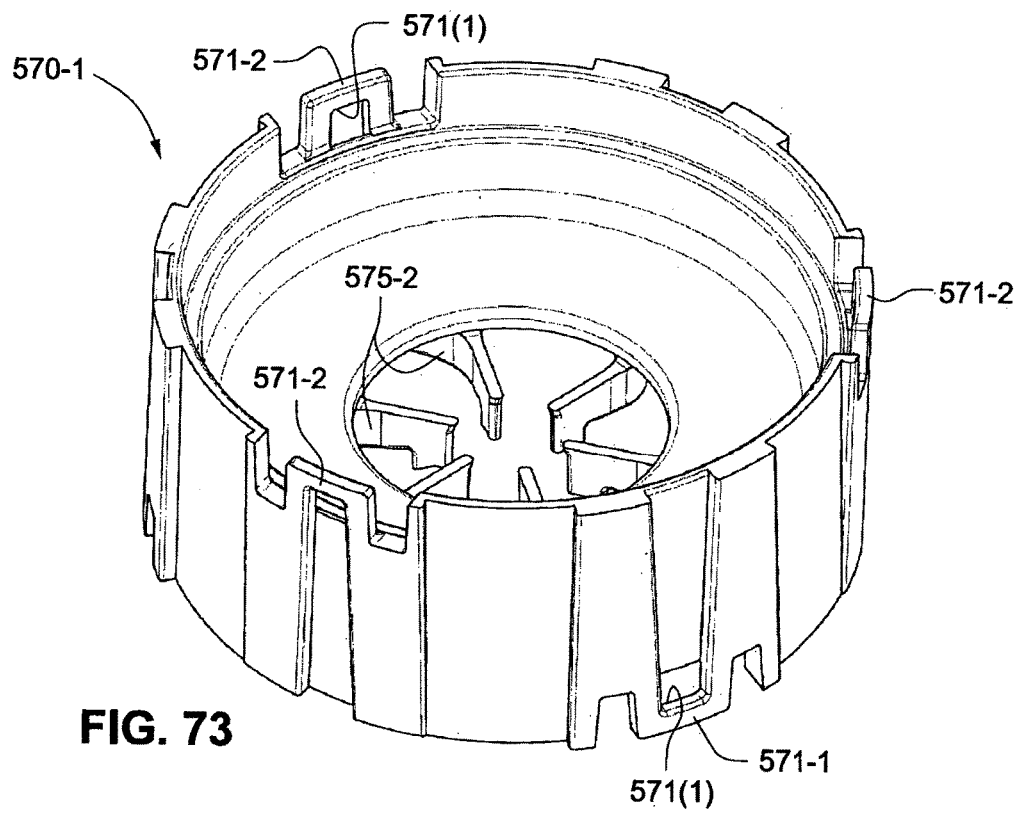
Figure 74:
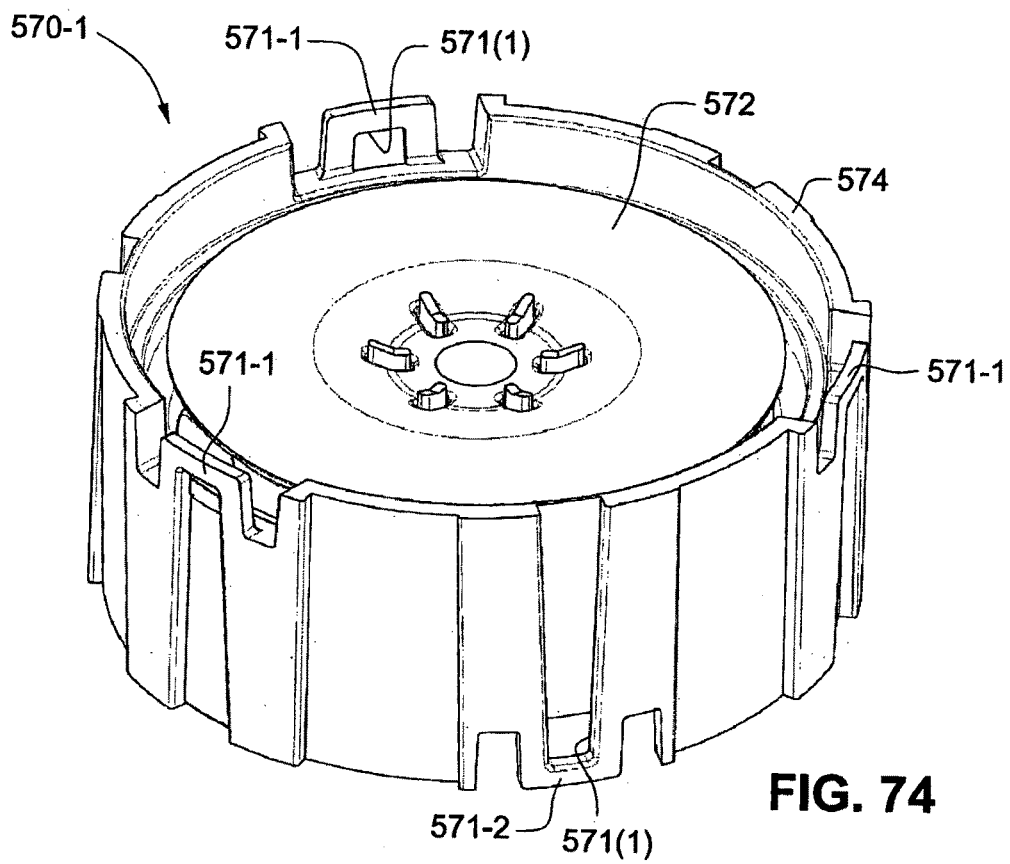
FIG. 74 is a perspective view showing an assembled first stationary component including the shield of FIGS. 68-70 assembled to the housing of FIGS. 71-73.
Figure 75:
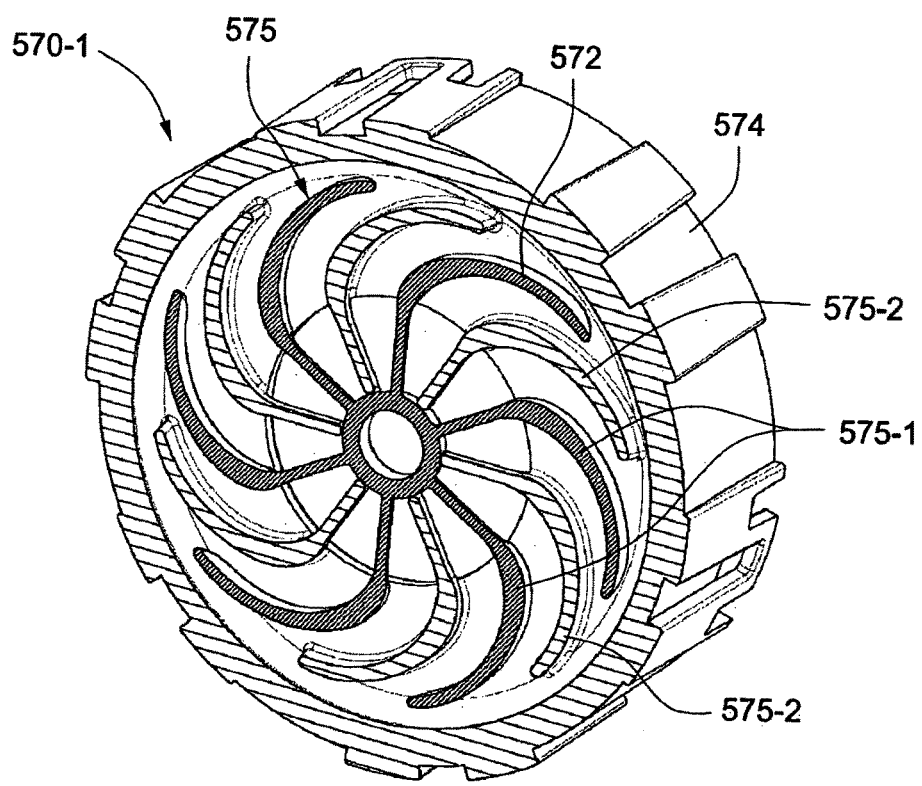
FIGS. 75 and 76 are cross-sectional views showing the assembled first stationary component of FIG. 74.
Figure 76:
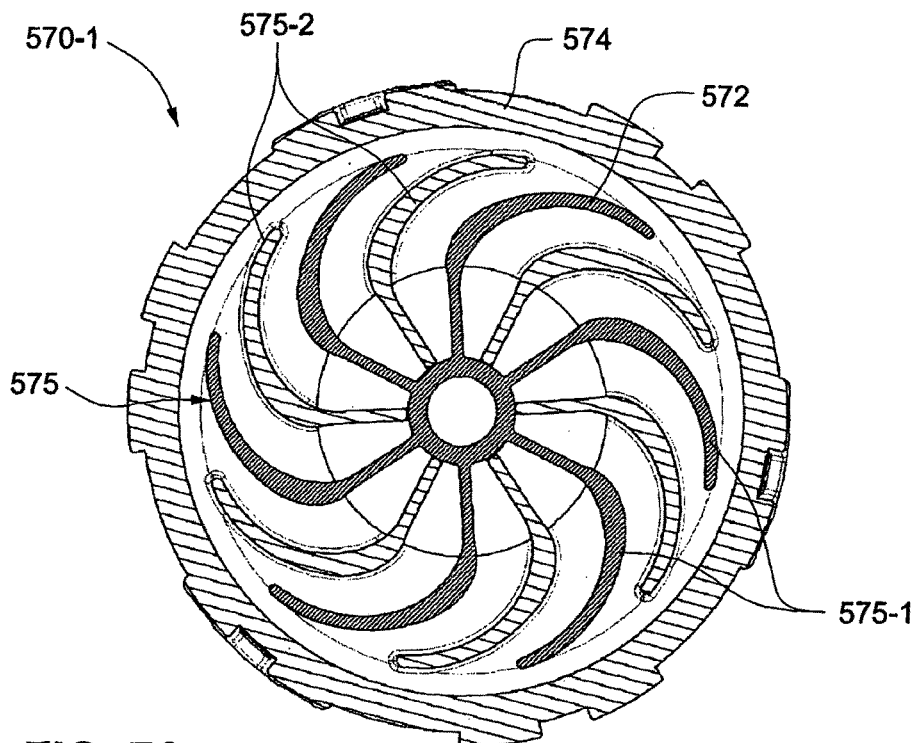

Similar to the example described above, the first stationary component 570-1 includes a shield 572 including a first set of stator vanes 575-1 (e.g., see FIGS. 68-70) and a housing 574 including a second set of stator vanes 575-2 (e.g., see FIGS. 71-73). When the shield 572 and housing 574 are assembled to one another, the first and second set of vanes 575-1, 575-2 provide the full or complete set of stator vanes 575 for air flow (e.g., see FIGS. 74-76). In this example, the housing 574 includes structure to interlock with the housing part 520 and the top portion 582 of the second stationary component 580.

Figure 77:
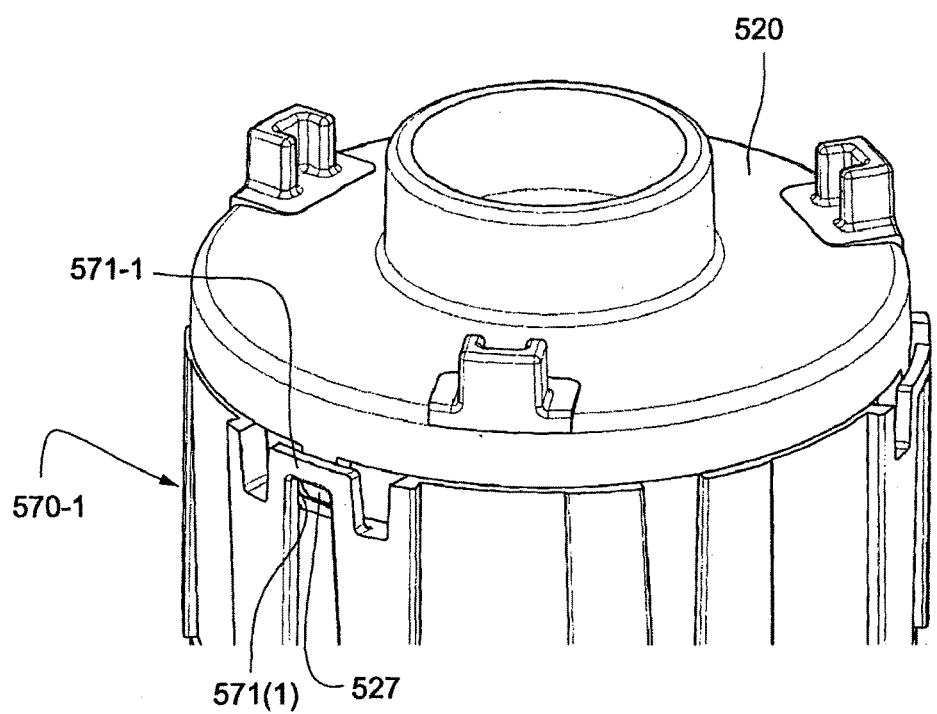
FIG. 77 is a perspective view showing a housing part attached to the housing of the first stationary component according to an example of the disclosed technology.
Figure 78:
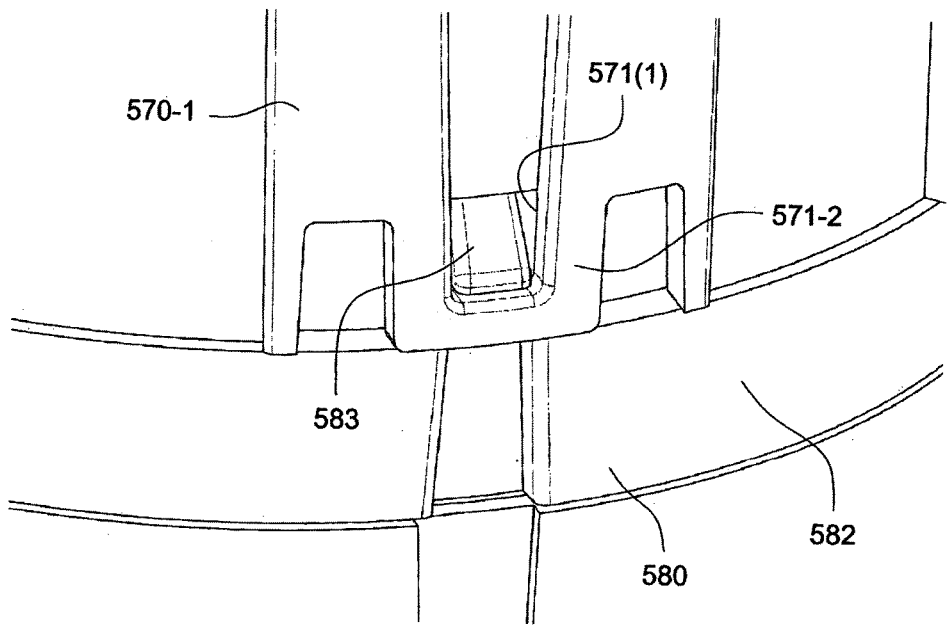
FIG. 78 is an enlarged perspective view showing the first stationary component attached to the second stationary component according to an example of the disclosed technology.

Specifically, one end of the housing 574 includes a plurality of resilient arm members 571-1 (e.g., three arm members as shown but may include two arm members or four or more arm members) each including an opening 571(1) adapted to receive a respective tab 527 provided to a side of the housing part 520 (e.g., see FIG. 77), e.g., with a snap-fit. Also, the opposite end of the housing 574 includes resilient a plurality of arm members 571-2 (e.g., three arm members as shown but may include two arm members or four or more arm members) each including an opening 571(1) adapted to receive a respective tab 583 provided to a side of the top portion 582 of the second stationary component 580 (e.g., see FIGS. 78 and 84-86), e.g., with a snap-fit. FIG. 78 is an enlarged view showing the snap-fit engagement between the tab 583 and a respective opening 571(1) of an arm member 571-2.

Figure 79:
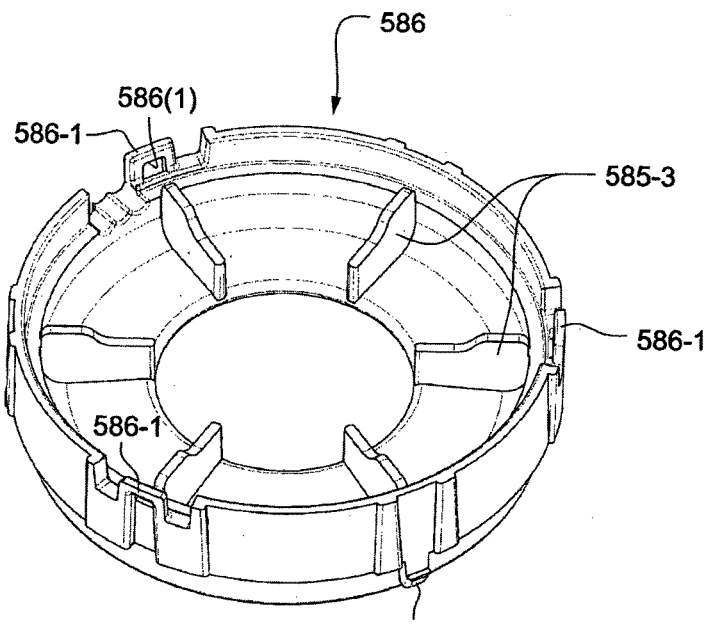
FIG. 79 is a perspective view of a bottom portion of a second stationary component according to an example of the disclosed technology.

Similar to the example described above, the second stationary component 580 includes a top portion 582 providing a first set of stator vanes 585-1 (e.g., see FIG. 67), an intermediate portion 584 providing a second set of stator vanes 585-2 (e.g., see FIG. 67), and a bottom portion 586 providing a third set of stator vanes 585-3 (e.g., see FIGS. 67 and 79). The top and intermediate portions 582, 584 cooperate to support and maintain the motor 530 in an operative position and to provide stator vanes structured to direct airflow in a generally axial direction down and around the motor. The bottom portion 586 is located below the motor and provides stator vanes to direct airflow radially to ensure that the airflow does not swirl as it enters the third stage.

Figure 92:
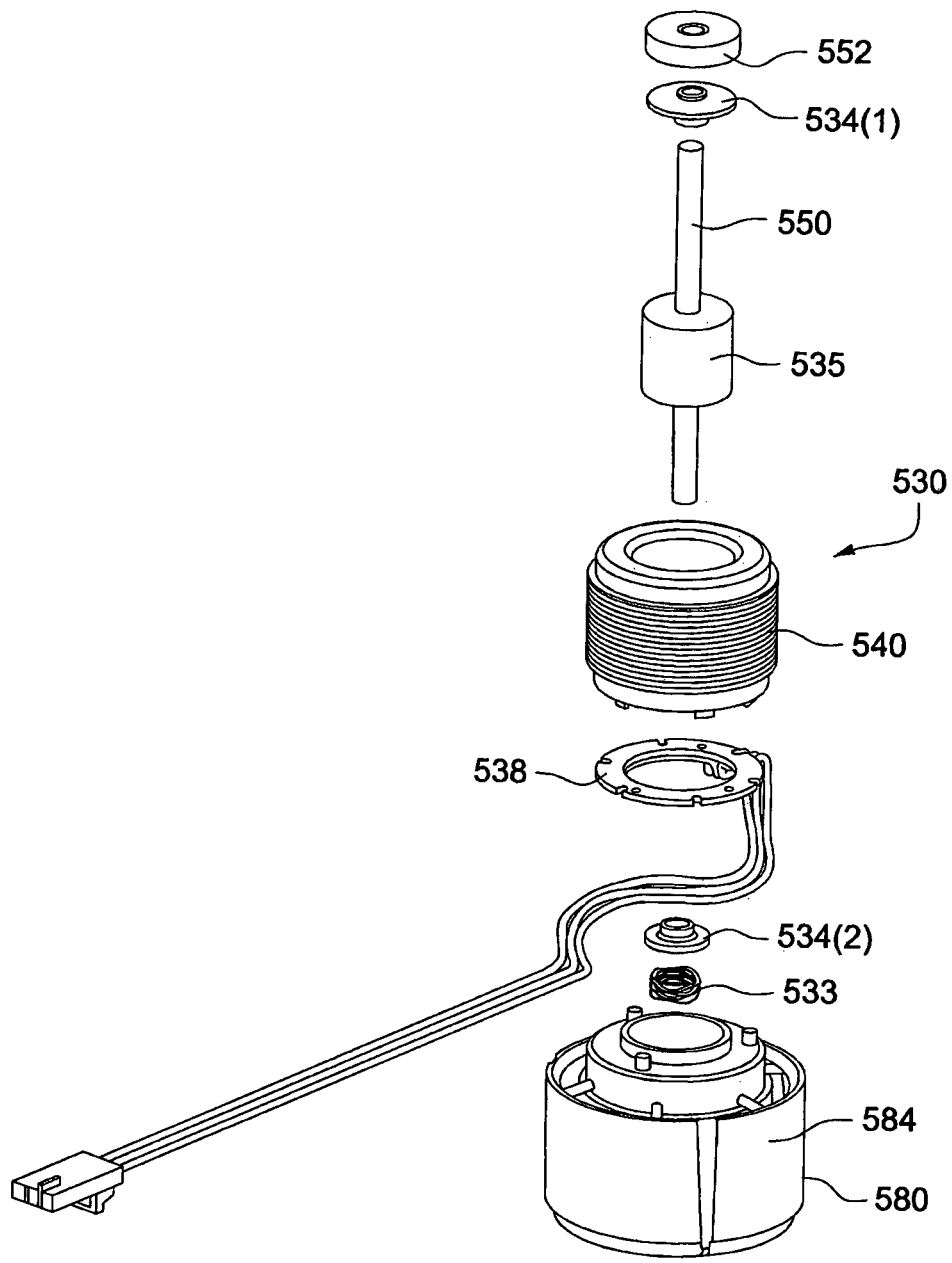
FIG. 92 is an exploded view of a motor and second stationary component according to an example of the disclosed technology.

FIG. 92 shows an example of motor 530 along with the intermediate portion 584 of the second stationary component 580. Similar to the example described above, the motor 530 includes rotor 550 with magnet 535 and a stator component 540. Also illustrated is bearing 552 for rotatably supporting one end of the rotor, flux getters 534(1), 534(2), preload spring 533, and printed circuit board assembly (PCBA) 538 to control the motor. In an example, the stator component and the PCBA may be overmolded with the intermediate portion of the second stationary component.

Figure 91:
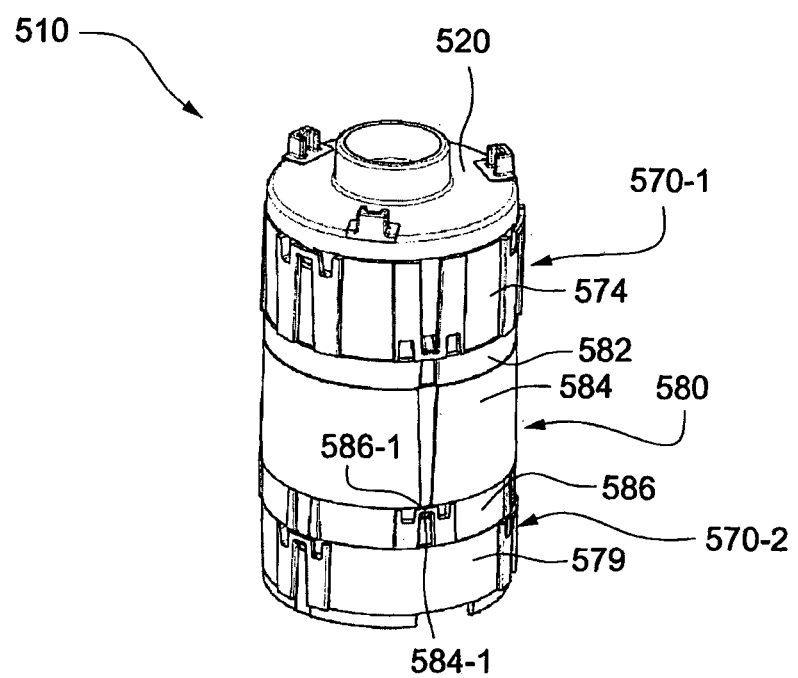
FIG. 91 is a perspective view of a blower according to an example of the disclosed technology.

In this example, the bottom portion 586 includes structure to interlock with the intermediate portion 584 of the second stationary component 580 and the third stationary component 570-2. Specifically, one end of the bottom portion 586 includes a plurality of resilient arm members 586-1 (e.g., three arm members as shown but may include two arm members or four or more arm members) each including an opening 586(1) adapted to receive a respective tab 584-1 provided to a side of the intermediate portion 584 (e.g., see FIGS. 67, 79, and 91), e.g., with a snap-fit. In an example, the top portion 582 may be secured to the intermediate portion 584 via heat staking, e.g., see FIGS. 83-84 showing stakes 582(1) on the intermediate portion 584 adapted to extend through respective openings in the top portion 582 and subsequently heat staked to secure the portions to one another.

Figure 80:
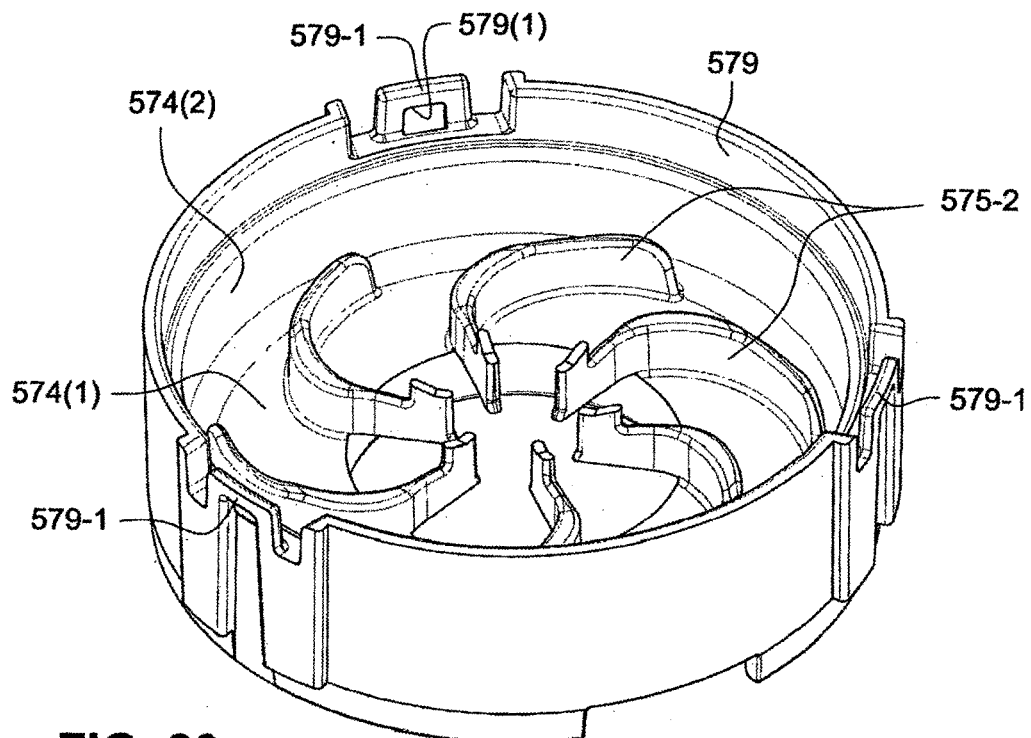
FIGS. 80-81 show various views of a housing of a third stationary component according to an example of the disclosed technology.
Figure 81:
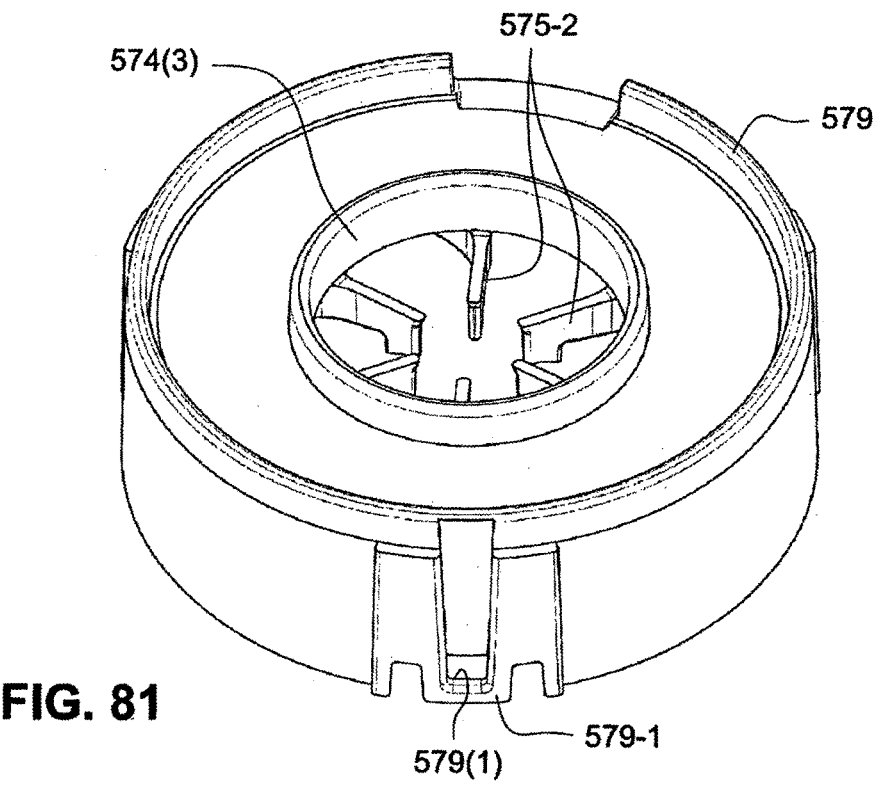
Figure 82:
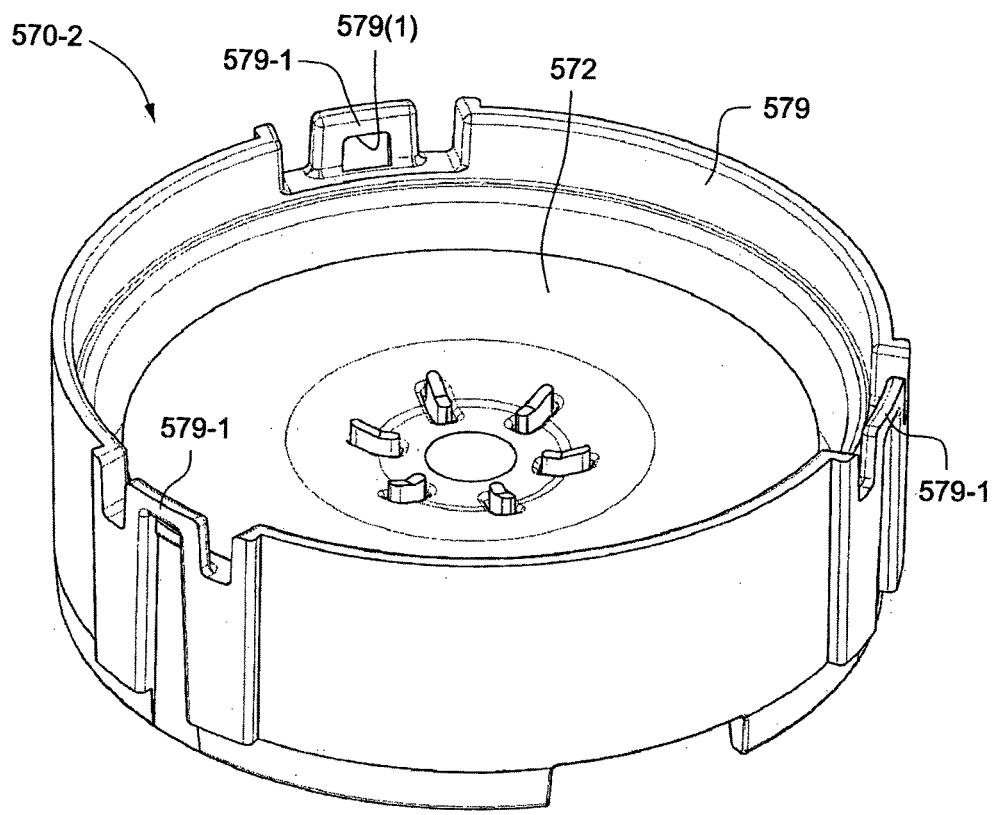
FIG. 82 is a perspective view showing an assembled third stationary component including the shield of FIGS. 68-70 assembled to the housing of FIGS. 80-81.

Similar to the example described above, the third stationary component 570-2 includes a shield 572 including a first set of stator vanes 575-1 (e.g., see FIGS. 68-70) and a housing 579 including a second set of stator vanes 575-2 (e.g., see FIGS. 80-81). When the shield 572 and housing 579 are assembled to one another (e.g., see FIG. 82), the first and second set of vanes 575-1, 575-2 provide the full or complete set of stator vanes for air flow. In this example, the housing 579 of the third stationary component 570-2 is different than the housing 574 of the first stationary component 570-1, e.g., bottom wall 574(1) supporting stator vanes 575-2 is recessed lower along the annular side wall 574(2) of the housing than the annular wall 574(3) provided along outlet. However, the shield 572 provided to the housings 574, 579 are similar.

In this example, the housing 579 includes structure to interlock with the bottom portion 586 of the second stationary component 580. Specifically, one end of the housing 579 includes a plurality of resilient arm members 579-1 (e.g., three arm members as shown but may include two arm members or four or more arm members) each including an opening 579(1) adapted to receive a respective tab 586-2 provided to a side of the bottom portion 586 (e.g., see FIGS. 79 and 90), e.g., with a snap-fit.

Figure 83:
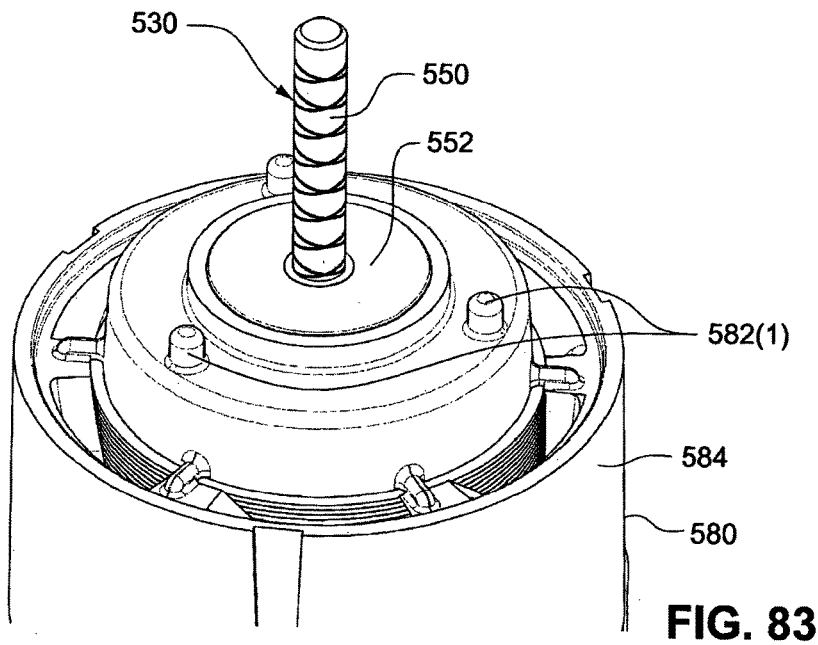
FIG. 83 is a perspective view showing an intermediate portion of the second stationary component engaged with motor according to an example of the disclosed technology.
Figure 84:
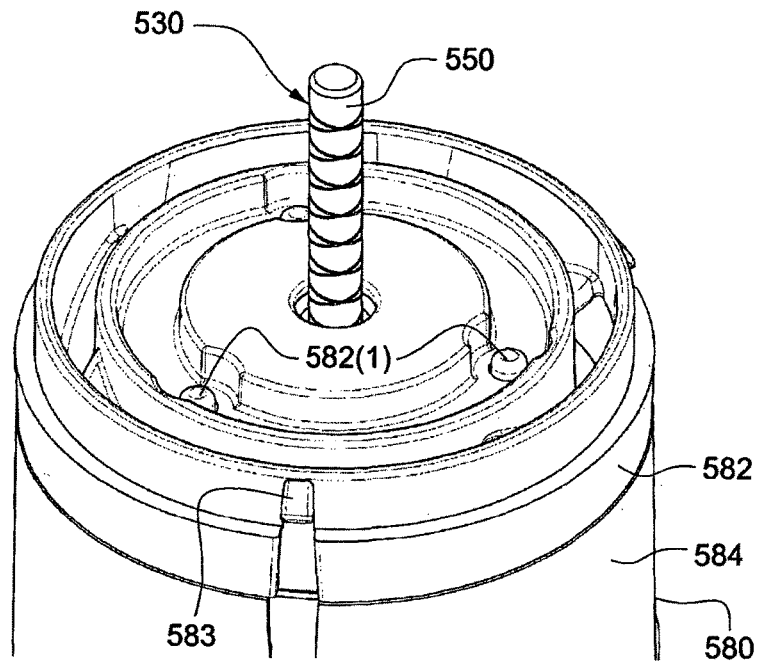
FIG. 84 is a perspective view showing the top portion engaged with the intermediate portion of the second stationary component according to an example of the disclosed technology.
Figure 85:
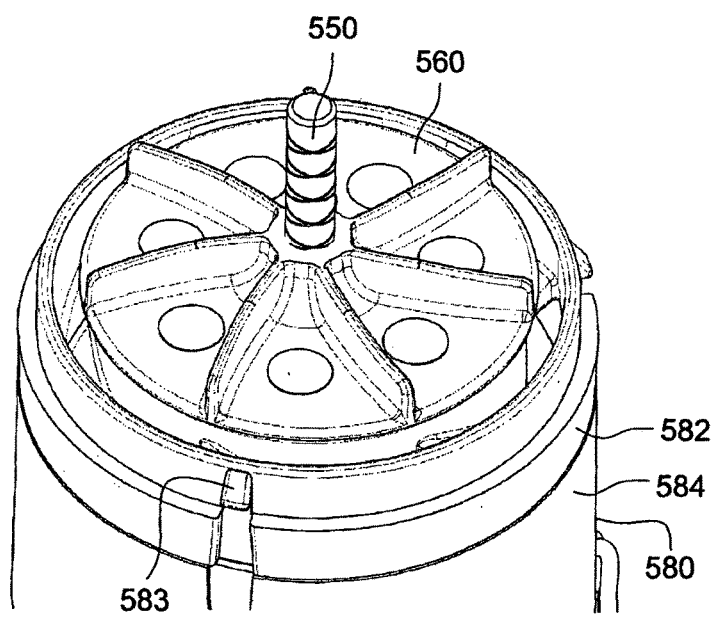
FIG. 85 is a perspective view showing an impeller provided to the rotor of the motor adjacent the top portion of the second stationary component according to an example of the disclosed technology.
Figure 86:
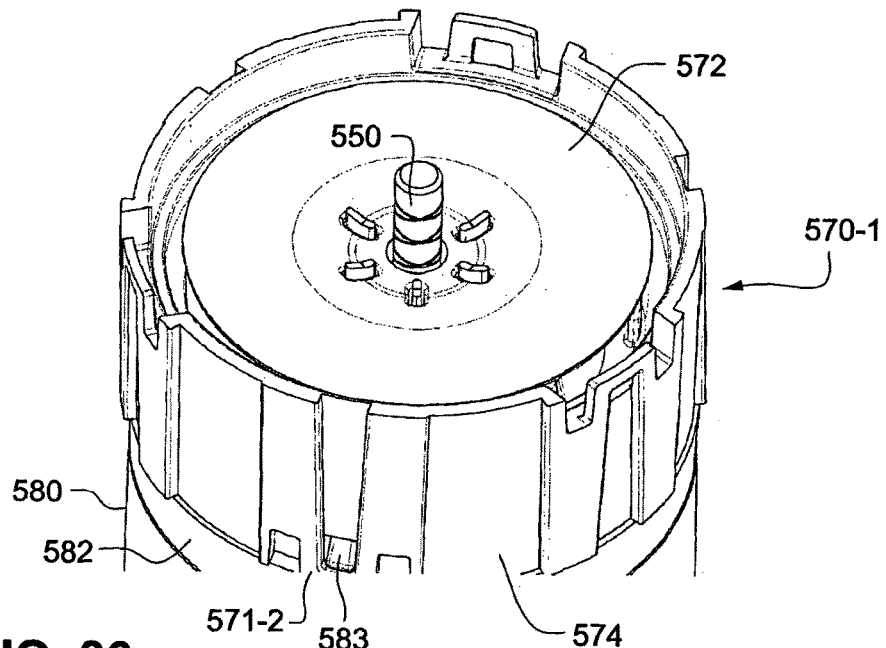
FIG. 86 is a perspective view showing the first stationary component and its housing engaged with the top portion of the second stationary component according to an example of the disclosed technology.
Figure 88:
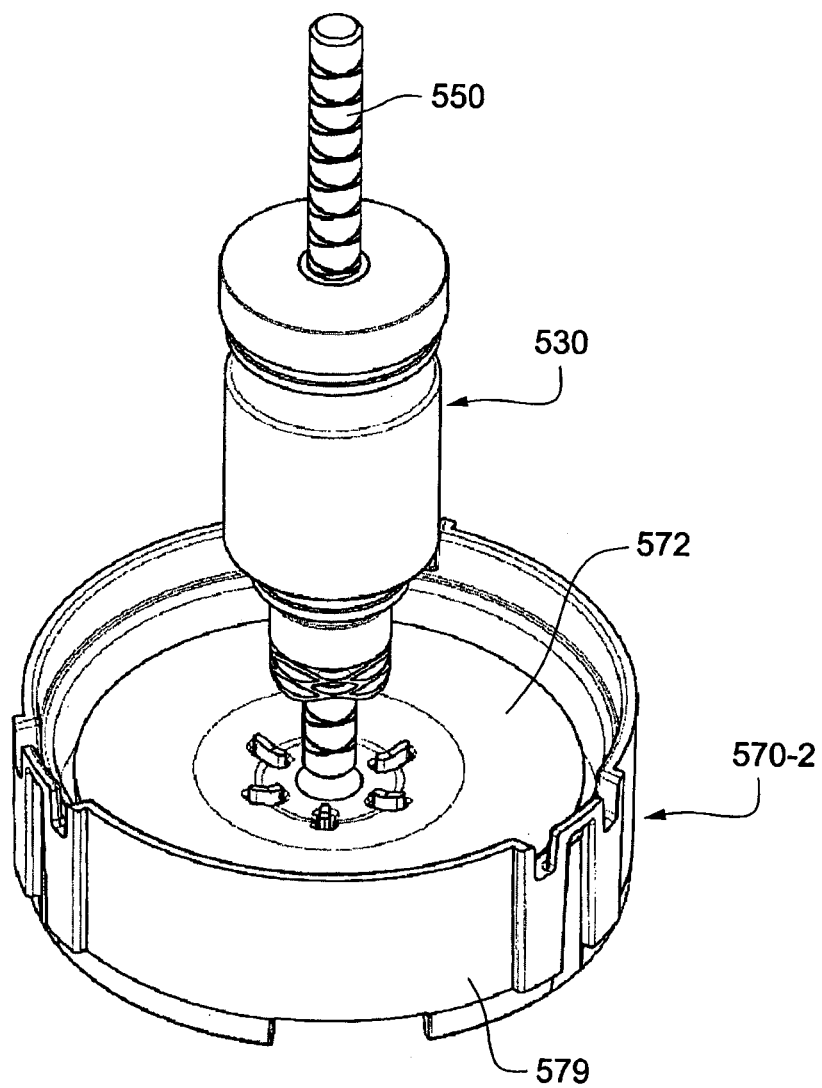
FIG. 88 is a perspective view showing the third stationary component in relation to the motor according to an example of the disclosed technology.
Figure 89:
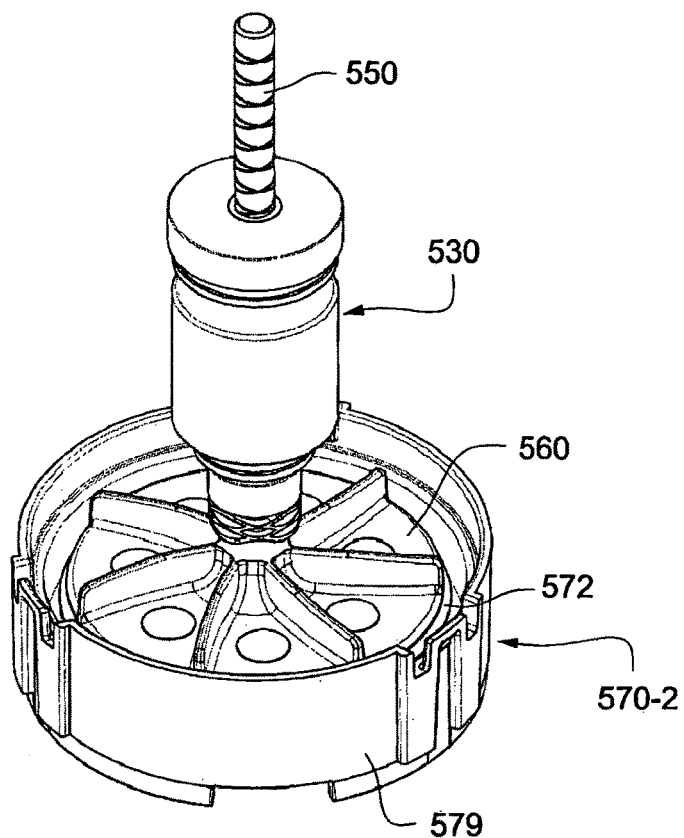
FIG. 89 is a perspective view showing an impeller provided to the rotor of the motor adjacent the shield of the third stationary component according to an example of the disclosed technology.
Figure 90:
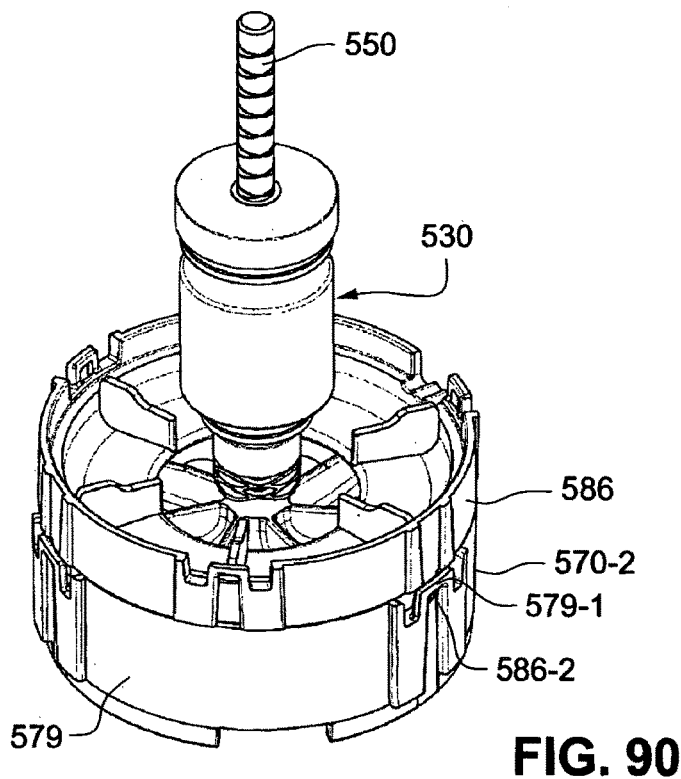
FIG. 90 is a perspective view showing the third stationary component engaged with the bottom portion of the second stationary-component according to an example of the disclosed technology.

FIGS. 83-91 show various sub-assembly views of the blower. For example, FIG. 83 shows the intermediate portion 584 of the second stationary component 580 engaged with motor 530, FIG. 84 shows the top portion 582 engaged with the intermediate portion 584 (e.g., heat staking, mechanical interlock, etc.), FIG. 85 shows impeller 560 provided to the rotor 550 adjacent the top portion 582, FIG. 86 shows the first stationary component 570-1 and its housing 574 engaged with the top portion 582 (e.g., via snap-fit as described above), and FIG. 87 shows impeller 560 provided to the rotor 550 adjacent the shield 572 of the first stationary component 570-1. FIG. 88 shows the third stationary component 570-2 in relation to the motor 530, FIG. 89 shows impeller 560 provided to the rotor 550 adjacent the shield 572 of the third stationary component 570-2, and FIG. 90 shows the third stationary component 570-2 engaged with the bottom portion 586 of the second stationary component 580 (e.g., via snap-fit as described above). FIGS. 91 and 93-95 show the assembled blower 510 with its housing part 520 and first, second and third stationary components 570-1, 580, 570-2 interlocked with one another.

However, it should be appreciated that the first and second housing parts may interlocked or otherwise secured to or relative to one another in other suitable manners.

1.5 Fluid Flow Path

As best shown in FIGS. 3 and 4, in the first stage, air enters the blower 10 at the inlet 21 and passes into the first impeller 60-1 where it is accelerated tangentially and directed radially outward. Air then flows with a large tangential velocity component and also an axial component passing through the gap 77-1 in the first stationary component 70-1 (defined by the outer edge of the shield 72 and the side wall of the housing 74). Air then enters the stator vanes 75 provided by the first stationary component 70-1 and is directed radially inwardly towards the outlet opening 76, and thereafter axially onto the second stage.

In the second stage, air passes into the second impeller 60-2 where it is accelerated tangentially and directed radially outward. Air then flows in a spiral manner with a large tangential velocity component and also an axial component passing through the annular gap 89 in the second stationary component 80. Air then enters the stator vanes 85-1, 85-2 that direct the air downwardly along the motor 30 and de-swirl the airflow and decelerate the air to increase the pressure. Air then converges at the bottom of the second stationary component 80 and is directed radially inwardly by the stator vanes 85-3, 85-4 towards the outlet opening 87, and thereafter axially onto the third stage.

In the third stage, air passes into the third impeller 60-3 where it is accelerated tangentially and directed radially outward. Air then flows with a large tangential velocity component and also an axial component passing through the gap 77-2 in the third stationary component 70-2 (defined by the outer edge of the shield 72 and the side wall of the housing 74). Air then enters the stator vanes 75 provided by the third stationary component 70-2 and is directed radially inwardly towards the outlet opening 76, and thereafter onto the blower outlet 26.

1.6 Heat Dissipation

In an example, the motor may spin up to 60,000 rpm. Due to the small size and high speeds from the motor, heat should be removed or dissipated from the motor, e.g., to reduce the possibility of drying lubricant grease. The use of thermally conductive plastics (e.g., Cool poly D5506, D5508, LCPs (liquid crystal polymer) and GLS LC 5000 TC LCP) for housings and/or impellers of the blower may provide some heat dissipation. Also, heat from the motor may be conducted along the shaft of the rotor to the airpath.

Figure 17:
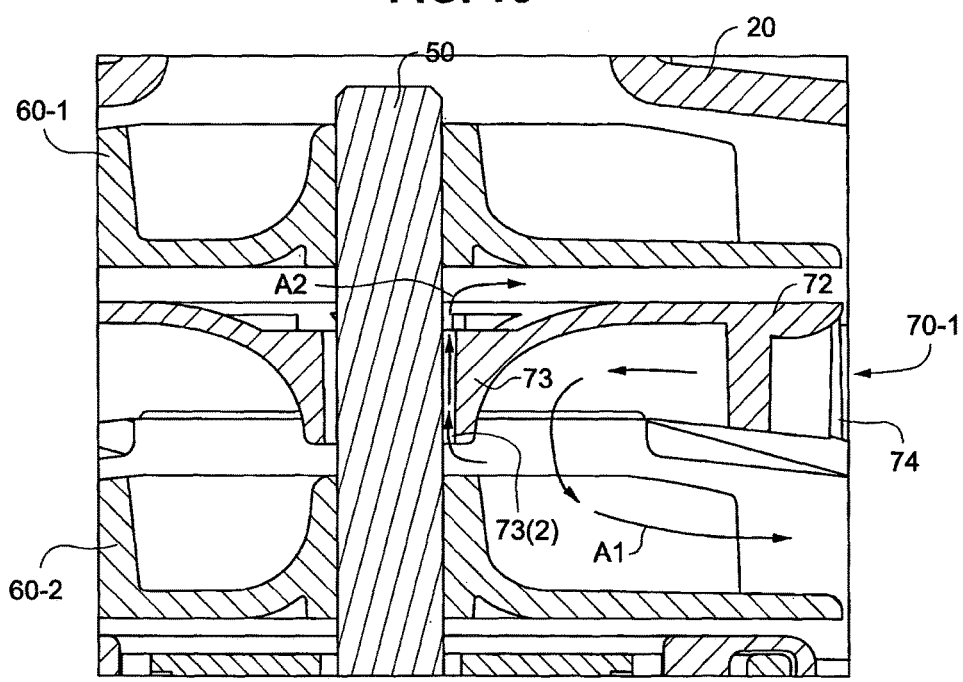
FIG. 17 is a cross-sectional view of a portion of the blower of FIG. 1.

For example, as best shown in FIG. 17, the first stationary component 70-1 positioned between the first and second impellers 60-1, 60-2 may provide structure to dissipate heat. As illustrated, the hub 73 of the shield 72 of the first stationary component includes an opening 73(2) to receive the shaft 50 therethrough, and such opening 73(2) is sufficiently larger than the diameter of the shaft to provide a space between the hub 73 and the shaft 50. This space allows heat to be removed from the shaft 50 due to the pressure differential generated above and below the stator vanes of the first stationary component. That is, air circulation or cooling airflow through the space assists in removing heat out of the shaft and the bearings. The arrows A1 represent the main airflow through the blower and the arrows A2 represent the cooling airflow through the space.

1.7 Suspension System

In an example, a suspension system is provided to the blower, e.g., to support the blower within the casing of a PAP device and/or to isolate vibration of the blower, reducing noise transmitted by vibration through the casing. The suspension system (e.g., constructed of an elastomeric material such as silicone) includes a dual suspension arrangement, i.e., a suspension located at each end of the blower, to provide seals for the airpath, isolate vibrations, and provide shock resistance. As shown in FIGS. 1-14, the suspension system includes an outlet end suspension 90 to support the blower adjacent the blower outlet and an inlet end suspension 95 to support the blower adjacent the blower inlet.

1.7.1 Outlet End Suspension

As shown in FIGS. 1-14, the outlet end suspension 90 (e.g., constructed of silicone or Thermoplastic elastomer (TPE)) includes a blower engaging portion 91, a tube portion 92, and a casing engaging portion 93.

As illustrated, the blower engaging portion 91 is in the form of a flange that extends radially outwardly from one end of the tube portion 92. The blower engaging portion is adapted to be sandwiched between the housing 74 of the third stationary component 70-2 and the second housing part 25 to secure the outlet end suspension to the blower.

The tube portion 92 provides an outlet path extending from the outlet 26 of the second housing part 25. As illustrated, tube portion 92 includes an inlet end 92(1) sealed against the outlet 26 as well as the outlet opening 76 of the third stationary component 70-2, and outlet end 92(2), e.g., see FIGS. 3 and 4. The tube portion 92 provides an expanding diameter or cross-section, i.e., diameter of the tube portion increases from the inlet end 92(1) to the outlet end 92(2). Also, a cone-shaped member 94 may be provided within the tube portion and includes an end adapted to engage within the hub 73 of the third stationary component 70-2. The cone-shaped member 94 allows air to decelerate or diffuse more gradually as air flows through the tube portion 92 towards the outlet end 92(2).

The casing engaging portion 93 extends outwardly from the opposite end of the tube portion 92. As described below, the casing engaging portion 93 is adapted to engage the casing or chassis of a PAP device to isolate vibrations and provide shock resistance. The casing engaging portion 93 includes a pressure port 93(4) (e.g., see FIGS. 1, 2, 5, 6) for interfacing with a pressure sensor 112 (e.g., see FIG. 42). An advantage of such arrangement is that no additional sealing component is required, i.e., a separate seal is not required between the airpath and the pressure sensor. Bellows or other compliant features may be included in the pressure port seal to aid assembly and ensure a good seal. A similar arrangement of a port and an optionally compliant seal may be implemented for any other sensor requirements, e.g., the flow sensor that straddles the flow plate following tubes 105 described below, a thermistor, etc.

In use, the outlet end suspension provides the following functions: vibration isolation from the PAP device casing to the blower; resist impact on shock; seal for the air path; blower clamp; and expansion outlet path of the blower.

The outlet end suspension may be secured to the blower in other suitable manners, i.e., outlet end suspension may not be clamped into the blower via blower engaging portion 91 described above. In an alternative example, the outlet end suspension may be structured to clamp to the outside of the blower, e.g., using one or more strap members.

For example, FIGS. 93-97 illustrate another example of an outlet end suspension 590 provided to the blower 510. The outlet end suspension 590 (e.g., constructed of silicone or Thermoplastic elastomer (TPE)) includes a blower engaging portion 591, a tube portion 592, and a casing engaging portion 593.

Similar to the example described above, the tube portion 592 provides an outlet path extending from the outlet of the third stationary component 570-2, i.e., tube portion 592 includes an inlet end 592(1) sealed against the annular wall 574(3) provided along the outlet of the third stationary component 570-2. Also, similar to the example described above, the casing engaging portion 593 is structured to engage the casing or chassis of a PAP device to isolate vibrations and provide shock resistance.

Figure 95:
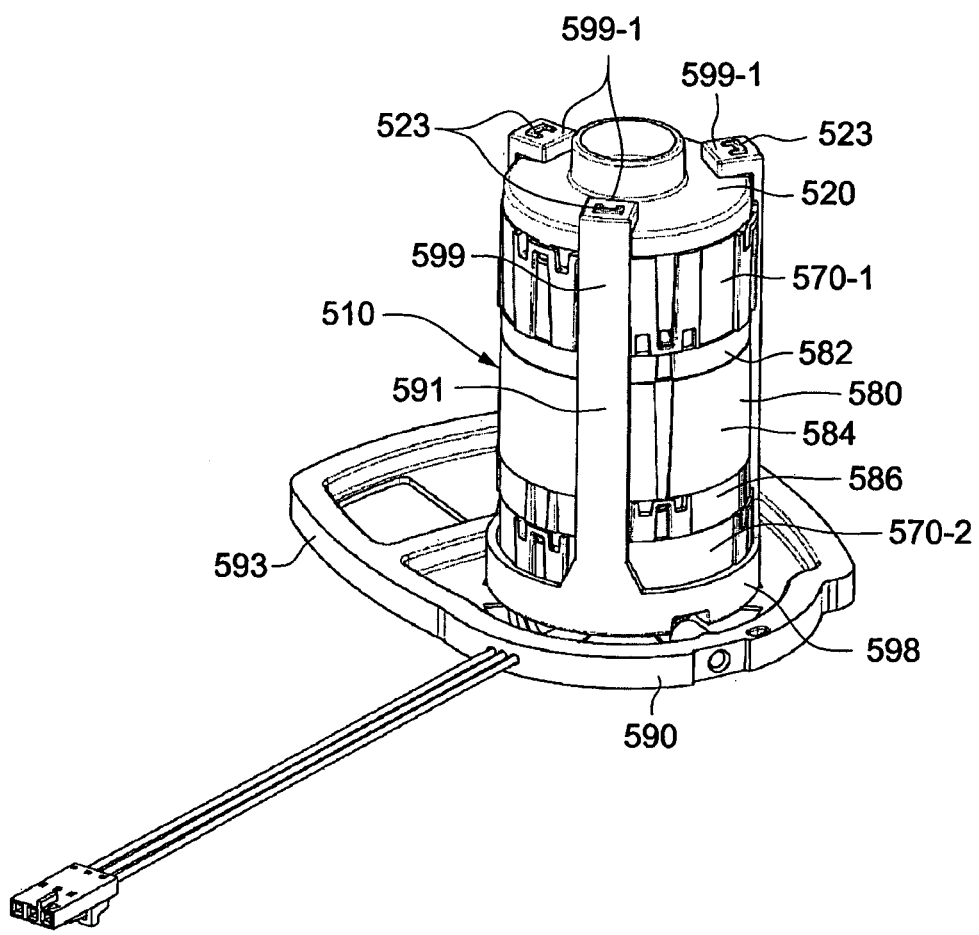
FIG. 95 is a perspective view of the blower of FIG. 93 with the inlet end suspension removed.
Figure 96:
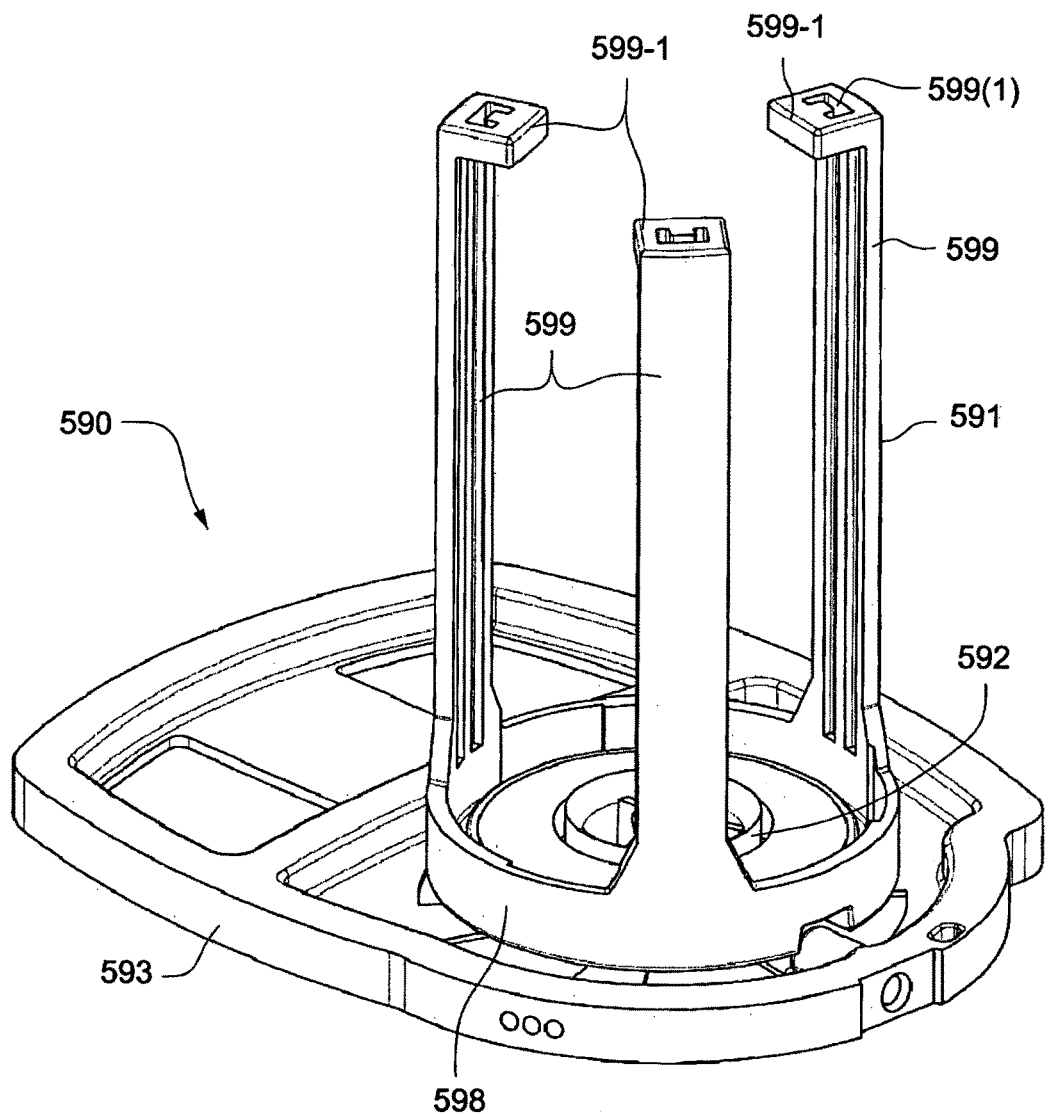
FIG. 96 is a perspective view showing an outlet end suspension for a blower according to an example of the disclosed technology.
Figure 97:
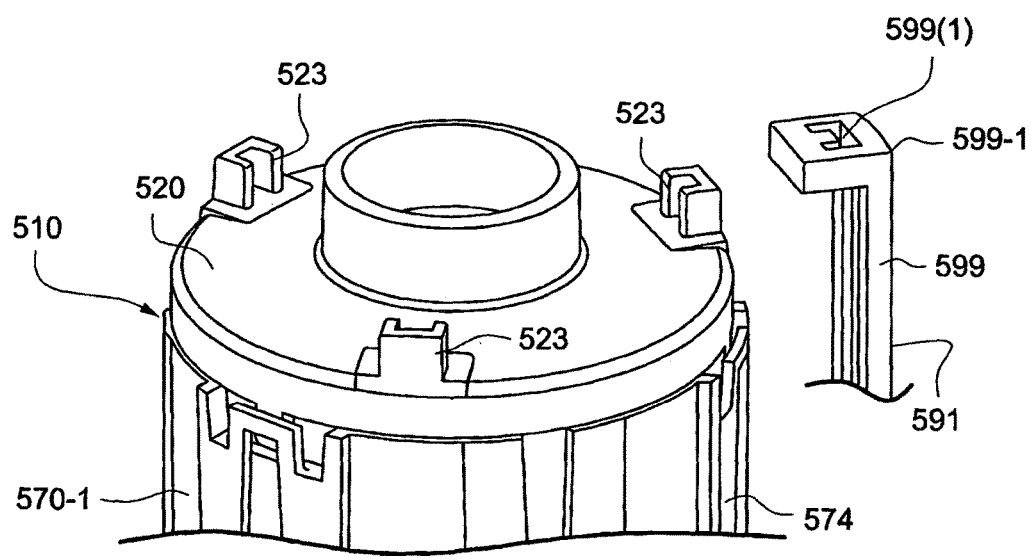
FIG. 97 is a perspective view showing an outlet end suspension being engaged with a blower according to an example of the disclosed technology.

In this example, the blower engaging portion 591 includes a bottom wall portion 598 adapted to engage the base of the blower along the third stationary component 570-2 and a plurality of elongated strap members 599 (e.g., 3 strap members illustrated but more or less strap members are possible, e.g., 2, 4, 5, or more strap members) extending in an axial direction from the bottom wall portion. The strap members 599 are resiliently flexible so that each strap member may be stretched to engage a respective tab 523 (e.g., U-shaped extrusion) provided to the housing part or inlet cover 520 (e.g., see FIGS. 95 and 97), which pulls the housing part downwardly to secure the blower components and suspension in position. As best shown in FIGS. 95-97, the free end of each strap member includes a catch portion 599-1 including an opening 599(1) adapted to receive a respective tab 523 provided to the housing part 520, e.g., generally U-shaped opening to receive generally U-shaped tab. However, it should be appreciated that the strap members may be secured with the housing part in other suitable manners. In an example, each strap may have an unstretched height (i.e., as molded height) of about 45-60 mm (e.g., 53.5 mm) and stretched height (i.e., as installed height) of about 60-75 mm (e.g., 68.5 mm), e.g., strap members provide at least about 5-25 mm (e.g., at least about 15 mm) of flexibility for installation.

1.7.2 Inlet End Suspension

As shown in FIG. 1-4, the inlet end suspension 95 (e.g., constructed of silicone or Thermoplastic elastomer (TPE)) includes a blower engaging portion 96 and a casing engaging portion 97. The blower engaging portion 96 includes an inner end 96(1) adapted to engage the upper wall and chimney portion of the first housing part 20 and an outer end 96(2) that wraps around the side wall of the first housing part 20 and/or the resilient arm members of the second housing part 25 to secure the inlet end suspension to the blower, e.g., see FIGS. 3 and 4.

The casing engaging portion 97 extends outwardly from the inner end 96(1) of the blower engaging portion 96. The casing engaging portion 97 may be resiliently flexible relative to the blower engaging portion 96. As described below, the casing engaging portion 97 is adapted to engage the casing of a PAP device to isolate vibrations, provide shock resistance, and seal the airpath.

Figure 93:
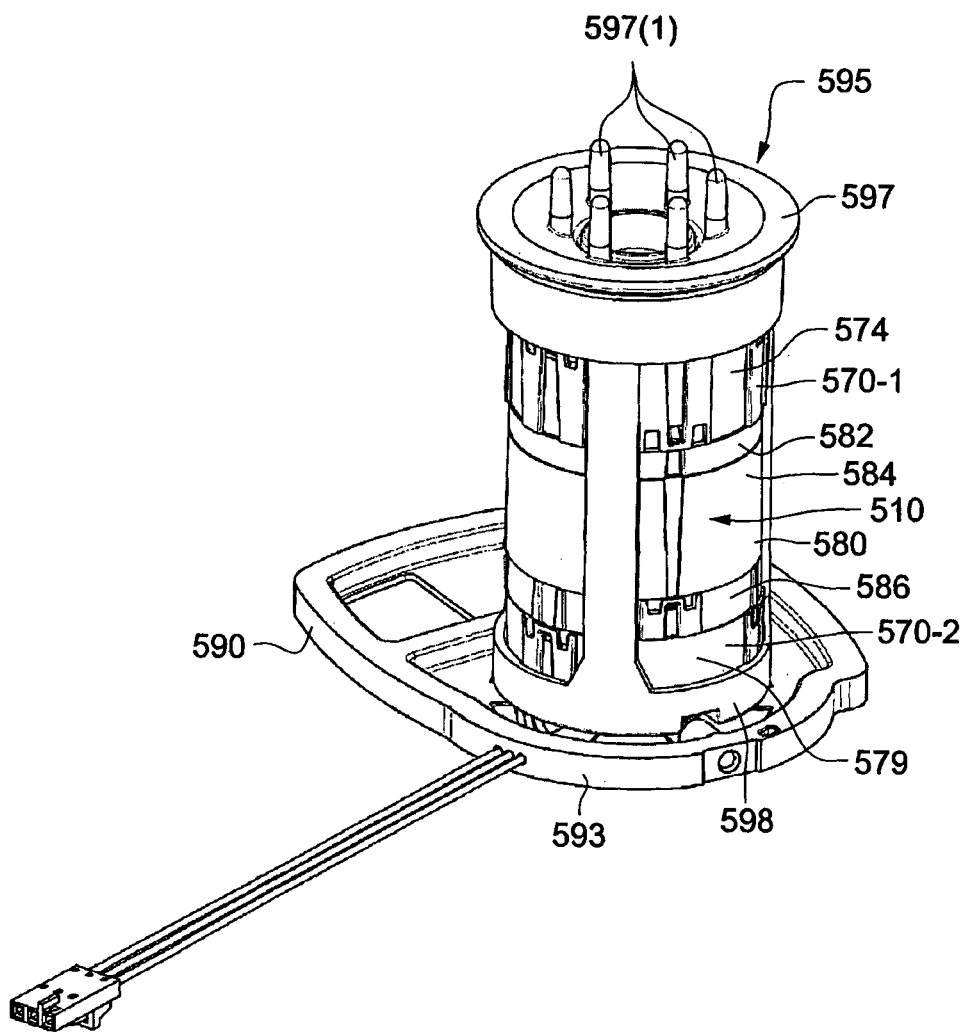
FIG. 93 is a perspective view of a blower including an inlet end suspension and an outlet end suspension according to an example of the disclosed technology.
Figure 94:
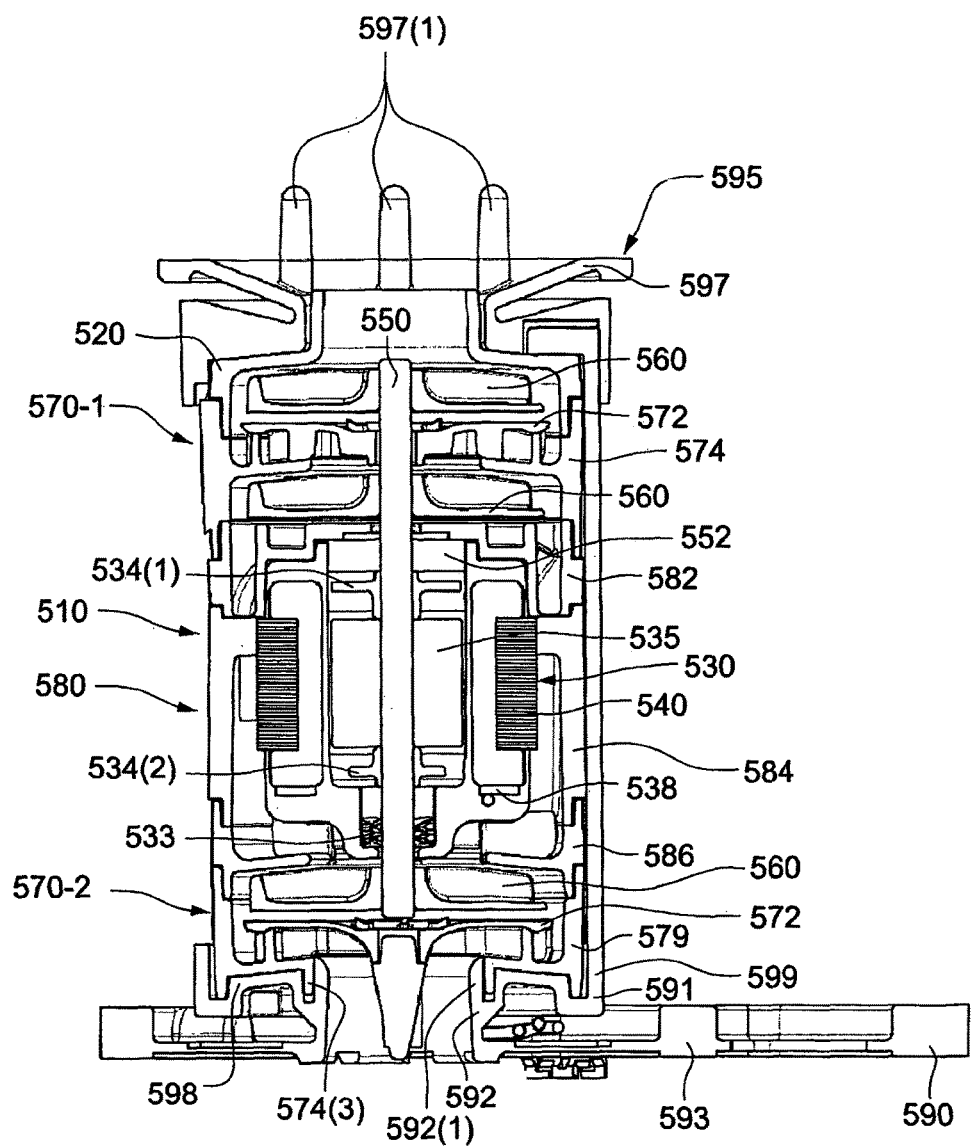
FIG. 94 is a cross-sectional view of the blower of FIG. 93.

FIGS. 93 and 94 shows another example of an inlet end suspension 595 provided to the blower 510. The inlet end suspension 595 is similar to that shown in FIGS. 1-4 described above. In this example, the casing engaging portion 597 of the inlet end suspension 595 includes a plurality of axially extending ribs 597(1) (e.g., 2, 3, 4, 5, 6, or more ribs), e.g., for axial shock absorption.

1.7.3 Single Suspension Component

In an example, a single suspension system may be provided to the blower. The single suspension system may be integrally formed as a one piece structure (e.g., molded of an elastomeric material such as silicone) structured to enclose or encase the blower. Thus, one or more functions of a suspension system may be embodied by a single (e.g., molded silicone) part. For example, the single suspension system may perform one or more of the following functions: vibration isolation from the PAP device casing to the blower; resist impact on shock; location of the blower in the casing; seal for the air path to divide the high pressure side (outlet chamber) and low pressure side (inlet chamber) of the blower; interface and seal to pressure sensor(s); interface and seal to flow sensor; and/or interfaces and seals to other sensors like a temperature sensor.

The single suspension system may include bumps on one or more outer, surfaces to provide shock absorption and axial movement. The bumps may also prevent foam, such as acoustic foam, from contacting the blower. The single suspension system may also include a shock absorption flange positioned adjacent ribs within the casing. A thickened portion of the shock absorption flange provides shock absorption in the radial direction. A membrane on the top of the single suspension system provides vibration isolation. In certain arrangements, the single suspension system may also include a chimney portion to surround the blower inlet. The single suspension system may also include one or more ports for sensors to allow sensors to be plugged into the side of the blower. For example, the single suspension system may include a pressure sensor port and two flow sensor ports. The single suspension system may also include an aperture configured to receive the wires from the motor and to provide a seal around the wires where they exit the blower.

Alternatives to sealing and sensor interfaces include over-moulded features on the casing; using a sufficiently soft/flexible casing material to connect directly to the sensors; and traditional silicone tubing connecting the sensors to features in the rigid case.

For example, FIGS. 135-153 show alternative examples of sensor interfaces or ports for pressure sensors and flow sensors. In examples, the pressure port is communicated with the blower outlet chamber and oriented perpendicular to the flow. In examples, a flow port is provided on each side of the flow plate, e.g., one communicated with the inlet chamber and one communicated with the blower inlet chamber.

Figure 135:
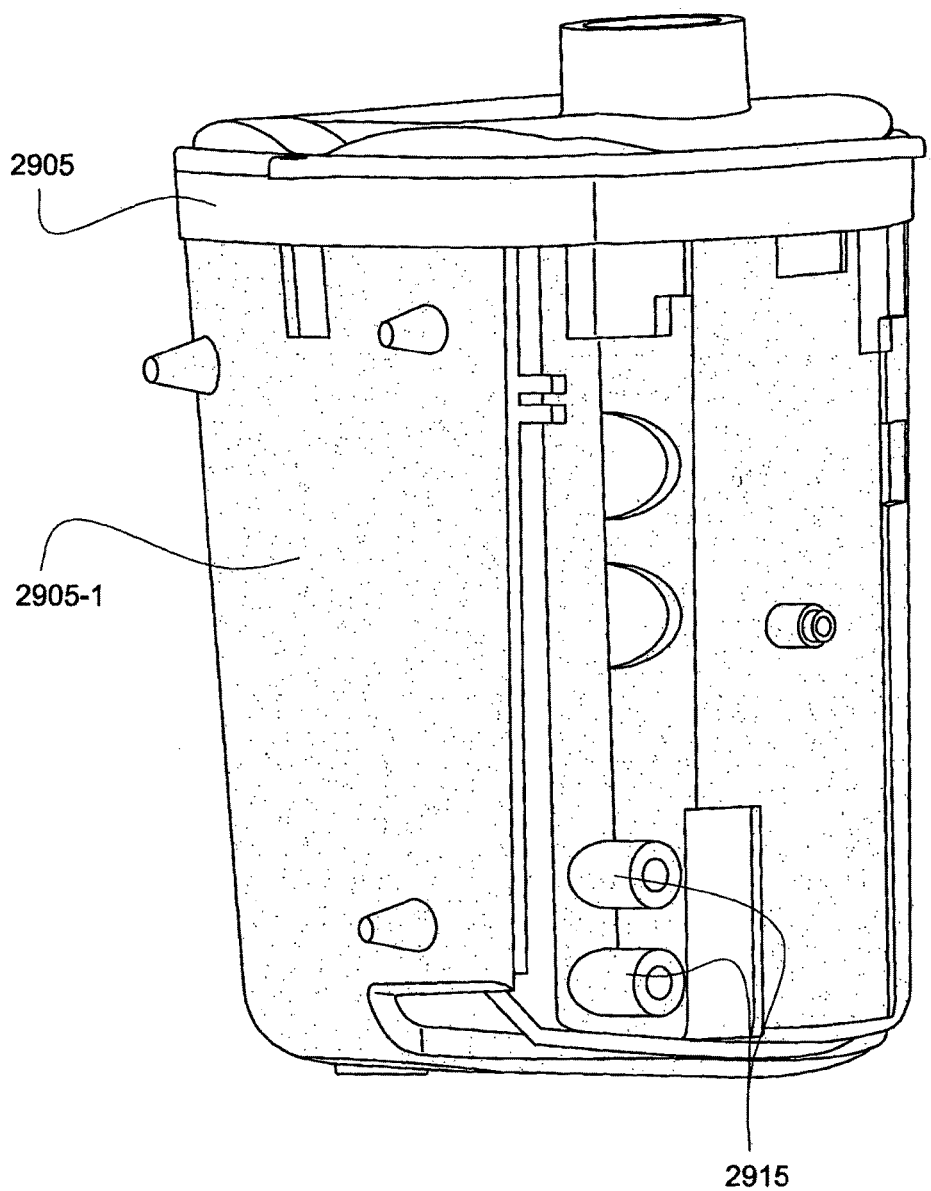
FIG. 135 is a perspective view of a PAP device including sensing ports in an over-molded layer of the casing according to an example of the disclosed technology.
Figure 136:
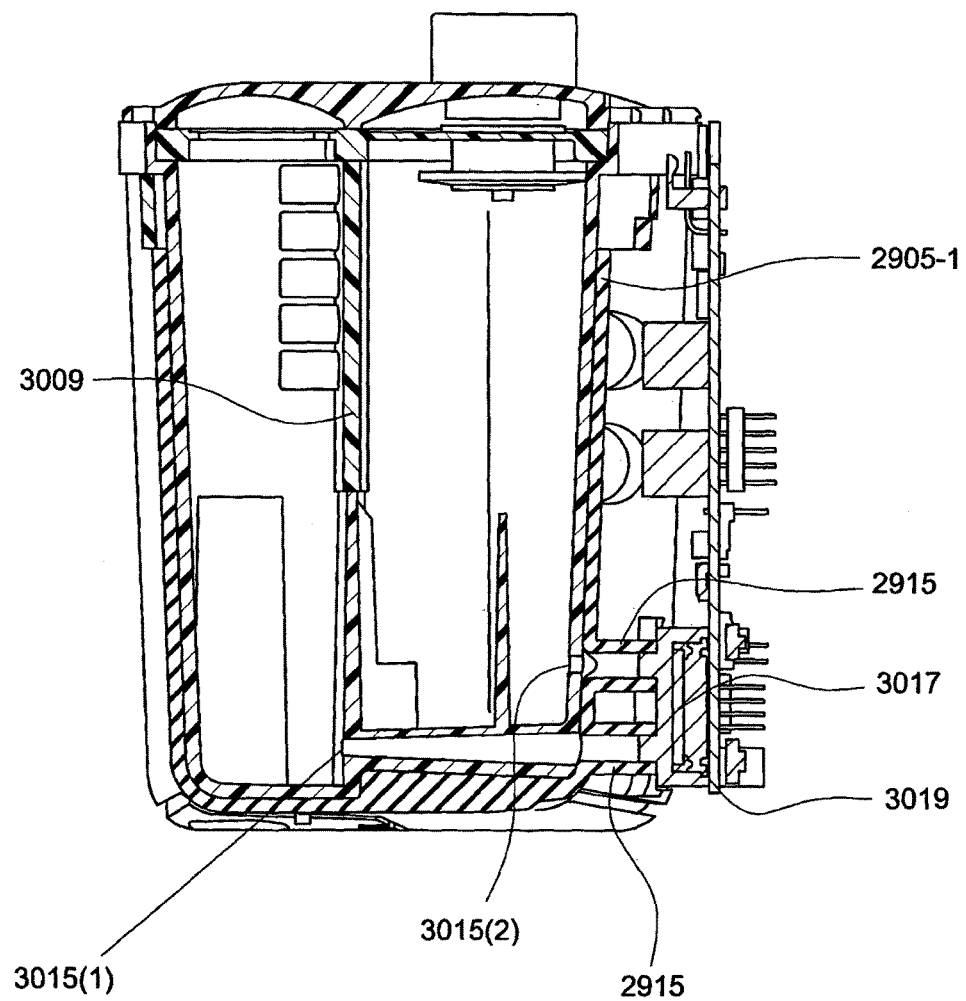
FIG. 136 is a cross-sectional view of a PAP device including flow sensor ports according to an example of the disclosed technology.

FIG. 135 shows a PAP device in which ports 2915 are provided in an over-molded layer 2905-1 of the casing 2905. FIG. 136 shows a port arrangement for a flow sensor 3017 in which the PCBA 3019 to which the flow sensor is provided is positioned at a side of the blower chamber distal to the flow plate 3009. As illustrated, one port 3015(1) is provided to the casing to communicate with the inlet chamber along the upstream side of the flow plate 3009 and the other port 3015(2) is provided to the casing to communicate with the blower inlet chamber along the downstream side of the flow plate 3009. Also, the ports 3015(1), 3015(2) in the casing communicate with respective ports 2915 provided in the over-molded layer 2905-1 as described above. FIG. 137 shows a port arrangement for a flow sensor 3117 in which the PCBA 3119 to which the flow sensor is provided is positioned adjacent to the inlet chamber/blower inlet chamber on each side of the flow plate 3109. As illustrated, the flow ports 3115(1), 3115(2) are provided to the casing on respective sides of the flow plate 3109.

Figure 140:
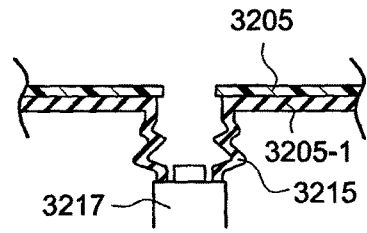
Figure 141:
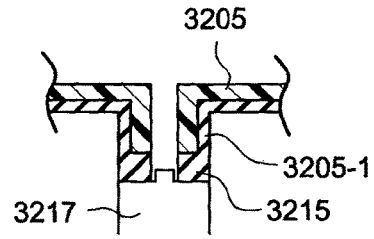
Figure 142:
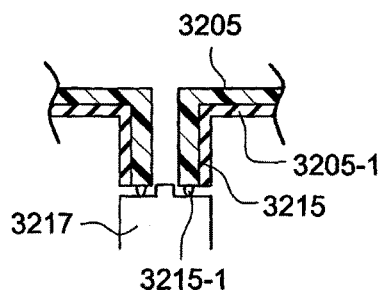
Figure 143:
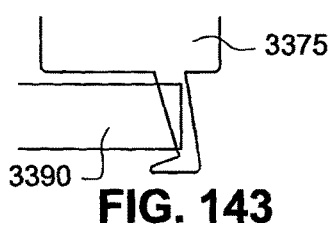
FIGS. 143-147 are schematic views of pressure sensor interfaces or seals provided between the pressure sensor and the blower suspension of a PAP device according to alternative examples of the disclosed technology.
Figure 146:
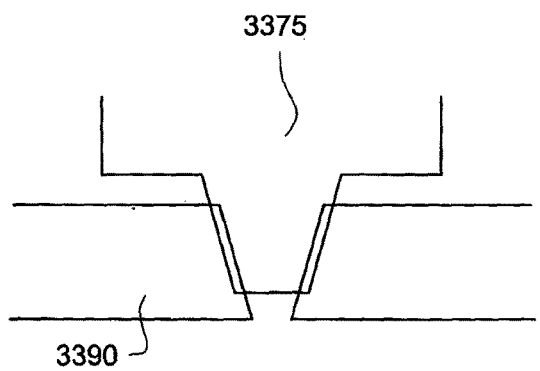
Figure 144:
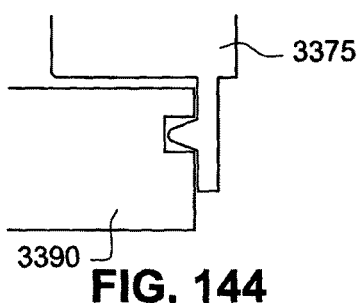
Figure 145:
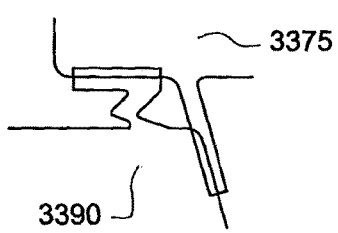
Figure 147:
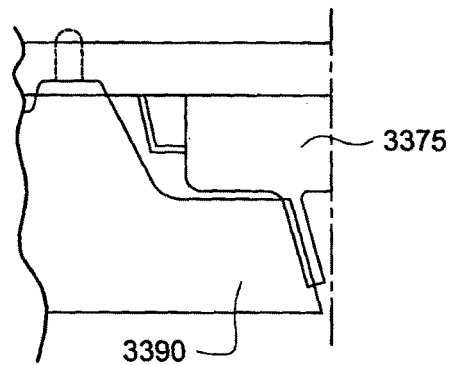

FIGS. 138-142 show alternative examples of flow sensor interfaces provided in an over-molded layer 3205-1 of the casing 3205. In FIG. 138, the port 3215 is structured to seal along an upper wall of the flow sensor 3217. In FIG. 139, the port 3215 is structured to seal along an upper wall and body or side wall of the flow sensor 3217. In FIG. 140, the port 3215 includes a gusset or spring-like arrangement to enhance flexibility and sealing with the flow sensor 3215. In FIG. 141, the port 3215 is provided with a shorter length to provide less creep. In FIG. 142, the port 3215 includes a bead seal 3215-1 for sealing with the flow sensor 3215.

FIGS. 143-147 show alternative examples of pressure sensor interfaces or seals provided between the pressure sensor 3375 and the blower suspension 3390 (e.g., constructed of silicone) that supports the blower within the PAP device. As illustrated the blower suspension 3390 and/or the pressure sensor 3375 may include structure (e.g., sealing arms, recesses, bellows arrangement) to interlock, engage, seal, or otherwise interface with one another.

Figure 152:
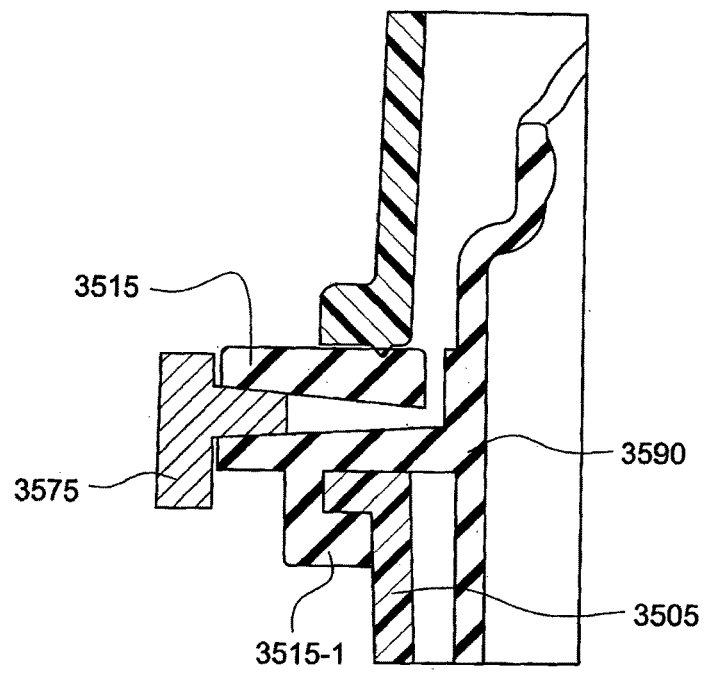
Figure 153:
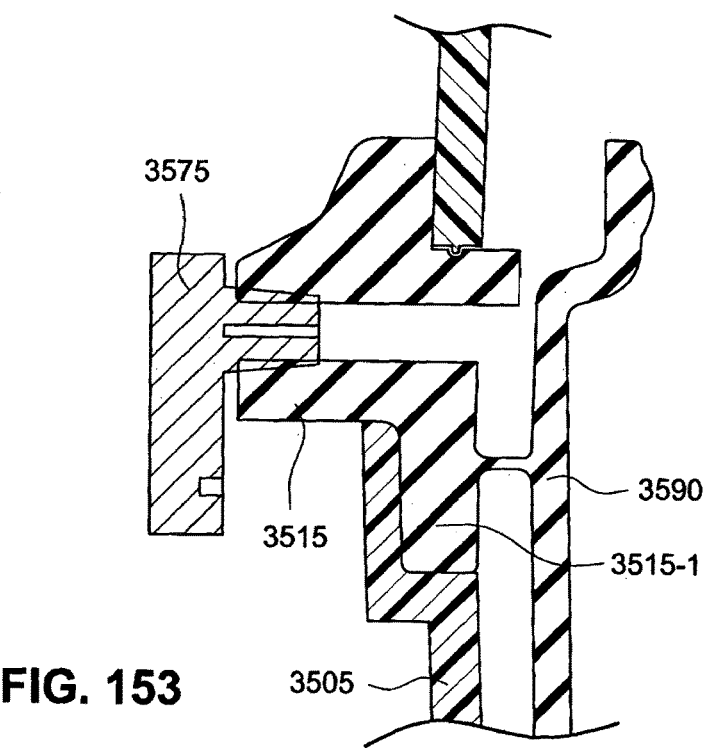
Figure 154:
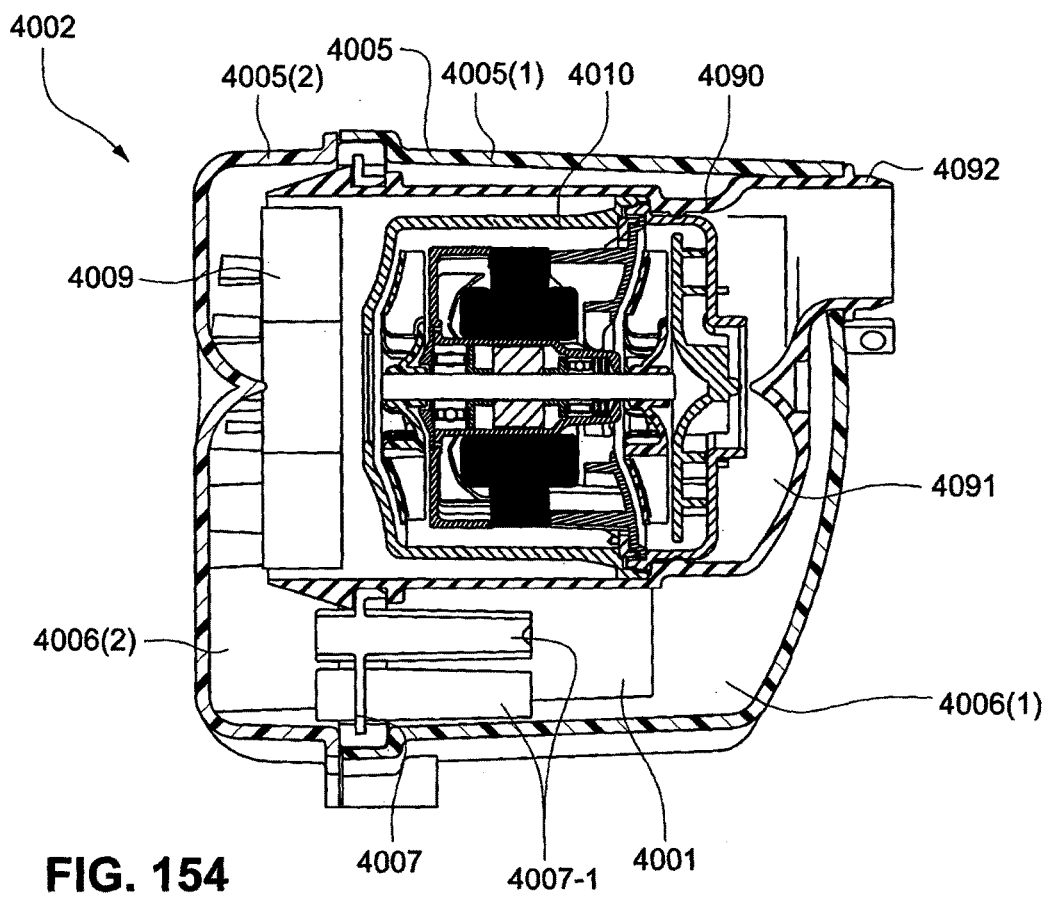
FIG. 154 is a cross-sectional view of a PAP device according to an example of the disclosed technology.
Figure 155:
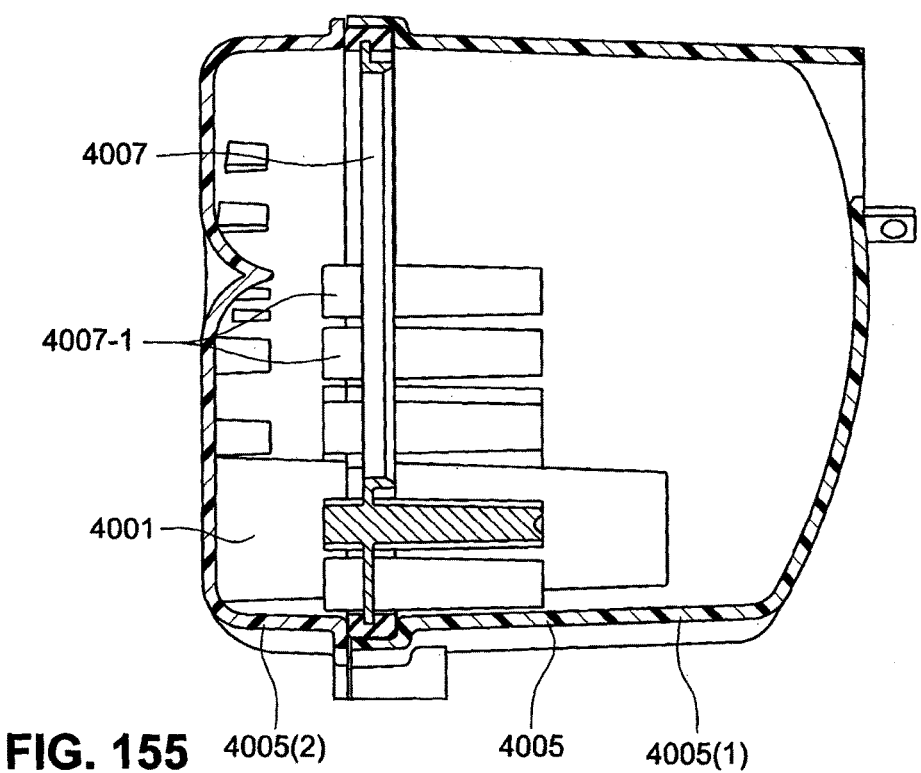
FIG. 155 is a cross-sectional view of the casing of the PAP device of FIG. 154.
Figure 156:
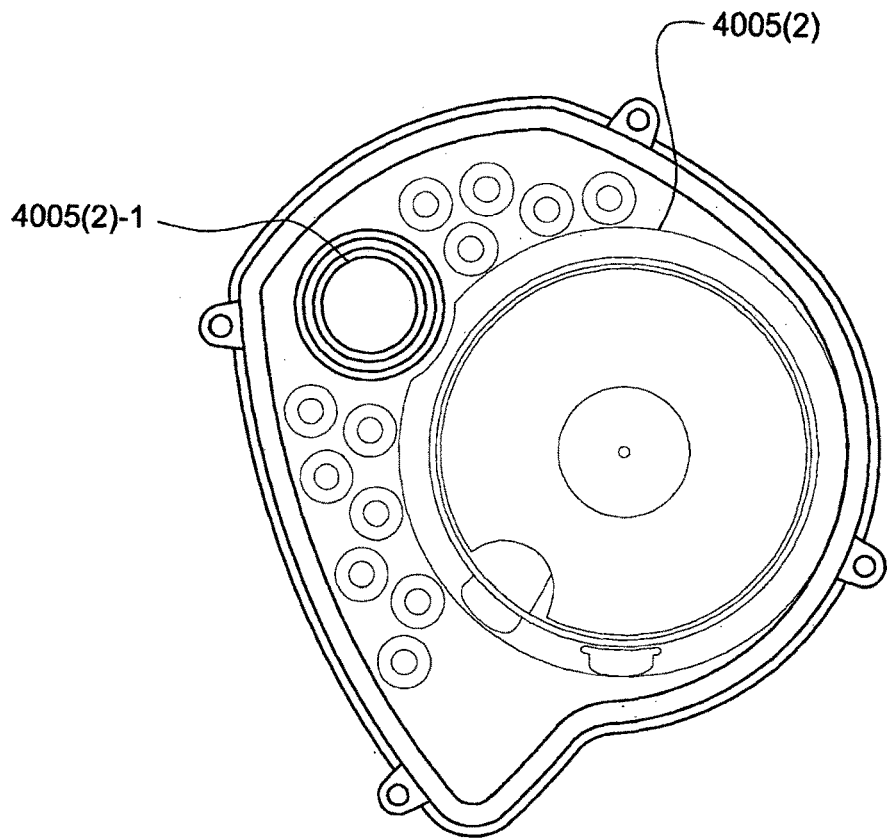
FIG. 156 is a view along the inlet of the PAP device of FIG. 154.
Figure 157:
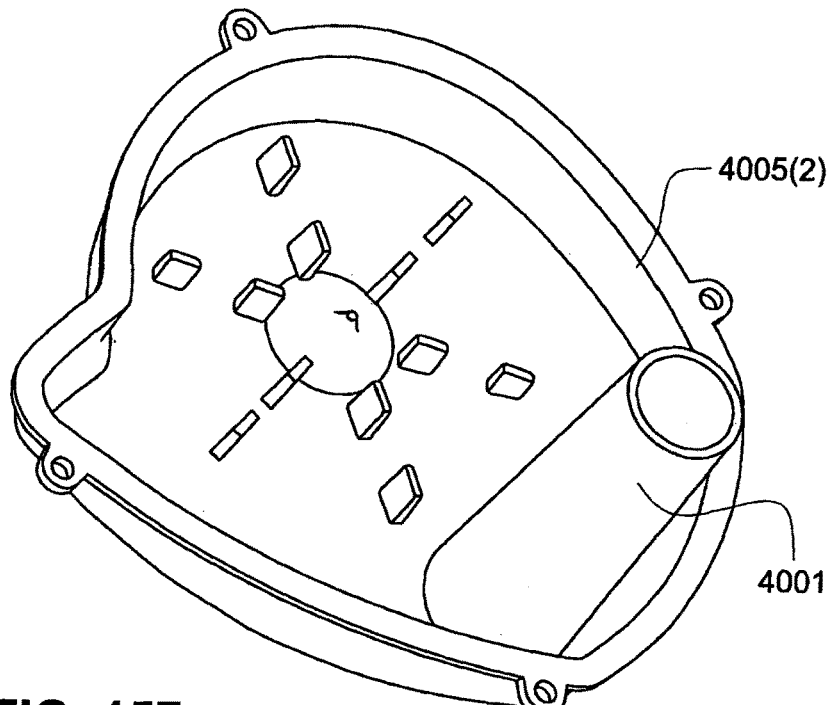
FIG. 157 is a perspective view of a cover of the PAP device of FIG. 154.
Figure 158:
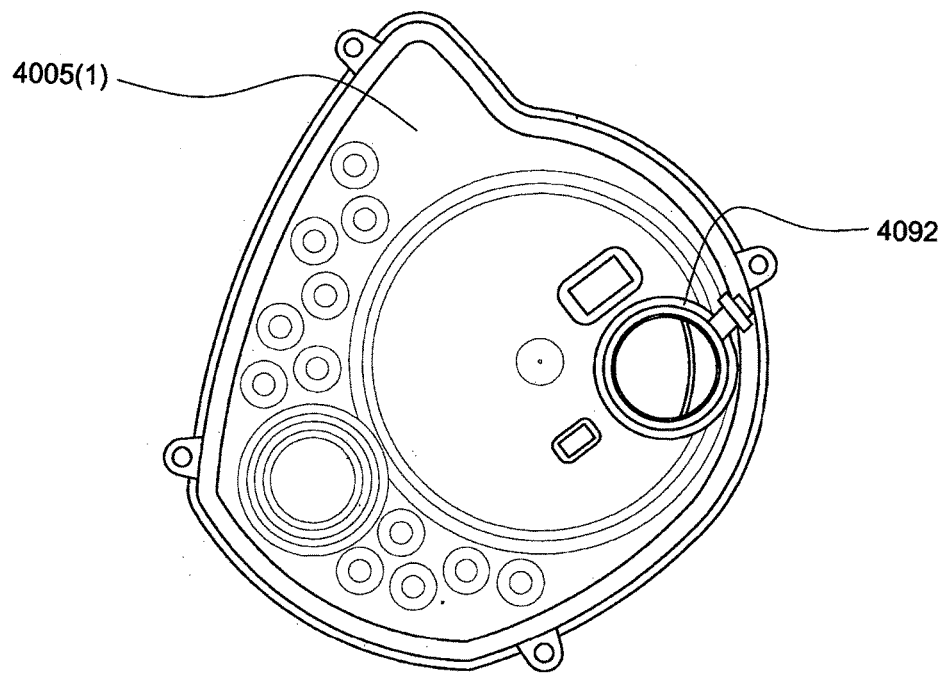
FIG. 158 is a view along the outlet of the PAP device of FIG. 154.
Figure 159:
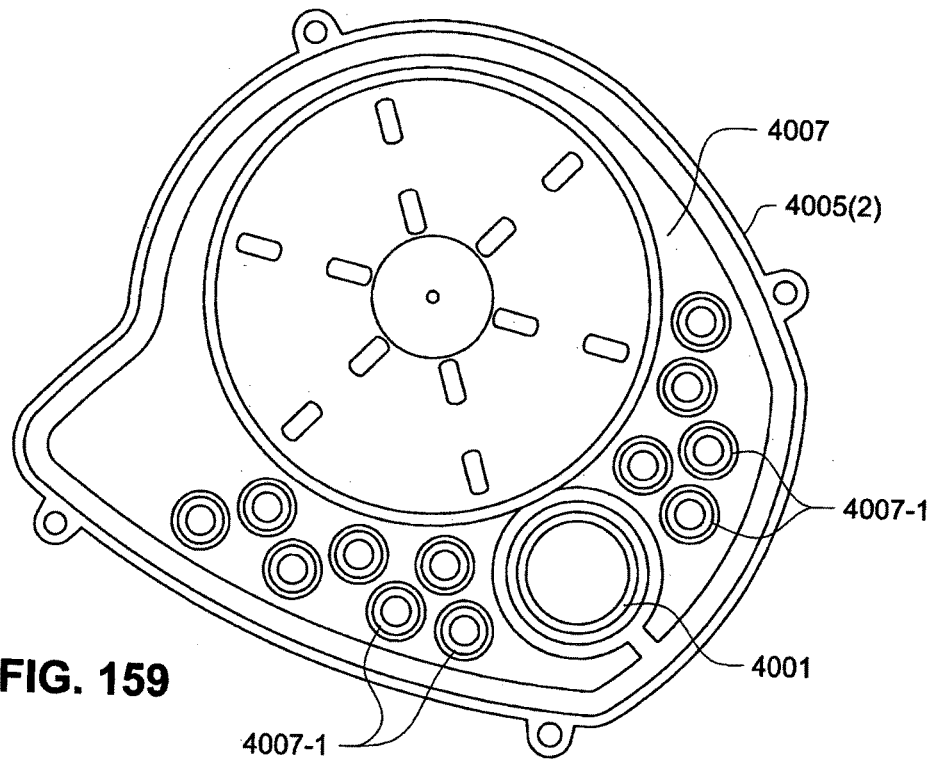
FIG. 159 is a cross-sectional view showing the flow plate of the PAP device of FIG. 154.
Figure 160:
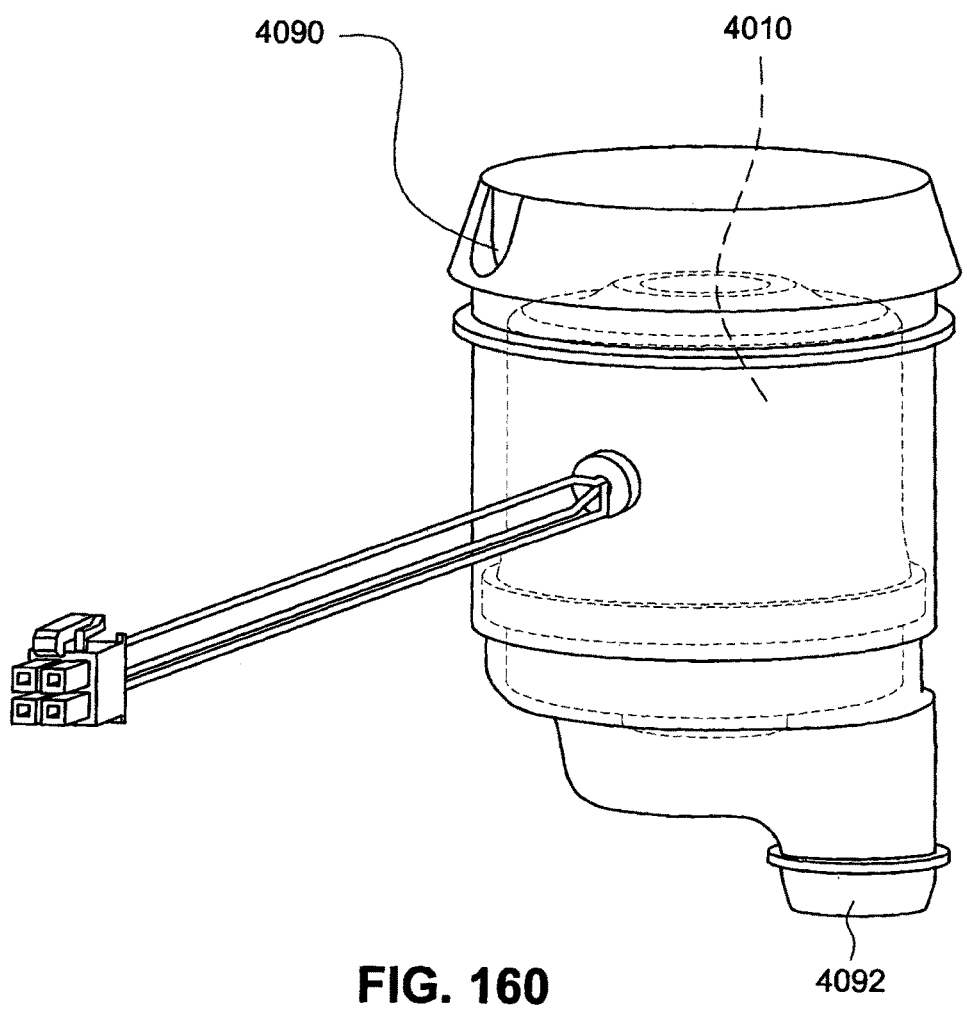
FIG. 160 is a perspective view of the suspension system of the PAP device of FIG. 154.
Figure 161:
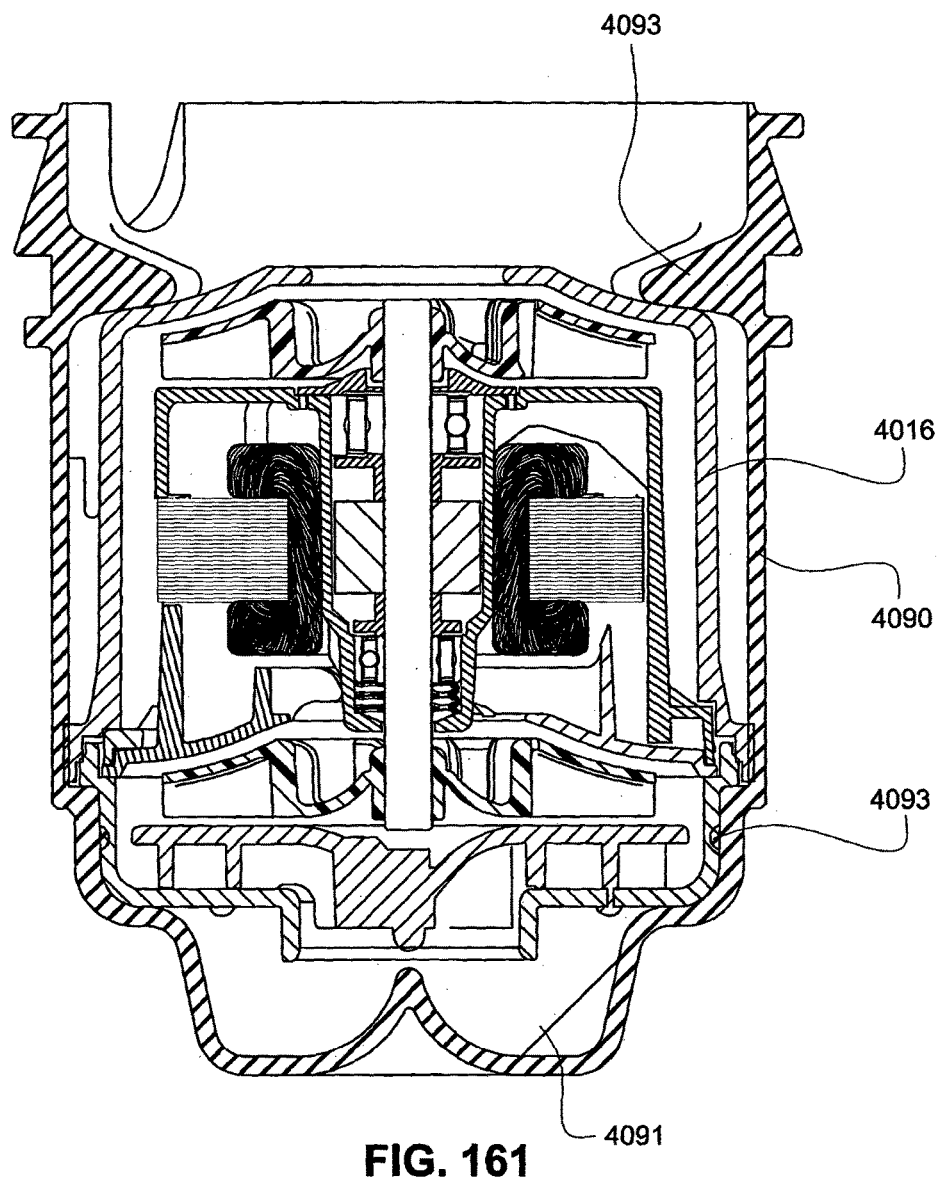
FIG. 161 is a cross-sectional view of the suspension system and blower of the PAP device of FIG. 154.

FIGS. 148-153 show alternative examples of sensor interfaces or seals provided to the blower suspension (e.g., one-piece suspension) that supports the blower. In FIGS. 148-150, the suspension 3490 for blower 3410 includes a plug-type port 3415 adapted to be inserted into an opening provided in the blower casing 3405. As shown in FIG. 150, the suspension along with the plug-type port may be molded flat, and then the plug-type port may be bent or flexed into engagement with the blower casing. In FIG. 151, the plug-type port 3515 extending (e.g., by thin, flexible web) from the blower suspension 3590 may include a flange 3515-1 (e.g., to prevent from pushing the port too far into the opening in the blower casing 3505) and a barb 3515-2 (e.g., to secure the port within the opening). As illustrated, the port 3515 provides a tapered opening into the casing and may include a gusset or spring-like arrangement to enhance flexibility and sealing with the pressure sensor 3575 and blower casing. In FIG. 152, the port 3515 extends from the blower suspension 3590 and includes structure 3515-1 that interlocks or otherwise engages an exterior of the blower casing 3505 to secure the port 3515 and pressure sensor 3575 in position. In FIG. 153, the port 3515 extends from the blower suspension 3590 and includes structure 3515-1 that interlocks or otherwise engages an interior of the blower casing 3505 to secure the port 3515 and pressure sensor 3575 in position.

Figure 121:
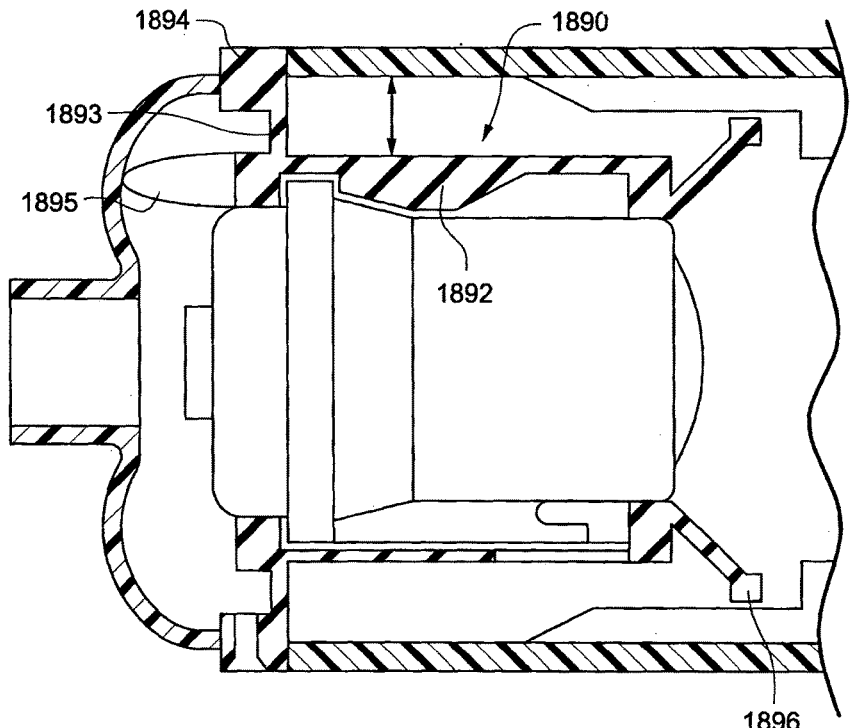
FIG. 121 shows a single suspension system for a blower according to an example of the disclosed technology.

FIG. 121 shows a single suspension system 1890 (e.g., constructed of silicone) for a blower according to an example of the disclosed technology. As illustrated, the blower includes a generally cylindrical side wall 1892 that encloses the blower which connects by a thin web 1893 to a thicker silicone seal 1894 around the perimeter of the case/cover interface of the casing. The web 1893 provides vibration isolation and divides the low and high pressure sides of the blower. Axial shock-absorbing features (e.g., bumps 1895) are provided at the blower outlet end of the suspension and axial and radial shock-absorbing features (e.g., flexible membrane 1896) are provided at the blower inlet end of the suspension.

Figure 2:
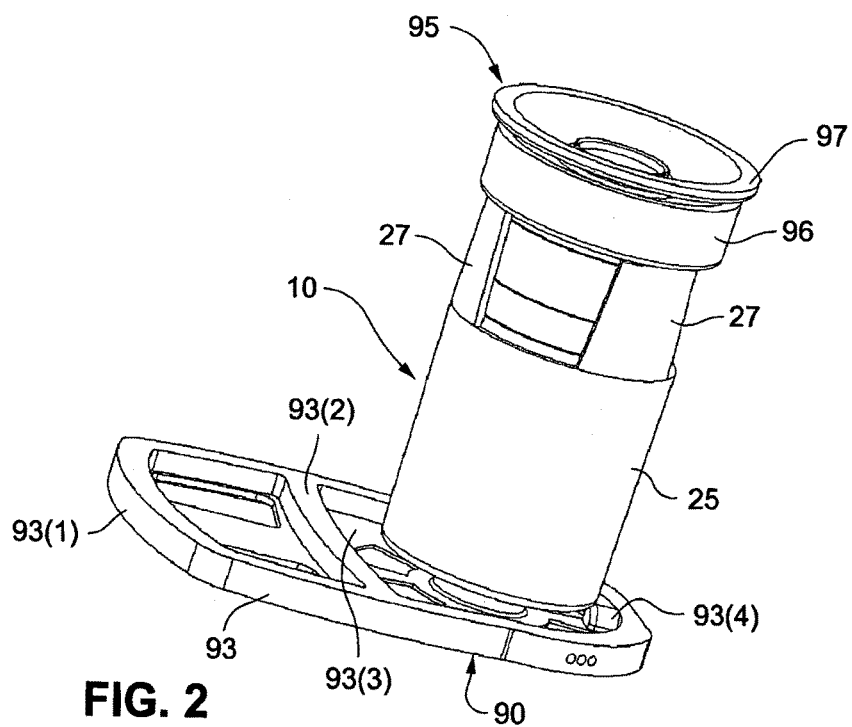
FIG. 2 is another perspective view of the blower of FIG. 1.
Figures 1, 122:
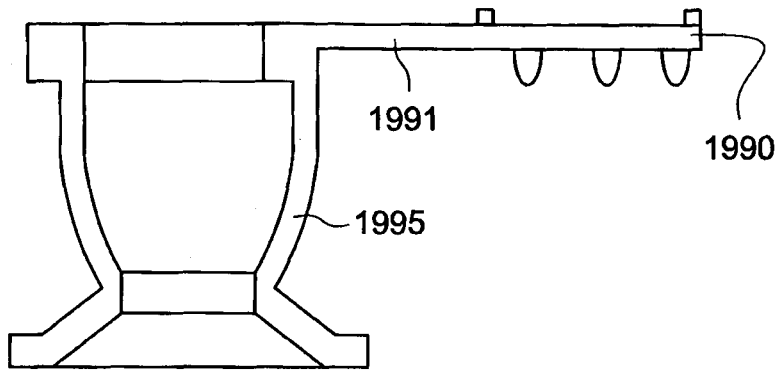
Figures 2, 122:
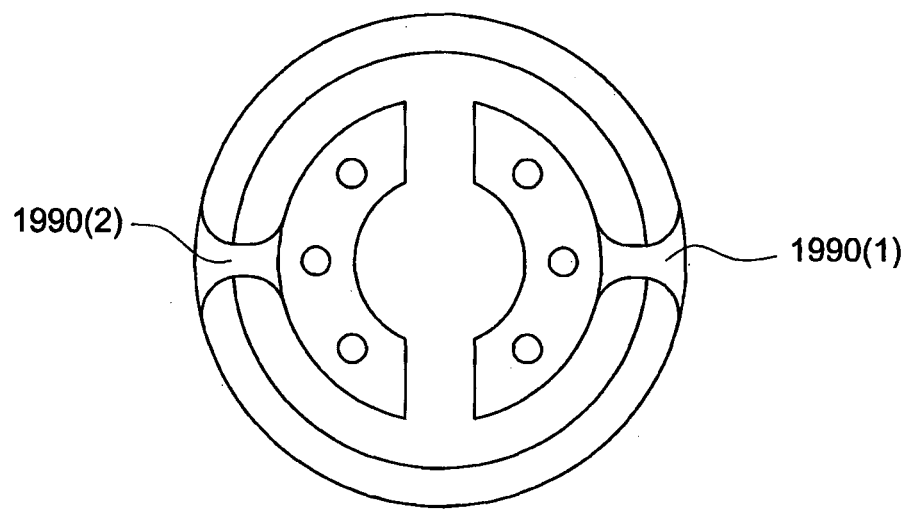

FIG. 122-1 shows a single suspension system (e.g., constructed of silicone) including an inlet end suspension portion 1990 and an outlet end suspension portion 1995 that are molded in one piece and coupled to one another by connector 1991. In use, the blower may be provided to the portion 1995 and then the portion 1990 may be folded over to enclose the blower within the suspension system. As shown in FIG. 122-2, the inlet end suspension portion may be provided as two parts 1990(1), 1990(2) that may be folded over to assemble.

1.8 PAP Device

As described below in more detail; the PAP device or pneumatic block is configured to provide the following functions: (i) house and protect a blower located within the PAP device; (ii) form the air path from the chassis or casing air inlet to the blower and from the blower to the chassis or casing outlet; (iii) to assist in attenuating noise, including radiated and airborne or inlet noise; and/or (iv) to provide an interface for one of more of the following: sensors, printed circuit board assembly (PCBA), humidifier, air delivery tube, inlet filter and/or user interface components.

It should be appreciated that the PAP device may be used with different blowers, e.g., three-stage blower 10 and two-stage blower 410 described herein, blowers described in U.S. Patent Application Publication No. US 2008/0304986 and U.S. Pat. No. 7,866,944, each of which is incorporated herein by reference in its entirety.

Figure 162:
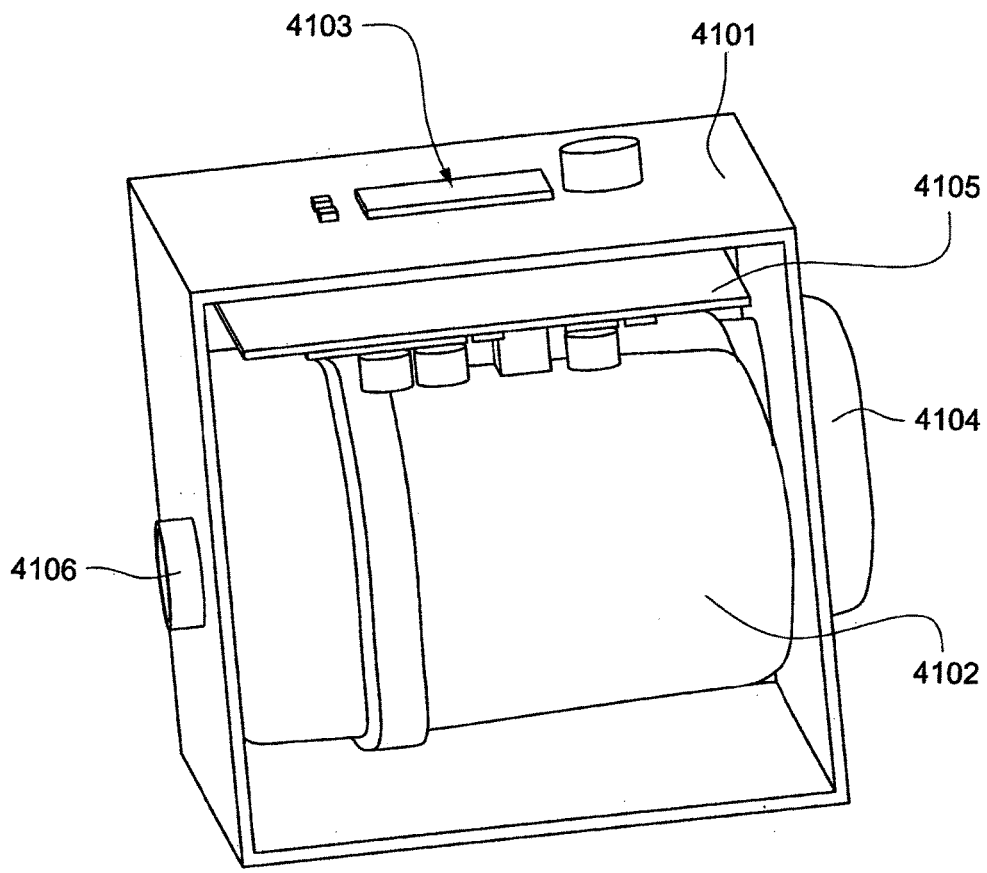
FIG. 162 is a perspective view of a PAP system according to an example of the disclosed technology.
Figure 163:
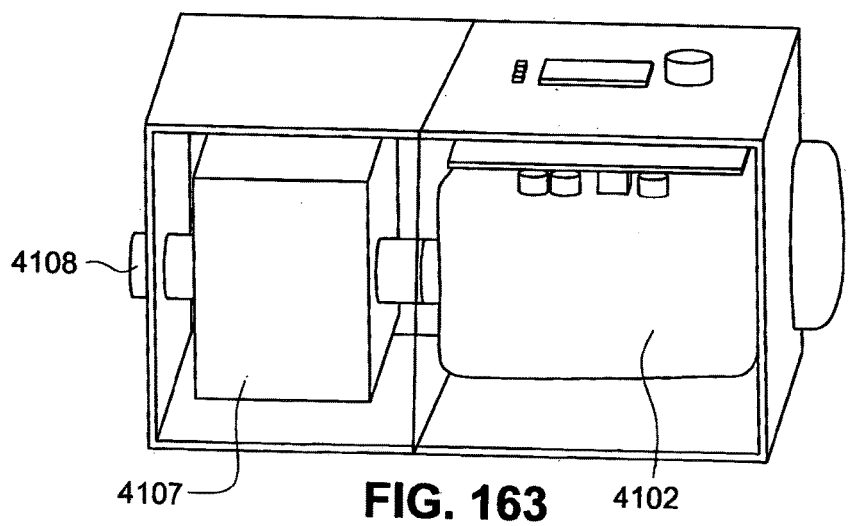
FIG. 163 is a perspective view of a PAP system according to an example of the disclosed technology.

Also, the PAP device may form part of a PAP system, e.g., PAP device or pneumatic block may be inserted into or otherwise interfaced with other components, such as a user interface, controls, and/or outer housing, to form a flow generator system. Alternatively, the PAP device, with one or more additional features, may be a stand-alone device. For example, the PAP device may be provided with one or more of the following features to provide a stand-alone device: non-rigid feet or other vibration isolation feature so that the device can be as intended when placed on a hard surface, enclosure for the PCBA, user-interface features/components, and/or filter cover. For example, FIG. 162 shows a PAP system including outer enclosure 4101 for enclosing PAP device 4102, user interface 4103 (e.g., screen, buttons, dial), inlet filter cover 4104 along inlet of the PAP device, PCBA 4105 including one or more sensors for interfacing with the PAP device. The outlet 4106 of the PAP device extends outside the enclosure or may be coupled to an outlet port to provide an outlet connector for a mask (e.g., via air tubing) or humidifier. FIG. 163 shows a PAP system similar to FIG. 162 with the outlet of the PAP device coupled to a humidifier. 4107 (enclosed within an outer enclosure). The outlet 4108 of the humidifier extends outside its enclosure to provide an outlet connector for a mask (e.g., via air tubing).

Figure 41:
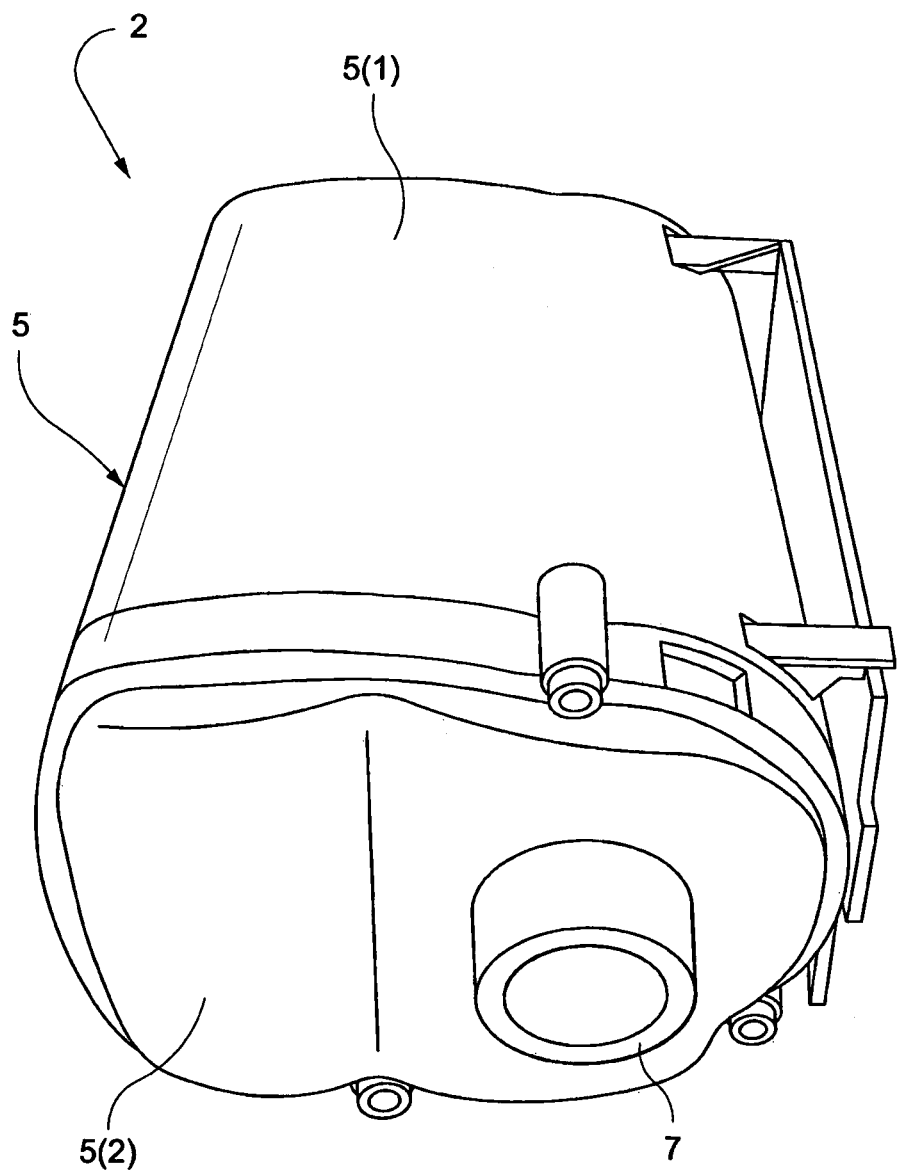
FIG. 41 is a perspective view of a PAP device according to an example of the disclosed technology.
Figure 42:
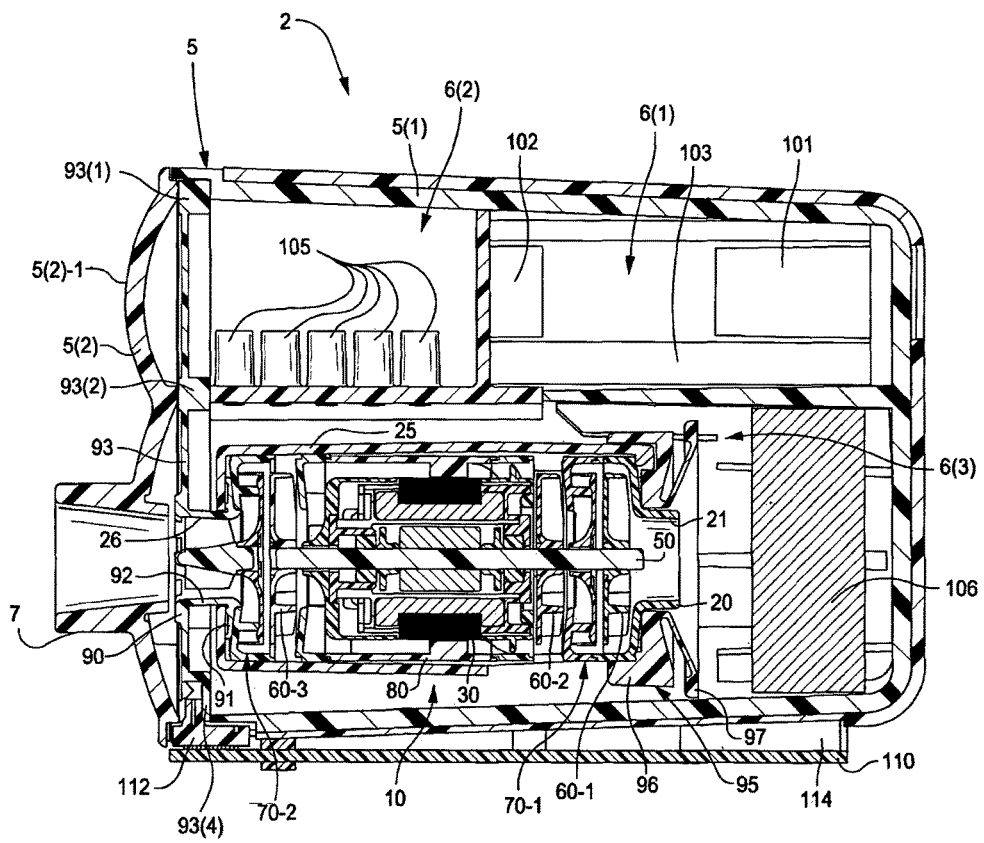
FIG. 42 is a cross-sectional view of the PAP device of FIG. 41.

FIGS. 41 and 42 show an example of a PAP device 2 including a casing or chassis 5 and the blower 10 supported within the casing 5 by the suspension system. In the illustrated example, the casing 5 includes three different expansion chambers to provide acoustic impedance for air flowing to the inlet of the blower, i.e., a first inlet muffler chamber 6(1), a second inlet muffler chamber 6(2), and a blower chamber 6(3). In an example, the relative volumes of the chambers may include similar or different volumes from one another, e.g., first inlet chamber 6(1) may be larger than the second inlet chamber 6(2). The air or gas flow between the different chambers is via at least one flow conduit or tube or pipe. There may be 1, 2, or more larger flow conduits or a plurality of smaller conduits or tubes as described in more detail below.

Figure 113:
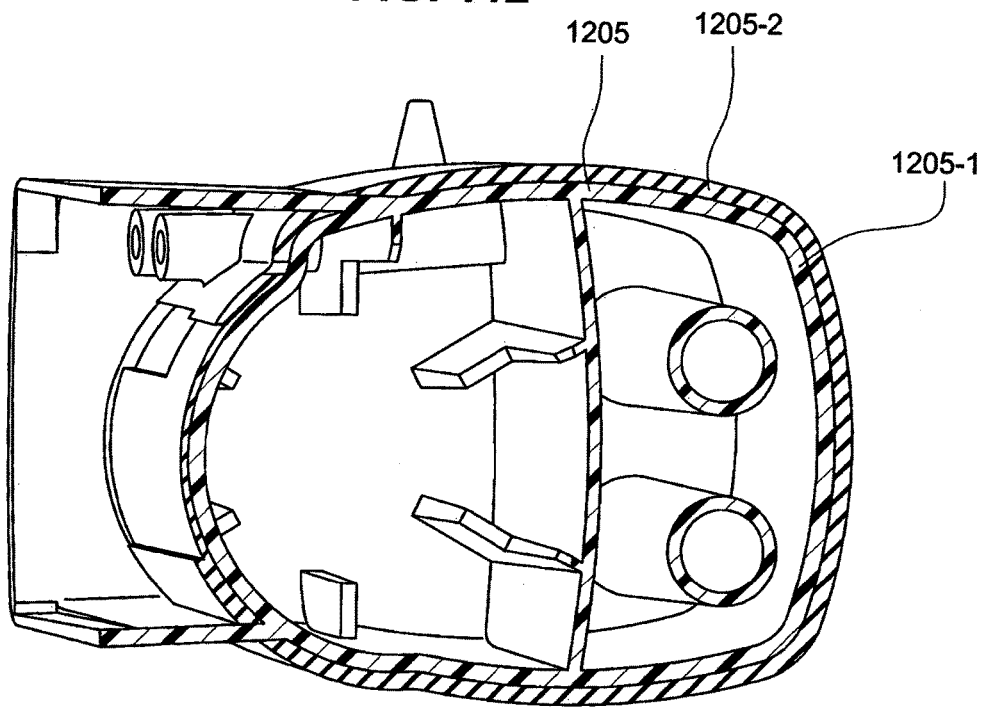
FIG. 113 is a cross-sectional view of a casing for a PAP device according to an example of the disclosed technology.

The casing may be constructed of a plastic material, polypropylene, polyamide, polybutylene terephthalate (PBT), polyethylene, polyethylene terephthalate (PET), high density polyethylene (HDPE), other semi-crystalline plastics, polycarbonate, acrylonitrile butadiene styrene (ABS), thermoset polymers (e.g., epoxy), thermoset elastomer (e.g., silicone, e.g., Shore D or above 70 Shore A hardness), MuCell gas-assisted microcellular injection molded foam, or thermoplastic elastomers (TPE) (e.g., Hytrel, Santoprene, TPU), or blends, alloys, or combinations thereof. However, other suitable materials are possible, e.g., metals, glasses, ceramics, hybrids). One or more surfaces or walls of the casing may be over-molded to attenuate wall-radiated noise. The over-moulding may be formed on either the inside or outside surface of the casing walls or both. For example, the casing may include a single layer material, over-molded or assembled with hard inside/soft outside, over-molded or assembled with soft inside/hard outside, or filled cavity or laminations of any combination of these materials or foam. FIG. 113 shows an example of a casing 1205 including a hard base 1205-1 for stiffness (e.g., polycarbonate, ABS) with a TPE overmold 1205-2 for damping. The casing may also or alternatively comprise one or more flexible walls, such as a silicone wall. Also, the casing material may be formed with increased damping properties. In an example, the flexural modulus for stiffness of the casing walls may be in the range of about 500-12,000 MPa. In another example, the stiffness may be 800-2000 MPa. The loss coefficient for the polymeric materials of the casing walls (not composites/metals) may be in the range 0.005 to 1.

The casing may also be shaped to include a plurality of curved surfaces rather than flat surfaces to provide increased stiffness to the walls and assist in attenuating radiating noise through the casing. In particular, the chambers upstream of and/or surrounding the blower may be irregularly shaped or axially asymmetrical relative to the blower to reduce chamber resonances that may result from the air flow, thus not cylindrical. For example, the chamber walls may include a plurality of convex and/or concave surfaces. Radiated noise may be attenuated by increasing the mass, stiffness and/or damping the casing walls.

In an alternative example, the wall separating the first and second chambers 6(1), 6(2) may be eliminated to provide only two chambers. In such example, the length of the inlet conduits 101 into the first chamber 6(1) (described below) may be increased. The chambers are arranged to attenuate airborne noise, i.e., to muffle the blower noise.

In an example, the PAP device includes an overall height of about 70 mm, and overall width of about 93.5 mm, and an overall length of about 118 mm. In an example, the volume of the PAP device is about 772,310 mm$^3$. However, the dimensions of the PAP device may be varied depending upon the type and size of the blower to be included within the PAP device. In certain arrangements, the overall height of the PAP device may be 110 mm, overall width of about 85 mm, and an overall length of about 140 mm.

Figure 109:
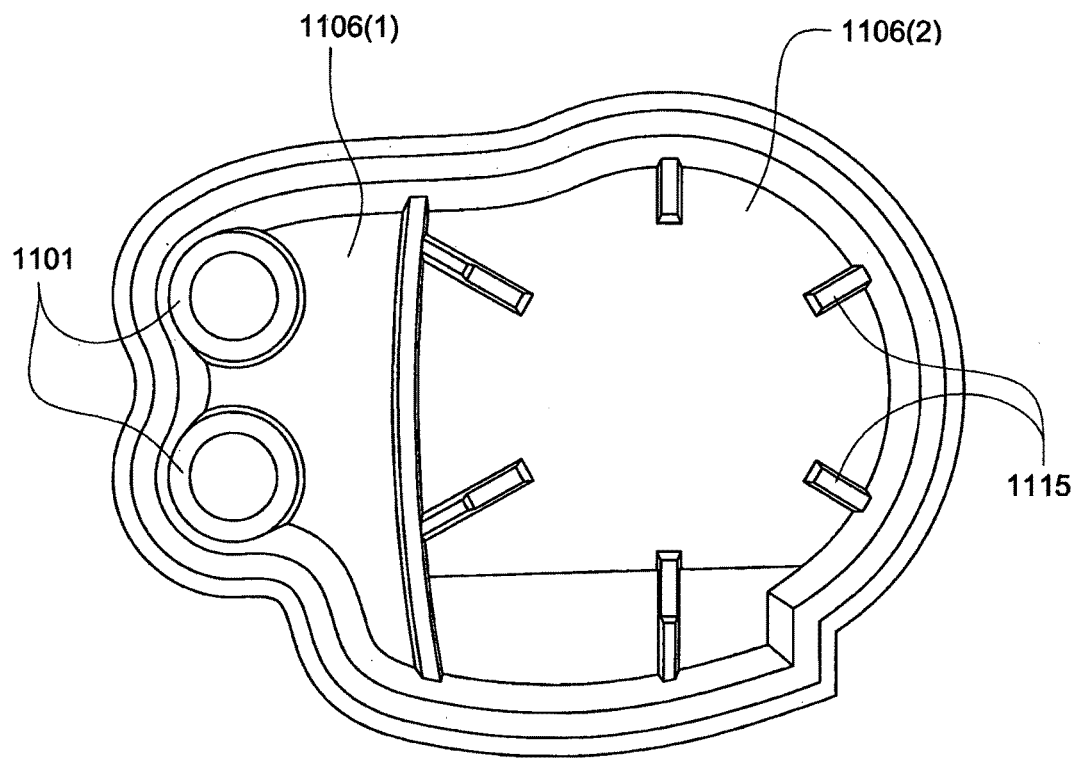
FIGS. 109 to 111 show different shapes for the inlet chamber and the blower chamber according to alternative examples of the disclosed technology.
Figure 110:
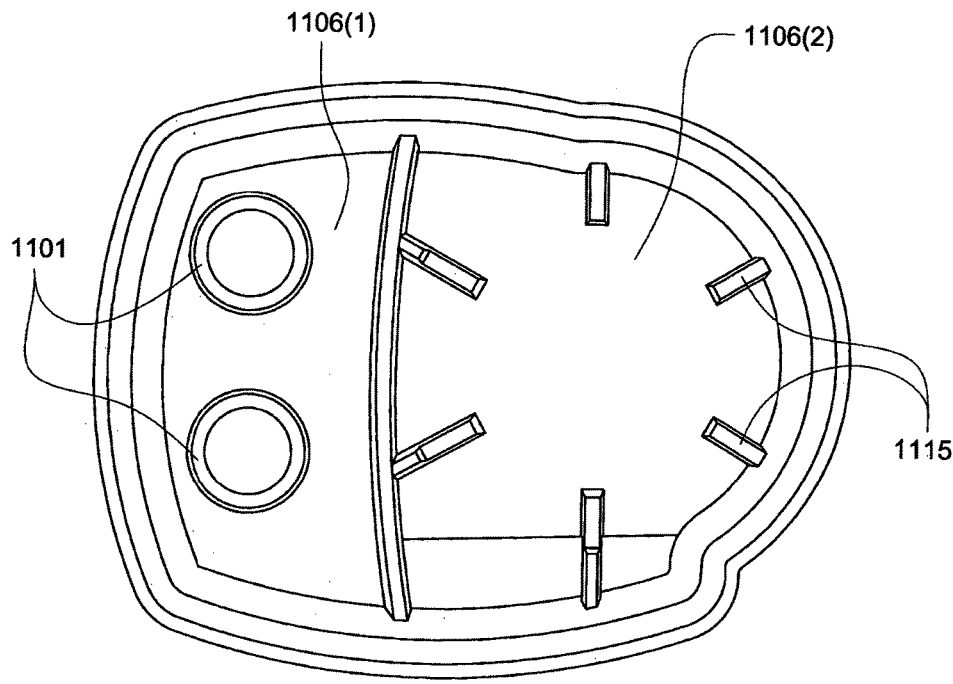
Figure 111:
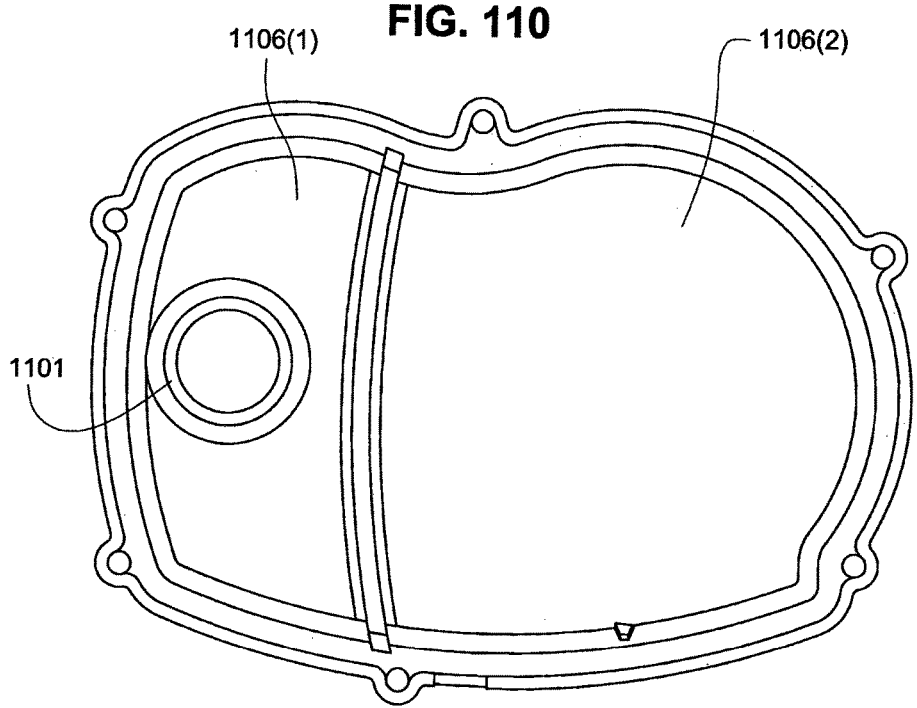

FIGS. 109 to 111 show different shapes for the inlet chamber 1106(1) and blower chamber 1106(2) according to alternative examples of the disclosed technology. As noted above, the shapes of the blower chambers may be configured to optimize: large muffler volume; small size casing; axially asymmetric blower chambers; curved walls for stiffness; space for interfacing sensors; and/or space for fastening. As described below, FIGS. 109 and 110 show an arrangement where two inlet chimneys 1101 extend into the inlet chamber, and FIG. 111 shows an arrangement where one inlet chimney 1101 extends into the inlet chamber. As illustrated, the casing may provide structure (e.g., retaining ribs 1115 as shown in FIGS. 109 and 110) to retain acoustic foam, e.g., within the blower chamber adjacent the blower inlet.

In an example, each chamber volume may be within the range of about 50,000-500,000 mm$^3$. For example, the inlet chamber volume may in the range of about 100,000-250,000 mm$^3$ (e.g., 120,000-130,000 mm$^3$ (e.g., 122,000 mm$^3$), 155,000-165,000 mm$^3$ (e.g., 160,600 mm$^3$), 220,000-230,000 mm$^3$ (e.g., 223,000 mm$^3$)), and the blower chamber volume may be in the range of about 150,000-170,000 mm$^3$ (e.g., 130,000-140,000 mm$^3$ (e.g., 132,700 mm$^3$), 155,000-165,000 mm$^3$ (e.g., 162,400 mm$^3$), 110,000-120,000 mm$^3$ (e.g., 112,900 mm$^3$). In one example, a chamber configuration for a blower includes an inlet chamber volume of about 122,000 mm$^3$ and a blower chamber volume of about 132,700 mm$^3$ for a total volume of about 254,700 mm$^3$. In another example, a chamber configuration for a blower includes an inlet chamber volume of about 160,600 mm$^3$ and a blower chamber volume of about 162,400 mm$^3$ for a total volume of about 323,000 mm$^3$. In another example, a chamber configuration for a blower includes an inlet chamber volume of about 223,000 mm$^3$ and a blower chamber volume of about 112,900 mm$^3$ for a total volume of about 335,900 mm$^3$. It should be appreciated that the chamber volumes may be varied depending upon the type and size of the blower to be included within the PAP device.

The first and second inlet muffler chambers 6(1), 6(2) are structured to attenuate airborne radiated noise. One or more inlet chimneys or, conduits 101, such as two or three or more (only one shown in FIG. 42), extend into the first inlet muffler chamber 6(1) to allow ambient air to enter the casing while providing acoustic impedance. The inlet chimney(s) 101 are shown arranged substantially parallel to the axis of the blower, however the inlet chimney(s) may be provided at any angle within the inlet chamber. The inlet chimney(s) 101 may have a generally cylindrical or tubular shape (however other suitable shapes are possible such as oval, rectangular, hexagonal, peanut-shaped, pill-shaped, etc.). A sharp entrance to the chimney(s) may result in pressure losses due to detached flow and a reduction in effective cross-sectional area.

To assist in reducing the radiated noise from the device, the inlet chimney conduit(s) are designed to have a high inertance and low flow resistance. Inertance is a measure of the pressure gradient in a fluid required to cause a change in flow-rate with time and for a circular conduit or tube is given by the formula:

$$I=\rho L/A \quad (1)$$

Wherein L is the length of the conduit or tube, $\rho$ is the density of air, and A is the cross-sectional area of the conduit or tube.

Figure 164:
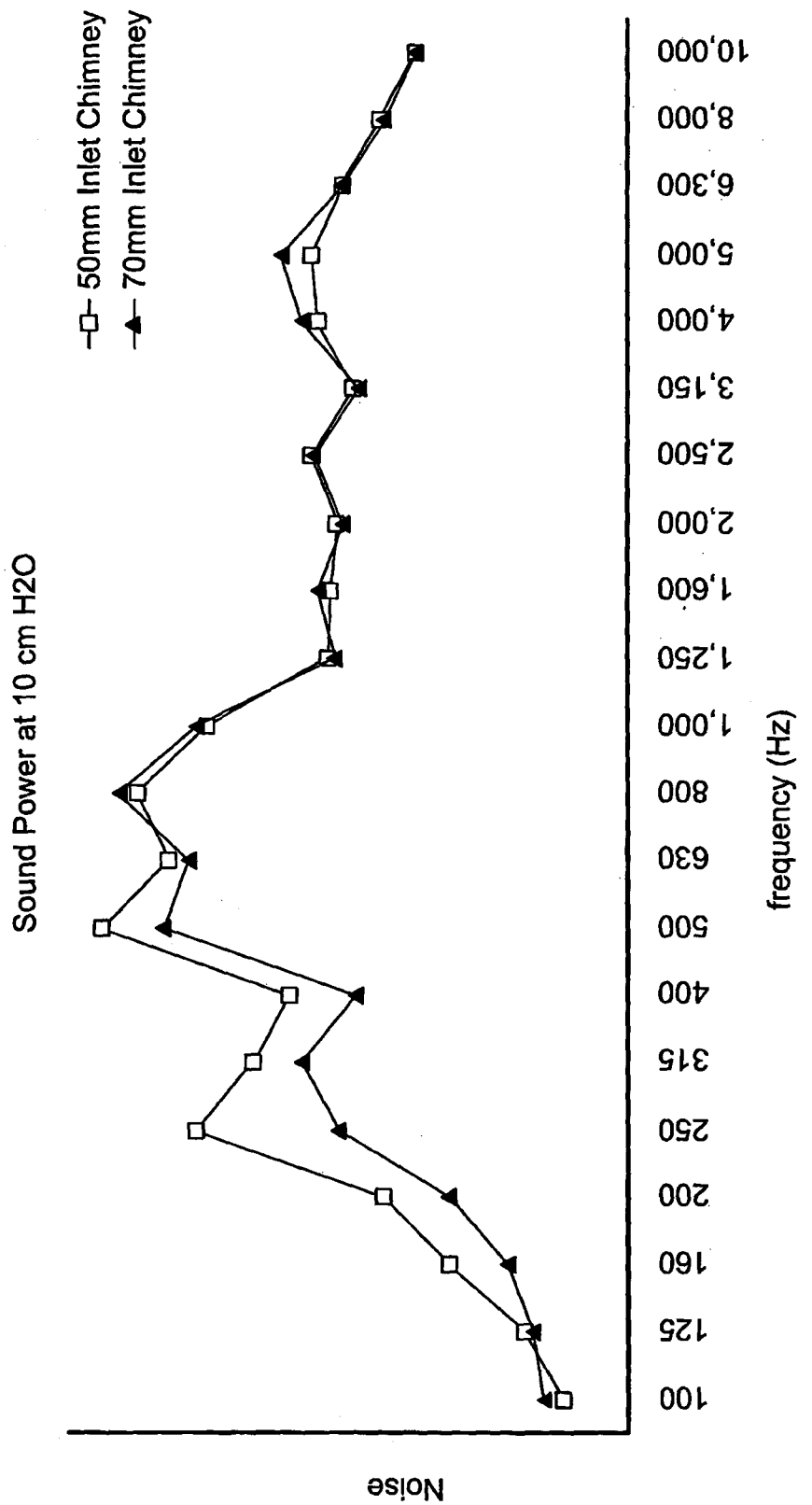
FIG. 164 is a graph of noise versus frequency for different inlet chimney lengths for a PAP device according to an example of the disclosed technology.

The inlet chimney(s) 101 may have a length of approximately 20 mm to 120 mm, such as 30 mm, 40 mm, 50 mm, 60 mm, 70 mm, 80 mm or 90 mm or any number therebetween. If a single inlet chimney 101 is used, then a longer length chimney may be provided, such as 60 mm to 120 mm, e.g., 70 mm. The inlet chimney(s) may have an internal diameter at the exit end of approximately 8 mm to 20 mm, such as 10 mm, 12 mm, 14.4 mm or 16 mm. The inlet chimney(s) may taper along its length such that the diameter at the inlet end of the inlet chimney 101 is larger than the diameter at the exit end of the inlet chimney 101, e.g., 1-2° draft angle for molding purposes. The inlet chimney may be structured to be as long as possible provided it does not impede or choke the airflow at the outlet. For example, the inlet chimney may have a length greater than 30% of the total length of the inlet chamber, or greater than 50% of the total length of the inlet chamber or longer such as 60% to 70% of the total length of the inlet chamber. A longer inlet chimney has been shown to provide less radiated noise emitted from the device. For example, FIG. 164 is a graph showing how a longer chimney may assist in reducing noise output, e.g., 70 mm inlet chimney (shown with triangular data points) provides less noise over a greater range of frequencies than 50 mm inlet chimney (shown in square data points). The inlet chimney is configured to provide an inertance of the conduit that is greater than 200 kg/m$^4$, or preferably greater than 300 kg/m$^4$ or more preferably greater than 400 kg/m$^4$.

As shown in FIG. 42, when two inlet muffler chambers 6(1), 6(2) are provided, a conduit or conduits 102 allows air to pass from the first inlet muffler chamber 6(1) to the second inlet muffler chamber 6(2). Such conduits 102 are not required if a single inlet muffler chamber is provided. Acoustic foam 103, 106 may optionally be provided in one or more chambers of the PAP device to reduce noise such as provided within the first inlet muffler chamber to reduce noise.

A flow plate including an array of conduits 105 (e.g., molded thermoplastic) is provided within the second inlet muffler chamber 6(2) to allow air to pass from the second inlet muffler chamber 6(2) to the blower chamber 6(3). The conduits 105 are structured to provide acoustic impedance as well as provide flow resistance to facilitate flow sensing or flow measurement by creating a defined pressure drop, for example a pressure drop of 0-5 cmH$_2$O. The array of conduits includes multiple parallel conduits or tubes, e.g., to provide laminar flow. In the illustrated example, the array includes 20 total tubes arranged in 4 rows of 5 tubes (only one row shown in FIG. 42). Such arrangement provides a good pressure difference signal even at low flow levels. However, it should be appreciated that the array may include other suitable numbers of conduits or tubes and arrangements, e.g., 5-50 tubes, such as 12 tubes, configured to meet the required pressure drop. The flow conduits may be arranged in one group or in multiple groups. For a casing including a plurality of inlet chimneys 101, the flow conduits 105 may be arranged in groups to match the number of inlet chimney. For example, if two inlet chimneys are provided, then two groups of flow conduits may be provided. The flow may be arranged such that each group includes the same number of flow conduits or a different number of flow conduits. The flow conduits are not required to be arranged symmetrically or to be formed in the same plane. However, for accurate flow sensing, the flow conduits 105 must be arranged such that air flows evenly through the conduits. The array of conduits may be more easily manufactured than the prior art (large conduit subdivided by many thin walls, such as a honeycomb configuration). In an alternative example, the casing may include a single chamber and the array of conduits provided between the chamber and atmosphere, e.g., combine plurality of conduits and inlet into one piece.

Figure 104:
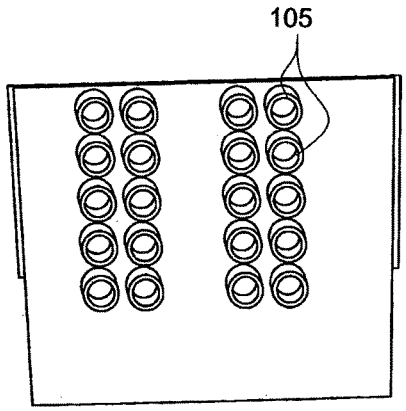
FIGS. 104 to 108 show flow plates with flow conduit arrangements according to alternative examples of the disclosed technology.
Figure 105:
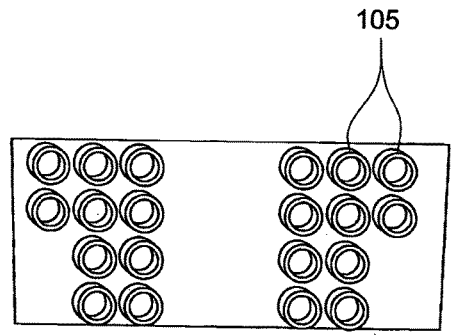
Figure 106:
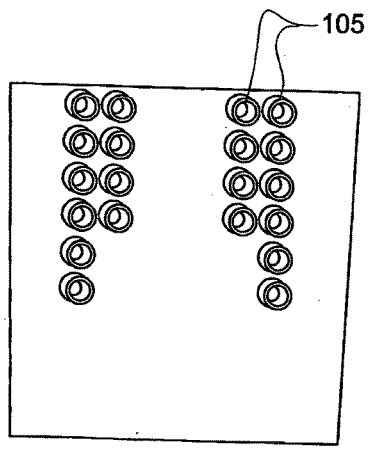
Figure 107:
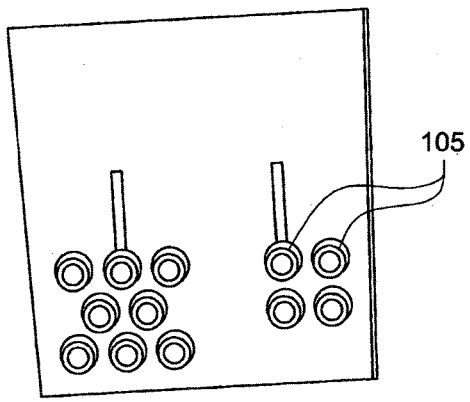
Figure 108:
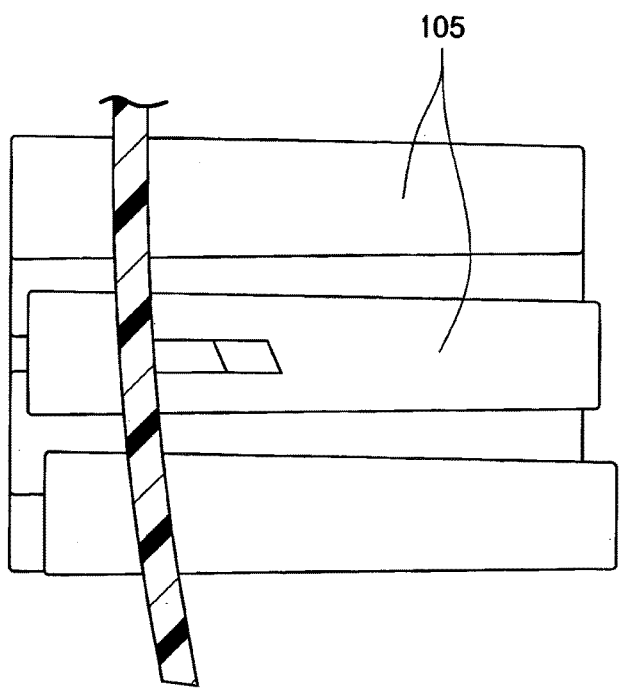

For example, FIGS. 104 to 108 show flow plates with alternative arrangements of flow conduits 105. FIGS. 104-106 show flow plates with two groups of flow conduits or tubes (one group per inlet chimney), with each group including the same number of flow conduits or tubes. In FIG. 104, each group includes 2 rows of 5 tubes. In FIG. 105, each group includes 3 rows with 2 of the rows including 4 tubes and 1 of the rows including 2 tubes, i.e., rows in each group may include different number of tubes. In FIG. 106, each group includes 2 rows with one of the rows including 4 tubes and the other of the rows including 6 tubes. FIG. 107 shows a flow plate with two groups of flow conduits or tubes (one group per inlet chimney), with each group including a different number of flow conduits or tubes, e.g., one group includes 2 rows of 2 tubes and the other group includes 8 total tubes in an offset arrangement. FIG. 108 shows flow tubes having different lengths and arranged in different planes.

The length of the flow conduits may be defined to provide a high inertance to assist in reducing radiated noise in a similar manner to that described above for the inlet chimney (s). The flow conduits 105 may have a length of approximately 5 mm to 55 mm, such as 11 mm, 20 mm, 25 mm, 33 mm or 40 mm or any length therebetween. The flow conduits may have an internal diameter at the exit end of the conduit of approximately 2 mm to 10 mm, such as 3.0 mm, 3.3 mm, 4.0 mm, 4.6 mm, 4.9 mm or 6 mm. The length of each flow conduit may vary within the set of flow conduits. The flow conduits may be tapered along their length from the inlet or entry end to the exit end, such that the inlet end is larger than the exit end, e.g., 1-2° draft angle for molding purposes.

In illustrated examples (e.g., see FIGS. 42, 98, 102, and 103), the flow conduits are provided upstream of the blower (i.e., upstream of the blower inlet). In an alternative example, the flow conduits may be provided downstream of the blower (i.e., downstream of the blower outlet).

Figure 112:
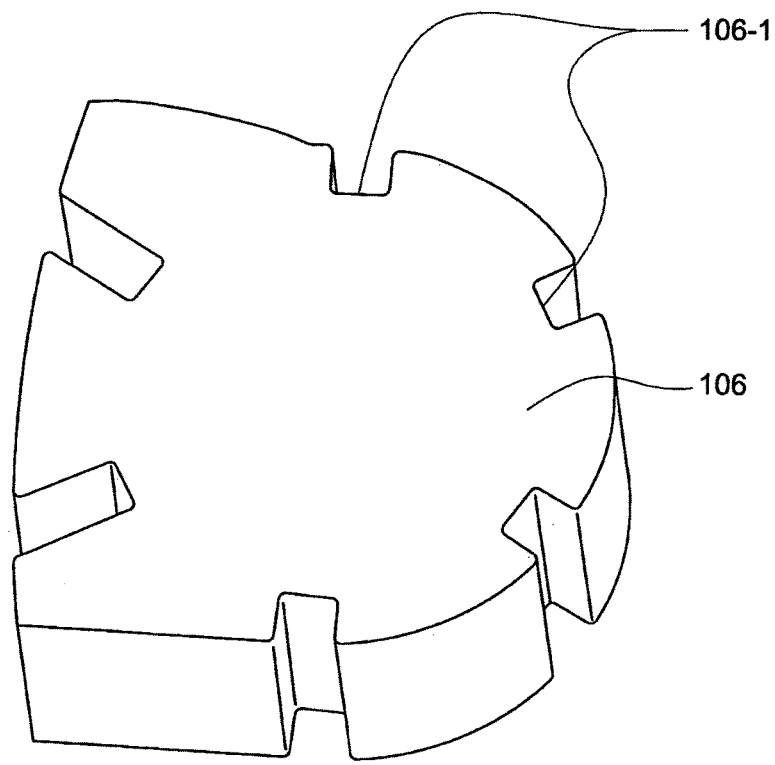
FIG. 112 is a perspective view of acoustic foam for a PAP device according to an example of the disclosed technology.

The blower 10 is supported by the outlet end and inlet end suspensions 90, 95 within the blower chamber 6(3) of the casing 5. As illustrated, the resiliently flexible, casing engaging portion 97 of the inlet end suspension 95 is adapted to engage interior walls of the blower chamber to stably support the inlet end of the blower 10 within the blower chamber. The casing engaging portion 97 seals the inlet 21 within the blower chamber and the resiliently flexible arrangement of the casing engaging portion 97 isolates vibrations and provides shock resistance. Acoustic foam 103, 106 (e.g., die cut, e.g., polyurethane foam) may also be provided within one or more chambers of the PAP device to reduce or dampen noise, such as in the blower chamber adjacent the inlet to reduce noise. In an example, as shown in FIG. 112, the foam 106 may include one or more cut-outs 106-1 along its perimeter (e.g., to receive retaining ribs 1115 as shown in FIGS. 109 and 110) for retaining and aligning the foam within chamber. In an example, foam may include a foam volume in the range of about 10,000-50,000 mm$^3$ (e.g., 15,000-20,000 mm$^3$ (e.g., 17,900 mm$^3$), 35,000-40,000 mm$^3$ (e.g., 38,200 mm$^3$)). The size of the foam may be varied depending upon the type and size of the blower to be included within the PAP device.

Figure 118:
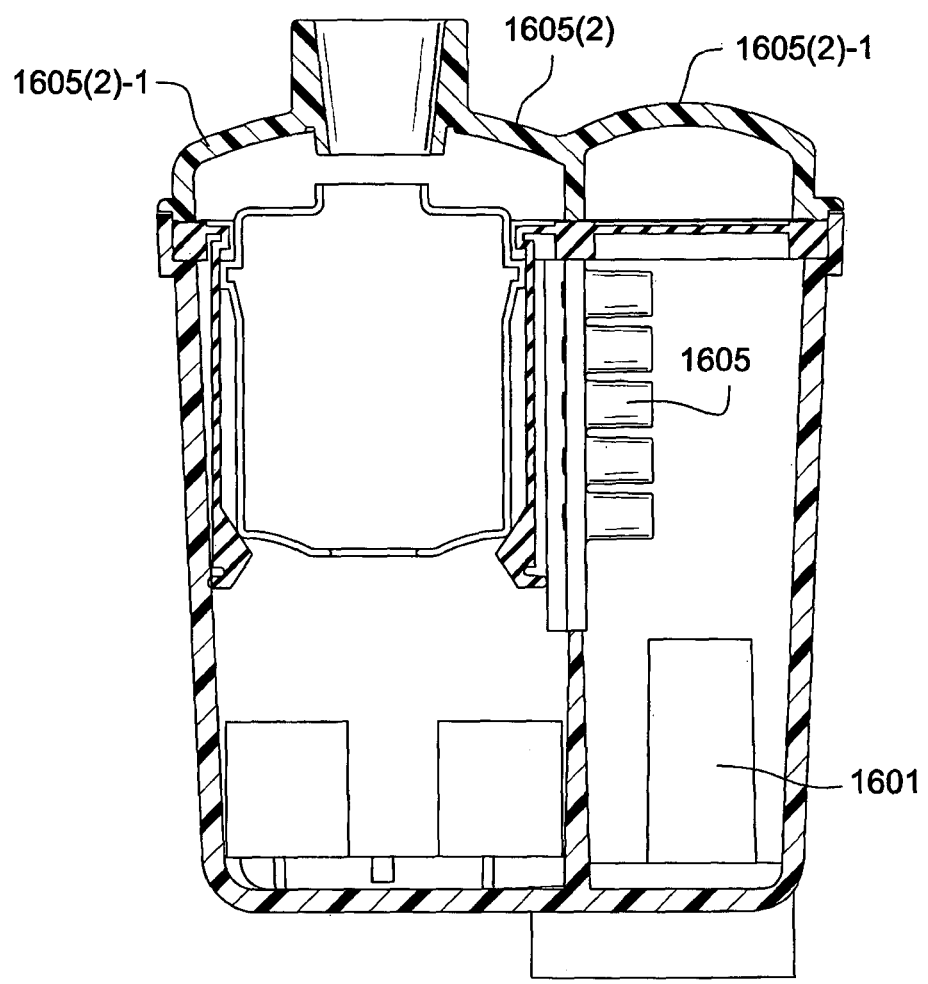
FIG. 118 is a cross-sectional view of a casing for a PAP device according to an example of the disclosed technology.
Figure 119:
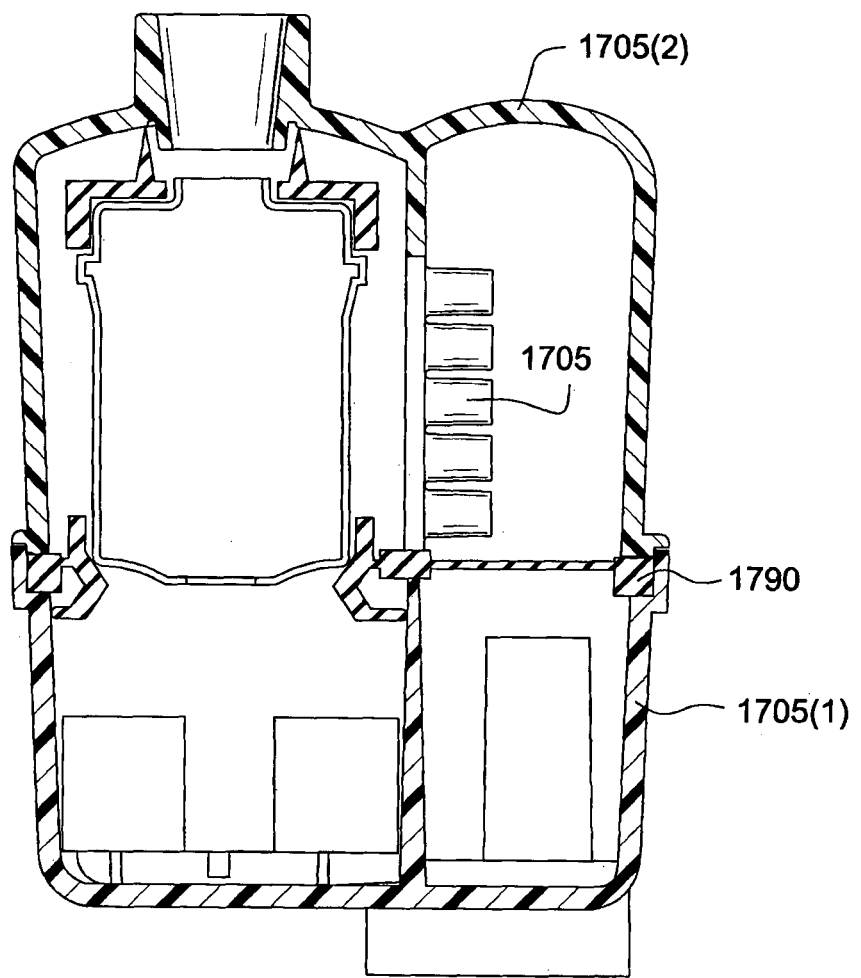
FIG. 119 is a cross-sectional view of a casing for a PAP device according to an example of the disclosed technology.
Figure 123:
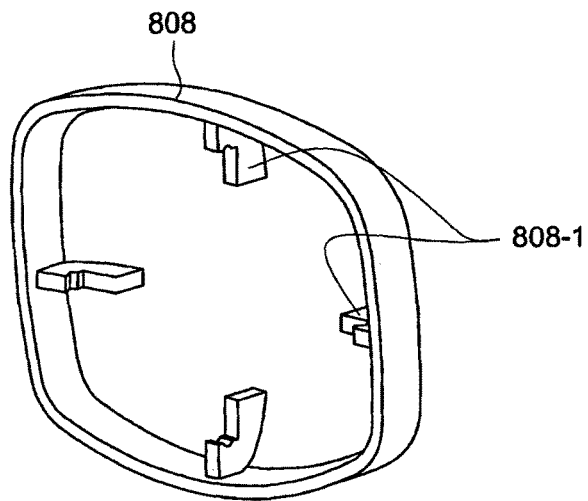
FIG. 123 is a perspective view of a filter cover for a PAP device according to an example of the disclosed technology.

The casing 5 includes a base 5(1) (providing the inlet airpath with three chambers, inlet chimneys) and an end wall or cover 5(2) provided to the base (providing airpath from blower outlet to air delivery tube or humidifier). The cover 5(2) may in the form of a cup-shaped lid or include curved surfaces to increase the strength, improve sealing and/or reduce radiated noise. For example, FIG. 42 shows a cover 5(2) including curved surfaces 5(2)-1, and FIG. 118 shows a cover 1605(2) with two cup-shaped portions 1605(2)-1 (e.g., flow tubes 1605 may be moved closer to inlet chimney 1601 to accommodate cover structure. FIG. 123 shows another example a cup-shaped cover 1705(2). In this example, the flow plate with flow tubes 1705 may be provided as a separate part, and the slit line between the cover 1705(2) and base 1705(1) is provided along a middle of the case, e.g., rear suspension 1790 for blower provides seal between base and cover. The cover 5(2) may be coupled to the base 5(1) using any known fastening method such as welding, heat staking, via adhesives, via screws, snaps or other such fasteners. Thus, the cover 5(2) may be coupled to the base 5(1) in a removable or permanent manner. The outlet end suspension 90 stably supports the outlet end of the blower 10 within the blower chamber and also provides a seal between the cover 5(2) and the base 5(1) of the casing 5.

Figure 131:
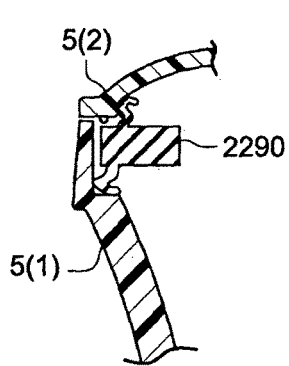
Figure 132:
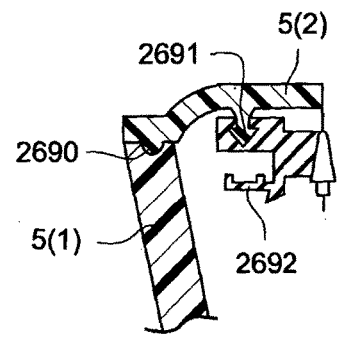
Figure 133:
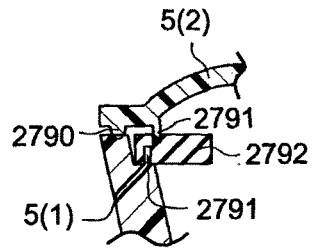

FIGS. 131 to 137 show alternative examples for sealing between the cover 5(2) and the base 5(1). For example, FIG. 131 127 shows a pressure-assisted seal 2190 with relatively thin lip seals, FIG. 128 shows cover/base interface that is internal to the casing with optional seals 2390(1) and/or 2390(2) provided to the cover 5(2) for sealing with the base, FIG. 129 shows cover 5(2) with snap-fit tab 2491 to secure cover to base 5(1) and a seal 2490 sandwiched between the cover and a ledge of the base 5(1), FIG. 130 shows a cover 5(2) with a barb or snap 2591 adapted to sealingly engage within an opening provided to the base 5(1), FIG. 131 shows a pressure-assisted seal 2290 with cushion type or questionmark shaped seals, FIG. 132 shows cover 5(2) with a seal 2690 to seal with the base 5(1) and a barb 2691 for engaging blower suspension 2692, and FIG. 133 shows cover 5(2) with a seal 2790 (e.g., seal in the form of bead, lip or bellows overmolded to cover) to seal with the base 5(1) and locating teeth 2791 on the cover/base to support the blower suspension 2792 within the casing.

Figure 120:
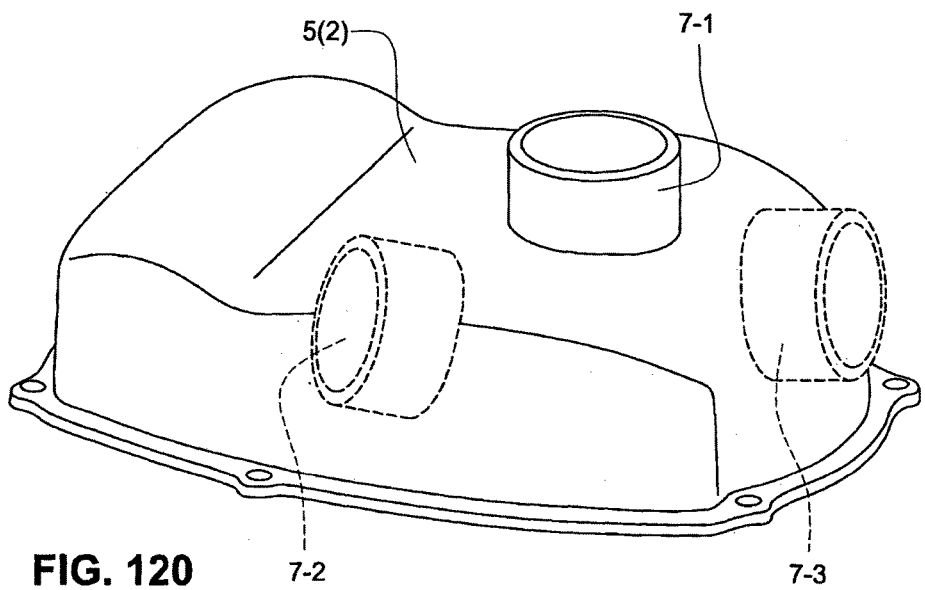
FIG. 120 is a perspective view of a cover for a PAP device casing according to an example of the disclosed technology.

As illustrated, the tube portion 92 of the outlet end suspension 90 is aligned and engaged with the outlet 7 provided to the end wall 5(2) to seal the airpath from the blower outlet 26 to the casing outlet 7. As illustrated, the outlet 7 may provide an expanding diameter which is substantially continuous with the expanding diameter of the tube portion 92. However, in other configurations, the outlet 7 may not include an expanding cross-section. Also, it should be appreciated that the outlet 7 may not directly align with blower outlet 26, e.g., outlet may be provided along any portion of the cover 5(2), e.g., for ease of interface with a humidifier, etc. For example, FIG. 120 show alternative locations for an outlet on cover 5(2), e.g., outlet 7-1, 7-2, or 7-3. Moreover, the casing engaging portion 93 of the outlet end suspension 90 includes an outer wall 93(1) to provide a seal between the end wall 5(2) and the outer wall of the base 5(1) and an inner wall 93(2) to provide a seal between the end wall 5(2) and an interior wall (e.g., interior chamber wall) of the base 5(1). A bottom wall 93(3) (e.g., with one or more openings) is provided between the outer wall 93(1) and each side of the inner wall 93(2), e.g., see FIGS. 1-7 and 9. The bottom wall 93(3) may be resiliently flexible so as to support the outlet end of the blower in a vibration isolating and shock resistance manner.

A printed circuit board assembly 110 (PCBA) is provided to the casing 5 (e.g., casing including one or more legs to hold PCBA) to control the motor 30. The PCBA 110 may include one or more sensors, e.g., pressure sensor 112, flow sensor 114 as shown in FIG. 42.

Figure 43:
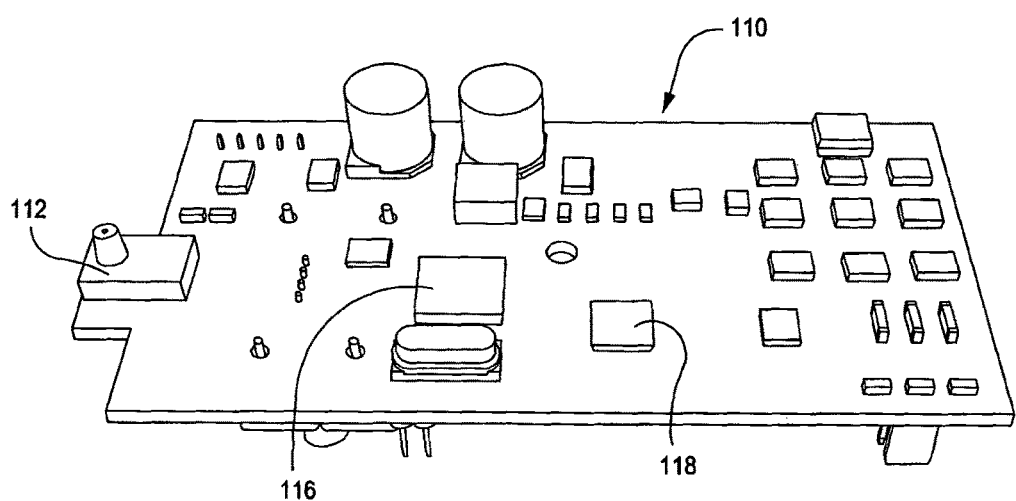
FIG. 43 is a perspective view of a printed circuit board assembly (PCBA) according to an example of the disclosed technology.
Figure 44:
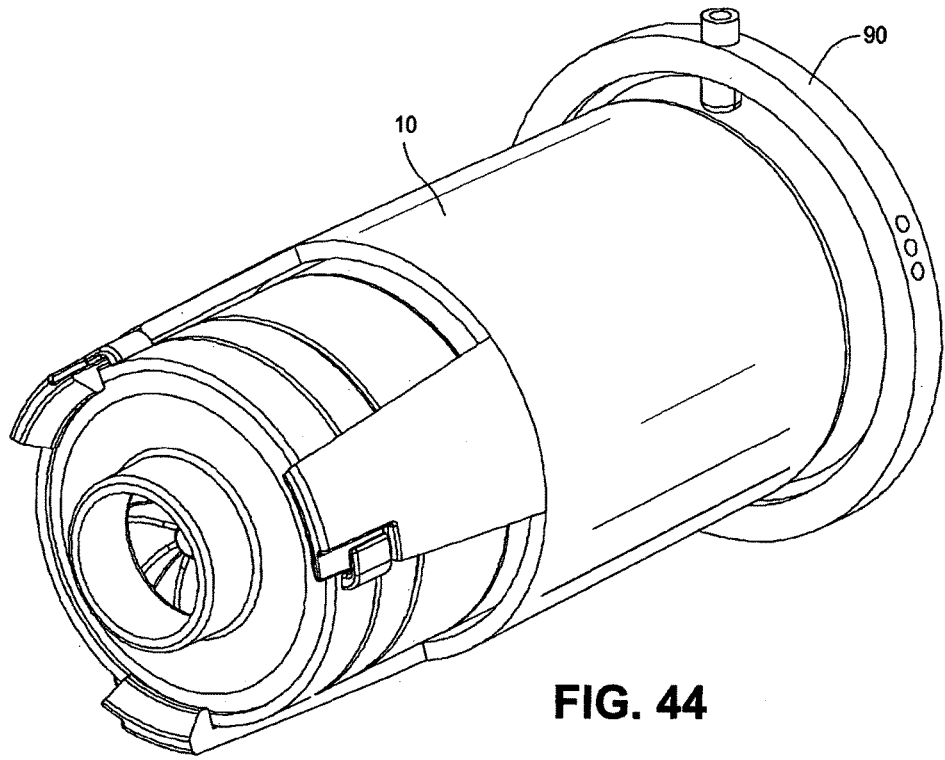
FIGS. 44-47 are perspective views of a blower with an outlet end suspension according to an example of the disclosed technology.
Figure 45:
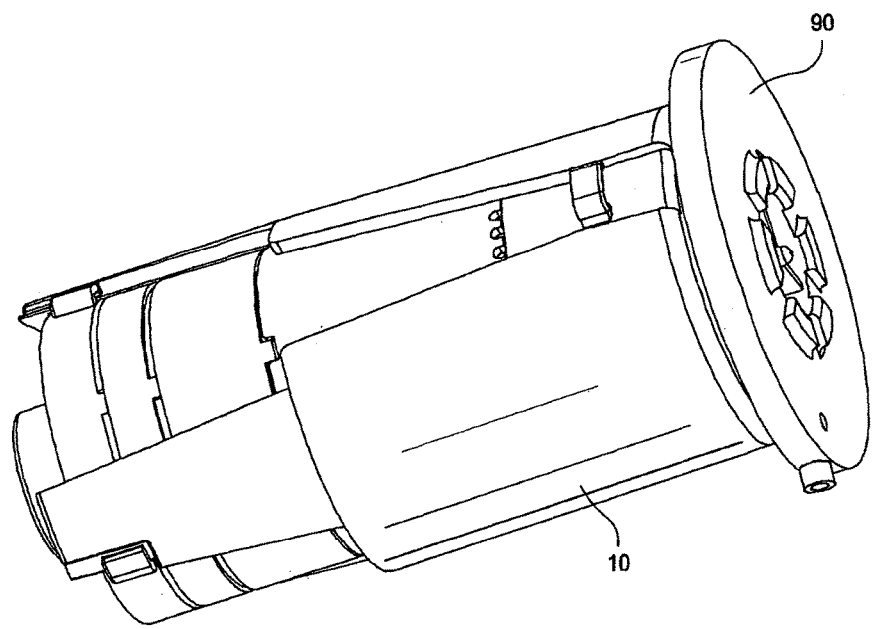
Figure 46:
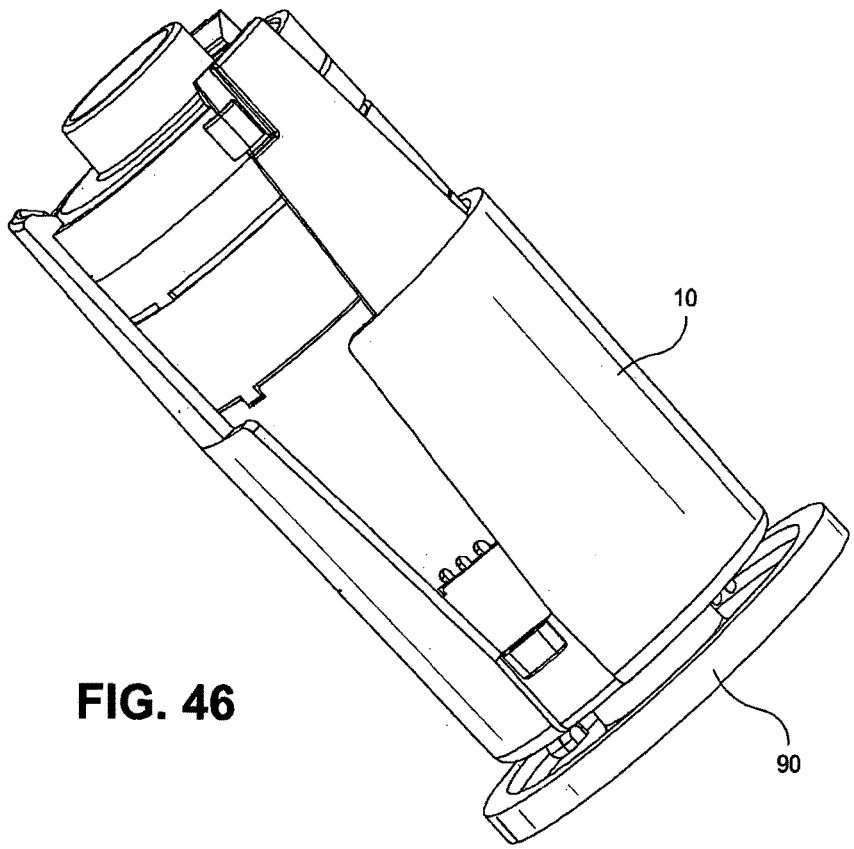
Figure 47:
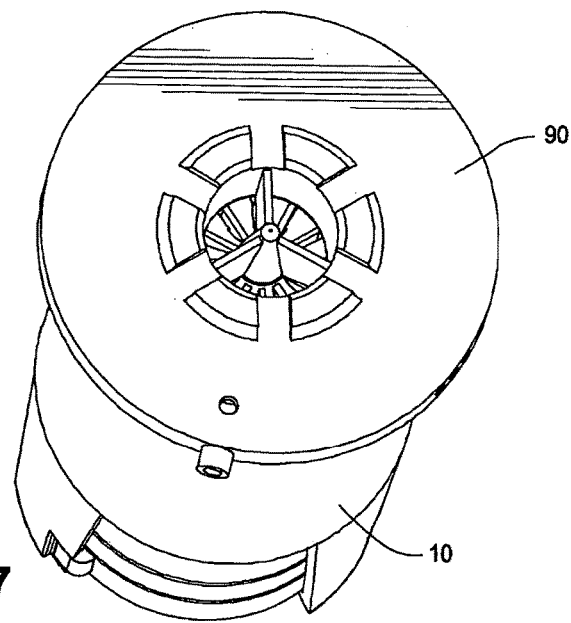
Figure 48:
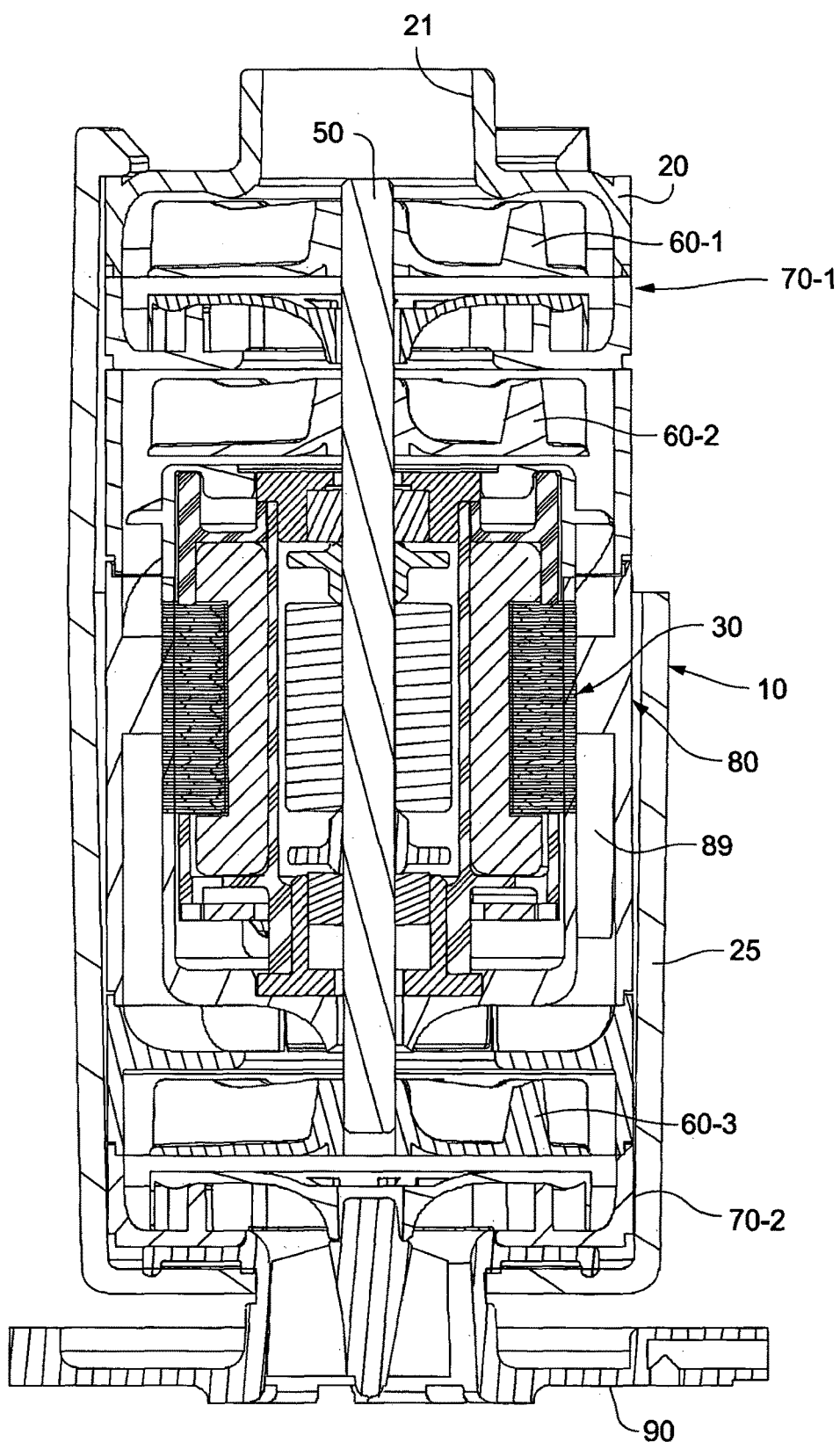
FIG. 48 is a cross-sectional view of the blower of FIGS. 44-47.

FIG. 43 shows a PCBA 110 according to an example of the present technology. In this example, the PCBA 110 may include a pressure sensor 112, electrically erasable programmable read-only memory (EEPROM), dedicated micro controller 116 (e.g., provide control and/or therapy), and/or hardware fault mitigations 118 via programmable mixed signal chip (fewer parts, more flexible).

Figure 98:
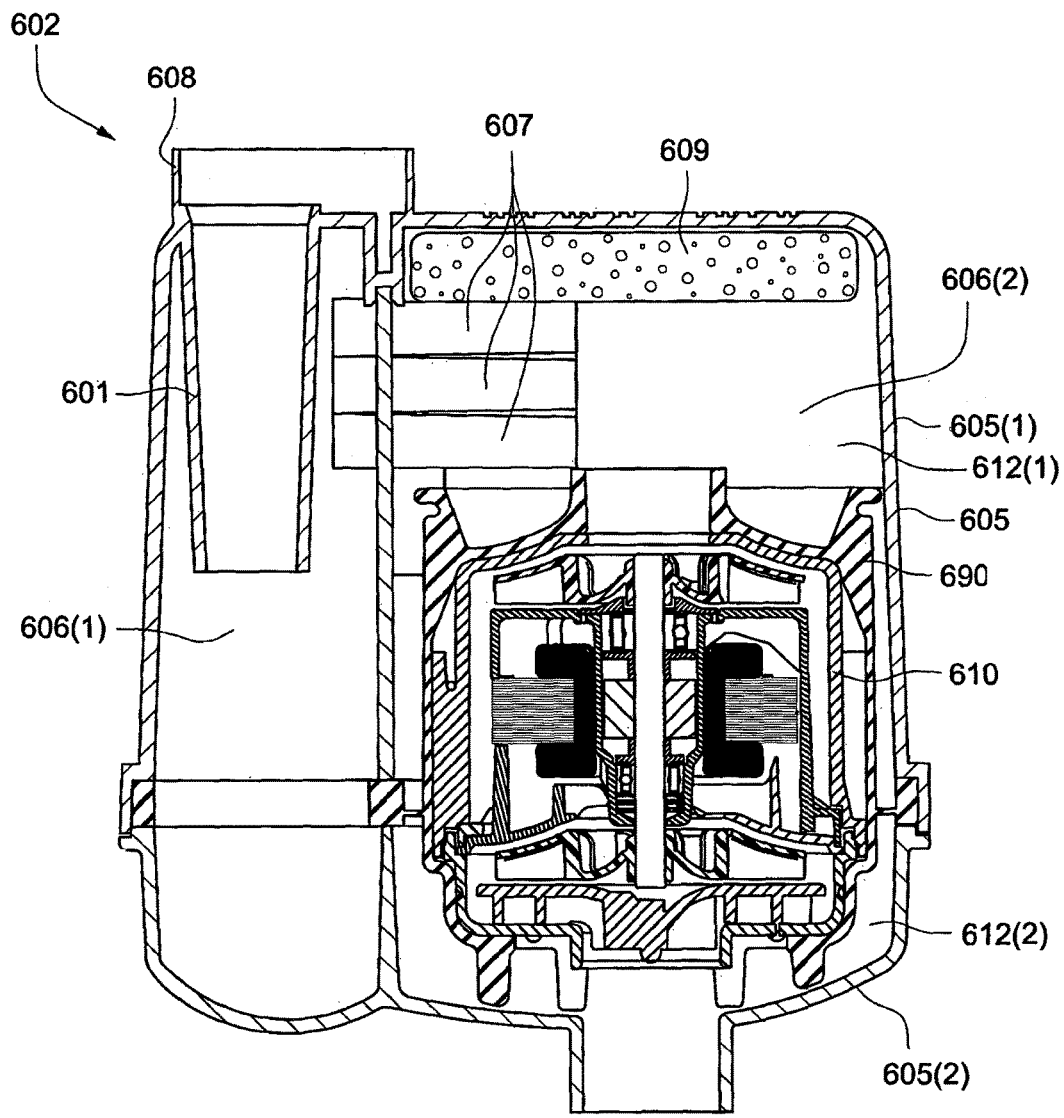
FIG. 98 is a cross-sectional view of a PAP device according to an example of the disclosed technology.

FIG. 98 shows another example of a PAP device 602 including casing 605 and blower 610 supported within the casing 605 by suspension system 690. In this example, the blower is similar to that described in U.S. Patent Application Publication No. US 2008/0304986, however it should be appreciated that the PAP device may be structured to support different blower designs. In this example, the casing 605 (including base or chassis 605(1) and cover 605(2)) provides two chambers, i.e., inlet chamber 606(1) and blower chamber 606(2). As described above, inlet conduit(s) or chimney (s) 601 (e.g., one 70 mm inlet chimney arranged parallel to the blower axis) extends from the inlet into the inlet chamber, and flow conduits 607 extend between the inlet chamber 606(1) and the blower chamber 606(2). In this example, the flow conduits 607 are provided to a similar side of the casing as the inlet chimney. Foam 609 is provided within the blower chamber adjacent the inlet to reduce noise. A filter interface 608 (e.g., wall support structure) may be provided to the inlet to support an inlet filter. As described above, the suspension system 690 may be in the form of a single suspension system structured to, e.g., provide a seal between the base 605(1) and cover 605(2), provide vibration isolation and impact resistance, and divide low pressure side 612(1) and high pressure side 612(2) leading to the outlet.

Figure 103:
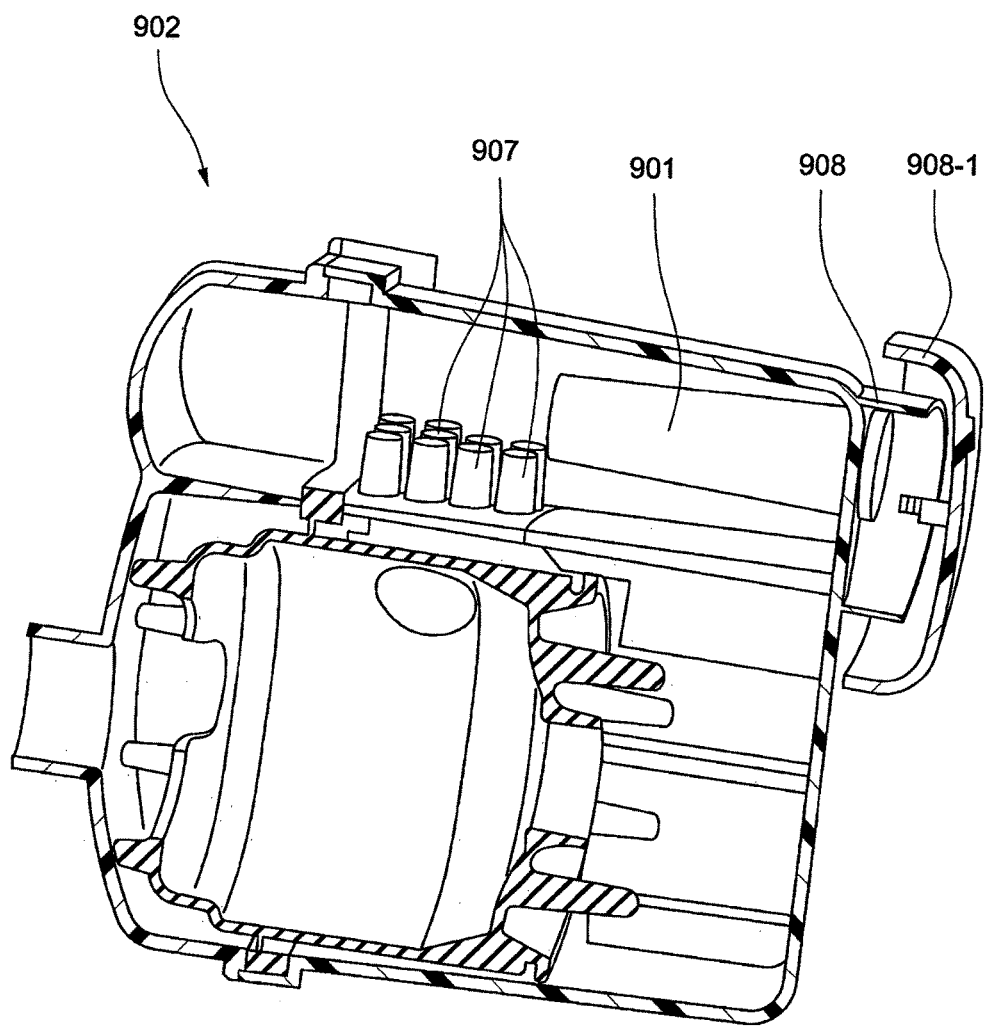
FIG. 103 is a cross-sectional view of a PAP device according to an example of the disclosed technology.

FIG. 103 shows a PAP device 902 similar to that shown in FIG. 98. In this example, the flow conduits 907 are provided adjacent an outlet side of the inlet chimney(s) 901. Also, a filter cover 908-1 is provided to the filter interface 908 at the casing inlet.

FIGS. 154-161 show another example of a PAP device 4002 including casing 4005 and blower 4010 supported within the casing 4005 by suspension system 4090. The casing 4005 (including base or chassis 4005(1) and cover 4005(2)) provide two chambers, i.e., first inlet chamber 4006(1) and second chamber 4006(2) or blower inlet chamber. The inlet chamber 4006(1) is relatively large compared to the second chamber 4006(2), e.g., to reduce noise, and the blower 4010 encased by single, one-piece suspension system 4090 is positioned within the inlet chamber 4006(1) but receives airflow at an inlet end of the blower from the second chamber 4006(2) or blower inlet chamber. The inlet chimney 4001 extends from the casing inlet 4005(2)-1 provided by the cover 4005(2) into the inlet chamber, and the flow plate 4007 including flow conduits 4007-1 is provided between the cover/base to divide the inlet chamber 4006(1) and the second chamber 4006(2). In this example, the inlet chimney and the flow conduits both extend parallel to the blower axis. Foam 4009 may be provided within the second chamber adjacent the blower inlet. The suspension system 4090 is in the form of a single, one-piece suspension system structured to, e.g., interlock and seal with the flow plate 4007, provide a silicone outlet chamber 4091 for the blower, provide an outlet conduit 4092 that extends through the casing outlet to outside the casing (e.g., outlet conduit is offset from blower outlet), divide low pressure side and high pressure side of blower, and provide vibration isolation and impact resistance (e.g., interior bumps 4093 to seal, retain, and isolate vibrations).

Figure 99:
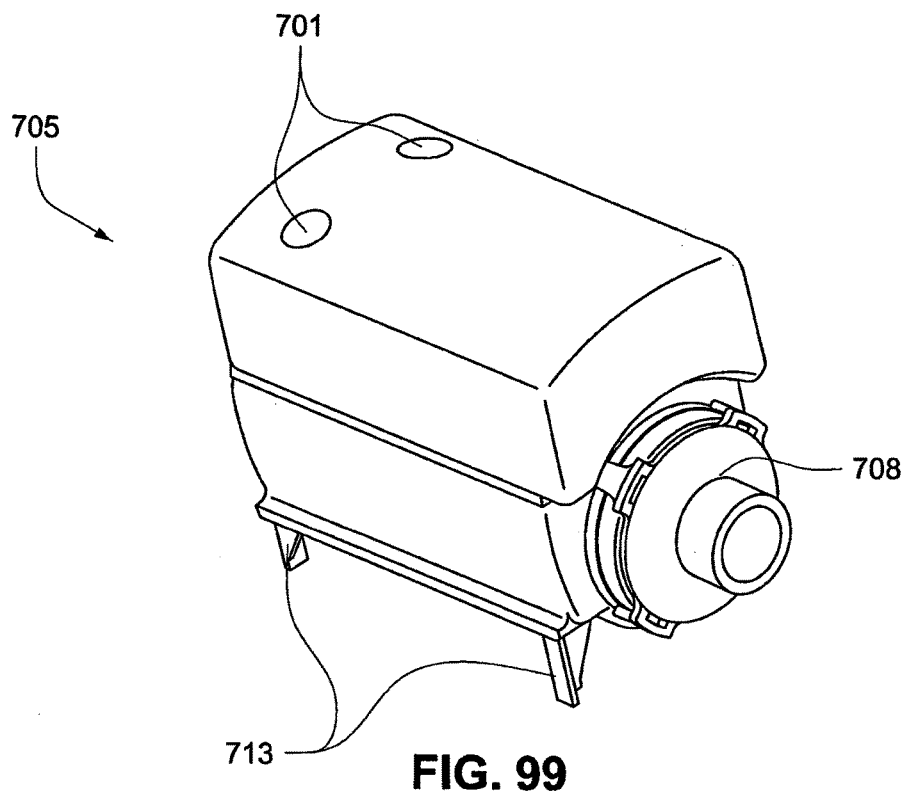
FIG. 99 is a perspective view of a PAP device according to an example of the disclosed technology.
Figure 100:
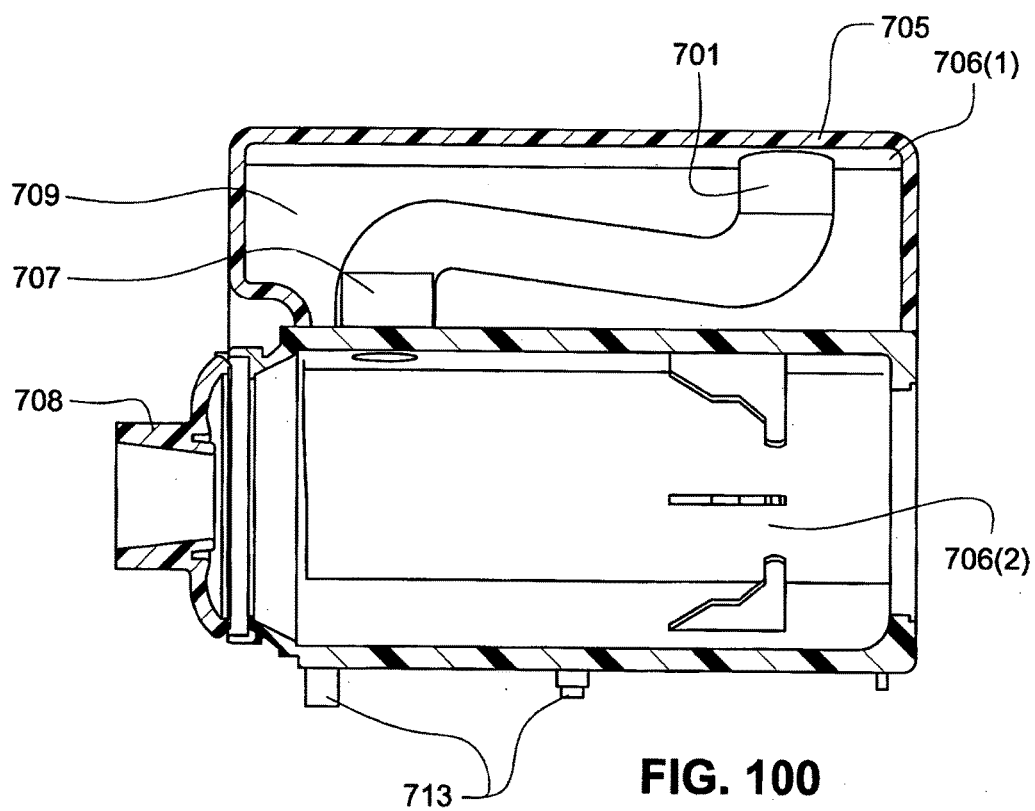
FIG. 100 is a cross-sectional view of the PAP device of FIG. 99.

FIGS. 99 and 100 show another example of a casing 705 for a PAP device including a two-piece chassis providing inlet chamber 706(1) and blower chamber 706(2), two inlet chimneys 701 (e.g., arranged perpendicular to the blower axis), two chimneys 707 between the inlet chamber and the blower chamber, foam 709 providing arcuate channels or bends to interconnect the chimneys 701, 707 while reducing noise, a snap-on outlet cover 708, and legs 713 to hold a PCBA. In this arrangement, the inlet chamber is provided by a separate casing component, which allows the chimneys to be molded on any surface of the inlet chamber, e.g., perpendicular to the blower axis. It should be appreciated that a separate casing component for the inlet chamber may be applicable to other PAP device examples, e.g., PAP device shown in FIGS. 41 and 42.

Figure 114:
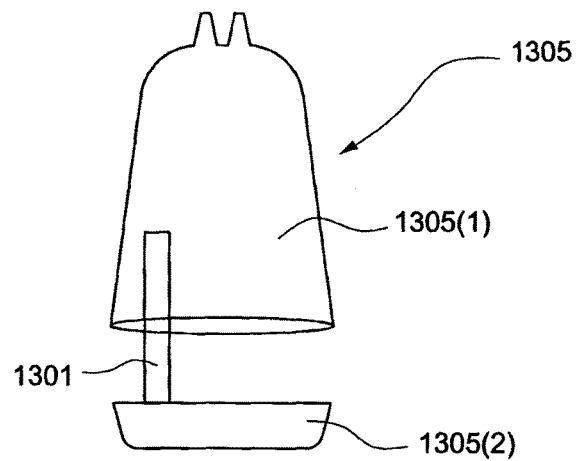
FIG. 114 is a schematic view of a casing for a PAP device according to an example of the disclosed technology.

FIG. 114 shows an example of a casing 1305 in which the split line between the base 1305(1) and the cover 1305(2) is provided along the inlet, i.e., not the outlet as in FIGS. 41 and 42. In an example, the cover 1305(2) may provide chimney(s) 1301, a filter cover, and closure for the base in a one-piece structure. As illustrated, relatively long chimney(s) 1301 may be molded (e.g., with side cores) along with the cover.

Figure 115:
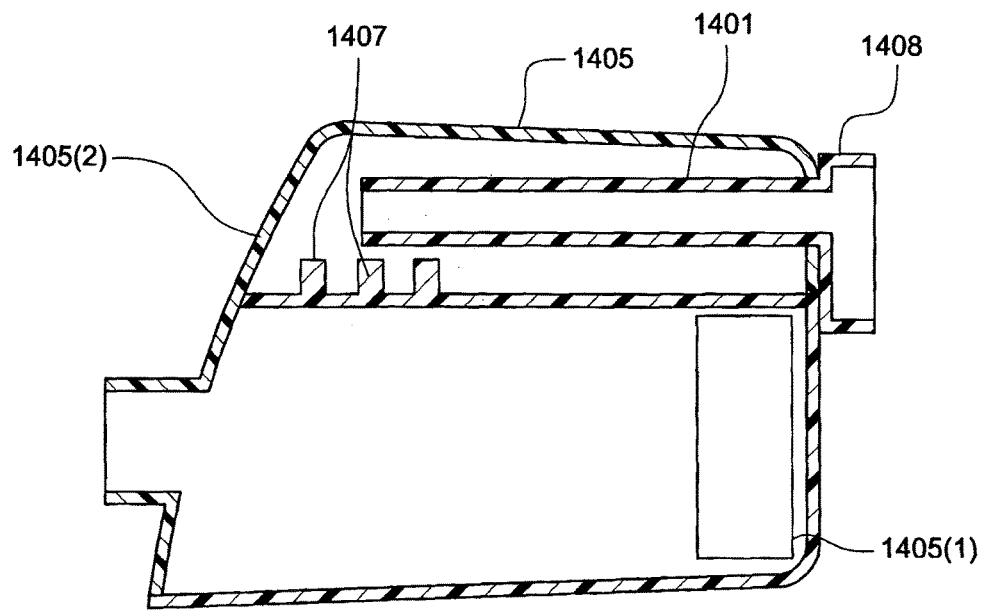
FIG. 115 is a cross-sectional view of a casing for a PAP device according to an example of the disclosed technology.

FIG. 115 shows an example of a casing 1405 in which the chimney 1401 and filter interface 1408 are provided as a separate component, e.g., which allows a relatively long chimney to be molded. As illustrated, the base 1405(1) includes the flow conduits 1407 and the cover 1405(2) provides the inlet chamber and the outlet cover.

Figure 116:
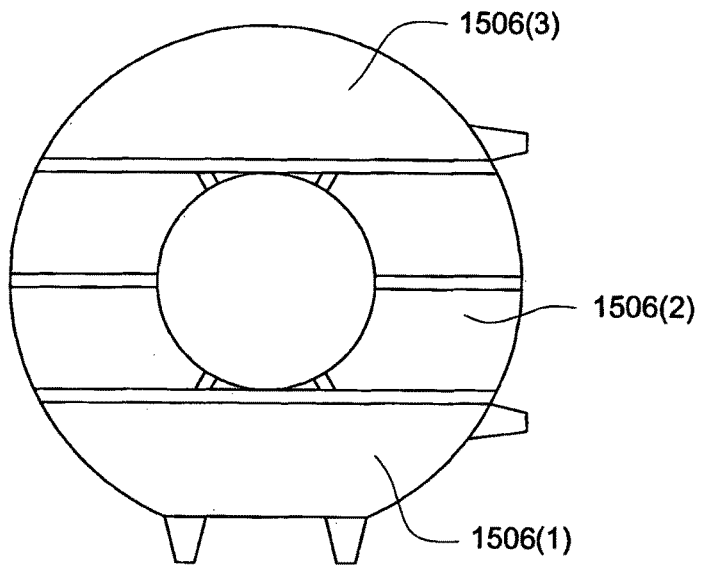
FIG. 116 is a schematic view of a casing for a PAP device according to an example of the disclosed technology.
Figure 117:
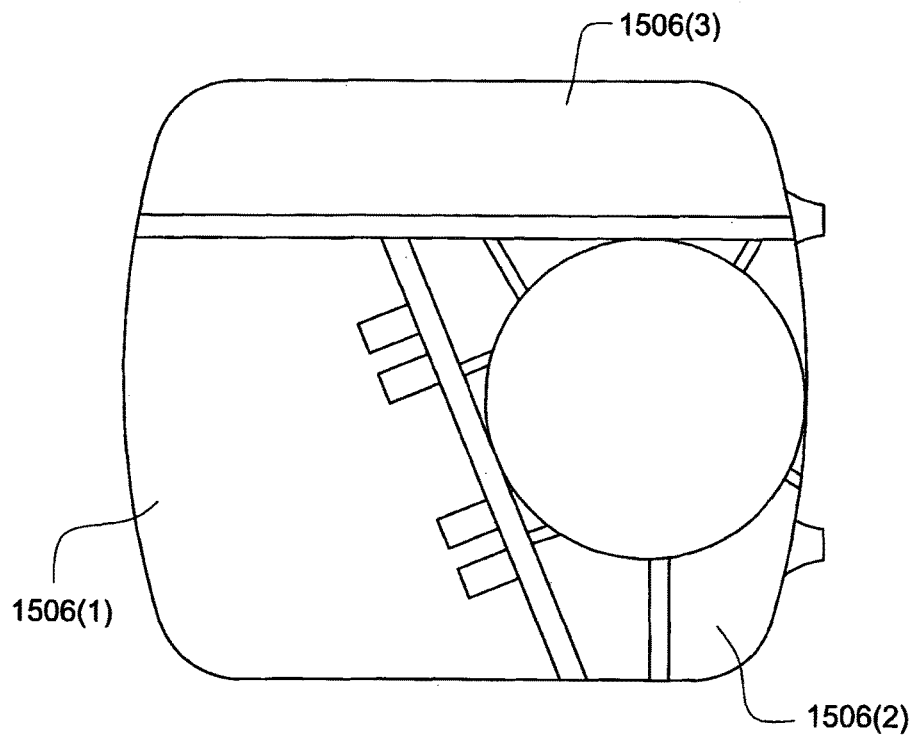
FIG. 117 is a schematic view of a casing for a PAP device according to an example of the disclosed technology.

FIGS. 116 and 117 show an example of a casing structured to accommodate PCBA, i.e., slot-in PCBA with no separate enclosure provided to the casing to enclose the PCBA. As illustrated, each casing includes an inlet chamber 1506(1), a blower chamber 1506(2), and a chamber 1506(3) to accommodate the PCBA.

Figure 101:
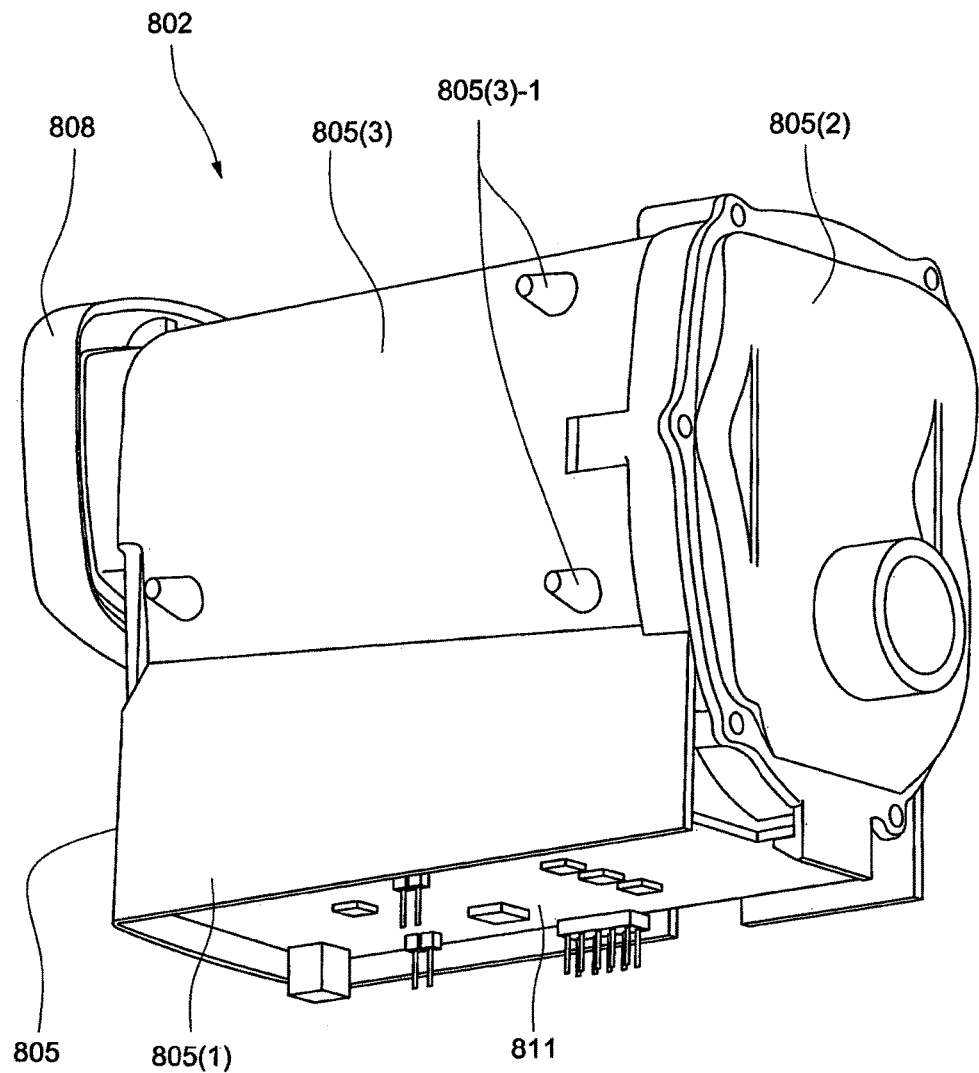
FIG. 101 is a perspective view of a PAP device according to an example of the disclosed technology.
Figure 102:
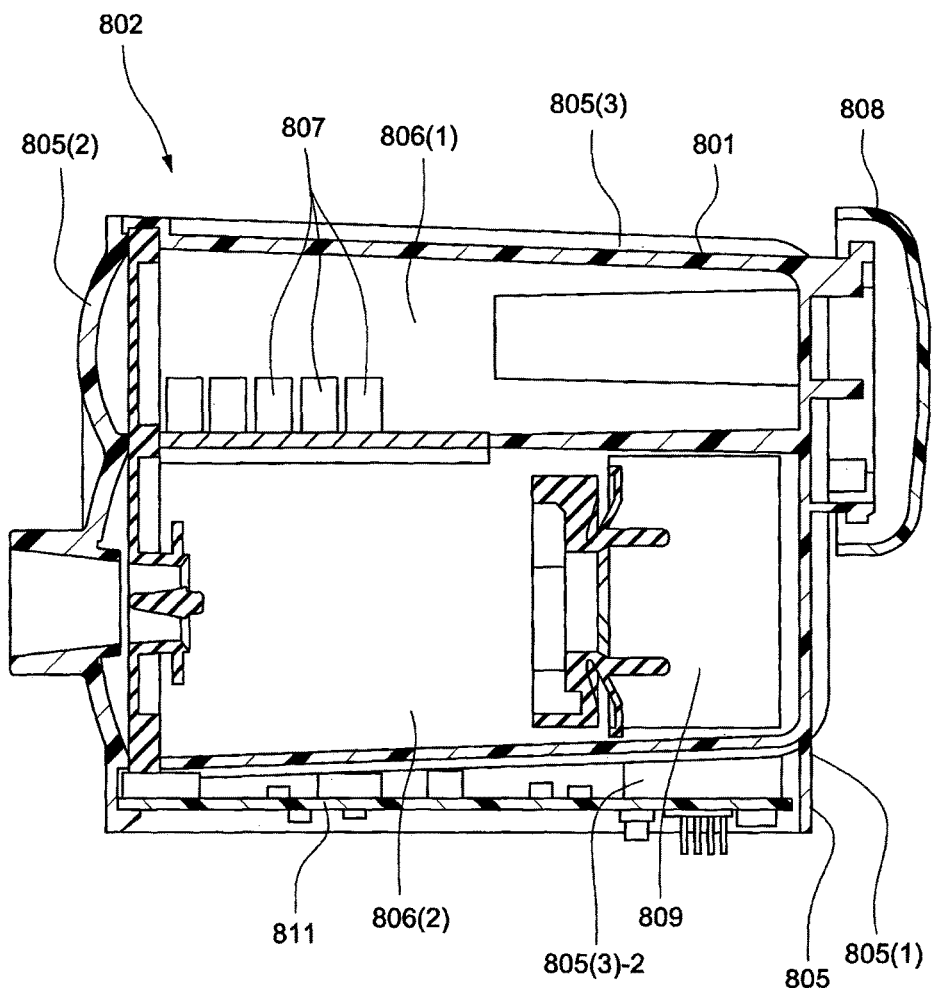
FIG. 102 is a cross-sectional view of the PAP device of FIG. 101.

FIGS. 101 and 102 show another example of a PAP device 802 which is similar to the PAP device 2 shown in FIGS. 41 and 42. In this example, the casing 805 (including base or chassis 805(1) and cover 805(2)) provides two chambers, i.e., inlet chamber 806(1) and blower chamber 806(2). As described above, inlet conduit(s) or chimney(s) 801 (e.g., two 50 mm inlet chimneys) extend from the inlet into the inlet chamber, flow conduits 807 extend between the inlet chamber and the blower chamber, and foam 809 is only provided within the blower chamber adjacent the blower inlet. The casing is structured to support and enclose a PCBA 811, e.g., base 805(1) includes enclosure walls to enclose and otherwise support sides and an end of the PCBA and cover 805(2) includes snap-fit tab to support an end of the PCBA and releasably secure the PCBA to the casing. Also, an overmold 805(3) is provided to the base of the casing and includes feet 805(3)-1 and flow ports 805(3)-2, e.g., for flow sensor. It should be appreciated that the shape and/or size of the device may vary to support different blower designs.

Figure 124:
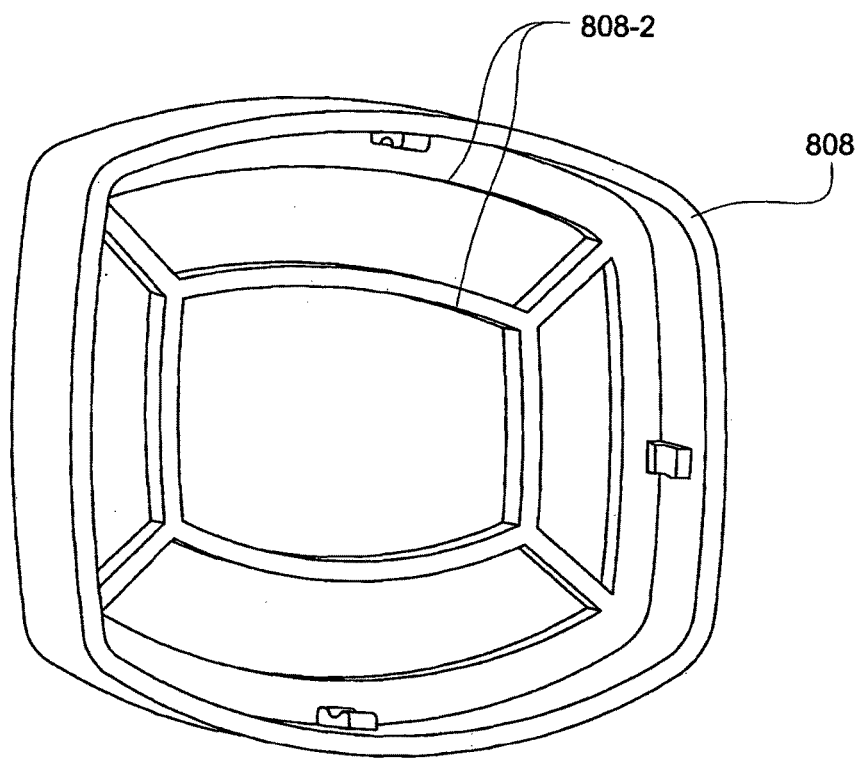
FIG. 124 is a perspective view of a filter cover for a PAP device according to an example of the disclosed technology.

A filter cover 808 is provided to the inlet of the casing to cover an inlet filter supported adjacent the inlet. As shown in FIG. 123, the filter cover 808 may include supports 808-1 to support the cover at the inlet of the casing. In an alternative example, as shown in FIG. 124, the filter cover 808 may include one or more inlet openings 808-2 along its top wall. In yet another example, as shown in FIGS. 125 and 126, the casing may be structured to support a filter insert 2008 adapted to be inserted into a slot adjacent the inlet/inlet chimney 2001 of the casing. As illustrated, the filter insert 2008 may include a filter portion 2008-1 and a cap or finger-grip portion 2008-2 adapted to support or retain the filter portion within the slot.

Figure 134:
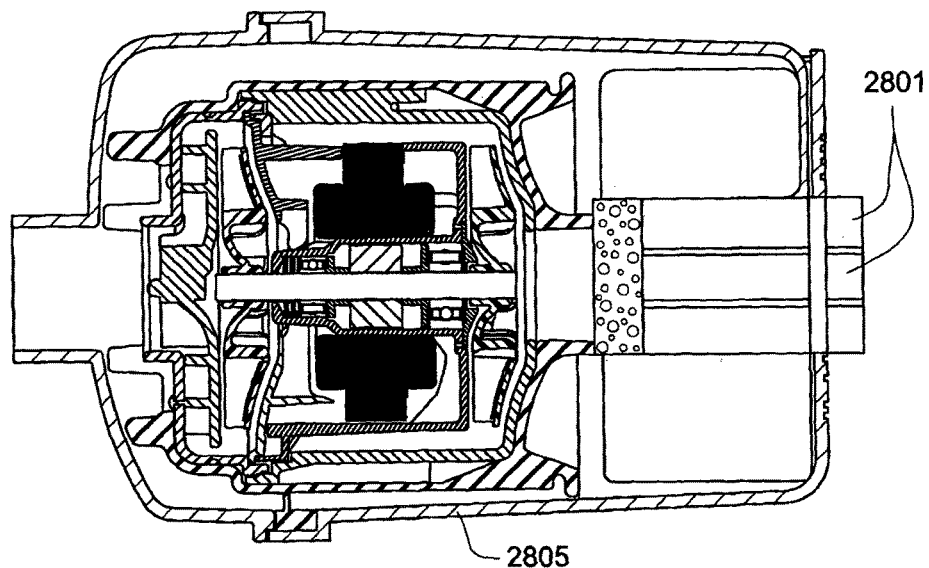
FIG. 134 is a cross-sectional view of a PAP device according to an example of the disclosed technology.

FIG. 134 shows an example in which inlet chimneys 2801 also provide flow conduits into a single chamber provided by the casing 2805.

1.8.1 Alternative Uses

Certain examples relate to systems in which the blower is adapted to be worn on the patient's head, is built into or incorporated into the patient interface or mask, is wearable or carried by the patient, is portable, is reduced in size or combinations thereof. In such examples, the blower may include the two stage variant as described above and its miniature size is especially beneficial (small overall product size).

1.9 Thin Wall Components

In an example, one or more components of the blower may include relatively thin walls, e.g., to enhance blower performance. For example, housing part walls, impeller blades of the impellers and/or stator vanes of the stationary components may include relatively thin walls or thin wall sections, while maintaining overall balance of the component. Also, thin vanes and impeller leading edges minimize pressure losses and provide small size (less bulky walls).

For example, as shown in FIG. 18, each impeller blade 62 of the impeller 60-1 may include a blade thickness at its base (i.e., where the blade meets the shroud 64) of about 0.7 mm and a blade thickness at its top (i.e., opposite end in the axial direction to the blade's base) of about 0.5 mm, i.e., blade tapers to a thinner thickness at its top, e.g., for molding purposes. FIG. 21 is another exemplary view showing thin and tapered blades of the impeller.

As shown in FIG. 25, each stator vane 75-1 of the shield 72 of the stationary component may include a vane thickness at its base in the range of about 0.4 mm to 1.2 mm and a vane thickness at its top in the range of about 0.25 mm to 1.1 mm.

Figure 28:
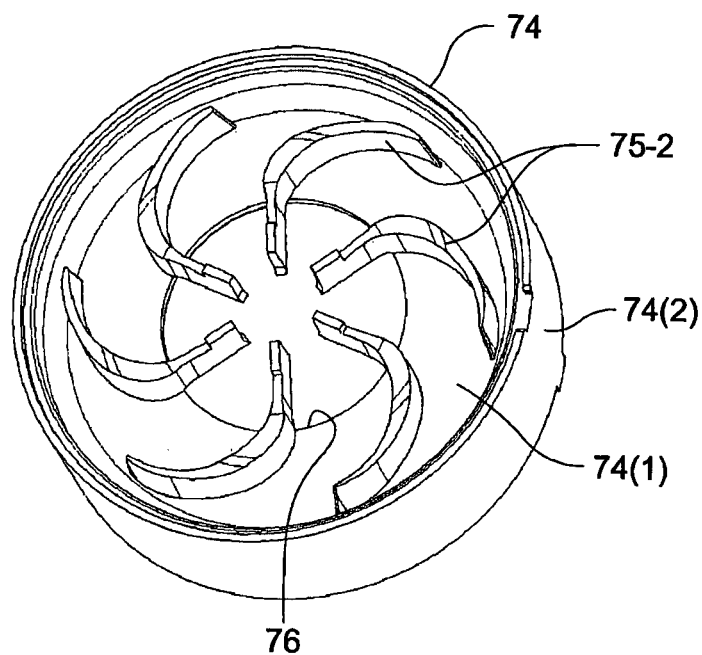
FIGS. 28 and 29 are perspective views of a housing of a stationary component according to an example of the disclosed technology.
Figure 29:
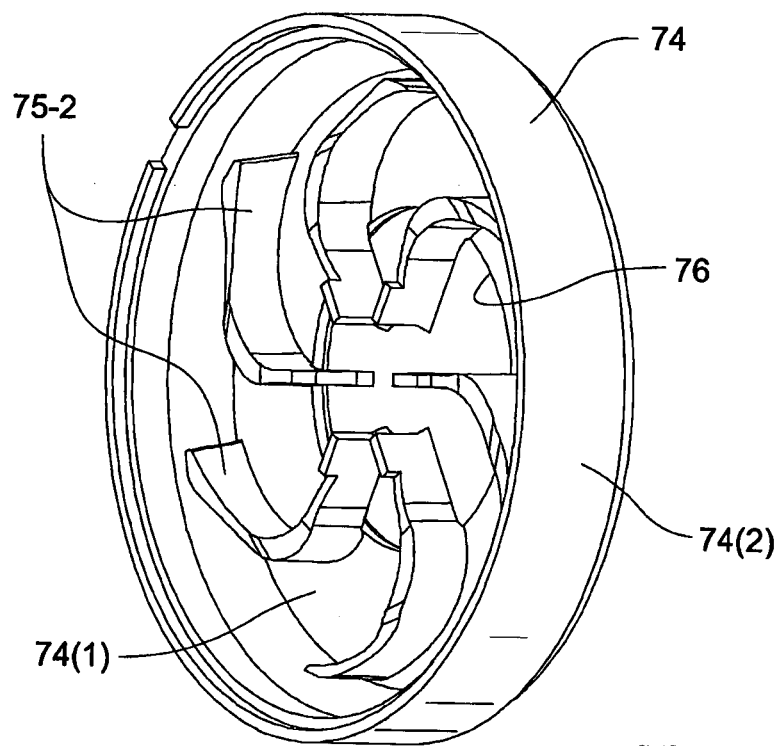
Figure 30:
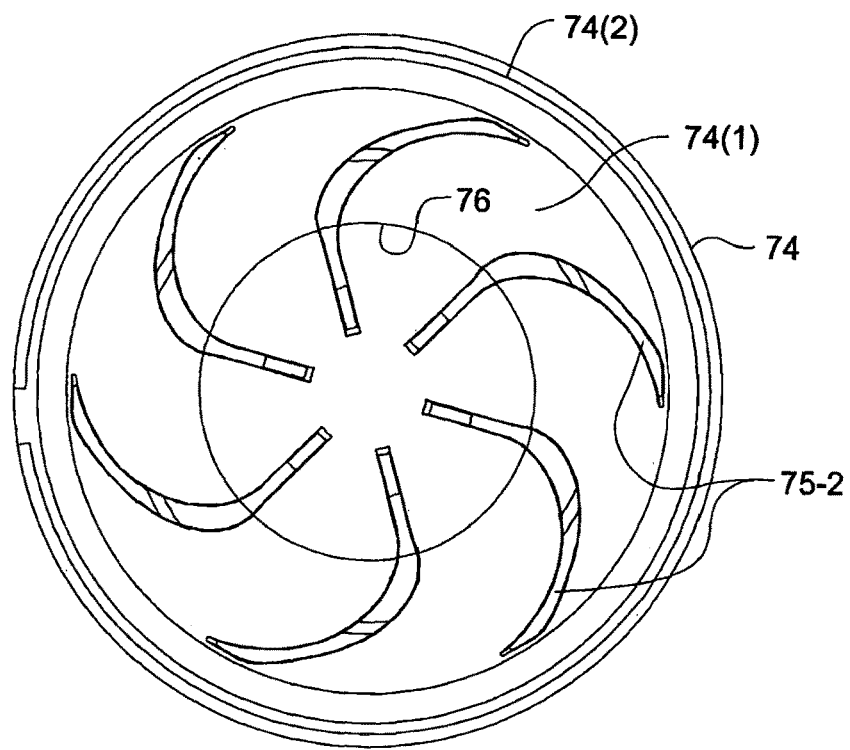
FIG. 30 is a top view of the housing of FIGS. 28 and 29.
Figure 31:
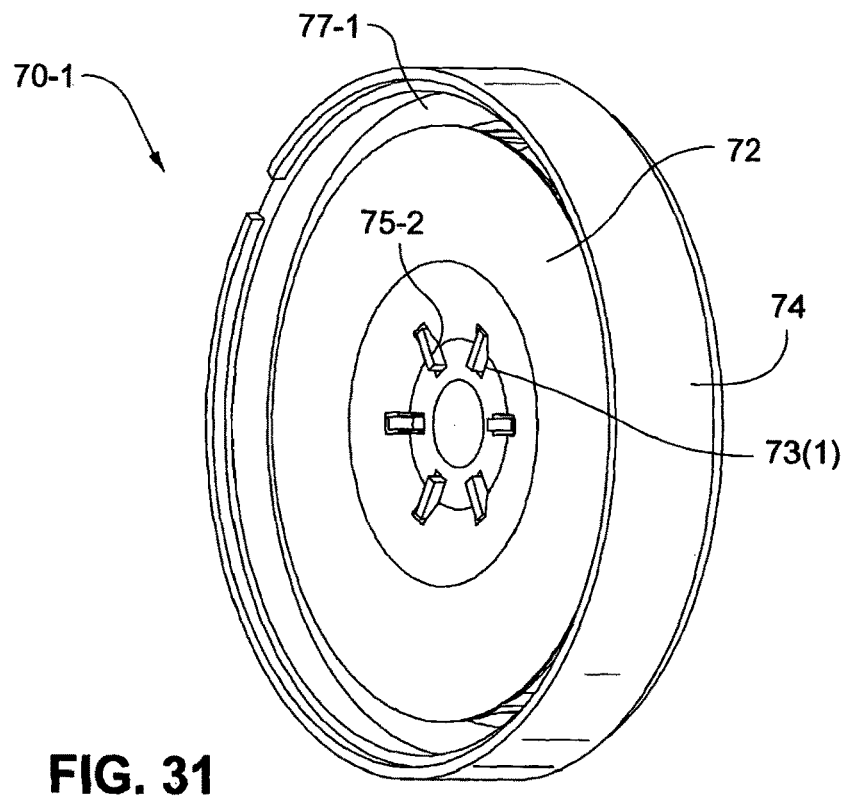
FIG. 31 is a perspective view showing an assembled stationary component including the shield of FIGS. 25-27 assembled to the housing of FIGS. 28-30.

As shown in FIG. 28, each stator vane 75-2 of the housing 74 of the stationary component may include a vane thickness at its base that varies from 0.25 mm at the tips to 1.3 mm at the center and a vane thickness at its top that varies from 0.25 mm at the tips to 1.2 mm at the center. FIG. 32 also illustrates thin and tapered vanes of the stationary component.

Exemplary reasons for varying vane thickness include: leading edge needs to be relatively thin to avoid losses as the air "splits" between entering the vane passage and recirculating; and/or keeping the vane passage expanding (or diffusing in order to obtain static regain), helps to allow the vane to become thicker towards the trailing edge, i.e., towards the outlet of the vane passage.

Exemplary steps to achieve relatively thin impeller blades/stator vanes (e.g., to provide good "fill" of the mold cavities that form the blades/vanes) include mold venting and high speed material injection. In mold venting, multi-section inserts may be provided to create vents on the blade side. Also, porous steel may be used as the material for blade/vane side insert. Porous steel may provide mat finish on parts because porous steel will not have as high a polish finish as traditional tool steel. Also, relatively thin impeller blades/stator vanes may be provided using specific materials, injection molding machines, machine settings, mold and material temperature, and/or material injection speeds.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A PAP device, comprising:
a casing; and
a blower,
the casing including an inlet chamber having a casing inlet configured to allow air to enter the casing, and the casing further including a blower inlet chamber that is peripheral to the inlet chamber such that the blower inlet chamber is outside or external to a periphery of the inlet chamber, the blower inlet chamber communicated with the inlet chamber and structured to support an inlet end of the blower, the inlet chamber configured to attenuate airborne radiated noise, wherein the blower is provided in the inlet chamber and receives airflow at the inlet end of the blower from the blower inlet chamber in use, and an outlet end of the blower is isolated from airflow within the inlet chamber.

2. A PAP device according to claim 1, wherein the blower is supported by a suspension system structured to divide low and high pressure sides of the blower.

3. A PAP device according to claim 2, wherein the suspension system includes an outlet end suspension to support an outlet end of the blower and an inlet end suspension to support the inlet end of the blower.

4. A PAP device according to claim 3, wherein the casing includes a base and an end wall provided to the base, and the outlet end suspension supports the outlet end of the blower within the casing and provides a seal between the end wall and the base.

5. A PAP device according to claim 1, wherein a casing outlet is located in the inlet chamber, the casing outlet is coupled to the outlet end of the blower and is isolated from the casing inlet by a suspension system.

6. A PAP device according to claim 1, wherein the inlet chamber is larger than the blower inlet chamber.

7. A PAP device according claim 2, wherein the suspension system includes one or more ports to interface with respective sensors.

8. A PAP device according to claim 2, wherein the suspension system is integrally formed as a one piece structure and structured to enclose or encase the blower.

9. A PAP device according to claim 8, wherein the suspension system is structured to interface and seal with one or more sensors.

10. A PAP device according to claim 2, wherein the suspension system includes a plurality of ribs or bumps on one or more outer surfaces.

11. A PAP device according to claim 1, wherein the casing includes at least one inlet conduit extending from the casing inlet into the inlet chamber to allow air to enter the inlet chamber.

12. A PAP device according to claim 11, wherein the at least one inlet conduit extends parallel to an axis of the blower.

13. A PAP device according to claim 11, wherein the at least one inlet conduit is tapered along its length such that its inlet end is larger than its exit end.

14. A PAP device according to claim 1, wherein the casing includes a plurality of conduits that allow air to pass from the inlet chamber to the blower inlet chamber.

15. A PAP device according to claim 14, further comprising a flow plate to support the plurality of conduits between the inlet chamber and the blower inlet chamber.

16. A PAP device according to claim 14, wherein the plurality of conduits extend parallel to an axis of the blower.

17. A PAP device according claim 14, wherein the plurality of conduits are provided upstream of the inlet end of the blower.

18. A PAP device according to claim 1, wherein the casing provides only two chambers including the inlet chamber and the blower inlet chamber.

19. A PAP device according to claim 2, wherein the suspension system includes an outlet conduit that extends through a casing outlet of the casing.

20. A PAP device according claim 19, wherein the casing outlet is offset from the outlet end of the blower.

21. A PAP device according to claim 1, wherein the casing includes a plurality of inlet conduits extending from the casing inlet into the inlet chamber to allow air to enter the inlet chamber.

22. A PAP device according to claim 11, wherein the at least one inlet conduit has a length greater than 30% of a total length of the inlet chamber.

23. A PAP device according to claim 22, wherein the at least one inlet conduit has a length greater than 50% of a total length of the inlet chamber.

24. A PAP device according to claim 11, wherein the at least one inlet conduit is configured to provide an inertance of greater than 200 kg/m$^4$.

25. A PAP device according to claim 24, wherein the at least one inlet conduit is configured to provide an inertance of greater than 300 kg/m⁴.

26. A PAP device according to claim 2, wherein the suspension system includes an outlet end suspension configured to isolate the outlet end of the blower from the airflow within the inlet chamber.

27. A PAP device according to claim 1, wherein the inlet chamber and the blower inlet chamber are arranged in series.

28. A PAP device according to claim 1, wherein the inlet end and the outlet end of the blower are aligned with an axis of the blower, and the casing inlet comprises an axis that is substantially parallel to the axis of the blower.

29. A PAP device according to claim 1, wherein the casing comprises a casing outlet configured to allow air to exit the casing, and the casing outlet comprises an axis that is substantially parallel to an axis of the casing inlet.

30. A PAP device according to claim 1, wherein the blower is supported by a suspension system within the inlet chamber, and the suspension system comprises a side wall configured to isolate the blower from air passing from the inlet chamber to the blower inlet chamber.

31. A PAP device, comprising:
a casing;
at least one inlet conduit;
an outlet; and
a blower provided within the casing,
the casing including at least an inlet chamber and a blower inlet chamber that is peripheral to the inlet chamber such that the blower inlet chamber is outside or external to a periphery of the inlet chamber, the blower inlet chamber communicated with the inlet chamber and configured to support an inlet end of the blower,
wherein the at least one inlet conduit is configured to deliver air into the inlet chamber, the outlet is arranged within the inlet chamber and in communication with an outlet end of the blower, and the outlet end of the blower is isolated from airflow within the inlet chamber.

32. A PAP device according to claim 31, wherein the at least one inlet conduit has a length of approximately 60 mm to 120 mm.

33. A PAP device according to claim 32, wherein the at least one inlet conduit has a length of approximately 95 mm.

34. A PAP device according to claim 31, wherein the at least one inlet conduit has a length greater than 50% of the length of the inlet chamber.

35. A PAP device according to claim 31, wherein the at least one inlet conduit is configured to provide an inertance of greater than 200 kg/m4.

36. A PAP device according to claim 35, wherein the at least one inlet conduit is configured to provide an inertance of greater than 300 kg/m4.

37. A PAP device according to claim 31, wherein the outlet end of the blower is isolated from the airflow within the inlet chamber by an outlet end suspension.

38. A PAP device according to claim 37, wherein the outlet end suspension is coupled between outlet and the outlet end of the blower.

39. A PAP device according to claim 37, wherein the outlet end suspension comprises a blower engaging portion, a tube portion and a casing engaging portion.

40. A PAP device according to claim 39, wherein the blower engaging portion is coupled to the outlet end of the blower and the casing engaging portion is coupled the outlet, the casing engaging portion being configured to isolate the casing from vibrations.

41. A PAP device according to claim 40, wherein the casing engaging portion includes a pressure port.

42. A PAP device according to claim 39, wherein the tube portion provides a sealed outlet path extending between the outlet end of the blower and the outlet.

43. A PAP device according to claim 42, wherein the outlet path has an expanding cross-section in the direction towards the outlet.

44. A PAP device according to claim 37, further comprising an inlet end suspension to support the inlet end of the blower.

45. A PAP device according to claim 44, wherein the outlet end suspension and/or the inlet end suspension is constructed of silicone or thermoplastic elastomer.

46. A PAP device according to claim 31, wherein the blower is located within the inlet chamber.

47. A PAP device according to claim 31, wherein the inlet conduit has an internal diameter of between approximately 8 mm and 20 mm.

48. A PAP device according to claim 47, wherein the inlet conduit tapers along its length such that the diameter at an inlet end is larger than the diameter at an exit end.

49. A PAP device, comprising:
a casing; and
a blower,
the casing including an inlet chamber having a casing inlet configured to allow air to enter the casing, and the casing further including a blower inlet chamber peripheral to the inlet chamber, the blower inlet chamber communicated with the inlet chamber and structured to support an inlet end of the blower, the inlet chamber configured to attenuate airborne radiated noise, wherein the blower is provided in the inlet chamber and receives airflow at the inlet end of the blower from the blower inlet chamber in use, and an outlet end of the blower is isolated from airflow within the inlet chamber,
wherein the casing includes a plurality of conduits arranged in parallel that allow air to pass from the inlet chamber to the blower inlet chamber.

50. A PAP device according to claim 49, wherein the plurality of conduits includes a plurality of parallel tubes to provide laminar flow.

51. A PAP device according to claim 49, further comprising a flow plate to support the plurality of conduits between the inlet chamber and the blower inlet chamber.

52. A PAP device according to claim 49, wherein an outlet end of the casing inlet and an inlet end of each of the plurality of conduits are provided in the inlet chamber.

53. A PAP device according to claim 49, wherein the inlet end and the outlet end of the blower are aligned with an axis of the blower, and the plurality of conduits are substantially parallel to the axis of the blower.

* * * * *